United States Patent
Glimcher et al.

(10) Patent No.: US 12,227,548 B2
(45) Date of Patent: Feb. 18, 2025

(54) USE OF IRE1α-XBP1 SIGNALING PATHWAY BIOMARKERS FOR MODULATING IMMUNE RESPONSES

(71) Applicant: Dana-Farber Cancer Institute, Inc., Boston, MA (US)

(72) Inventors: Laurie H. Glimcher, Boston, MA (US); Han Dong, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 796 days.

(21) Appl. No.: 17/294,477

(22) PCT Filed: Nov. 11, 2019

(86) PCT No.: PCT/US2019/060749
§ 371 (c)(1),
(2) Date: May 17, 2021

(87) PCT Pub. No.: WO2020/106483
PCT Pub. Date: May 28, 2020

(65) Prior Publication Data
US 2022/0023341 A1    Jan. 27, 2022

Related U.S. Application Data

(60) Provisional application No. 62/800,706, filed on Feb. 4, 2019, provisional application No. 62/769,265, filed on Nov. 19, 2018.

(51) Int. Cl.
*C07K 14/47*    (2006.01)
*A61K 39/00*    (2006.01)
(Continued)

(52) U.S. Cl.
CPC ...... *C07K 14/4705* (2013.01); *A61K 39/4613* (2023.05); *A61K 39/4644* (2023.05);
(Continued)

(58) Field of Classification Search
CPC .... A61K 35/17; A61K 45/06; A61K 2239/38; A61K 39/4613; A61K 2239/31;
(Continued)

(56) References Cited

U.S. PATENT DOCUMENTS

| 2012/0015841 A1* | 1/2012 | Shekdar ............ A61P 3/10 435/6.12 |
| 2013/0280269 A1 | 10/2013 | Samali et al. |
| 2018/0298079 A1 | 10/2018 | Lefrancois et al. |

FOREIGN PATENT DOCUMENTS

WO    WO-2020/106483 A1    5/2020

OTHER PUBLICATIONS

Sun, J., Beilke, J. & Lanier, L. Adaptive immune features of natural killer cells. Nature 457, 557-561 (2009). (Year: 2009).*
Berrou et al., "Natural Killer Cell Function, an Important Target for Infection and Tumor Protection, Is Impaired in Type 2 Diabetes," Plos One, 8(4): e62418 (2013).
(Continued)

*Primary Examiner* — Jeremy C Flinders
*Assistant Examiner* — Thomas R. Amick
(74) *Attorney, Agent, or Firm* — Foley Hoag LLP; DeAnn F. Smith; Philip S. Choi

(57) ABSTRACT

The present invention is based, in part, on the identification of an IRE1α-XBP1-cMyc axis in NK cell immunity. The present invention provides compositions and methods for treating conditions that would benefit from modulating (e.g., upregulating or downregulating) an immune response using an agent that modulates the IRE1α-XBP1 pathway, or a composition comprising modified NK cells.

12 Claims, 71 Drawing Sheets
Specification includes a Sequence Listing.

(51) Int. Cl.
  *A61K 45/06* (2006.01)
  *A61P 35/00* (2006.01)
  *C12N 5/0783* (2010.01)
  *C12N 15/11* (2006.01)
  *C12N 15/113* (2010.01)
  *C12Q 1/6886* (2018.01)

(52) U.S. Cl.
  CPC ...... *A61K 39/464838* (2023.05); *A61K 45/06* (2013.01); *A61P 35/00* (2018.01); *C12N 5/0646* (2013.01); *C12N 15/111* (2013.01); *C12N 15/113* (2013.01); *C12Q 1/6886* (2013.01); *A61K 2239/31* (2023.05); *A61K 2239/38* (2023.05); *A61K 2239/57* (2023.05); *C12Q 2600/106* (2013.01); *C12Q 2600/158* (2013.01)

(58) Field of Classification Search
  CPC ............ A61K 2239/57; A61K 39/4644; A61K 39/464838; A61P 35/00; C07K 14/4705; C12N 15/111; C12N 15/113; C12N 2501/2302; C12N 2501/2312; C12N 2501/2315; C12N 2501/2318; C12N 2501/998; C12Q 1/6886; C12Q 2600/106; C12Q 2600/158
  See application file for complete search history.

(56) References Cited

OTHER PUBLICATIONS

Dong et al., "The IRE1 endoplasmic reticulum stress sensor activates natural killer cell immunity in part by regulating c-Myc," Nature Immunology, 20(7): 865-878 (2019).
Hosomi et al., "New Insights Into the Regulation of Natural-Killer Group 2 Member D (NKG2d) and NKG2d-Ligands: Endoplastic Reticulum Stress and CEA-Related Cell Adhesion Molecule," Front Immunol, 9(1324):1-8 (2018).
International Search Report and Written Opinion for International Application No. PCT/US2019/060749 mailed Apr. 9, 2020.
Invitation to Pay Additional Fees for International Application No. PCT/US19/60749 dated Feb. 13, 2020.
Kamimura et al.,"Endoplasmic Reticulum Stress Regulator XBP-1 Contributes to Effector CD8 T Cell Differentiation during Acute Infection," The Journal of Immunology, 181(8): 5433-5441 (2008).
Leong et al., "Preactivation with IL-12, IL-15, and IL-18 Induces CD25 and a Functional High-Affinity IL-2 Receptor on Human Cytokine-Induced Memory-like Natural Killer Cells," Bio Blood Marrow Transplant, 20(4): 463-473 (2014).
Poli et al., "CD56bright natural killer (NK) cells: an important NK cell subset," Immunology, 126(4): 458-465 (2009).
Wu et al., "Developmental and Functional Control of Natural Killer Cells by Cytokines," Frontiers In Immunology, 8: Article 930 (2017).

* cited by examiner

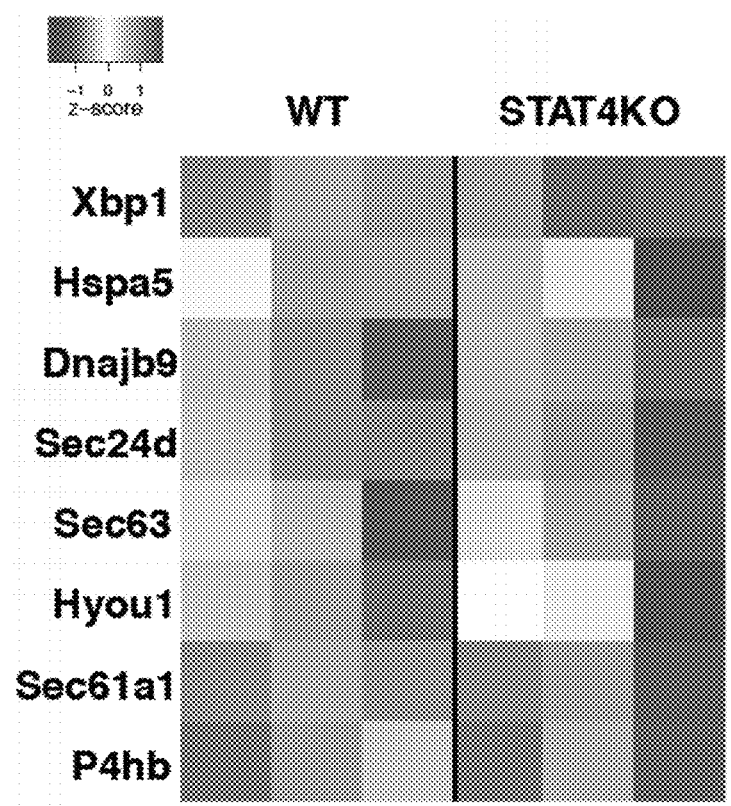

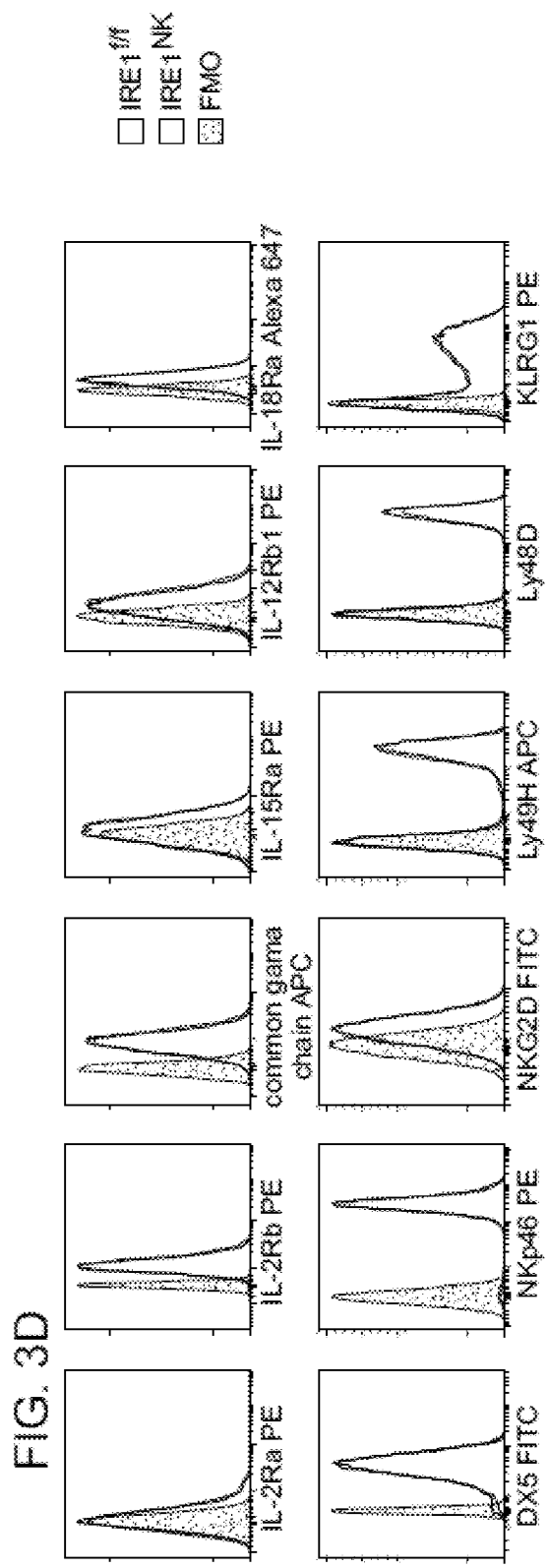

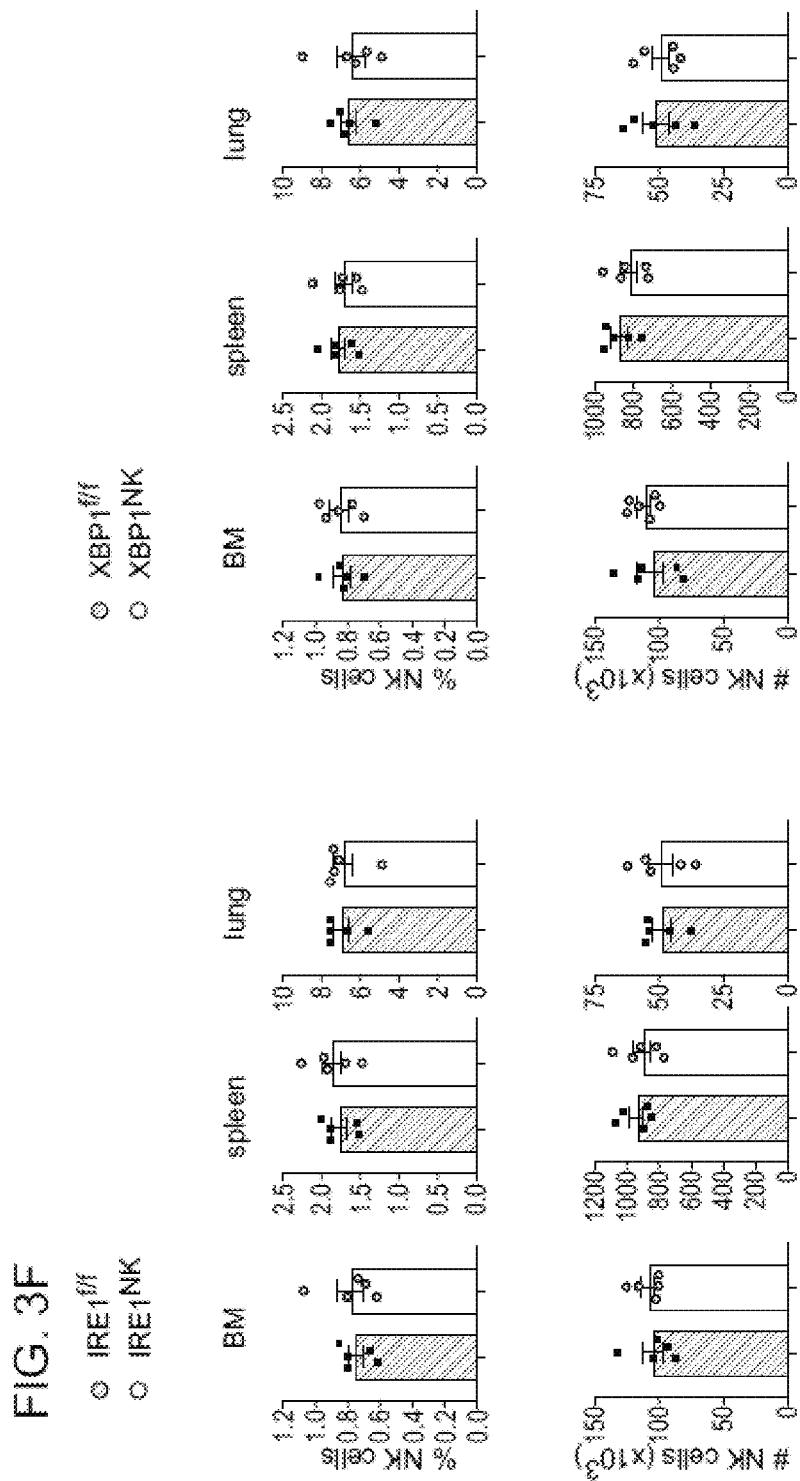

FIG. 4C
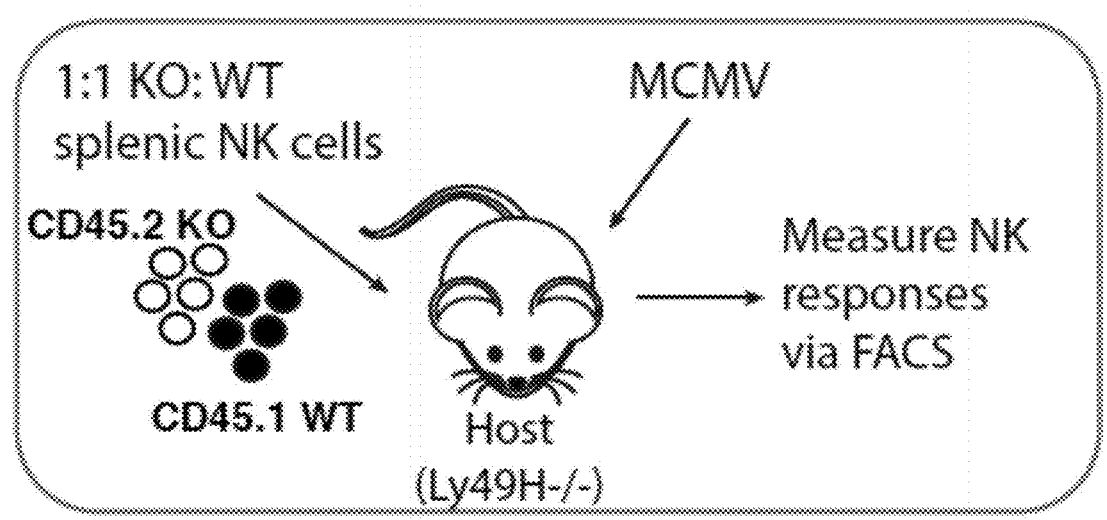
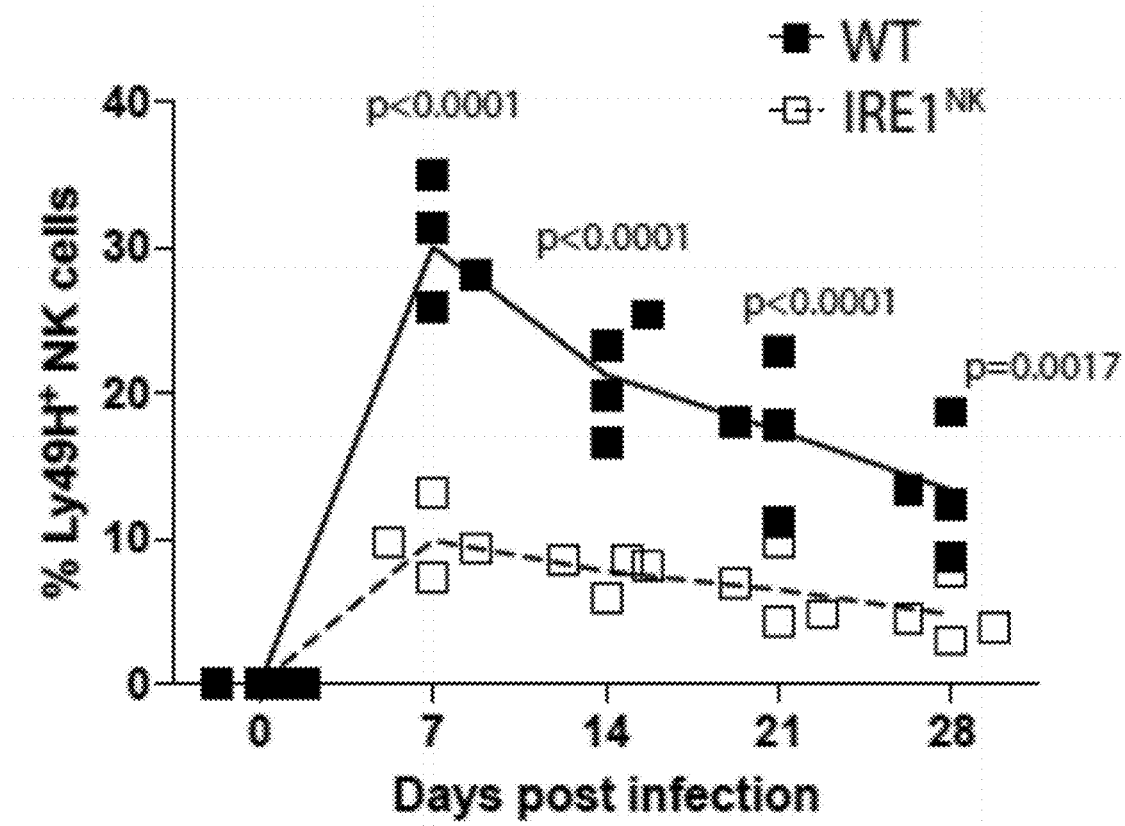
FIG. 4D

FIG. 5D con't
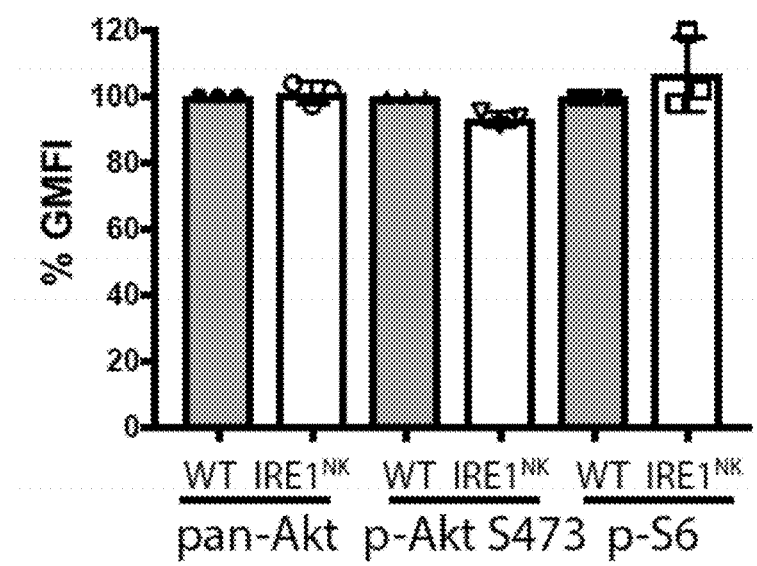

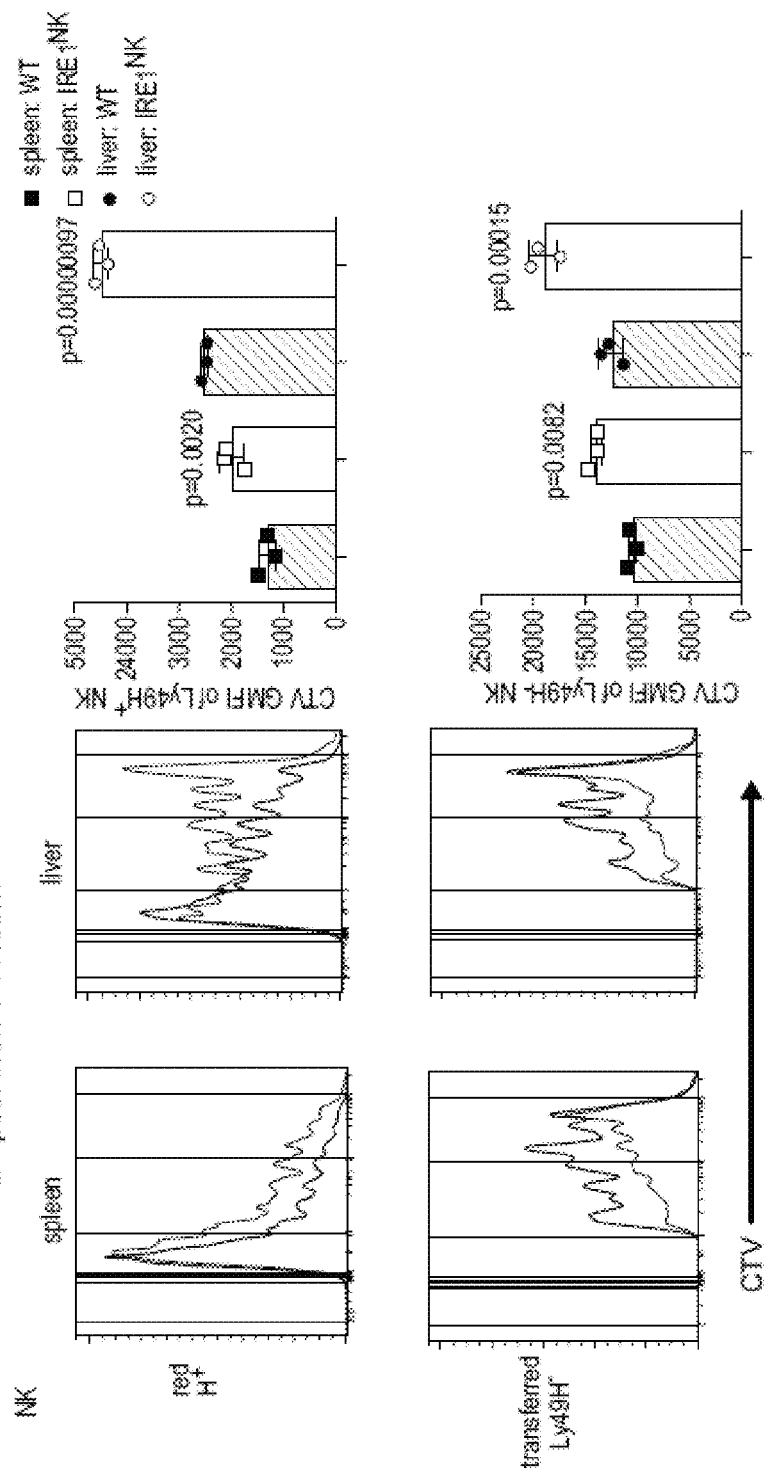

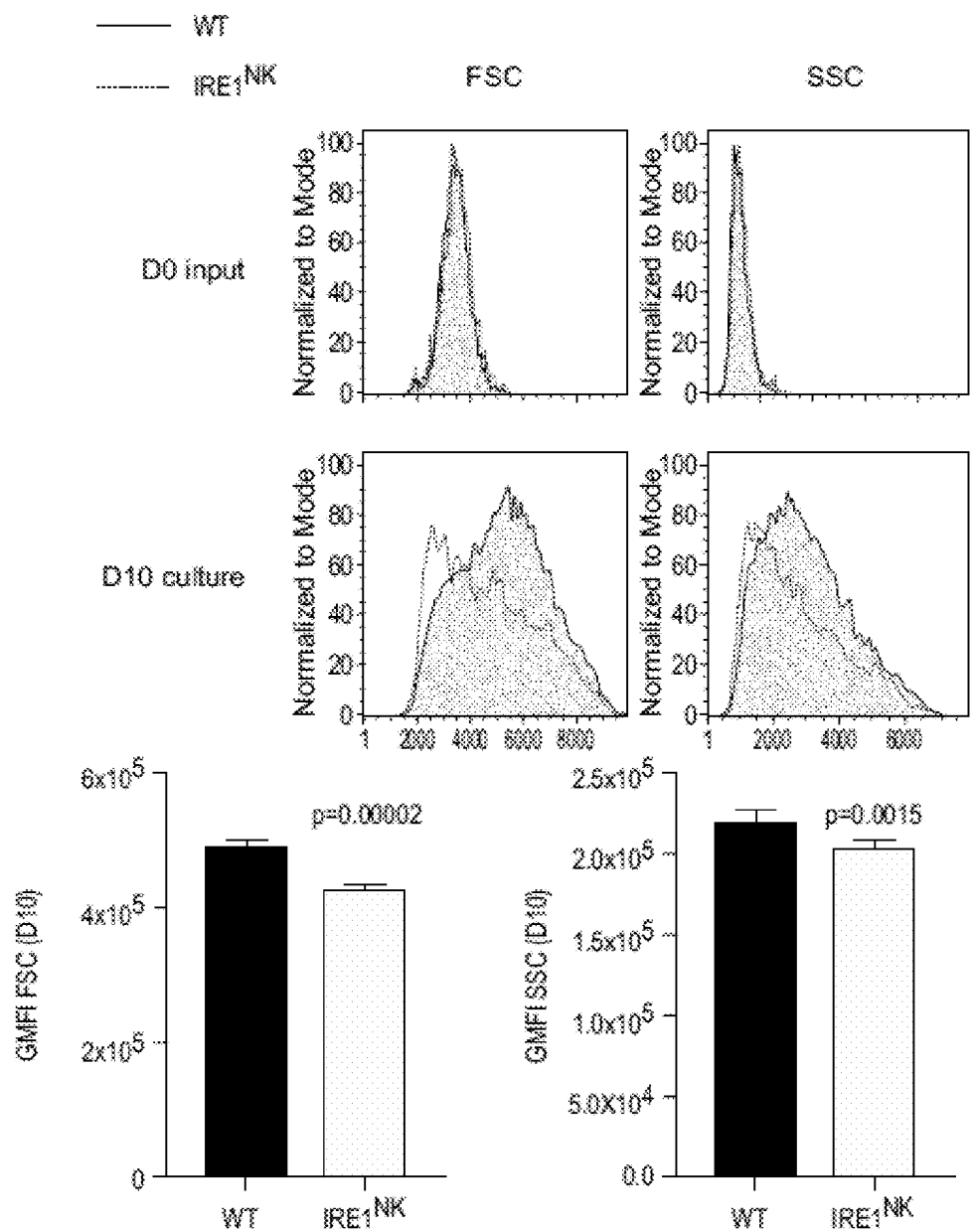

| Upstream Regulator | Molecule Type | Predicted Activity | Activation z-score | P-value |
|---|---|---|---|---|
| XBP1 | transcription factor | inhibited | -7.624 | 2.66E-38 |
| MYCN | transcription factor | inhibited | -6.347 | 3.93E-28 |
| KDM5A | transcription factor | Activated | 5.488 | 1.14E-12 |
| IGF1R | transcription factor | inhibited | -2.762 | 3.60E-09 |
| MYC | transcription factor | inhibited | -3.008 | 4.75E-08 |
| ERN1 | kinase | inhibited | -4.277 | 6.23E-08 |

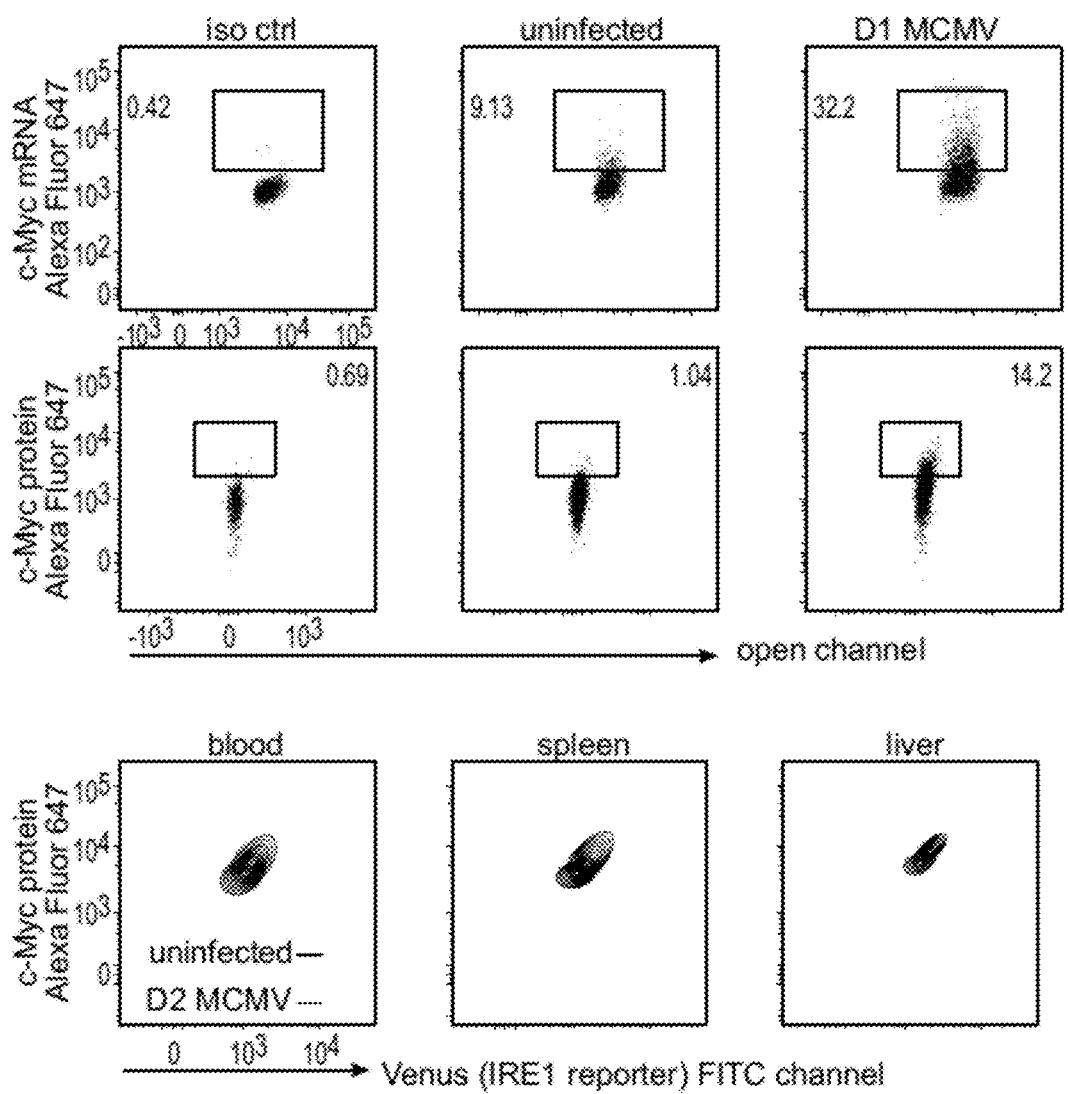

— WT (Mycf/+Ncr1Cre-)
---- HET (Mycf/+Ncr1Cre+)

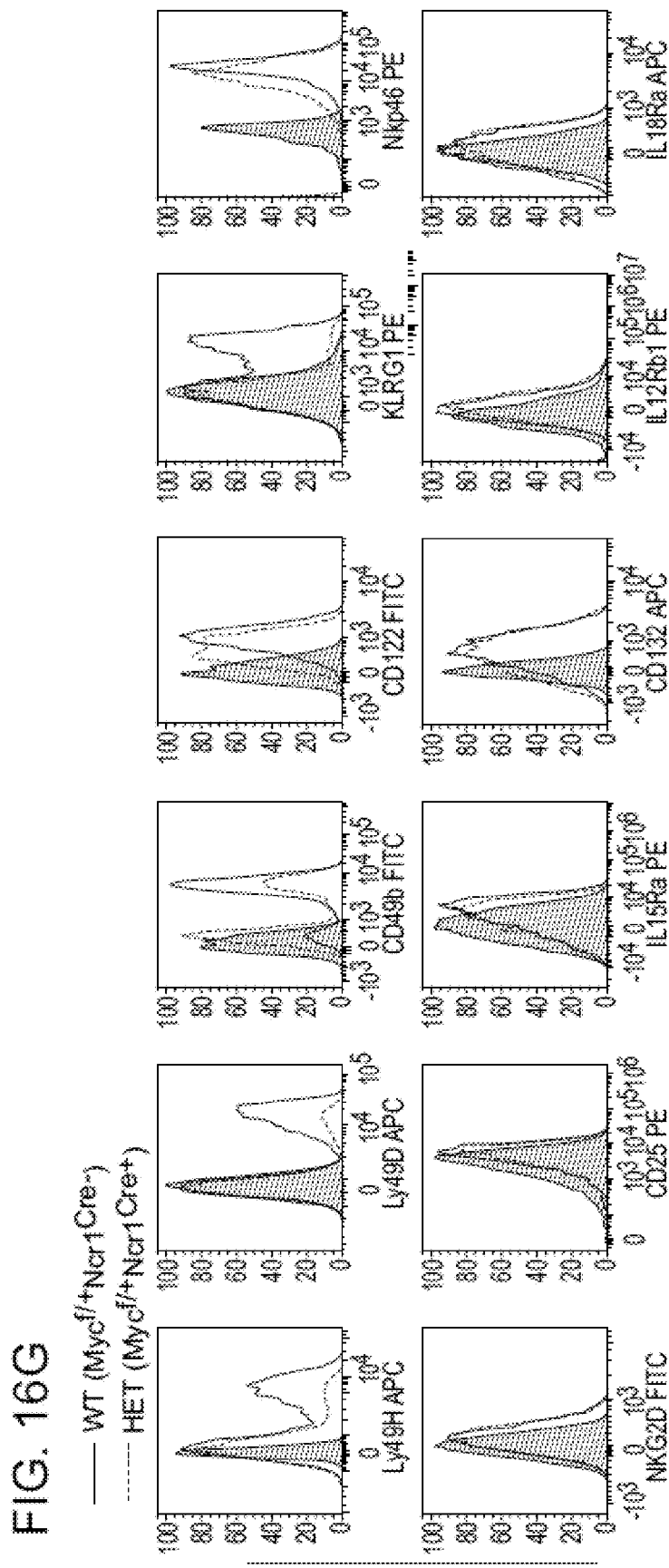

SEQUENCE LISTING

```
<160> NUMBER OF SEQ ID NOS: 68

<210> SEQ ID NO 1
<211> LENGTH: 7910
<212> TYPE: DNA
<213> ORGANISM: Homo sapiens

<400> SEQUENCE: 1
tgcctagtca gttctgcgtc cgctgaggct cggtcaccgc ctcgctgtcg tcgcggcgcc      60
cccgccccgt cctctgtccg taccgccccc ggagccaggg ccgagtcctc gccatgccgg     120
cccggcggct gctgctgctg ctgacgctgc tgctgcccgg cctcgggatt tttgaagta      180 ccagcacagt gacgcttcct gaaaccttgt tgtttgtgtc aacgctggat ggaagtttgc     240
atgctgtcag caagaggaca ggctcaatca aatggacttt aaaagaagat ccagtcctgc     300
aggtcccaac acatgtggaa gagcctgcct ttctcccaga tcctaatgat ggcagcctgt     360
atacgcttgg aagcaagaat aatgaaggcc tgacgaaact tccttttacc atcccagaat     420
tggtgcaggc atccccatgc cgaagttcag atggaatcct ctacatgggt aaaaagcagg     480
acatctggta tgttattgac ctcctgaccg gagagaagca gcagactttg tcatcggcct     540
ttgcagatag tctctgccca tcaacctctc ttctgtatct tgggcgaaca gaatacacca     600
tcaccatgta cgacaccaaa acccgagagc tccggtggaa tgccacctac tttgactatg     660
cggcctcact gcctgaggac gacgtggact acaagatgtc ccactttgtg tccaatggtg     720
atgggctggt ggtgactgtg gacagtgaat ctgggacgt cctgtggatc caaaactacg     780 cctccctgt ggtggctttt tatgtctggc agcgggaggg tctgaggaag gtgatgcaca     840
tcaatgtcgc tgtggagacc ctgcgctatc tgaccttcat gtctggggag gtggggcgca     900
tcacaaagtg gaagtacccg ttccccaagg agacagaggc caagagcaag ctgacgccca     960
ctctgtatgt tgggaaatac tctaccagcc tctatgcctc tccctcaatg gtacacgagg    1020
gggttgctgt cgtgccccgc ggcagcacac ttcctttgct ggaagggccc cagactgatg    1080
gcgtcaccat tggggacaag ggggagtgtg tgatcacgcc cagcacggac gtcaagtttg    1140 atccccggact caaaagcaag aacaagctca actacttgag gaattactgg cttctgatag    1200
```

```
gacaccatga aaccccactg tctgcgtcta ccaagatgct ggagagattt cccaacaatc   1260
tacccaaaca tcgggaaaat gtgattcctg ctgattcaga gaaaagagc tttgaggaag    1320 ttatcaacct ggttgaccag acttcagaaa acgcacctac caccgtgtct cgggatgtgg   1380
aggagaagcc cgcccatgcc cctgcccggc ccgaggcccc cgtggactcc atgcttaagg   1440
acatggctac catcatcctg agccccttcc tgctgattgg ctgggtggcc ttcatcatca   1500
cctatcccct gagcatgcat cagcagcagc agctccagca ccagcagttc cagaaggaac   1560
tggagaagat ccagctcctg cagcagcagc agcagcagct gcccttccac ccacctggag   1620
acacggctca ggacggcgag ctcctggaca cgtctggccc gtactcagag agctcgggca   1680
ccagcagccc cagcacgtcc cccagggcct caaccactc gctctgctcc ggcagctctg    1740
cctccaaggc tggcagcagc ccctcccctgg aacaagacga tggagatgag gaaaccagcg   1800
tggtgatagt tgggaaaatt tccttctgtc ccaaggatgt cctgggccat ggagctgagg   1860
gcacaattgt gtaccggggc atgtttgaca accgcgacgt ggccgtgaag aggatcctcc   1920
ccgagtgttt tagcttcgca gaccgtgagg tccagctgtt gcgagaatcg gatgagcacc   1980
cgaacgtgat ccgctacttc tgcacggaga aggaccggca attccagtac attgccatcg   2040
agctgtgtgc agccaccctg caagagtatg tggagcagaa ggactttgcg catctcggcc   2100
tggagcccat caccttgctg cagcagacca cctcgggcct ggcccacctc cactccctca   2160
acatcgttca cagagaccta aagccacaca acatcctcat atccatgccc aatgcacacg   2220
gcaagatcaa ggccatgatc tccgactttg gcctctgcaa gaagctggca gtgggcagac   2280
acagtttcag ccgccgatct ggggtgcctg gcacagaagg ctggatcgct ccagagatgc   2340
tgagcgaaga ctgtaaggag aaccctacct acacggtgga catcttttct gcaggctgcg   2400
tcttttacta cgtaatctct gagggcagcc accccttttgg caagtccctg cagcggcagg   2460
ccaacatcct cctgggtgcc tgcagccttg actgcttgca cccagagaag cacgaagacg   2520
tcattgcacg tgaattgata gagaagatga ttgcgatgga tcctcagaaa cgcccctcag   2580
cgaagcatgt gctcaaacac ccgttcttct ggagcctaga gaagcagctc cagttcttcc   2640
aggacgtgag cgacagaata gaaaaggaat ccctggatgg cccgatcgtg aagcagttag   2700
agagaggcgg gagagccgtg gtgaagatgg actggcggga gaacatcact gtcccctcc    2760 agacagacct gcgtaaattc aggacctata aggtggttc tgtcagagat ctcctccgag    2820
ccatgagaaa taagaagcac cactaccggg agctgcctgc agaggtgcgg gagacgctgg   2880
ggtccctccc cgacgacttc gtgtgctact tcacatctcg cttccccac ctcctcgcac    2940 acacctaccg ggccatggag ctgtgcagcc acgagagact cttccagccc tactacttcc   3000 acgagcccc agagcccag ccccagtga ctccagacgc cctctgagcg agggcggccc      3060
ctctgttctg gtggcccag ctgtgactga gggcctggtc accacaatta gagcttgatg    3120
cctcccggct ttgcagggag accaggcttc caaaccaag tgccttgagc tgcctgctct    3180
gcagcccaca gaggacagtg ctgaccccag gaagtgggag aagtggcccc tcgtgaccta   3240
cagggaactg ggaagatgct ggccccaaaa gccttacggt catgatgtct gcaaaggagg   3300
gcctcagaga cagcgcgagt agcaccccca gccatctact ggataaactt gcttcagact   3360 tttttaaattc ctgcttaatg tcagtctaca ggcctttcag gaagggagag gagggaatcg   3420
tacattttgc ttgcgtgctg ggacagctag gctgagatgc accaagtaca gccttcactg   3480
gagaccggaa ttgagaggtg gggatgctg aggaggggga ggacggagtt cagagggtgt    3540
```

| | |
|---|---|
| cgtcctgcag tgtgagattt ctcattgatc acagatgtgc ccagagtagc ccaggtcact | 3600 |
| gttaactagt gtttctgcag aggcagcagg agccatgagc atgaggtgtg cattaggga | 3660 |
| ctggtcagct atgcatgctg gcaggtgggg ttgtgtctgc aggtctcaga aatgaagagg | 3720 |
| ctgctctgtt ctggaggcag ccgtggccca gtgccagtgg ccagaacagt ggcctttggt | 3780 |
| gggtgtgtcc cgggccatct cggggtggtg ctcaggagcg cctggggcaa gaggtaaaga | 3840 |
| gttccctggc cttcaaggag agcagcgaag acccagacag gggccagcct tcaggaccag | 3900 |
| agggaggccg ccgaatggga ccctcctggt caccaggaga aagccctggg ccagcgagta | 3960 |
| ggcagtcaaa ctccttcgtc cccaaggccg gtggaacaag aggctcgtgg tgagtcaggg | 4020 |
| ccagggtggg tggccaaggc cagggtcacc gtgtgcttca tgggccagct ttttgtttt | 4080 |
| tcttggcaaa ttttaataac tatattttga ttatactgta gaatgctatg tcagcataag | 4140 |
| taagctaaac ttgaagcttt cttgtgaaga ataaatgcaa gatagaatac atcttctatt | 4200 |
| ttttgtggta ccaaaaatca ccatcccctc aagagtgttc atgtatagaa cattctctaa | 4260 |
| tgctgaagag taaaacatta tagcaacact atgtaaatgt attgaacagt atcaaagaaa | 4320 |
| tagtctctaa attgtttgta ccatattttt ttttctaaac ttaacataat ttttagcttt | 4380 |
| agtttcagtc aaaactttgt cttttctctc ccgagagcct tagaggttaa aatgcaatca | 4440 |
| gcctaccgtg taaggagatg ttgtccatgt actttctcca gccagttggg ggatcattgc | 4500 |
| agctcaggcc tggtgaactc agagattcca ttcagtatta agaatgggat tgttgaattt | 4560 |
| tactcacaga gaaatcactg tttcttcatg ttgtaagatg ttttctgttt gtgtatttgt | 4620 |
| atcatggtta ctcatcaaaa gctctcattc tgcctttgta gaattcagtt cccttccttt | 4680 |
| catcatagct aaagtgactt tttccctac tattaacgtg atcctacatc cttaaatctc | 4740 |
| atcgattacc tcacttaggc cttggaacct tggcccttgg tcggtgtcct tggcgtcttc | 4800 |
| taagcaaggc tgtgcgttgt tcagaaacgt ggccagaccg catttcctgc tgctcccatg | 4860 |
| ccgcatgcca ggtggcctga gacagagctc cccatacggc tgcaaggtgc tttacctgtg | 4920 |
| ggctttggca gtaacccaag agaggatcag aaggtggaga aggtgccacg agtgatttaa | 4980 |
| caggcctgcc acagggagtg cccccagccc agctcgttct cagcacaggt tttctctttg | 5040 |
| ggagtaccca ggtgatttct agtgacccaa ttttgtgtca tctccctgtt ttagccccac | 5100 |
| ttgcctagag acaactgttt ccgatgcctt ttctgcttat catactagtt tctaaccacg | 5160 |
| cagatttctc aaaatcattt attcaatgta ttttatttga gcacttagtg tattgagcta | 5220 |
| ggcaggatat agggtgccgg agatacagcg atgaacaaga caggcaaaac ttctgctttc | 5280 |
| ctaaaacttg tgatgagaga gaacaataaa aaagtgttgc tgccacaaag aaaccaaagt | 5340 |
| gtgtggggaa gggcgcgtgt ttgcggttta catctcttct gtcccagaat cacagggatc | 5400 |
| tggtccggtc acctctggtc tttcctctta gtcgccttta ggagccctgg ttcccgtcca | 5460 |
| tcctctgggg ggtttgtttg aagagatctc gtgtgggtac ttgtcatgaa acaccttgg | 5520 |
| gcatcatctg gtgtatccag ttctagtctc gagaattctg gtttcccact gtgctcagca | 5580 |
| agtggaaagt tcttttcagg ccagaacagc tctgcaccat cacatatcgt gttgcggctt | 5640 |
| agctgtttgg tctgtagttc aggttatggg acttctccaa tcctggaagg ctgttgagct | 5700 |
| ttttagaagt actgtacgct atcttcaaga tggagcttgg tcacatctgt taggaatcca | 5760 |
| aaggacacta tgacttattt aaatcttgtc ttactaaacc tctcttgggc acgtgtgcca | 5820 |
| gaatttctct tgttgcttct tgagtctttt taatttcagt gttttttcgt ttgttttttg | 5880 |
| tttttttgag acagagtctc gctctgtcac ccaggctgga gtgcagtggc acgacctcag | 5940 |

```
ctcactgcaa cctccgcctc cttggttcaa gcaattctcc tgcctcagcc tcccgagtag    6000
ctgggattac aggtgtgtgc caccacgctc ggctaatttt ttatattttt tttagtagag    6060
acggggtttc cccatgttag gcaggatggt ctcgatctcc taacctcgtg atccgcctgc    6120
ctcagcctcc caaagtgctg ggattacagg cttgagccac cgcacccggc ctaatctcag    6180
tttttgaagt gctccacaag tcattaggca ccaaaacatt ttcacctggg aacactggc     6240 atttccctga ttagctgtga agcaatctag tggctaagtg tgaaatcctg ggtgcgcagg    6300
tgttctcact cccgccgtgt tctcagtgca gtggtggtca gaggcccttc caaggagaca    6360
tcactctgat cagttacaga tagatgttct ggaagatctg caggtgagta gatccagcag    6420
agtttcttcc caccaactct agaagaaagg gccttatcag agttgaccct gagcctttgg    6480
taaggttttg tgtgcatgcg attcagttat ctttggcaat tcttttcttg ctgcagtgag    6540
agattaattg gttgctgatc aaaccgttca tgcagatggg gggaccttg gattgtacgg     6600 ctttctcctc ttggctgctt tcttttcagg aagttggact ttggccaggt ttggcttcc    6660 cagagccgtt cctttctctg tcctttcctt gggtcctcat ggtgtgccca ttggatcctt    6720
ggccttgtga tcctctggga actggggcc agttccactt ttgcagcctt ctgtgctgga    6780
agagaagccc agcgccctgg aaggagcctc tttaagtccc ccatgtcgct ttctctctct    6840
gctcttttag tgtctgagat tgcctttctt tgaatttccc agtgtttctt ttccttgtcc    6900
cttccctcac caacctggag ttattttggt tgactatgtc ctggctttgg cttctcctgg    6960
caggaagtca tcaggcatcc tctccaggtg agccgaaatt ccaccctccc aggttggaca    7020
tcatctttta aacccaatgg tctactcccc tccttcttta tgaaacagtg atttcccgtg    7080
agtaactctg gttctgattt tttgtaccgg cgcttaaatt ctttctgtag acgttggaaa    7140
gccacaaaga acgtgactgc agtgagcctc ccactggagc agccttaacc aacactttgg    7200
ccaaagcccc cccacctccc ctgtgtactg tgtgtgtgtt tggtggatac agtattcctt    7260
ttcagtgtcc ctaaagctgt gatggggagt ccccacttac ctagaaagca ttaccagtca    7320
cctactctgc attctcagat gtaaaccttg tgtagtgttc ttttttgcaat gacctattta    7380 tttaacctat ttatatttat ttaatttta ctctgaaatg tatccagtta caattgtact     7440
tgcttaaagc acatcagatt tgttttggac aacaccttg accatttaa aactggaaaa     7500 gtgatactgt atccttccat gggatggatg ctttacagta gtcttattat taagggtga    7560 ttaatttggt cggggtaaaa tgttaatttt taggtgatttt ttaagaattc tgtgccatta    7620
tgtcttctgt gtggatggtt aattgttaa ttagtacgtg ttaattgtgt gatacagtct     7680
tctttgtgga acccaaaatc ctcttttag ctttatattt tataaactgc cagattgtac      7740
aacttttatg tgcatttta aagcttgaag acatgagggt cattatctaa gttaaacagc     7800 ctattttgt gcctcctgta cagttttata attctgctga tggcggcatc ttatgtcgag     7860
ccaaccacaa taaggtagt tttagatttt ggaaaaaaaa aaaaaaaaa                  7910
```

<210> SEQ ID NO 2
<211> LENGTH: 977
<212> TYPE: PRT
<213> ORGANISM: Homo sapiens

<400> SEQUENCE: 2

Met Pro Ala Arg Arg Leu Leu Leu Leu Thr Leu Leu Pro Gly
1               5                   10                  15

Leu Gly Ile Phe Gly Ser Thr Ser Thr Val Thr Leu Pro Glu Thr Leu

-continued

```
                20                  25                  30
Leu Phe Val Ser Thr Leu Asp Gly Ser Leu His Ala Val Ser Lys Arg
             35                  40                  45
Thr Gly Ser Ile Lys Trp Thr Leu Lys Glu Asp Pro Val Leu Gln Val
 50                  55                  60
Pro Thr His Val Glu Glu Pro Ala Phe Leu Pro Asp Pro Asn Asp Gly
 65                  70                  75                  80
Ser Leu Tyr Thr Leu Gly Ser Lys Asn Asn Glu Gly Leu Thr Lys Leu
                 85                  90                  95
Pro Phe Thr Ile Pro Glu Leu Val Gln Ala Ser Pro Cys Arg Ser Ser
                100                 105                 110
Asp Gly Ile Leu Tyr Met Gly Lys Lys Gln Asp Ile Trp Tyr Val Ile
                115                 120                 125
Asp Leu Leu Thr Gly Glu Lys Gln Gln Thr Leu Ser Ser Ala Phe Ala
                130                 135                 140
Asp Ser Leu Cys Pro Ser Thr Ser Leu Leu Tyr Leu Gly Arg Thr Glu
145                 150                 155                 160
Tyr Thr Ile Thr Met Tyr Asp Thr Lys Thr Arg Glu Leu Arg Trp Asn
                165                 170                 175
Ala Thr Tyr Phe Asp Tyr Ala Ala Ser Leu Pro Glu Asp Asp Val Asp
                180                 185                 190
Tyr Lys Met Ser His Phe Val Ser Asn Gly Asp Gly Leu Val Val Thr
                195                 200                 205
Val Asp Ser Glu Ser Gly Asp Val Leu Trp Ile Gln Asn Tyr Ala Ser
                210                 215                 220
Pro Val Val Ala Phe Tyr Val Trp Gln Arg Glu Gly Leu Arg Lys Val
225                 230                 235                 240
Met His Ile Asn Val Ala Val Glu Thr Leu Arg Tyr Leu Thr Phe Met
                245                 250                 255
Ser Gly Glu Val Gly Arg Ile Thr Lys Trp Lys Tyr Pro Phe Pro Lys
                260                 265                 270
Glu Thr Glu Ala Lys Ser Lys Leu Thr Pro Thr Leu Tyr Val Gly Lys
                275                 280                 285
Tyr Ser Thr Ser Leu Tyr Ala Ser Pro Ser Met Val His Glu Gly Val
                290                 295                 300
Ala Val Val Pro Arg Gly Ser Thr Leu Pro Leu Leu Glu Gly Pro Gln
305                 310                 315                 320
Thr Asp Gly Val Thr Ile Gly Asp Lys Gly Glu Cys Val Ile Thr Pro
                325                 330                 335
Ser Thr Asp Val Lys Phe Asp Pro Gly Leu Lys Ser Lys Asn Lys Leu
                340                 345                 350
Asn Tyr Leu Arg Asn Tyr Trp Leu Leu Ile Gly His His Glu Thr Pro
                355                 360                 365
Leu Ser Ala Ser Thr Lys Met Leu Glu Arg Phe Pro Asn Asn Leu Pro
                370                 375                 380
Lys His Arg Glu Asn Val Ile Pro Ala Asp Ser Glu Lys Lys Ser Phe
385                 390                 395                 400
Glu Glu Val Ile Asn Leu Val Asp Gln Thr Ser Glu Asn Ala Pro Thr
                405                 410                 415
Thr Val Ser Arg Asp Val Glu Glu Lys Pro Ala His Ala Pro Ala Arg
                420                 425                 430
Pro Glu Ala Pro Val Asp Ser Met Leu Lys Asp Met Ala Thr Ile Ile
                435                 440                 445
```

```
Leu Ser Thr Phe Leu Leu Ile Gly Trp Val Ala Phe Ile Ile Thr Tyr
450                 455                 460

Pro Leu Ser Met His Gln Gln Gln Leu Gln His Gln Gln Phe Gln
465                 470                 475                 480

Lys Glu Leu Glu Lys Ile Gln Leu Leu Gln Gln Gln Gln Gln Leu
                485                 490                 495

Pro Phe His Pro Pro Gly Asp Thr Ala Gln Asp Gly Glu Leu Leu Asp
                500                 505                 510

Thr Ser Gly Pro Tyr Ser Glu Ser Ser Gly Thr Ser Ser Pro Ser Thr
                515                 520                 525

Ser Pro Arg Ala Ser Asn His Ser Leu Cys Ser Gly Ser Ser Ala Ser
530                 535                 540

Lys Ala Gly Ser Ser Pro Ser Leu Glu Gln Asp Asp Gly Asp Glu Glu
545                 550                 555                 560

Thr Ser Val Val Ile Val Gly Lys Ile Ser Phe Cys Pro Lys Asp Val
                565                 570                 575

Leu Gly His Gly Ala Glu Gly Thr Ile Val Tyr Arg Gly Met Phe Asp
                580                 585                 590

Asn Arg Asp Val Ala Val Lys Arg Ile Leu Pro Glu Cys Phe Ser Phe
595                 600                 605

Ala Asp Arg Glu Val Gln Leu Leu Arg Glu Ser Asp Glu His Pro Asn
610                 615                 620

Val Ile Arg Tyr Phe Cys Thr Glu Lys Asp Arg Gln Phe Gln Tyr Ile
625                 630                 635                 640

Ala Ile Glu Leu Cys Ala Ala Thr Leu Gln Glu Tyr Val Glu Gln Lys
                645                 650                 655

Asp Phe Ala His Leu Gly Leu Glu Pro Ile Thr Leu Leu Gln Gln Thr
                660                 665                 670

Thr Ser Gly Leu Ala His Leu His Ser Leu Asn Ile Val His Arg Asp
                675                 680                 685

Leu Lys Pro His Asn Ile Leu Ile Ser Met Pro Asn Ala His Gly Lys
690                 695                 700

Ile Lys Ala Met Ile Ser Asp Phe Gly Leu Cys Lys Lys Leu Ala Val
705                 710                 715                 720

Gly Arg His Ser Phe Ser Arg Arg Ser Gly Val Pro Gly Thr Glu Gly
                725                 730                 735

Trp Ile Ala Pro Glu Met Leu Ser Glu Asp Cys Lys Glu Asn Pro Thr
                740                 745                 750

Tyr Thr Val Asp Ile Phe Ser Ala Gly Cys Val Phe Tyr Tyr Val Ile
                755                 760                 765

Ser Glu Gly Ser His Pro Phe Gly Lys Ser Leu Gln Arg Gln Ala Asn
770                 775                 780

Ile Leu Leu Gly Ala Cys Ser Leu Asp Cys Leu His Pro Glu Lys His
785                 790                 795                 800

Glu Asp Val Ile Ala Arg Glu Leu Ile Glu Lys Met Ile Ala Met Asp
                805                 810                 815

Pro Gln Lys Arg Pro Ser Ala Lys His Val Leu Lys His Pro Phe Phe
                820                 825                 830

Trp Ser Leu Glu Lys Gln Leu Gln Phe Phe Gln Asp Val Ser Asp Arg
                835                 840                 845

Ile Glu Lys Glu Ser Leu Asp Gly Pro Ile Val Lys Gln Leu Glu Arg
850                 855                 860
```

```
Gly Gly Arg Ala Val Val Lys Met Asp Trp Arg Glu Asn Ile Thr Val
865                 870                 875                 880

Pro Leu Gln Thr Asp Leu Arg Lys Phe Arg Thr Tyr Lys Gly Gly Ser
                885                 890                 895

Val Arg Asp Leu Leu Arg Ala Met Arg Asn Lys Lys His His Tyr Arg
            900                 905                 910

Glu Leu Pro Ala Glu Val Arg Glu Thr Leu Gly Ser Leu Pro Asp Asp
        915                 920                 925

Phe Val Cys Tyr Phe Thr Ser Arg Phe Pro His Leu Leu Ala His Thr
    930                 935                 940

Tyr Arg Ala Met Glu Leu Cys Ser His Glu Arg Leu Phe Gln Pro Tyr
945                 950                 955                 960

Tyr Phe His Glu Pro Pro Glu Pro Gln Pro Pro Val Thr Pro Asp Ala
                965                 970                 975

Leu

<210> SEQ ID NO 3
<211> LENGTH: 3976
<212> TYPE: DNA
<213> ORGANISM: Mus musculus

<400> SEQUENCE: 3
tccgtgtcca ccgatcctcc gccggtgccg cgctgtcgtt gcggcgcccc cgtccagccc    60
tctgttcgcg cgggctccag aaccggccgg cggggcccgg agtcagggcc acgtcctgcc   120
atgccggccc ggtggctgtt gctcctgctg gcgctgctgc taccgccgcc ggccccgggg   180
agttttggaa gaaccagcac agttacactg cctgagacct tgttgtttgt ctcgaccctg   240 gatgaagct tgcatgctgt tagcaagagg acgggctcca tcaagtggac tttaaaagaa   300
gatccagtcc tgcaggtccc aacacacgtg gaagagccgg ctttcctccc agatcccaat   360
gatggcagtc tgtacacact ggaggcaag acaacgaag gcctgacgaa acttcccttt   420
accatcccag aattggttca ggcctcccca tgccgaagtt cagatggaat cctctacatg   480
ggtaaaaagc aagatatttg gtatgttatc gacctcctga ctggcgagaa gcagcagact   540
ttgtcatcgg cctttgctga tagtctctgc ccatcaactt cccttctata tcttggacgg   600
acagaataca ccatcaccat gtatgacacc aagacccggg agctccgctg gaatgccacc   660
tattttgact atgcagcctc actgccggaa gacgacgtgg actacaagat gtcccacttt   720
gtgtccaatg gcgatggact ggtggtaact gtggacagtg aatctgggga tgtcctgtgg   780
atccaaaact atgcctctcc tgtggtggcc ttctacgtct ggcaggggga ggtcctgaga   840
aaggtggtgc acatcaacgt tgctgtggag actctacgct acttgacctt catgtctggg   900
gaagtggggc gcatcaccaa gtggaagtat ccattcccca ggagacaga ggccaagagc   960 aagctaacgc ctactctgta tgttgggaag tattccacca gcctctatgc ctctccctca  1020
atggtgcatg agggggttgc tgtcgtgcct cgaggcagca ctcttccttt gctgaaggc   1080 ccccagacag atggcgtcac cattggagac aaaggagagt gtgtgatcac tcccagcaca  1140
gacctcaagt ttgaccctgg actcaaaggg aagagcaagc tgaactactt gaggaattac  1200
tggcttctca taggacacca tgaaactcct ctgtctgcat ccaccaagat gctggagaga  1260
tttcctaaca acctgcccaa acatcgagaa aatgtgattc ctgctgattc agaaaaaagg  1320
agctttgagg aagttatcaa catagttggc cagacttcag acaacacacc gaccaccgta  1380
tctcaggatg tggaggagaa gctcgctcgc gcccctgcca gcctgaggc ccccgtggac  1440
```

```
tccatgctca aggacatggc taccattatc ctgagcacct tcctgctggt tggatgggtg    1500
gcgttcatca tcacttaccc cctgagcgtg catcagcagc gtcagctcca gcaccaacag    1560
ttccagaagg agctggagaa gattcagctc ctgcagcagc agcagctgcc cttccaccca    1620
cacggagacc ttacccagga ccctgagttc ctggattcat ctggccccct ctcagagagc    1680
tctggcacca gcagccccag cccatccccc agagcctcca accactccct ccaccccagc    1740
agctctgcct ccagggccgg caccagcccc tctctggagc aggatgatga ggatgaggaa    1800
accagaatgg tgattgttgg gaaaatttca ttctgcccca aggatgtcct gggtcatgga    1860
gctgagggca caattgtata caaaggtatg tttgacaacc gagatgtggc cgtgaagagg    1920
atcctccctg agtgttttag ctttgccgac cgtgaggtcc agctgcttcg agaatcagac    1980
gagcacccaa atgtgatccg ctacttttgc acagagaagg accggcagtt ccagtacatt    2040
gctatcgagc tgtgtgcagc caccctacaa gagtatgtgg agcagaagga ctttgcccac    2100
cttggcctcg agcccatcac cctgcttcat cagaccacct caggcctggc acacctgcat    2160
tctctcaaca ttgttcacag agacctgaag ccccacaaca ttctcctctc catgcccaac    2220
gcacatggca ggatcaaggc gatgatctct gactttggcc tctgcaagaa gctggcagtg    2280
ggcaggcaca gtttcagccg ccgttcaggg gtacctggac tgaagggtg gatcgcccca    2340
gagatgctga gtgaagactg taaggacaac cctacctaca cggtggacat ctttctgca    2400
ggctgtgtct tttactatgt catctctgag gcaaccatc cttttggcaa atccttgcag    2460
cggcaggcca acatcctcct gggcgcctgc aaccttgact gtttccactc agacaagcat    2520
gaggacgtca ttgctcgtga attgatagag aaaatgattg ctatggatcc ccagcagcgt    2580
ccctctgcaa agcacgtgct gaaacacccc ttcttctgga gcctggagaa gcagctccag    2640
tttttccagg atgtaagtga ccgaatagaa aaggaggcct tggacggtcc aatcgtacgg    2700
cagttggaga gaggcgggag agctgtggtc aagatggact ggcgggagaa catcactgtc    2760
cccctgcaga cagatctgcg caaattcaga acctacaaag gtggctctgt gagagacctc    2820
ctccgagcca tgagaaacaa gaaacaccac taccgggagc tccccgtgga ggttcaggag    2880
acgctgggct ccatcccgga tgactttgtg cgctacttca cttcccgctt cccccaccttc   2940
ctctctcaca cctaccaagc catggagctg tgcagacatg agagactctt tcagacctac    3000
tactggcacg agcccacaga accccagcct ccagtgattc catatgccct ctgagctagg    3060
gcagccctct ggtctggtgg ccccaataat gaccatgggc ccgatctctg cagtcatagt    3120
ttgttgcctc tgggattagc aggaagacta agcttcgcaa atcaagtgcc ttgagctgct    3180
gatctgcagc cagaagagga taacgctgat cctaggacgc aggggaagat ggtccctcat    3240
gactacagag acctgaggag atgtggcccct gaaaccttgt agtgaaggac gtctacgaag    3300
gcagcctgtc ccagaggctg caaaggaaac agcatcagcc tttcaccgga tgagcttgct    3360
cccacttctc tttcttttcta aaattcctgt gggatggcat tttgggggc ctttcagtga    3420
gagtagagga atctggtttt gcctgcatgg tggaagcagc ctggttgggg tattgcatgt    3480
gcagcctctg atagaaatgg tttgagagat gtgggtgct aaggaagaga tgttcagagg    3540
tgttgccatg gggataggag gcacctccaa gttactgata gcccgtgttg cctcatgcag    3600
caagttgtga gagtgggttg tggagactcg ttagcaatgc tgtggacact gacatgtgct    3660
gtgggtctgg aagatgaagc agacactcag ttctggatgt ggtgctggcc cagcacagtg    3720
gcctaaaatag tggcccctga taggttgaat cctggctatg tgggcagag atgagtttcc    3780
tggccaccag gtggcagcta agaccagaca gggacagaga cagattgtca gggccagaga    3840
```

```
ggagcaacta gagggagctt cccagtcact caaagatgct aagaactaga aggtgagtga    3900
tatggtccct ctaccccaga ggccagcaga ttagcgcata gattatgaat caaggccctg    3960
ggggtagaga gccaag                                                    3976
```

<210> SEQ ID NO 4
<211> LENGTH: 977
<212> TYPE: PRT
<213> ORGANISM: Mus musculus

<400> SEQUENCE: 4

```
Met Pro Ala Arg Trp Leu Leu Leu Leu Ala Leu Leu Leu Pro Pro
1               5                   10                  15

Pro Gly Pro Gly Ser Phe Gly Arg Thr Ser Thr Val Thr Leu Pro Glu
            20                  25                  30

Thr Leu Leu Phe Val Ser Thr Leu Asp Gly Ser Leu His Ala Val Ser
        35                  40                  45

Lys Arg Thr Gly Ser Ile Lys Trp Thr Leu Lys Glu Asp Pro Val Leu
    50                  55                  60

Gln Val Pro Thr His Val Glu Glu Pro Ala Phe Leu Pro Asp Pro Asn
65                  70                  75                  80

Asp Gly Ser Leu Tyr Thr Leu Gly Gly Lys Asn Asn Glu Gly Leu Thr
                85                  90                  95

Lys Leu Pro Phe Thr Ile Pro Glu Leu Val Gln Ala Ser Pro Cys Arg
            100                 105                 110

Ser Ser Asp Gly Ile Leu Tyr Met Gly Lys Lys Gln Asp Ile Trp Tyr
        115                 120                 125

Val Ile Asp Leu Leu Thr Gly Glu Lys Gln Gln Thr Leu Ser Ser Ala
    130                 135                 140

Phe Ala Asp Ser Leu Cys Pro Ser Thr Ser Leu Leu Tyr Leu Gly Arg
145                 150                 155                 160

Thr Glu Tyr Thr Ile Thr Met Tyr Asp Thr Lys Thr Arg Glu Leu Arg
                165                 170                 175

Trp Asn Ala Thr Tyr Phe Asp Tyr Ala Ala Ser Leu Pro Glu Asp Asp
            180                 185                 190

Val Asp Tyr Lys Met Ser His Phe Val Ser Asn Gly Asp Gly Leu Val
        195                 200                 205

Val Thr Val Asp Ser Glu Ser Gly Asp Val Leu Trp Ile Gln Asn Tyr
    210                 215                 220

Ala Ser Pro Val Val Ala Phe Tyr Val Trp Gln Gly Glu Val Leu Arg
225                 230                 235                 240

Lys Val Val His Ile Asn Val Ala Val Glu Thr Leu Arg Tyr Leu Thr
                245                 250                 255

Phe Met Ser Gly Glu Val Gly Arg Ile Thr Lys Trp Lys Tyr Pro Phe
            260                 265                 270

Pro Lys Glu Thr Glu Ala Lys Ser Lys Leu Thr Pro Thr Leu Tyr Val
        275                 280                 285

Gly Lys Tyr Ser Thr Ser Leu Tyr Ala Ser Pro Ser Met Val His Glu
    290                 295                 300

Gly Val Ala Val Val Pro Arg Gly Ser Thr Leu Pro Leu Leu Glu Gly
305                 310                 315                 320

Pro Gln Thr Asp Gly Val Thr Ile Gly Asp Lys Gly Glu Cys Val Ile
                325                 330                 335

Thr Pro Ser Thr Asp Leu Lys Phe Asp Pro Gly Leu Lys Gly Lys Ser
```

-continued

```
                340                 345                 350
Lys Leu Asn Tyr Leu Arg Asn Tyr Trp Leu Leu Ile Gly His His Glu
            355                 360                 365

Thr Pro Leu Ser Ala Ser Thr Lys Met Leu Glu Arg Phe Pro Asn Asn
        370                 375                 380

Leu Pro Lys His Arg Glu Asn Val Ile Pro Ala Asp Ser Glu Lys Arg
385                 390                 395                 400

Ser Phe Glu Glu Val Ile Asn Ile Val Gly Gln Thr Ser Asp Asn Thr
                405                 410                 415

Pro Thr Thr Val Ser Gln Asp Val Glu Glu Lys Leu Ala Arg Ala Pro
            420                 425                 430

Ala Lys Pro Glu Ala Pro Val Asp Ser Met Leu Lys Asp Met Ala Thr
        435                 440                 445

Ile Ile Leu Ser Thr Phe Leu Leu Val Gly Trp Val Ala Phe Ile Ile
    450                 455                 460

Thr Tyr Pro Leu Ser Val His Gln Gln Arg Gln Leu Gln His Gln Gln
465                 470                 475                 480

Phe Gln Lys Glu Leu Glu Lys Ile Gln Leu Leu Gln Gln Gln Gln Leu
                485                 490                 495

Pro Phe His Pro His Gly Asp Leu Thr Gln Asp Pro Glu Phe Leu Asp
            500                 505                 510

Ser Ser Gly Pro Phe Ser Glu Ser Ser Gly Thr Ser Ser Pro Ser Pro
        515                 520                 525

Ser Pro Arg Ala Ser Asn His Ser Leu His Pro Ser Ser Ser Ala Ser
    530                 535                 540

Arg Ala Gly Thr Ser Pro Ser Leu Glu Gln Asp Asp Glu Asp Glu Glu
545                 550                 555                 560

Thr Arg Met Val Ile Val Gly Lys Ile Ser Phe Cys Pro Lys Asp Val
                565                 570                 575

Leu Gly His Gly Ala Glu Gly Thr Ile Val Tyr Lys Gly Met Phe Asp
            580                 585                 590

Asn Arg Asp Val Ala Val Lys Arg Ile Leu Pro Glu Cys Phe Ser Phe
        595                 600                 605

Ala Asp Arg Glu Val Gln Leu Leu Arg Glu Ser Asp Glu His Pro Asn
    610                 615                 620

Val Ile Arg Tyr Phe Cys Thr Glu Lys Asp Arg Gln Phe Gln Tyr Ile
625                 630                 635                 640

Ala Ile Glu Leu Cys Ala Ala Thr Leu Gln Glu Tyr Val Glu Gln Lys
                645                 650                 655

Asp Phe Ala His Leu Gly Leu Glu Pro Ile Thr Leu Leu His Gln Thr
            660                 665                 670

Thr Ser Gly Leu Ala His Leu His Ser Leu Asn Ile Val His Arg Asp
        675                 680                 685

Leu Lys Pro His Asn Ile Leu Leu Ser Met Pro Asn Ala His Gly Arg
    690                 695                 700

Ile Lys Ala Met Ile Ser Asp Phe Gly Leu Cys Lys Lys Leu Ala Val
705                 710                 715                 720

Gly Arg His Ser Phe Ser Arg Arg Ser Gly Val Pro Gly Thr Glu Gly
                725                 730                 735

Trp Ile Ala Pro Glu Met Leu Ser Glu Asp Cys Lys Asp Asn Pro Thr
            740                 745                 750

Tyr Thr Val Asp Ile Phe Ser Ala Gly Cys Val Phe Tyr Tyr Val Ile
        755                 760                 765
```

```
Ser Glu Gly Asn His Pro Phe Gly Lys Ser Leu Gln Arg Gln Ala Asn
    770             775                 780
Ile Leu Leu Gly Ala Cys Asn Leu Asp Cys Phe His Ser Asp Lys His
785             790                 795                 800
Glu Asp Val Ile Ala Arg Glu Leu Ile Glu Lys Met Ile Ala Met Asp
                805                 810                 815
Pro Gln Gln Arg Pro Ser Ala Lys His Val Leu Lys His Pro Phe Phe
                820                 825                 830
Trp Ser Leu Glu Lys Gln Leu Gln Phe Phe Gln Asp Val Ser Asp Arg
            835                 840                 845
Ile Glu Lys Glu Ala Leu Asp Gly Pro Ile Val Arg Gln Leu Glu Arg
    850                 855                 860
Gly Gly Arg Ala Val Lys Met Asp Trp Arg Glu Asn Ile Thr Val
865             870                 875                 880
Pro Leu Gln Thr Asp Leu Arg Lys Phe Arg Thr Tyr Lys Gly Gly Ser
                885                 890                 895
Val Arg Asp Leu Leu Arg Ala Met Arg Asn Lys Lys His His Tyr Arg
                900                 905                 910
Glu Leu Pro Val Glu Val Gln Glu Thr Leu Gly Ser Ile Pro Asp Asp
            915                 920                 925
Phe Val Arg Tyr Phe Thr Ser Arg Phe Pro His Leu Leu Ser His Thr
    930                 935                 940
Tyr Gln Ala Met Glu Leu Cys Arg His Glu Arg Leu Phe Gln Thr Tyr
945             950                 955                 960
Tyr Trp His Glu Pro Thr Glu Pro Gln Pro Pro Val Ile Pro Tyr Ala
                965                 970                 975
Leu
```

<210> SEQ ID NO 5
<211> LENGTH: 2954
<212> TYPE: DNA
<213> ORGANISM: Rattus norvegicus

<400> SEQUENCE: 5

```
atgcgcaggt gcaatgacat acaaagtttt ggaagagcca gcacagtaac actgcctgaa      60
gccttgttat ttgttccac cctggacgga agtttgcatg ctgtcagcaa gaggacaggc     120
tccatcaagt ggactttaaa agaagatcca gtcctgcagg tcccaacaca cgtggaagag     180
cctgctttcc tcccagaccc caatgatggc agtctgtaca cacttggagg caagaacaat     240
gaaggcctga cgaaacttcc ctttaccatc ccggaattgg ttcaggcatc cccatgccga     300
agttcagatg gaattctcta catgggtaag aagcaagaca tttggtatgt catcgacctc     360
ctgactggcg agaagcagca gactttgtca tcagccttcg cagacagtct gtgcccgtca     420
acttcccttc tgtatcttgg acggacagaa tacaccatca ccatgtatga caccaagacc     480
cgggagctcc gctggaatgc cacctatttt gactatgcag cctcacttcc cgaggatgac     540
gtggactaca gatgtcccca ctttgtgtcc aatggcgatg gactggtggt aactgtggac     600
agtgaatctg gggatgtctt gtggatccaa aactatgcct ctcctgtggt ggccttctac     660
atctggcagc gggagggcct gagaaaggtg gtgcacatca cgttgctgt ggagacccta     720
cgctatttga ccttcatgtc tggggaagtg gggcgcatca ccaagtggaa atatccattc     780
cccaaggaga cagaggccaa gagcaaactg acgcccactc tgtatgtggg gaagtactcc     840
accagcctct atgcctcgcc ctcgatggtg cacgaggggg tcgctgttgt gcctcgaggc     900
```

| | | | |
|---|---|---|---|
| agcactcttc ctttgctcga aggaccccag acagatggtg tcaccattgg agacaaagga | 960 |
| gaatgtgtga tcactcccag cacagacctc aagtttgacc ctggactcaa aggcaagagc | 1020 |
| aagctgaact acctgaggaa ttactggctt ctcataggac accatgaaac tcctctgtct | 1080 |
| gcatccacca agatgctgga gagatttcct aacaatcttc ccaaacatcg agaaaacgtg | 1140 |
| attcctgctg attcggagaa aaggagcttt gaggaggtta tcaacctagt tggccagact | 1200 |
| tcagaaaaca caccaaccac tgtgtctcag gatgtagaag agaagctgcc ccgtgccccc | 1260 |
| gccaagccag aggcccccgt ggactccatg ctcaaggaca tggctactat tatcctgagc | 1320 |
| accttcctgc tggtcggatg ggtggcgttc atcatcactt accccctgag catgcatcag | 1380 |
| cagcgccagc tccagcacca gcagttccag aaggaactgg agaaaattca gctccttcag | 1440 |
| caacagcagc tgcccttcca cccacacgga gaccttaccc aggaccctga cttcctggat | 1500 |
| tcatctggcc tcttctcgga gagctcaggc accagcagcc ccagcccatc ccccagagcc | 1560 |
| tccaaccact cactcaactc tagcagctct gcctccaagg ctggcaccag tccctccctg | 1620 |
| gagccagatg acgaggatga ggaaaaccaga atggtgattg ttgggaaaat ctcattctgc | 1680 |
| cccaaggatg tcctgggcca tggagctgag ggcacaattg tatacaaagg tatgtttgac | 1740 |
| aaccgtgatg tggccgtgaa gaggatcctc cctgagtgtt ttagctttgc agaccgagag | 1800 |
| gtccagctgc ttcgagaatc agacgagcat ccgaatgtga tccgctactt ttgcacagag | 1860 |
| aaggaccggc agttccagta cattgccatt gagctgtgtg cagctaccct gcaggagtat | 1920 |
| gtggagcaga aggacttcgc ccaccttggc ctagagccca tcaccttgct tcatcagacc | 1980 |
| acctcaggcc tggcgcacct gcattccctc aacattgttc acagagacct gaagcccac | 2040 |
| aacattctcc tctccatgcc caacgcacat ggcaggatca aggcgatgat ctcagacttt | 2100 |
| ggcctctgca agaagctggc agtgggcagg catagtttca gccgccgttc aggggtgcct | 2160 |
| ggcactgaag gttggatcgc cccagagatg ctgagtgaag actgcaagga gaaccctacc | 2220 |
| tacacagtgg acatcttctc tgcaggctgt gtctttttact atgtcatctc tgagggcaac | 2280 |
| catcctttg gcaaatcctt gcagcggcag gccaacatcc tcctgggcgc ctgcagcctt | 2340 |
| gactgcttcc actcagacaa gcacgaggac gtcattgctc gtgagttgat agagaaaatg | 2400 |
| attgcaatgg atccgcagca gcgaccctcg gcaaagcacg tgctaaaaca cccattcttc | 2460 |
| tggagcctgg aaaagcagct ccagttcttc caggatgtga gtgaccgaat agaaaaggag | 2520 |
| tccttggatg gcccgatcgt gcggcagttg gagagaggcg ggagagctgt ggttaagatg | 2580 |
| gactggcggg agaacatcac tgtccccctg cagacagatc tgcgcaaatt cagaacctat | 2640 |
| aaaggtggct ccgtccggga tctcctccga gccatgagga ataagagaca ccactaccgg | 2700 |
| gagctccctc tggaggttca ggagacgctg gctccatcc ctgatgactt cgtgcgctac | 2760 |
| ttcacatcac gtttcccca cctcctctct cacacctacc gagccatgga actgtgcaga | 2820 |
| catgagagac ttttccagac ctactactgg cacgagccca cagaagccca gcctccaggg | 2880 |
| attccagatg ccctctgagc gagggcagcc ctctggtctg gtggcccaa caaggaccat | 2940 |
| gggcctgatc tctg | 2954 |

<210> SEQ ID NO 6
<211> LENGTH: 965
<212> TYPE: PRT
<213> ORGANISM: Rattus norvegicus

<400> SEQUENCE: 6

-continued

```
Met Arg Arg Cys Asn Asp Ile Gln Ser Phe Gly Arg Ala Ser Thr Val
1               5                   10                  15

Thr Leu Pro Glu Ala Leu Leu Phe Val Ser Thr Leu Asp Gly Ser Leu
            20                  25                  30

His Ala Val Ser Lys Arg Thr Gly Ser Ile Lys Trp Thr Leu Lys Glu
                35                  40                  45

Asp Pro Val Leu Gln Val Pro Thr His Val Glu Glu Pro Ala Phe Leu
        50                  55                  60

Pro Asp Pro Asn Asp Gly Ser Leu Tyr Thr Leu Gly Lys Asn Asn
65                  70                  75                  80

Glu Gly Leu Thr Lys Leu Pro Phe Thr Ile Pro Glu Leu Val Gln Ala
                85                  90                  95

Ser Pro Cys Arg Ser Ser Asp Gly Ile Leu Tyr Met Gly Lys Lys Gln
            100                 105                 110

Asp Ile Trp Tyr Val Ile Asp Leu Leu Thr Gly Glu Lys Gln Gln Thr
            115                 120                 125

Leu Ser Ser Ala Phe Ala Asp Ser Leu Cys Pro Ser Thr Ser Leu Leu
    130                 135                 140

Tyr Leu Gly Arg Thr Glu Tyr Thr Ile Thr Met Tyr Asp Thr Lys Thr
145                 150                 155                 160

Arg Glu Leu Arg Trp Asn Ala Thr Tyr Phe Asp Tyr Ala Ala Ser Leu
                165                 170                 175

Pro Glu Asp Asp Val Asp Tyr Lys Met Ser His Phe Val Ser Asn Gly
            180                 185                 190

Asp Gly Leu Val Val Thr Val Asp Ser Glu Ser Gly Asp Val Leu Trp
    195                 200                 205

Ile Gln Asn Tyr Ala Ser Pro Val Val Ala Phe Tyr Ile Trp Gln Arg
    210                 215                 220

Glu Gly Leu Arg Lys Val Val His Ile Asn Val Ala Val Glu Thr Leu
225                 230                 235                 240

Arg Tyr Leu Thr Phe Met Ser Gly Glu Val Gly Arg Ile Thr Lys Trp
                245                 250                 255

Lys Tyr Pro Phe Pro Lys Glu Thr Glu Ala Lys Ser Lys Leu Thr Pro
            260                 265                 270

Thr Leu Tyr Val Gly Lys Tyr Ser Thr Ser Leu Tyr Ala Ser Pro Ser
        275                 280                 285

Met Val His Glu Gly Val Ala Val Pro Arg Gly Ser Thr Leu Pro
    290                 295                 300

Leu Leu Glu Gly Pro Gln Thr Asp Gly Val Thr Ile Gly Asp Lys Gly
305                 310                 315                 320

Glu Cys Val Ile Thr Pro Ser Thr Asp Leu Lys Phe Asp Pro Gly Leu
            325                 330                 335

Lys Gly Lys Ser Lys Leu Asn Tyr Leu Arg Asn Tyr Trp Leu Leu Ile
            340                 345                 350

Gly His His Glu Thr Pro Leu Ser Ala Ser Thr Lys Met Leu Glu Arg
        355                 360                 365

Phe Pro Asn Asn Leu Pro Lys His Arg Glu Asn Val Ile Pro Ala Asp
    370                 375                 380

Ser Glu Lys Arg Ser Phe Glu Glu Val Ile Asn Leu Val Gly Gln Thr
385                 390                 395                 400

Ser Glu Asn Thr Pro Thr Thr Val Ser Gln Asp Val Glu Glu Lys Leu
            405                 410                 415

Pro Arg Ala Pro Ala Lys Pro Glu Ala Pro Val Asp Ser Met Leu Lys
```

```
                420             425             430
Asp Met Ala Thr Ile Ile Leu Ser Thr Phe Leu Leu Val Gly Trp Val
            435             440             445
Ala Phe Ile Ile Thr Tyr Pro Leu Ser Met His Gln Gln Arg Gln Leu
            450             455             460
Gln His Gln Gln Phe Gln Lys Glu Leu Glu Lys Ile Gln Leu Leu Gln
465             470             475             480
Gln Gln Gln Leu Pro Phe His Pro His Gly Asp Leu Thr Gln Asp Pro
            485             490             495
Asp Phe Leu Asp Ser Ser Gly Leu Phe Ser Glu Ser Ser Gly Thr Ser
            500             505             510
Ser Pro Ser Pro Ser Pro Arg Ala Ser Asn His Ser Leu Asn Ser Ser
            515             520             525
Ser Ser Ala Ser Lys Ala Gly Thr Ser Pro Ser Leu Glu Pro Asp Asp
            530             535             540
Glu Asp Glu Glu Thr Arg Met Val Ile Val Gly Lys Ile Ser Phe Cys
545             550             555             560
Pro Lys Asp Val Leu Gly His Gly Ala Glu Gly Thr Ile Val Tyr Lys
            565             570             575
Gly Met Phe Asp Asn Arg Asp Val Ala Val Lys Arg Ile Leu Pro Glu
            580             585             590
Cys Phe Ser Phe Ala Asp Arg Glu Val Gln Leu Leu Arg Glu Ser Asp
            595             600             605
Glu His Pro Asn Val Ile Arg Tyr Phe Cys Thr Glu Lys Asp Arg Gln
            610             615             620
Phe Gln Tyr Ile Ala Ile Glu Leu Cys Ala Ala Thr Leu Gln Glu Tyr
625             630             635             640
Val Glu Gln Lys Asp Phe Ala His Leu Gly Leu Glu Pro Ile Thr Leu
            645             650             655
Leu His Gln Thr Thr Ser Gly Leu Ala His Leu His Ser Leu Asn Ile
            660             665             670
Val His Arg Asp Leu Lys Pro His Asn Ile Leu Leu Ser Met Pro Asn
            675             680             685
Ala His Gly Arg Ile Lys Ala Met Ile Ser Asp Phe Gly Leu Cys Lys
            690             695             700
Lys Leu Ala Val Gly Arg His Ser Phe Ser Arg Arg Ser Gly Val Pro
705             710             715             720
Gly Thr Glu Gly Trp Ile Ala Pro Glu Met Leu Ser Glu Asp Cys Lys
            725             730             735
Glu Asn Pro Thr Tyr Thr Val Asp Ile Phe Ser Ala Gly Cys Val Phe
            740             745             750
Tyr Tyr Val Ile Ser Glu Gly Asn His Pro Phe Gly Lys Ser Leu Gln
            755             760             765
Arg Gln Ala Asn Ile Leu Leu Gly Ala Cys Ser Leu Asp Cys Phe His
            770             775             780
Ser Asp Lys His Glu Asp Val Ile Ala Arg Glu Leu Ile Glu Lys Met
785             790             795             800
Ile Ala Met Asp Pro Gln Gln Arg Pro Ser Ala Lys His Val Leu Lys
            805             810             815
His Pro Phe Phe Trp Ser Leu Glu Lys Gln Leu Gln Phe Phe Gln Asp
            820             825             830
Val Ser Asp Arg Ile Glu Lys Glu Ser Leu Asp Gly Pro Ile Val Arg
            835             840             845
```

Gln Leu Glu Arg Gly Gly Arg Ala Val Val Lys Met Asp Trp Arg Glu
    850                 855                 860

Asn Ile Thr Val Pro Leu Gln Thr Asp Leu Arg Lys Phe Arg Thr Tyr
865                 870                 875                 880

Lys Gly Gly Ser Val Arg Asp Leu Leu Arg Ala Met Arg Asn Lys Arg
            885                 890                 895

His His Tyr Arg Glu Leu Pro Leu Glu Val Gln Glu Thr Leu Gly Ser
        900                 905                 910

Ile Pro Asp Asp Phe Val Arg Tyr Phe Thr Ser Arg Phe Pro His Leu
    915                 920                 925

Leu Ser His Thr Tyr Arg Ala Met Glu Leu Cys Arg His Glu Arg Leu
    930                 935                 940

Phe Gln Thr Tyr Tyr Trp His Glu Pro Thr Glu Ala Gln Pro Pro Gly
945                 950                 955                 960

Ile Pro Asp Ala Leu
            965

<210> SEQ ID NO 7
<211> LENGTH: 1810
<212> TYPE: DNA
<213> ORGANISM: Homo sapiens

<400> SEQUENCE: 7

```
ggcgctgggc ggctgcggcg cgcggtgcgc ggtgcgtagt ctggagctat ggtggtggtg      60
gcagccgcgc cgaacccggc cgacgggacc cctaaagttc tgcttctgtc ggggcagccc     120
gcctccgccg ccggagcccc ggccggccag gccctgccgc tcatggtgcc agcccagaga     180
ggggccagcc cggaggcagc gagcgggggg ctgccccagg cgcgcaagcg acagcgcctc     240
acgcacctga gccccgagga aaggcgctg aggaggaaac tgaaaaacag agtagcagct     300
cagactgcca gagatcgaaa gaaggctcga atgagtgagc tggaacagca agtggtagat     360
ttagaagaag agaaccaaaa acttttgcta gaaaatcagc ttttacgaga gaaaactcat     420
ggccttgtag ttgagaacca ggagttaaga cagcgcttgg ggatggatgc cctggttgct     480
gaagaggagg cggaagccaa ggggaatgaa gtgaggccag tggccgggtc tgctgagtcc     540
gcagcaggtg caggcccagt tgtcaccct ccagaacatc tccccatgga ttctggcggt     600
attgactctt cagattcaga gtctgatatc ctgttgggca ttctggacaa cttgacccca     660
gtcatgttct tcaaatgccc ttccccagag cctgccagcc tggaggagct cccagaggtc     720
tacccagaag gacccagttc cttaccagcc tcccttttctc tgtcagtggg gacgtcatca     780
gccaagctgg aagccattaa tgaactaatt cgttttgacc acatatatac caagccccta     840
gtcttagaga taccctctga gacagagagc caagctaatg tggtagtgaa atcgaggaa     900
gcacctctca gccctcaga gaatgatcac cctgaattca ttgtctcagt gaaggaagaa     960
cctgtagaa atgacctcgt tccggagctg ggtatctcaa atctgctttc atccagccac    1020
tgcccaaagc catcttcctg cctactggat gcttacagtg actgtggata cgggggttcc    1080
cttttcccat tcagtgacat gtcctctctg cttggtgtaa accattcttg ggaggacact    1140
tttgccaatg aactctttcc ccagctgatt agtgtctaag gaatgatcca atactgttgc    1200
cccttttcctt gactattaca ctgcctggag gatagcagag aagcctgtct gtacttcatt    1260
caaaaagcca aaatagagag tatacagtcc tagagaattc ctctatttgt tcagatctca    1320
tagatgaccc ccaggtattg tcttttgaca tccagcagtc caaggtattg agacatatta    1380
```

-continued

```
ctggaagtaa gaaatattac tataattgag aactacagct tttaagattg tacttttatc   1440 ttaaagggt ggtagttttc cctaaaatac ttattatgta agggtcatta gacaaatgtc    1500
ttgaagtaga catggaattt atgaatggtt ctttatcatt tctcttcccc cttttggca    1560 tcctggcttg cctccagttt taggtccttt agtttgcttc tgtaagcaac gggaacacct   1620 gctgagggg ctctttcccct catgtatact tcaagtaaga tcaagaatct tttgtgaaat   1680
tatagaaatt tactatgtaa atgcttgatg gaattttttc ctgctagtgt agcttctgaa   1740
aggtgctttc tccatttatt taaaactacc catgcaatta aaaggtacaa tgcaaaaaaa   1800
aaaaaaaaaa                                                         1810
```

<210> SEQ ID NO 8
<211> LENGTH: 376
<212> TYPE: PRT
<213> ORGANISM: Homo sapiens

<400> SEQUENCE: 8

```
Met Val Val Val Ala Ala Pro Asn Pro Ala Asp Gly Thr Pro Lys
1               5                   10                  15

Val Leu Leu Leu Ser Gly Gln Pro Ala Ser Ala Gly Ala Pro Ala
            20                  25                  30

Gly Gln Ala Leu Pro Leu Met Val Pro Ala Gln Arg Gly Ala Ser Pro
        35                  40                  45

Glu Ala Ala Ser Gly Gly Leu Pro Gln Ala Arg Lys Arg Gln Arg Leu
50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Asn Gln Lys Leu
                100                 105                 110

Leu Leu Glu Asn Gln Leu Leu Arg Glu Lys Thr His Gly Leu Val Val
            115                 120                 125

Glu Asn Gln Glu Leu Arg Gln Arg Leu Gly Met Asp Ala Leu Val Ala
        130                 135                 140

Glu Glu Glu Ala Glu Ala Lys Gly Asn Glu Val Arg Pro Val Ala Gly
145                 150                 155                 160

Ser Ala Glu Ser Ala Ala Gly Ala Gly Pro Val Val Thr Pro Pro Glu
                165                 170                 175

His Leu Pro Met Asp Ser Gly Gly Ile Asp Ser Ser Ser Glu Ser
                180                 185                 190

Asp Ile Leu Leu Gly Ile Leu Asp Asn Leu Asp Pro Val Met Phe Phe
            195                 200                 205

Lys Cys Pro Ser Pro Glu Pro Ala Ser Leu Glu Glu Leu Pro Glu Val
        210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255

Asp His Ile Tyr Thr Lys Pro Leu Val Leu Glu Ile Pro Ser Glu Thr
                260                 265                 270

Glu Ser Gln Ala Asn Val Val Val Lys Ile Glu Glu Ala Pro Leu Ser
            275                 280                 285

Pro Ser Glu Asn Asp His Pro Glu Phe Ile Val Ser Val Lys Glu Glu
```

```
                290                 295                 300
Pro Val Glu Asp Asp Leu Val Pro Glu Leu Gly Ile Ser Asn Leu Leu
305                 310                 315                 320

Ser Ser Ser His Cys Pro Lys Pro Ser Ser Cys Leu Leu Asp Ala Tyr
            325                 330                 335

Ser Asp Cys Gly Tyr Gly Gly Ser Leu Ser Pro Phe Ser Asp Met Ser
            340                 345                 350

Ser Leu Leu Gly Val Asn His Ser Trp Glu Asp Thr Phe Ala Asn Glu
        355                 360                 365

Leu Phe Pro Gln Leu Ile Ser Val
    370                 375

<210> SEQ ID NO 9
<211> LENGTH: 1820
<212> TYPE: DNA
<213> ORGANISM: Homo sapiens

<400> SEQUENCE: 9
ggcgctgggc ggctgcggcg cgcggtgcgc ggtgcgtagt ctggagctat ggtggtggtg      60
gcagccgcgc cgaacccggc cgacgggacc cctaaagttc tgcttctgtc ggggcagccc     120
gcctccgccg ccggagcccc ggccggccag gccctgccgc tcatggtgcc agcccagaga     180
ggggccagcc cggaggcagc gagcgggggg ctgccccagg cgcgcaagcg acagcgcctc     240
acgcacctga gccccgagga aaggcgctg aggaggaaac tgaaaaacag agtagcagct     300
cagactgcca gagatcgaaa gaaggctcga atgagtgagc tggaacagca agtggtagat     360
ttagaagaag agaaccaaaa acttttgcta gaaaatcagc ttttacgaga gaaaactcat     420
ggccttgtag ttgagaacca ggagttaaga cagcgcttgg ggatggatgc cctggttgct     480
gaagaggagg cggaagccaa ggggaatgaa gtgaggccag tggccgggtc tgctgagtcc     540
gcagcactca gactacgtgc acctctgcag caggtgcagg cccagttgtc accctccag     600 aacatctccc catggattct ggcggtattg actcttcaga ttcagagtct gatatcctgt     660
tgggcattct ggacaacttg gacccagtca tgttcttcaa atgcccttcc ccagagcctg     720
ccagcctgga ggagctccca gaggtctacc agaaggacc cagttcctta ccagcctccc     780
tttctctgtc agtggggacg tcatcagcca agctggaagc cattaatgaa ctaattcgtt     840 tgaccacat atataccaag cccctagtct tagagatacc ctctgagaca gagagccaag     900
ctaatgtggt agtgaaaatc gaggaagcac ctctcagccc ctcagagaat gatcaccctg     960
aattcattgt ctcagtgaag gaagaacctg tagaagatga cctcgttccg gagctgggta    1020
tctcaaatct gctttcatcc agccactgcc caaagccatc ttcctgccta ctggatgctt    1080
acagtgactg tggatacggg ggttcccttt ccccattcag tgacatgtcc tctctgcttg    1140
gtgtaaacca ttcttgggag gacactttg ccaatgaact cttccccag ctgattagtg    1200 tctaaggaat gatccaatac tgttgcccct tccttgact attacactgc ctggaggata    1260
gcagagaagc ctgtctgtac ttcattcaaa aagccaaaat agagagtata cagtcctaga    1320
gaattcctct atttgttcag atctcataga tgaccccag gtattgtctt ttgacatcca    1380
gcagtccaag gtattgagac atattactgg aagtaagaaa tattactata attgagaact    1440 acagcttta agattgtact tttatcttaa aagggtggta gttttcccta aaatacttat    1500
tatgtaaggg tcattagaca aatgtcttga agtagacatg gaatttatga atggttcttt    1560
atcatttctc ttcccccttt ttggcatcct ggcttgcctc cagttttagg tcctttagtt    1620
```

```
tgcttctgta agcaacggga acacctgctg aggggggctct ttccctcatg tatacttcaa    1680
gtaagatcaa gaatcttttg tgaaattata gaaatttact atgtaaatgc ttgatggaat    1740 ttttcctgc tagtgtagct tctgaaaggt gctttctcca tttatttaaa actacccatg    1800
caattaaaag gtacaatgca                                                1820
```

<210> SEQ ID NO 10
<211> LENGTH: 261
<212> TYPE: PRT
<213> ORGANISM: Homo sapiens

<400> SEQUENCE: 10

```
Met Val Val Val Ala Ala Pro Asn Pro Ala Asp Gly Thr Pro Lys
1               5                   10                  15

Val Leu Leu Leu Ser Gly Gln Pro Ala Ser Ala Gly Ala Pro Ala
            20                  25                  30

Gly Gln Ala Leu Pro Leu Met Val Pro Ala Gln Arg Gly Ala Ser Pro
        35                  40                  45

Glu Ala Ala Ser Gly Gly Leu Pro Gln Ala Arg Lys Arg Gln Arg Leu
50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Asn Gln Lys Leu
            100                 105                 110

Leu Leu Glu Asn Gln Leu Leu Arg Glu Lys Thr His Gly Leu Val Val
        115                 120                 125

Glu Asn Gln Glu Leu Arg Gln Arg Leu Gly Met Asp Ala Leu Val Ala
    130                 135                 140

Glu Glu Glu Ala Glu Ala Lys Gly Asn Glu Val Arg Pro Val Ala Gly
145                 150                 155                 160

Ser Ala Glu Ser Ala Ala Leu Arg Leu Arg Ala Pro Leu Gln Gln Val
                165                 170                 175

Gln Ala Gln Leu Ser Pro Leu Gln Asn Ile Ser Pro Trp Ile Leu Ala
            180                 185                 190

Val Leu Thr Leu Gln Ile Gln Ser Leu Ile Ser Cys Trp Ala Phe Trp
        195                 200                 205

Thr Thr Trp Thr Gln Ser Cys Ser Ser Asn Ala Leu Pro Gln Ser Leu
    210                 215                 220

Pro Ala Trp Arg Ser Ser Gln Arg Ser Thr Gln Lys Asp Pro Val Pro
225                 230                 235                 240

Tyr Gln Pro Pro Phe Leu Cys Gln Trp Gly Arg His Gln Pro Ser Trp
                245                 250                 255

Lys Pro Leu Met Asn
            260
```

<210> SEQ ID NO 11
<211> LENGTH: 2264
<212> TYPE: DNA
<213> ORGANISM: Mus musculus

<400> SEQUENCE: 11

```
ctagggtaaa accgtgagac tcggtctgga aatctggcct gagaggacag cctggcaatc    60
ctcagccggg gtggggacgt ctgccgaaga tccttggact ccagcaacca gtggtcgcca    120
```

| | |
|---|---|
| ccgtccatcc acccctaaggc ccagtttgca cggcggagaa cagctgtgca gccacgctgg | 180 |
| acactcaccc cgcccgagtt gagcccgccc ccgggactac aggaccaata agtgatgaat | 240 |
| atacccgcgc gtcacggagc accggccaat cgcggacggc cacgaccccta gaaaggctgg | 300 |
| gcgcggcagg aggccacggg gcggtggcgg cgctggcgta gacgtttcct ggctatggtg | 360 |
| gtggtggcag cggcgccgag cgcggccacg gcggccccca aagtgctact cttatctggc | 420 |
| cagcccgcct ccggcggccg ggcgctgccg ctcatggtac ccgtccgcg ggcagcaggg | 480 |
| tcggaggcga gcgggacacc gcaggctcgc aagcggcagc ggctcacgca cctgagcccg | 540 |
| gaggagaaag cgctgcggag gaaactgaaa aacagagtag cagcgcagac tgctcgagat | 600 |
| agaaagaaag cccggatgag cgagctggag cagcaagtgg tggatttgga agaagagaac | 660 |
| cacaaactcc agctagaaaa tcagctttta cgggagaaaa ctcacggcct tgtggttgag | 720 |
| aaccaggagt taagaacacg cttgggaatg gacacgctgg atcctgacga ggttccagag | 780 |
| gtggaggcca aggggagtgg agtaaggctg gtggccgggt ctgctgagtc cgcagcactc | 840 |
| agactatgtg cacctctgca gcaggtgcag gcccagttgt cacctcccca gaacatcttc | 900 |
| ccatggactc tgacactgtt gcctcttcag attctgagtc tgatatcctt ttgggcattc | 960 |
| tggacaagtt ggaccctgtc atgttttca aatgtccttc cccagagtct gctagtctgg | 1020 |
| aggaactccc agaggtctac ccagaaggac ctagttcctt accagcctcc ctttctctgt | 1080 |
| cagtggggac ctcatcagcc aagctggaag ccattaatga actcattcgt tttgaccatg | 1140 |
| tatacaccaa gcctctagtt ttagagatcc cctctgagac agagagtcaa actaacgtgg | 1200 |
| tagtgaaaat tgaggaagca cctctaagct cttcagaaga ggatcaccct gaattcattg | 1260 |
| tctcagtgaa gaaagagcct ttggaagatg acttcatccc agagctgggc atctcaaacc | 1320 |
| tgctttcatc cagccattgt ctgagaccac cttcttgcct gctggacgct cacagtgact | 1380 |
| gtggatatga gggctcccct tctcccttca gtgacatgtc ttctccactt ggtacagacc | 1440 |
| actcctggga ggatactttt gccaatgaac ttttccccca gctgattagt gtctaaagag | 1500 |
| ccacataaca ctgggcccct ttccctgacc atcacattgc ctagaggata gcataggcct | 1560 |
| gtctctttcg ttaaaagcca aagtagaggc tgtctggcct tagaagaatt cctctaaagt | 1620 |
| atttcaaatc tcatagatga cttccaagta ttgtcgtttg acactcagct gtctaaggta | 1680 |
| ttcaaaggta ttccagtact acagcttttg agattctagt ttatcttaaa ggtggtagta | 1740 |
| tactctaaat cgcagggagg gtcatttgac agttttttcc cagcctggct tcaaactatg | 1800 |
| tagccgaggc taggcagaaa cttctgaccc tcttgacccc acctcccaag tgctgggctt | 1860 |
| caccaggtgt gcacctccac acctgccccc ccgacatgtc aggtggacat gggattcatg | 1920 |
| aatggccctt agcatttctt tctccactct ctgcttccca ggtttcgtaa cctgaggggg | 1980 |
| cttgtttcc cttatgtgca tttaaatga agatcaagaa tctttgtaaa atgatgaaaa | 2040 |
| tttactatgt aaatgcttga tggatcttct tgctagtgta gcttctagaa ggtgctttct | 2100 |
| ccatttattt aaaactaccc ttgcaattaa aaaaaaagca acacagcgtc ctgttctgtg | 2160 |
| atttctaggg ctgttgtaat ttctctttat tgttggctaa aggagtaatt tatccaacta | 2220 |
| aagtgagcat accacttttt aaagtcaaaa aaaaaaaaaa aaaa | 2264 |

<210> SEQ ID NO 12
<211> LENGTH: 267
<212> TYPE: PRT
<213> ORGANISM: Mus musculus

<400> SEQUENCE: 12

```
Met Val Val Val Ala Ala Pro Ser Ala Thr Ala Ala Pro Lys
1               5                   10                  15

Val Leu Leu Leu Ser Gly Gln Pro Ala Ser Gly Gly Arg Ala Leu Pro
                20                  25                  30

Leu Met Val Pro Gly Pro Arg Ala Ala Gly Ser Glu Ala Ser Gly Thr
            35                  40                  45

Pro Gln Ala Arg Lys Arg Gln Arg Leu Thr His Leu Ser Pro Glu Glu
        50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn His Lys Leu Gln Leu Glu Asn Gln Leu Leu
                100                 105                 110

Arg Glu Lys Thr His Gly Leu Val Val Glu Asn Gln Glu Leu Arg Thr
                115                 120                 125

Arg Leu Gly Met Asp Thr Leu Asp Pro Asp Glu Val Pro Glu Val Glu
            130                 135                 140

Ala Lys Gly Ser Gly Val Arg Leu Val Ala Gly Ser Ala Glu Ser Ala
145                 150                 155                 160

Ala Leu Arg Leu Cys Ala Pro Leu Gln Gln Val Gln Ala Gln Leu Ser
                165                 170                 175

Pro Pro Gln Asn Ile Phe Pro Trp Thr Leu Thr Leu Pro Leu Gln
            180                 185                 190

Ile Leu Ser Leu Ile Ser Phe Trp Ala Phe Trp Thr Ser Trp Thr Leu
                195                 200                 205

Ser Cys Phe Ser Asn Val Leu Pro Gln Ser Leu Leu Val Trp Arg Asn
                210                 215                 220

Ser Gln Arg Ser Thr Gln Lys Asp Leu Val Pro Tyr Gln Pro Pro Phe
225                 230                 235                 240

Leu Cys Gln Trp Gly Pro His Gln Pro Ser Trp Lys Pro Leu Met Asn
                245                 250                 255

Ser Phe Val Leu Thr Met Tyr Thr Pro Ser Leu
            260                 265

<210> SEQ ID NO 13
<211> LENGTH: 2238
<212> TYPE: DNA
<213> ORGANISM: Mus musculus

<400> SEQUENCE: 13
ctagggtaaa accgtgagac tcggtctgga aatctggcct gagaggacag cctggcaatc      60
ctcagccggg gtggggacgt ctgccgaaga tccttggact ccagcaacca gtggtcgcca     120
ccgtccatcc accctaaggc ccagtttgca cggcggagaa cagctgtgca gccacgctgg     180
acactcaccc cgcccgagtt gagcccgccc ccgggactac aggaccaata agtgatgaat     240 ataccegege gtcacggage acceggccaat egeggacgge cacgaceeta gaaaggetgg     300 gcgcggcagg aggccacggg gcggtggcgg cgctggcgta gacgtttcct ggctatggtg     360
gtggtggcag cggcgccgag cgcggccacg gcggccccca aagtgctact cttatctggc     420 cagccegect ceggeggeeg ggegetgeeg ctcatggtac eegteegeg ggcageaggg     480 tcggaggcga gcgggacacc gcaggctcgc aagcggcagc ggctcacgca cctgagcccg     540
gaggagaaag cgctgcggag gaaactgaaa aacagagtag cagcgcagac tgctcgagat     600
```

```
agaaagaaag cccggatgag cgagctggag cagcaagtgg tggatttgga agaagagaac      660
cacaaactcc agctagaaaa tcagctttta cgggagaaaa ctcacggcct tgtggttgag      720
aaccaggagt taagaacacg cttgggaatg gacacgctgg atcctgacga ggttccagag      780
gtggaggcca aggggagtgg agtaaggctg gtggccgggt ctgctgagtc cgcagcaggt      840
gcaggcccag ttgtcacctc cccagaacat cttcccatgg actctgacac tgttgcctct      900
tcagattctg agtctgatat ccttttgggc attctggaca agttggaccc tgtcatgttt      960
ttcaaatgtc cttccccaga gtctgctagt ctggaggaac tcccagaggt ctacccagaa     1020
ggacctagtt ccttaccagc ctcccttttct ctgtcagtgg ggacctcatc agccaagctg     1080
gaagccatta atgaactcat tcgttttgac catgtataca ccaagcctct agttttagag     1140
atcccctctg agacagagag tcaaactaac gtggtagtga aaattgagga agcacctcta     1200
agctcttcag aagaggatca ccctgaattc attgtctcag tgaagaaaga gcctttggaa     1260
gatgacttca tcccagagct gggcatctca aacctgcttt catccagcca ttgtctgaga     1320
ccaccttctt gcctgctgga cgctcacagt gactgtggat atgagggctc cccttctccc     1380
ttcagtgaca tgtcttctcc acttggtaca gaccactcct gggaggatac ttttgccaat     1440
gaacttttcc cccagctgat tagtgtctaa agagccacat aacactgggc ccctttccct     1500
gaccatcaca ttgcctagag gatagcatag gcctgtctct ttcgttaaaa gccaaagtag     1560
aggctgtctg gccttagaag aattcctcta aagtatttca aatctcatag atgacttcca     1620
agtattgtcg tttgacactc agctgtctaa ggtattcaaa ggtattccag tactacagct     1680
tttgagattc tagtttatct taaaggtggt agtatactct aaatcgcagg gagggtcatt     1740
tgacagtttt ttcccagcct ggcttcaaac tatgtagccg aggctaggca gaaacttctg     1800
accctcttga ccccacctcc caagtgctgg gcttcaccag gtgtgcacct ccacacctgc     1860
cccccgaca tgtcaggtgg acatgggatt catgaatggc ccttagcatt tctttctcca     1920
ctctctgctt cccaggtttc gtaacctgag ggggcttgtt ttcccttatg tgcattttaa     1980
atgaagatca agaatctttg taaaatgatg aaaatttact atgtaaatgc ttgatggatc     2040
ttcttgctag tgtagcttct agaaggtgct ttctccattt atttaaaact acccttgcaa     2100
ttaaaaaaaa agcaacacag cgtcctgttc tgtgatttct agggctgttg taatttctct     2160
ttattgttgg ctaaaggagt aatttatcca actaaagtga gcataccact tttaaagtc     2220
aaaaaaaaaa aaaaaaa                                                    2238
```

<210> SEQ ID NO 14
<211> LENGTH: 371
<212> TYPE: PRT
<213> ORGANISM: Mus musculus

<400> SEQUENCE: 14

Met Val Val Ala Ala Ala Pro Ser Ala Ala Thr Ala Ala Pro Lys
1               5                   10                  15

Val Leu Leu Leu Ser Gly Gln Pro Ala Ser Gly Gly Arg Ala Leu Pro
            20                  25                  30

Leu Met Val Pro Gly Pro Arg Ala Ala Gly Ser Glu Ala Ser Gly Thr
        35                  40                  45

Pro Gln Ala Arg Lys Arg Gln Arg Leu Thr His Leu Ser Pro Glu Glu
    50                  55                  60

Lys Ala Leu Arg Arg Lys Leu Lys Asn Arg Val Ala Ala Gln Thr Ala
65                  70                  75                  80

```
Arg Asp Arg Lys Lys Ala Arg Met Ser Glu Leu Glu Gln Gln Val Val
                85                  90                  95
Asp Leu Glu Glu Glu Asn His Lys Leu Gln Leu Glu Asn Gln Leu Leu
            100                 105                 110
Arg Glu Lys Thr His Gly Leu Val Val Glu Asn Gln Glu Leu Arg Thr
        115                 120                 125
Arg Leu Gly Met Asp Thr Leu Asp Pro Asp Glu Val Pro Glu Val Glu
    130                 135                 140
Ala Lys Gly Ser Gly Val Arg Leu Val Ala Gly Ser Ala Glu Ser Ala
145                 150                 155                 160
Ala Gly Ala Gly Pro Val Val Thr Ser Pro Glu His Leu Pro Met Asp
                165                 170                 175
Ser Asp Thr Val Ala Ser Ser Asp Ser Glu Ser Asp Ile Leu Leu Gly
            180                 185                 190
Ile Leu Asp Lys Leu Asp Pro Val Met Phe Phe Lys Cys Pro Ser Pro
        195                 200                 205
Glu Ser Ala Ser Leu Glu Glu Leu Pro Glu Val Tyr Pro Glu Gly Pro
    210                 215                 220
Ser Ser Leu Pro Ala Ser Leu Ser Leu Ser Val Gly Thr Ser Ser Ala
225                 230                 235                 240
Lys Leu Glu Ala Ile Asn Glu Leu Ile Arg Phe Asp His Val Tyr Thr
                245                 250                 255
Lys Pro Leu Val Leu Glu Ile Pro Ser Glu Thr Glu Ser Gln Thr Asn
            260                 265                 270
Val Val Val Lys Ile Glu Glu Ala Pro Leu Ser Ser Ser Glu Glu Asp
        275                 280                 285
His Pro Glu Phe Ile Val Ser Val Lys Lys Gly Pro Leu Glu Asp Asp
    290                 295                 300
Phe Ile Pro Glu Leu Gly Ile Ser Asn Leu Leu Ser Ser Ser His Cys
305                 310                 315                 320
Leu Arg Pro Pro Ser Cys Leu Leu Asp Ala His Ser Asp Cys Gly Tyr
                325                 330                 335
Glu Gly Ser Pro Ser Pro Phe Ser Asp Met Ser Ser Pro Leu Gly Thr
            340                 345                 350
Asp His Ser Trp Glu Asp Thr Phe Ala Asn Glu Leu Phe Pro Gln Leu
        355                 360                 365
Ile Ser Val
370

<210> SEQ ID NO 15
<211> LENGTH: 1870
<212> TYPE: DNA
<213> ORGANISM: Rattus norvegicus

<400> SEQUENCE: 15
cgctggcgta gacgtttcct ggctatggtg gtggtggcag cggcgccgag cgcggcctcg      60
gcggccccca agtgctact cctatctggt cagcccgcct ccggcggccg agcgctgccg     120
ctcatggttc cgggcccgcg agccgcaggg tcggaggcga gcgggacacc gcaggctcgc     180
aagcggcagc gcctcacgca cctgagcccg gaggagaaag cgctgcggag gaaactgaaa     240
aacagagtag cagcacagac tgcgcgagat agaagaaag cccggatgag cgagctggag     300
cagcaagtgt tggatttgga agaagagaac cagaaactcc agctagaaaa tcagctttta     360
cgagagaaaa ctcatgggct tgtgattgag aaccaggagt taaggacacg cttggggatg     420
```

-continued

```
aatgccctgg ttactgaaga ggtctcagag gcagagtcca aggggaatgg agtaaggctg     480
gtggccgggt ctgctgagtc cgcagcactc agactacgtg cgcctctgca gcaggtgcag     540
gcccagttgt cacctcccca gaacatcttc ccatggattc tgacgctgtt gcctcttcag     600
attctgagtc tgatatcctt ttgggcattc tggacaagtt ggaccctgtc atgttttca      660 aatgtccttc cccagagtct gctaatctgg aggaactccc agaggtctac ccagaaggac     720
ctagttcctt accagcctcc ctttctctgt cagtggggac ctcatcagcc aagctggaag     780
ccattaatga actcattcgt tttgaccatg tatacaccaa gcctctagtc ttagagatcc     840
cctctgagac agagagccaa actaatgtgg tagtgaaaat tgaggaagca cctctaagct     900
cttcagaaga ggatcaccct gaattcattg tctcagtgaa gaaagaacct ttggatgatg     960
acttcattcc cgagctgggc atctcaaacc tgctttcatc cagccattgt ctgagaccac    1020
cttcctgcct gctggatgct cacagtgact gtggatatga gggctcccct tctcccttca    1080
gcgacatgtc ttctccactt ggtacagacc actcctggga ggacactttt gccaacgaac    1140
ttttccccca gctgattagt gtctaaagcc acccaccact gggctccttc cctgatcatc    1200
acactgccta gaggatagca taggcctgtc tgcttcacta aaagccaaag tagaggctat    1260
ctggccttat aagaattcct ctaaagtatt tcaaacctct tagatgactt ccaagtattg    1320
tcttttgaca ctcagctgtc tgaggtcttc aaaggtattc aatactaca gcttttgaga     1380 ttctcattat cttaaaggtg gtagcatgct ctaaatcata gggaaagtca tctgacagtt    1440
atcgttcagc ctggctatgt agccgaggct aagctgaaac ttgtgaccct cttgacccca    1500
ctcccaagtg ctggactta ccaggtgtgc agctccacac cggcctcttc acatgtcctg     1560
aagtagacat gagagtcacc agttctttct ctcctccccg ccccacaggt ttcttttgtt    1620
tccttctaca agcagagaaa cagcaacctg aggggcctgt ccttccttat gtccagttca    1680
agtgaagatc aagaatcttt gtaaaattat tggaaattta ctgtgtaaat gcttgatgga    1740
atcttcttgc tagtgtagct tctagaaggt gctttctcca tttatttaaa actacccatg    1800
caattaaaaa agcaacgcag catccccgtt gaatgatttt aaaaaaaaaa aaaaaaaaa     1860 aaaaaaaaaa                                                           1870
```

<210> SEQ ID NO 16
<211> LENGTH: 267
<212> TYPE: PRT
<213> ORGANISM: Rattus norvegicus

<400> SEQUENCE: 16

```
Met Val Val Val Ala Ala Pro Ser Ala Ala Ser Ala Ala Pro Lys
1               5                   10                  15

Val Leu Leu Leu Ser Gly Gln Pro Ala Ser Gly Gly Arg Ala Leu Pro
                20                  25                  30

Leu Met Val Pro Gly Pro Arg Ala Ala Gly Ser Glu Ala Ser Gly Thr
            35                  40                  45

Pro Gln Ala Arg Lys Arg Gln Arg Leu Thr His Leu Ser Pro Glu Glu
        50                  55                  60

Lys Ala Leu Arg Arg Lys Leu Lys Asn Arg Val Ala Ala Gln Thr Ala
    65                  70                  75                  80

Arg Asp Arg Lys Lys Ala Arg Met Ser Glu Leu Glu Gln Gln Val Val
                85                  90                  95

Asp Leu Glu Glu Glu Asn Gln Lys Leu Gln Leu Glu Asn Gln Leu Leu
            100                 105                 110
```

Arg Glu Lys Thr His Gly Leu Val Ile Glu Asn Gln Glu Leu Arg Thr
        115                 120                 125

Arg Leu Gly Met Asn Ala Leu Val Thr Glu Glu Val Ser Glu Ala Glu
    130                 135                 140

Ser Lys Gly Asn Gly Val Arg Leu Val Ala Gly Ser Ala Glu Ser Ala
145                 150                 155                 160

Ala Leu Arg Leu Arg Ala Pro Leu Gln Gln Val Gln Ala Gln Leu Ser
                165                 170                 175

Pro Pro Gln Asn Ile Phe Pro Trp Ile Leu Thr Leu Pro Leu Gln
            180                 185                 190

Ile Leu Ser Leu Ile Ser Phe Trp Ala Phe Trp Thr Ser Trp Thr Leu
                195                 200                 205

Ser Cys Phe Ser Asn Val Leu Pro Gln Ser Leu Leu Ile Trp Arg Asn
        210                 215                 220

Ser Gln Arg Ser Thr Gln Lys Asp Leu Val Pro Tyr Gln Pro Pro Phe
225                 230                 235                 240

Leu Cys Gln Trp Gly Pro His Gln Pro Ser Trp Lys Pro Leu Met Asn
                245                 250                 255

Ser Phe Val Leu Thr Met Tyr Thr Pro Ser Leu
            260                 265

<210> SEQ ID NO 17
<211> LENGTH: 1844
<212> TYPE: DNA
<213> ORGANISM: Rattus norvegicus

<400> SEQUENCE: 17
cgctggcgta gacgtttcct ggctatggtg gtggtggcag cggcgccgag cgcggcctcg      60
gcggccccca aagtgctact cctatctggt cagcccgcct ccggcggccg agcgctgccg     120
ctcatggttc cgggcccgcg agccgcaggg tcggaggcga gcgggacacc gcaggctcgc     180
aagcggcagc gcctcacgca cctgagcccg gaggagaaag cgctgcggag gaaactgaaa     240
aacagagtag cagcacagac tgcgcgagat agaaagaaag cccggatgag cgagctggag     300
cagcaagtgg tggatttgga agaagagaac cagaaactcc agctagaaaa tcagctttta     360
cgagagaaaa ctcatgggct tgtgattgag aaccaggagt taaggacacg cttggggatg     420
aatgccctgg ttactgaaga ggtctcagag gcagagtcca aggggaatgg agtaaggctg     480
gtggccgggt ctgctgagtc cgcagcaggt gcaggcccag ttgtcacctc cccagaacat     540
cttcccatgg attctgacgc tgttgcctct tcagattctg agtctgatat ccttttgggc     600
attctggaca gttggaccc tgtcatgttt ttcaaatgtc cttccccaga gtctgctaat     660
ctggaggaac tcccagaggt ctacccagaa ggacctagtt ccttaccagc ctccctttct     720
ctgtcagtgg ggacctcatc agccaagctg gaagccatta tgaactcat tcgttttgac     780 catgtataca ccaagcctct agtcttagag atcccctctg agacagagag ccaaactaat     840
gtggtagtga aaattgagga agcacctcta agctcttcag aagaggatca ccctgaattc     900
attgtctcag tgaagaaaga acctttggat gatgacttca ttcccgagct gggcatctca     960
aacctgcttt catccagcca ttgtctgaga ccaccttcct gcctgctgga tgctcacagt    1020
gactgtggat atgagggctc cccttctccc ttcagcgaca tgtcttctcc acttggtaca    1080
gaccactcct gggaggacac ttttgccaac gaacttttcc cccagctgat tagtgtctaa    1140
agccacccac cactgggctc cttccctgat catcacactg cctagaggat agcataggcc    1200

-continued

```
tgtctgcttc actaaaagcc aaagtagagg ctatctggcc ttataagaat tcctctaaag    1260
tatttcaaac ctcttagatg acttccaagt attgtctttt gacactcagc tgtctgaggt    1320
cttcaaaggt attccaatac tacagctttt gagattctca ttatcttaaa ggtggtagca    1380
tgctctaaat catagggaaa gtcatctgac agttatcgtt cagcctggct atgtagccga    1440
ggctaagctg aaacttgtga ccctcttgac cccactccca agtgctggac tttaccaggt    1500
gtgcagctcc acaccggcct cttcacatgt cctgaagtag acatgagagt caccagttct    1560
ttctctcctc cccgccccac aggtttcttt tgtttccttc tacaagcaga gaaacagcaa    1620
cctgaggggc ctgtccttcc ttatgtccag ttcaagtgaa gatcaagaat ctttgtaaaa    1680
ttattggaaa tttactgtgt aaatgcttga tggaatcttc ttgctagtgt agcttctaga    1740
aggtgctttc tccatttatt taaaactacc catgcaatta aaaagcaac gcagcatccc     1800 cgttgaatga ttttaaaaaa aaaaaaaaaa aaaaaaaaaa aaaa                      1844
```

<210> SEQ ID NO 18
<211> LENGTH: 371
<212> TYPE: PRT
<213> ORGANISM: Rattus norvegicus

<400> SEQUENCE: 18

```
Met Val Val Ala Ala Ala Pro Ser Ala Ala Ser Ala Ala Pro Lys
1               5                   10                  15

Val Leu Leu Leu Ser Gly Gln Pro Ala Ser Gly Gly Arg Ala Leu Pro
            20                  25                  30

Leu Met Val Pro Gly Pro Arg Ala Ala Gly Ser Glu Ala Ser Gly Thr
        35                  40                  45

Pro Gln Ala Arg Lys Arg Gln Arg Leu Thr His Leu Ser Pro Glu Glu
    50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn Gln Lys Leu Gln Leu Glu Asn Gln Leu Leu
            100                 105                 110

Arg Glu Lys Thr His Gly Leu Val Ile Glu Asn Gln Glu Leu Arg Thr
        115                 120                 125

Arg Leu Gly Met Asn Ala Leu Val Thr Glu Glu Val Ser Glu Ala Glu
    130                 135                 140

Ser Lys Gly Asn Gly Val Arg Leu Val Ala Gly Ser Ala Glu Ser Ala
145                 150                 155                 160

Ala Gly Ala Gly Pro Val Val Thr Ser Pro Glu His Leu Pro Met Asp
                165                 170                 175

Ser Asp Ala Val Ala Ser Ser Asp Ser Glu Ser Asp Ile Leu Leu Gly
            180                 185                 190

Ile Leu Asp Lys Leu Asp Pro Val Met Phe Phe Lys Cys Pro Ser Pro
        195                 200                 205

Glu Ser Ala Asn Leu Glu Glu Leu Pro Glu Val Tyr Pro Glu Gly Pro
    210                 215                 220

Ser Ser Leu Pro Ala Ser Leu Ser Leu Ser Val Gly Thr Ser Ser Ala
225                 230                 235                 240

Lys Leu Glu Ala Ile Asn Glu Leu Ile Arg Phe Asp His Val Tyr Thr
                245                 250                 255

Lys Pro Leu Val Leu Glu Ile Pro Ser Glu Thr Glu Ser Gln Thr Asn
```

```
                  260                 265                 270
Val Val Val Lys Ile Glu Glu Ala Pro Leu Ser Ser Glu Glu Asp
            275                 280                 285

His Pro Glu Phe Ile Val Ser Val Lys Lys Glu Pro Leu Asp Asp Asp
            290                 295                 300

Phe Ile Pro Glu Leu Gly Ile Ser Asn Leu Leu Ser Ser Ser His Cys
305                 310                 315                 320

Leu Arg Pro Pro Ser Cys Leu Leu Asp Ala His Ser Asp Cys Gly Tyr
                325                 330                 335

Glu Gly Ser Pro Ser Pro Phe Ser Asp Met Ser Ser Pro Leu Gly Thr
            340                 345                 350

Asp His Ser Trp Glu Asp Thr Phe Ala Asn Glu Leu Phe Pro Gln Leu
            355                 360                 365

Ile Ser Val
        370

<210> SEQ ID NO 19
<211> LENGTH: 4518
<212> TYPE: DNA
<213> ORGANISM: Homo sapiens

<400> SEQUENCE: 19
ggagtttatt cataacgcgc tctccaagta tacgtggcaa tgcgttgctg ggttatttta      60
atcattctag gcatcgtttt cctccttatg cctctatcat tcctccctat ctacactaac     120
atcccacgct ctgaacgcgc gcccattaat accctccttt cctccactct ccctgggact     180
cttgatcaaa gcgcggccct ttccccagcc ttagcgaggc gccctgcagc ctggtacgcg     240
cgtggcgtgg cggtgggcgc gcagtgcgtt ctcggtgtgg agggcagctg ttccgcctgc     300
gatgatttat actcacagga caaggatgcg gtttgtcaaa cagtactgct acggaggagc     360
agcagagaaa gggagagggt ttgagaggga gcaaaagaaa atggtaggcg cgcgtagtta     420
attcatgcgg ctctcttact ctgtttacat cctagagcta gagtgctcgg ctgcccggct     480
gagtctcctc cccaccttcc caccctcccc accctccccc ataagcgccc ctcccgggtt     540
cccaaagcag agggcgtggg ggaaaagaaa aaagatcctc tctcgctaat ctccgcccac     600 cggccccttta taatgcgagg gtctggacgg ctgaggaccc ccgagctgtg ctgctcgcgg     660
ccgccaccgc cgggccccgg ccgtccctgg ctcccctcct gcctcgagaa gggcagggct     720
tctcagaggc ttggcgggaa aaagaacgga gggagggatc gcgctgagta taaaagccgg     780
ttttcggggc tttatctaac tcgctgtagt aattccagcg agaggcagag ggagcgagcg     840 gcggccggc tagggtggaa gagccgggcg agcagagctg cgctgcgggc gtcctgggaa     900
gggagatccg gagcgaatag ggggcttcgc ctctggccca gccctcccgc tgatccccca     960
gccagcggtc cgcaacccctt gccgcatcca cgaaactttg cccatagcag cgggcgggca    1020
ctttgcactg gaacttacaa cacccgagca aggacgcgac tctcccgacg cggggaggct    1080
attctgccca tttggggaca cttccccgcc gctgccagga cccgcttctc tgaaaggctc    1140
tccttgcagc tgcttagacg ctggattttt ttcgggtagt ggaaaaccag cagcctcccg    1200
cgacgatgcc cctcaacgtt agcttcacca acaggaacta tgacctcgac tacgactcgg    1260
tgcagccgta tttctactgc gacgaggagg agaacttcta ccagcagcag cagcagagcg    1320
agctgcagcc cccggcgccc agcgaggata tctggaagaa attcgagctg ctgcccaccc    1380
cgcccctgtc ccctagccgc cgctccgggc tctgctcgcc ctcctacgtt gcggtcacac    1440
```

-continued

```
ccttctccct tcggggagac aacgacggcg gtggcgggag cttctccacg gccgaccagc    1500
tggagatggt gaccgagctg ctgggaggag acatggtgaa ccagagtttc atctgcgacc    1560
cggacgacga gaccttcatc aaaaacatca tcatccagga ctgtatgtgg agcggcttct    1620
cggccgccgc caagctcgtc tcagagaagc tggcctccta ccaggctgcg cgcaaagaca    1680
gcggcagccc gaacccgcc cgcggccaca gcgtctgctc cacctccagc ttgtacctgc    1740
aggatctgag cgccgccgcc tcagagtgca tcgacccctc ggtggtcttc ccctaccctc    1800
tcaacgacag cagctcgccc aagtcctgcg cctcgcaaga ctccagcgcc ttctctccgt    1860
cctcggattc tctgctctcc tcgacggagt cctccccgca gggcagcccc gagcccctgg    1920
tgctccatga ggagacaccg cccaccacca gcagcgactc tgaggaggaa caagaagatg    1980
aggaagaaat cgatgttgtt tctgtggaaa agaggcaggc tcctggcaaa aggtcagagt    2040
ctggatcacc ttctgctgga ggccacagca acctcctca cagcccactg gtcctcaaga    2100
ggtgccacgt ctccacacat cagcacaact acgcagcgcc tccctccact cggaaggact    2160
atcctgctgc caagagggtc aagttggaca gtgtcagagt cctgagacag atcagcaaca    2220
accgaaaatg caccagcccc aggtcctcgg acaccgagga gaatgtcaag aggcgaacac    2280
acaacgtctt ggagcgccag aggaggaacg agctaaaacg gagcttttt gccctgcgtg    2340 accagatccc ggagttggaa aacaatgaaa aggcccccaa ggtagttatc cttaaaaaag    2400
ccacagcata catcctgtcc gtccaagcag aggagcaaaa gctcatttct gaagaggact    2460
tgttgcggaa acgacgagaa cagttgaaac acaaacttga acagctacgg aactcttgtg    2520
cgtaaggaaa agtaaggaaa acgattcctt ctaacagaaa tgtcctgagc aatcacctat    2580
gaacttgttt caaatgcatg atcaaatgca acctcacaac cttggctgag tcttgagact    2640
gaaagattta gccataatgt aaactgcctc aaattggact ttgggcataa aagaactttt    2700
ttatgcttac catctttttt ttttctttaa cagatttgta tttaagaatt gttttaaaa    2760 aattttaaga tttacacaat gtttctctgt aaatattgcc attaaatgta ataactttta    2820
ataaaacgtt tatagcagtt acacagaatt tcaatcctag tatatagtac ctagtattat    2880
aggtactata aaccctaatt tttttattt aagtacattt tgcttttaa agttgatttt    2940 tttctattgt ttttagaaaa aataaaataa ctggcaaata tatcattgag ccaaatctta    3000
agttgtgaat gttttgtttc gtttcttccc cctcccaacc accaccatcc ctgtttgttt    3060
tcatcaattg ccccttcaga gggtggtctt aagaaaggca agagttttcc tctgttgaaa    3120
tgggtctggg ggccttaagg tctttaagtt cttggaggtt ctaagatgct tcctggagac    3180
tatgataaca gccagagttg acagttagaa ggaatggcag aaggcaggtg agaaggtgag    3240
aggtaggcaa aggagataca agaggtcaaa ggtagcagtt aagtacacaa agaggcataa    3300
ggactgggga gttgggagga aggtgaggaa gaaactcctg ttactttagt taaccagtgc    3360
cagtcccctg ctcactccaa acccaggaat tctgcccagt tgatggggac acggtgggaa    3420
ccagcttctg ctgccttcac aaccaggcgc cagtcctgtc catgggttat ctcgcaaacc    3480
ccagaggatc tctgggagga atgctactat taaccctatt tcacaaacaa ggaaatagaa    3540
gagctcaaag aggttatgta acttatctgt agccacgcag ataatacaaa gcagcaatct    3600
ggacccattc tgttcaaaac acttaaccct tcgctatcat gccttggttc atctgggtct    3660
aatgtgctga gatcaagaag gtttaggacc taatggacag actcaagtca taacaatgct    3720
aagctctatt tgtgtcccaa gcactcctaa gcatttatc cctaactcta catcaacccc    3780
atgaaggaga tactgttgat ttccccatat tagaagtaga gagggaagct gaggcacaca    3840
```

```
aagactcatc cacatgccca agattcactg atagggaaaa gtggaagcga gatttgaacc    3900
caggctgttt actcctaacc tgtccaagcc acctctcaga cgacggtagg aatcagctgg    3960
ctgcttgtga gtacaggagt tacagtccag tgggttatgt ttttaagtc tcaacatcta     4020 agcctggtca ggcatcagtt cccctttttt tgtgatttat tttgttttta ttttgttgtt    4080
cattgtttaa ttttccttt tacaatgaga aggtcaccat cttgactcct accttagcca    4140
tttgttgaat cagactcatg acggctcctg ggaagaagcc agttcagatc ataaaataaa    4200
acatatttat tctttgtcat gggagtcatt attttagaaa ctacaaactc tccttgcttc    4260
catccttttt tacatactca tgacacatgc tcatcctgag tccttgaaaa ggtattttg     4320 aacatgtgta ttaattataa gcctctgaaa acctatggcc caaaccagaa atgatgttga    4380
ttatataggt aaatgaagga tgctattgct gttctaatta cctcattgtc tcagtctcaa    4440
agtaggtctt cagctccctg tactttggga ttttaatcta ccaccaccca taaatcaata    4500
aataattact ttctttga                                                  4518
```

<210> SEQ ID NO 20
<211> LENGTH: 454
<212> TYPE: PRT
<213> ORGANISM: Homo sapiens

<400> SEQUENCE: 20

```
Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
```

| | | | | | | | | | | | |
|---|---|---|---|---|---|---|---|---|---|---|---|
| | | 245 | | | 250 | | | 255 | | | |
| Glu | Glu | Thr | Pro | Pro | Thr | Thr | Ser | Ser | Asp | Ser | Glu |
| Glu | Glu | Gln | Glu | | | | | | | | |
| | | 260 | | | | 265 | | | 270 | | |
| Asp | Glu | Glu | Ile | Asp | Val | Val | Ser | Val | Glu | Lys | Arg |
| Gln | Ala | Pro | | | | | | | | | |
| | | 275 | | | 280 | | | | 285 | | |
| Gly | Lys | Arg | Ser | Glu | Ser | Gly | Ser | Pro | Ser | Ala | Gly |
| Gly | His | Ser | Lys | | | | | | | | |
| | | 290 | | | | 295 | | | 300 | | |
| Pro | Pro | His | Ser | Pro | Leu | Val | Leu | Lys | Arg | Cys | His |
| Val | Ser | Thr | His | | | | | | | | |
| 305 | | | | 310 | | | | 315 | | | 320 |
| Gln | His | Asn | Tyr | Ala | Ala | Pro | Pro | Ser | Thr | Arg | Lys |
| Asp | Tyr | Pro | Ala | | | | | | | | |
| | | | 325 | | | | 330 | | | | 335 |
| Ala | Lys | Arg | Val | Lys | Leu | Asp | Ser | Val | Arg | Val | Leu |
| Arg | Gln | Ile | Ser | | | | | | | | |
| | | | 340 | | | | 345 | | | 350 | |
| Asn | Asn | Arg | Lys | Cys | Thr | Ser | Pro | Arg | Ser | Ser | Asp |
| Thr | Glu | Glu | Asn | | | | | | | | |
| | | 355 | | | | 360 | | | 365 | | |
| Val | Lys | Arg | Arg | Thr | His | Asn | Val | Leu | Glu | Arg | Gln |
| Arg | Arg | Asn | Glu | | | | | | | | |
| | | 370 | | | | 375 | | | 380 | | |
| Leu | Lys | Arg | Ser | Phe | Phe | Ala | Leu | Arg | Asp | Gln | Ile |
| Pro | Glu | Leu | Glu | | | | | | | | |
| 385 | | | | 390 | | | | 395 | | | 400 |
| Asn | Asn | Glu | Lys | Ala | Pro | Lys | Val | Val | Ile | Leu | Lys |
| Lys | Ala | Thr | Ala | | | | | | | | |
| | | | 405 | | | | 410 | | | | 415 |
| Tyr | Ile | Leu | Ser | Val | Gln | Ala | Glu | Glu | Gln | Lys | Leu |
| Ile | Ser | Glu | Glu | | | | | | | | |
| | | | 420 | | | | 425 | | | 430 | |
| Asp | Leu | Leu | Arg | Lys | Arg | Arg | Glu | Gln | Leu | Lys | His |
| Lys | Leu | Glu | Gln | | | | | | | | |
| | | | 435 | | | | 440 | | | | 445 |
| Leu | Arg | Asn | Ser | Cys | Ala | | | | | | |
| | | 450 | | | | | | | | | |

<210> SEQ ID NO 21
<211> LENGTH: 4515
<212> TYPE: DNA
<213> ORGANISM: Homo sapiens

<400> SEQUENCE: 21

| | |
|---|---|
| ggagtttatt cataacgcgc tctccaagta tacgtggcaa tgcgttgctg ggttatttta | 60 |
| atcattctag gcatcgtttt cctccttatg cctctatcat tcctccctat ctacactaac | 120 |
| atcccacgct ctgaacgcgc gcccattaat acccttcttt cctccactct ccctgggact | 180 |
| cttgatcaaa gcgcggccct ttccccagcc ttagcgaggc gccctgcagc ctggtacgcg | 240 |
| cgtggcgtgg cggtgggcgc gcagtgcgtt ctcggtgtgg agggcagctg ttccgcctgc | 300 |
| gatgatttat actcacagga caaggatgcg gtttgtcaaa cagtactgct acggaggagc | 360 |
| agcagagaaa gggagagggt tgagaggga gcaaaagaaa atggtaggcg cgcgtagtta | 420 |
| attcatgcgg ctctcttact ctgtttacat cctagagcta gagtgctcgg ctgcccggct | 480 |
| gagtctcctc cccaccttcc caccctcccc accctcccc ataagcgccc ctcccgggtt | 540 |
| cccaaagcag agggcgtggg ggaaaagaaa aaagatcctc tctcgctaat ctccgcccac | 600 |
| cggcccttta taatgcgagg gtctggacgg ctgaggaccc ccgagctgtg ctgctcgcgg | 660 |
| ccgccaccgc cgggccccgg ccgtccctgg ctcccctcct gcctcgagaa gggcagggct | 720 |
| tctcagaggc ttgcgggaa aaagaacgga gggagggatc gcgctgagta taaaagccgg | 780 |
| ttttcggggt tttatctaac tcgctgtagt aattccagcg agaggcagag ggagcgagcg | 840 |
| ggcggccggc tagggtggaa gagccgggcg agcagagctg cgctgcgggc gtcctgggaa | 900 |

```
gggagatccg gagcgaatag ggggcttcgc ctctggccca gccctcccgc tgatccccca    960
gccagcggtc cgcaacccct gccgcatcca cgaaactttg cccatagcag cgggcgggca   1020
ctttgcactg gaacttacaa cacccgagca aggacgcgac tctcccgacg cggggaggct   1080
attctgccca tttggggaca cttccccgcc gctgccagga cccgcttctc tgaaaggctc   1140
tccttgcagc tgcttagacg ctggattttt tcgggtagt ggaaaaccag cctcccgcga    1200
cgatgcccct caacgttagc ttcaccaaca ggaactatga cctcgactac gactcggtgc   1260
agccgtattt ctactgcgac gaggaggaga acttctacca gcagcagcag cagagcgagc   1320
tgcagccccc ggcgcccagc gaggatatct ggaagaaatt cgagctgctg cccacccgc    1380
ccctgtcccc tagccgccgc tccgggctct gctcgccctc ctacgttgcg gtcacaccct   1440
tctcccttcg gggagacaac gacggcggtg gcgggagctt ctccacggcc gaccagctgg   1500
agatggtgac cgagctgctg ggaggagaca tggtgaacca gagtttcatc tgcgacccgg   1560
acgacgagac cttcatcaaa aacatcatca tccaggactg tatgtggagc ggcttctcgg   1620
ccgccgccaa gctcgtctca gagaagctgg cctcctacca ggctgcgcgc aaagacagcg   1680
gcagcccgaa ccccgcccgc ggccacagcg tctgctccac ctccagcttg tacctgcagg   1740
atctgagcgc cgccgcctca gagtgcatcg acccctcggt ggtcttcccc taccctctca   1800
acgacagcag ctcgcccaag tcctgcgcct cgcaagactc cagcgccttc tctccgtcct   1860
cggattctct gctctcctcg acggagtcct ccccgcaggg cagccccgag ccctggtgc    1920
tccatgagga gacaccgccc accaccagca gcgactctga ggaggaacaa gaagatgagg   1980
aagaaatcga tgttgtttct gtggaaaaga ggcaggctcc tggcaaaagg tcagagtctg   2040
gatcaccttc tgctggaggc cacagcaaac ctcctcacag cccactggtc ctcaagaggt   2100
gccacgtctc cacacatcag cacaactacg cagcgcctcc ctccactcgg aaggactatc   2160
ctgctgccaa gagggtcaag ttggacagtg tcagagtcct gagacagatc agcaacaacc   2220
gaaaatgcac cagccccagg tcctcggaca ccgaggagaa tgtcaagagg cgaacacaca   2280
acgtcttgga gcgccagagg aggaacgagc taaaacggag cttttttgcc ctgcgtgacc   2340
agatcccgga gttggaaaac aatgaaaagg ccccaaggt agttatcctt aaaaaagcca   2400
cagcatacat cctgtccgtc aagcagagg agcaaaagct catttctgaa gaggacttgt   2460
tgcggaaacg acgagaacag ttgaaacaca aacttgaaca gctacggaac tcttgtgcgt   2520
aaggaaaagt aaggaaaacg attccttcta acagaaatgt cctgagcaat cacctatgaa   2580
cttgttttcaa atgcatgatc aaatgcaacc tcacaacctt ggctgagtct tgagactgaa   2640
agatttagcc ataatgtaaa ctgcctcaaa ttggactttg gcataaaaag aacttttta    2700
tgcttaccat ctttttttt tcttaacag atttgtattt aagaattgtt ttaaaaaat     2760
tttaagattt acacaatgtt tctctgtaaa tattgccatt aaatgtaaat aactttaata   2820
aaacgtttat agcagttaca cagaatttca atcctagtat atagtaccta gtattatagg   2880
tactataaac cctaattttt tttatttaag tacattttgc tttttaaagt tgatttttt    2940
ctattgtttt tagaaaaaat aaaataactg gcaaatatat cattgagcca atcttaagt    3000
tgtgaatgtt ttgtttcgtt tcttccccct cccaaccacc accatccctg tttgttttca   3060
tcaattgccc cttcagaggg tggtcttaag aaaggcaaga gttttcctct gttgaaatgg   3120
gtctggggc cttaaggtct ttaagttctt ggaggttcta agatgcttcc tggagactat   3180
gataacagcc agagttgaca gttagaagga atggcagaag gcaggtgaga aggtgagagg   3240
taggcaaagg agatacaaga ggtcaaaggt agcagttaag tacacaaaga ggcataagga   3300
```

```
ctggggagtt gggaggaagg tgaggaagaa actcctgtta ctttagttaa ccagtgccag    3360 tccctgctc actccaaacc caggaattct gcccagttga tggggacacg gtgggaacca     3420
gcttctgctg ccttcacaac caggcgccag tcctgtccat gggttatctc gcaaacccca    3480
gaggatctct gggaggaatg ctactattaa ccctatttca caaacaagga aatagaagag    3540
ctcaaagagg ttatgtaact tatctgtagc cacgcagata atacaaagca gcaatctgga    3600
cccattctgt tcaaaacact taaccccttcg ctatcatgcc ttggttcatc tgggtctaat    3660
gtgctgagat caagaaggtt taggacctaa tggacagact caagtcataa caatgctaag    3720
ctctatttgt gtcccaagca ctcctaagca ttttatccct aactctacat caaccccatg    3780
aaggagatac tgttgatttc cccatattag aagtagagag ggaagctgag gcacacaaag    3840
actcatccac atgcccaaga ttcactgata gggaaaagtg gaagcgagat ttgaacccag    3900
gctgtttact cctaacctgt ccaagccacc tctcagacga cggtaggaat cagctggctg    3960
cttgtgagta caggagttac agtccagtgg gttatgtttt ttaagtctca acatctaagc    4020
ctggtcaggc atcagttccc ctttttttgt gatttatttt gtttttattt tgttgttcat    4080
tgtttaattt ttcctttttac aatgagaagg tcaccatctt gactcctacc ttagccattt    4140
gttgaatcag actcatgacg gctcctggga agaagccagt tcagatcata aaataaaaca    4200
tatttattct ttgtcatggg agtcattatt ttagaaacta caaactctcc ttgcttccat    4260
ccttttttac atactcatga cacatgctca tcctgagtcc ttgaaaaggt attttttgaac    4320 atgtgtatta attataagcc tctgaaaacc tatgggccca accagaaatg atgttgatta    4380
tataggtaaa tgaaggatgc tattgctgtt ctaattacct cattgtctca gtctcaaagt    4440
aggtcttcag ctccctgtac tttgggattt taatctacca ccacccataa atcaataaat    4500
aattactttc tttga                                                    4515
```

<210> SEQ ID NO 22
<211> LENGTH: 453
<212> TYPE: PRT
<213> ORGANISM: Homo sapiens

<400> SEQUENCE: 22

Met Asp Phe Phe Arg Val Val Glu Asn Gln Pro Pro Ala Thr Met Pro
1               5                   10                  15

Leu Asn Val Ser Phe Thr Asn Arg Asn Tyr Asp Leu Asp Tyr Asp Ser
            20                  25                  30

Val Gln Pro Tyr Phe Tyr Cys Asp Glu Glu Asn Phe Tyr Gln Gln
        35                  40                  45

Gln Gln Gln Ser Glu Leu Gln Pro Pro Ala Pro Ser Glu Asp Ile Trp
    50                  55                  60

Lys Lys Phe Glu Leu Leu Pro Thr Pro Pro Leu Ser Pro Ser Arg Arg
65                  70                  75                  80

Ser Gly Leu Cys Ser Pro Ser Tyr Val Ala Val Thr Pro Phe Ser Leu
                85                  90                  95

Arg Gly Asp Asn Asp Gly Gly Gly Gly Ser Phe Ser Thr Ala Asp Gln
            100                 105                 110

Leu Glu Met Val Thr Glu Leu Leu Gly Gly Asp Met Val Asn Gln Ser
        115                 120                 125

Phe Ile Cys Asp Pro Asp Asp Glu Thr Phe Ile Lys Asn Ile Ile Ile
    130                 135                 140

Gln Asp Cys Met Trp Ser Gly Phe Ser Ala Ala Ala Lys Leu Val Ser

-continued

```
            145                 150                 155                 160
Glu Lys Leu Ala Ser Tyr Gln Ala Ala Arg Lys Asp Ser Gly Ser Pro
                165                 170                 175
Asn Pro Ala Arg Gly His Ser Val Cys Ser Thr Ser Leu Tyr Leu
            180                 185                 190
Gln Asp Leu Ser Ala Ala Ala Ser Glu Cys Ile Asp Pro Ser Val Val
            195                 200                 205
Phe Pro Tyr Pro Leu Asn Asp Ser Ser Pro Lys Ser Cys Ala Ser
            210                 215                 220
Gln Asp Ser Ser Ala Phe Ser Pro Ser Ser Asp Ser Leu Leu Ser Ser
225                 230                 235                 240
Thr Glu Ser Ser Pro Gln Gly Ser Pro Glu Pro Leu Val Leu His Glu
                245                 250                 255
Glu Thr Pro Pro Thr Thr Ser Ser Asp Ser Glu Glu Gln Glu Asp
            260                 265                 270
Glu Glu Glu Ile Asp Val Val Ser Val Glu Lys Arg Gln Ala Pro Gly
            275                 280                 285
Lys Arg Ser Glu Ser Gly Ser Pro Ser Ala Gly Gly His Ser Lys Pro
            290                 295                 300
Pro His Ser Pro Leu Val Leu Lys Arg Cys His Val Ser Thr His Gln
305                 310                 315                 320
His Asn Tyr Ala Ala Pro Pro Ser Thr Arg Lys Asp Tyr Pro Ala Ala
                325                 330                 335
Lys Arg Val Lys Leu Asp Ser Val Arg Val Leu Arg Gln Ile Ser Asn
                340                 345                 350
Asn Arg Lys Cys Thr Ser Pro Arg Ser Ser Asp Thr Glu Glu Asn Val
            355                 360                 365
Lys Arg Arg Thr His Asn Val Leu Glu Arg Gln Arg Asn Glu Leu
            370                 375                 380
Lys Arg Ser Phe Phe Ala Leu Arg Asp Gln Ile Pro Glu Leu Glu Asn
385                 390                 395                 400
Asn Glu Lys Ala Pro Lys Val Val Ile Leu Lys Lys Ala Thr Ala Tyr
                405                 410                 415
Ile Leu Ser Val Gln Ala Glu Glu Gln Lys Leu Ile Ser Glu Glu Asp
            420                 425                 430
Leu Leu Arg Lys Arg Arg Glu Gln Leu Lys His Lys Leu Glu Gln Leu
            435                 440                 445
Arg Asn Ser Cys Ala
    450

<210> SEQ ID NO 23
<211> LENGTH: 2399
<212> TYPE: DNA
<213> ORGANISM: Mus musculus

<400> SEQUENCE: 23
cccgcccacc cgccctttat attccggggg tctgcgcggc cgaggacccc tgggctgcgc      60
tgctctcagc tgccgggtcc gactcgcctc actcagctcc cctcctgcct cctgaagggc     120
agggcttcgc cgacgcttgg cgggaaaaag aaggaggggg agggatcctg agtcgcagta     180 taaagaagc ttttcgggcg ttttttttctg actcgctgta gtaattccag cgagagacag     240
agggagtgag cggacggttg gaagagccgt gtgtgcagag ccgcgctccg ggcgaccta      300 agaaggcagc tctggagtga gaggggcttt gcctccgagc ctgccgccca ctctcccaa      360
```

```
cccctgcgact gacccaacat cagcggccgc aaccctcgcc gccgctggga aactttgccc    420
attgcagcgg gcagacactt ctcactggaa cttacaatct gcgagccagg acaggactcc    480
ccaggctccg gggagggaat ttttgtctat ttggggacag tgttctctgc ctctgcccgc    540
gatcagctct cctgaaaaga gctcctcgag ctgtttgaag ctggatttc ctttgggcgt     600
tggaaccccc gcagacagcc acgacgatgc ccctcaacgt gaacttcacc aacaggaact    660
atgacctcga ctacgactcc gtacagccct atttcatctg cgacgaggaa gagaatttct    720
atcaccagca acagcagagc gagctgcagc cgcccgcgcc cagtgaggat atctggaaga    780
aattcgagct gcttcccacc ccgccccgtg ccccgagccg ccgctccggg ctctgctctc    840
catcctatgt tgcggtcgct acgtccttct ccccaaggga agacgatgac ggcggcggtg    900
gcaacttctc caccgccgat cagctggaga tgatgaccga gttacttgga ggagacatgg    960
tgaaccagag cttcatctgc gatcctgacg acgagacctt catcaagaac atcatcatcc   1020
aggactgtat gtggagcggt ttctcagccc ctgccaagct ggtctcggag aagctggcct   1080
cctaccaggc tgcgcgcaaa gacagcacca gcctgagccc cgcccgcggg cacagcgtct   1140
gctccacctc cagcctgtac ctgcaggacc tcaccgccgc cgcgtccgag tgcattgacc   1200
cctcagtggt ctttccctac ccgctcaacg acagcagctc gcccaaatcc tgtacctcgt   1260
ccgattccac ggccttctct ccttcctcgg actcgctgct gtcctccgag tcctccccac   1320
gggccagccc tgagcccta gtgctgcatg aggagacacc gccaccacc agcagcgact     1380
ctgaagaaga gcaagaagat gaggaagaaa ttgatgtggt gtctgtggag aagaggcaaa   1440
cccctgccaa gaggtcggag tcgggctcat ctccatcccg aggccacagc aaacctccgc   1500
acagcccact ggtcctcaag aggtgccacg tctccactca ccagcacaac tacgccgcac   1560
cccctccac aaggaaggac tatccagctg ccaagagggc caagtggac agtggcaggg    1620
tcctgaagca gatcagcaac aaccgcaagt gctccagccc caggtcctca gacacggagg   1680
aaaacgacaa gaggcggaca cacaacgtct tggaacgtca gaggaggaac gagctgaagc   1740
gcagcttttt tgccctgcgt gaccagatcc ctgaattgga aaacaacgaa aaggccccca   1800
aggtagtgat cctcaaaaaa gccaccgcct acatcctgtc cattcaagca gacgagcaca   1860
agctcacctc tgaaaaggac ttattgagga acgacgaga cagttgaaa cacaaactcg     1920
aacagcttcg aaactctggt gcataaactg acctaactcg aggaggagct ggaatctctc   1980
gtgagagtaa ggagaacggt tccttctgac agaactgatg cgctggaatt aaaatgcatg   2040
ctcaaagcct aacctcacaa ccttggctgg ggctttggga ctgtaagctt cagccataat   2100
tttaactgcc tcaaacttaa atagtataaa agaactttt tttatgcttc ccatctttt    2160
tcttttcct tttaacagat ttgtatttaa ttgtttttt aaaaaatct taaaatctat      2220
ccaattttcc catgtaaata gggccttgaa atgtaaataa ctttaataaa acgtttataa   2280
cagttacaaa agattttaag acatgtacca taatttttt tatttaaaga cattttcatt    2340
tttaaagttg atttttttct attgttttta gaaaaaaata aaataattgg aaaaaatac    2399
```

<210> SEQ ID NO 24
<211> LENGTH: 454
<212> TYPE: PRT
<213> ORGANISM: Mus musculus

<400> SEQUENCE: 24

Met Asp Phe Leu Trp Ala Leu Glu Thr Pro Gln Thr Ala Thr Thr Met
1               5                   10                  15

-continued

```
Pro Leu Asn Val Asn Phe Thr Asn Arg Asn Tyr Asp Leu Asp Tyr Asp
             20                  25                  30

Ser Val Gln Pro Tyr Phe Ile Cys Asp Glu Glu Asn Phe Tyr His
         35                  40                  45

Gln Gln Gln Gln Ser Glu Leu Gln Pro Pro Ala Pro Ser Glu Asp Ile
     50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Ala Thr Ser Phe
                 85                  90                  95

Ser Pro Arg Glu Asp Asp Asp Gly Gly Gly Gly Asn Phe Ser Thr Ala
            100                 105                 110

Asp Gln Leu Glu Met Met Thr Glu Leu Leu Gly Gly Asp Met Val Asn
            115                 120                 125

Gln Ser Phe Ile Cys Asp Pro Asp Asp Glu Thr Phe Ile Lys Asn Ile
        130                 135                 140

Ile Ile Gln Asp Cys Met Trp Ser Gly Phe Ser Ala Ala Ala Lys Leu
145                 150                 155                 160

Val Ser Glu Lys Leu Ala Ser Tyr Gln Ala Ala Arg Lys Asp Ser Thr
                165                 170                 175

Ser Leu Ser Pro Ala Arg Gly His Ser Val Cys Ser Thr Ser Ser Leu
            180                 185                 190

Tyr Leu Gln Asp Leu Thr Ala Ala Ala Ser Glu Cys Ile Asp Pro Ser
        195                 200                 205

Val Val Phe Pro Tyr Pro Leu Asn Asp Ser Ser Pro Lys Ser Cys
210                 215                 220

Thr Ser Ser Asp Ser Thr Ala Phe Ser Pro Ser Ser Asp Ser Leu Leu
225                 230                 235                 240

Ser Ser Glu Ser Ser Pro Arg Ala Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Thr Pro
        275                 280                 285

Ala Lys Arg Ser Glu Ser Gly Ser Ser Pro Ser Arg Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Ala Lys Leu Asp Ser Gly Arg Val Leu Lys Gln Ile Ser
            340                 345                 350

Asn Asn Arg Lys Cys Ser Ser Pro Arg Ser Ser Asp Thr Glu Glu Asn
        355                 360                 365

Asp Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Ile Gln Ala Asp Glu His Lys Leu Thr Ser Glu Lys
            420                 425                 430

Asp Leu Leu Arg Lys Arg Arg Glu Gln Leu Lys His Lys Leu Glu Gln
```

Leu Arg Asn Ser Gly Ala
    450

<210> SEQ ID NO 25
<211> LENGTH: 2399
<212> TYPE: DNA
<213> ORGANISM: Mus musculus

<400> SEQUENCE: 25

| | | | | | |
|---|---|---|---|---|---|
| cccgcccacc | cgcccttat | attccggggg | tctgcgcggc | cgaggacccc | tgggctgcgc | 60 |
| tgctctcagc | tgccgggtcc | gactcgcctc | actcagctcc | cctcctgcct | cctgaagggc | 120 |
| agggcttcgc | cgacgcttgg | cgggaaaaag | aagggagggg | agggatcctg | agtcgcagta | 180 |
| taaaagaagc | ttttcgggcg | ttttttttctg | actcgctgta | gtaattccag | cgagagacag | 240 |
| agggagtgag | cggacggttg | gaagagccgt | gtgtgcagag | ccgcgctccg | ggcgaccta | 300 |
| agaaggcagc | tctggagtga | gaggggcttt | gcctccgagc | ctgccgccca | ctctccccaa | 360 |
| ccctgcgact | gacccaacat | cagcggccgc | aaccctcgcc | gccgctggga | aactttgccc | 420 |
| attgcagcgg | gcagacactt | ctcactggaa | cttacaatct | gcgagccagg | acaggactcc | 480 |
| ccaggctccg | gggagggaat | ttttgtctat | ttggggacag | tgttctctgc | ctctgcccgc | 540 |
| gatcagctct | cctgaaaaga | gctcctcgag | ctgtttgaag | gctggatttc | ctttgggcgt | 600 |
| tggaaacccc | gcagacagcc | acgacgatgc | ccctcaacgt | gaacttcacc | aacaggaact | 660 |
| atgacctcga | ctacgactcc | gtacagcccct | atttcatctg | cgacgaggaa | gagaatttct | 720 |
| atcaccagca | acagcagagc | gagctgcagc | cgcccgcgcc | cagtgaggat | atctggaaga | 780 |
| aattcgagct | gcttcccacc | ccgcccctgt | ccccgagccg | ccgctccggg | ctctgctctc | 840 |
| catcctatgt | tgcggtcgct | acgtccttct | ccccaaggga | agacgatgac | ggcggcggtg | 900 |
| gcaacttctc | caccgccgat | cagctggaga | tgatgaccga | gttacttgga | ggagacatgg | 960 |
| tgaaccagag | cttcatctgc | gatcctgacg | acgagacctt | catcaagaac | atcatcatcc | 1020 |
| aggactgtat | gtggagcggt | ttctcagccg | ctgccaagct | ggtctcggag | aagctggcct | 1080 |
| cctaccaggc | tgcgcgcaaa | gacagcacca | gcctgagccc | cgcccgcggg | cacagcgtct | 1140 |
| gctccacctc | cagcctgtac | ctgcaggacc | tcaccgccgc | cgcgtccgag | tgcattgacc | 1200 |
| cctcagtggt | ctttcccctac | ccgctcaacg | acagcagctc | gcccaaatcc | tgtacctcgt | 1260 |
| ccgattccac | ggccttctct | ccttcctcgg | actcgctgct | gtcctccgag | tcctccccac | 1320 |
| gggccagccc | tgagccccta | gtgctgcatg | aggagacacc | gccaccacc | agcagcgact | 1380 |
| ctgaagaaga | gcaagaagat | gaggaagaaa | ttgatgtggt | gtctgtggag | aagaggcaaa | 1440 |
| cccctgccaa | gaggtcggag | tcgggctcat | ctccatcccg | aggccacagc | aaacctccgc | 1500 |
| acagcccact | ggtcctcaag | aggtgccacg | tctccactca | ccagcacaac | tacgccgcac | 1560 |
| cccctccac | aaggaaggac | tatccagctg | ccaagagggc | caagtggac | agtggcaggg | 1620 |
| tcctgaagca | gatcagcaac | aaccgcaagt | gctccagccc | caggtcctca | gacacggagg | 1680 |
| aaaacgacaa | gaggcggaca | cacaacgtct | tggaacgtca | gaggaggaac | gagctgaagc | 1740 |
| gcagctttt | tgccctgcgt | gaccagatcc | ctgaattgga | aaacaacgaa | aaggccccca | 1800 |
| aggtagtgat | cctcaaaaaa | gccaccgcct | acatcctgtc | cattcaagca | gacgagcaca | 1860 |
| agctcacctc | tgaaaaggac | ttattgagga | acgacgaga | acagttgaaa | cacaaactcg | 1920 |
| aacagcttcg | aaactctggt | gcataaactg | acctaactcg | aggaggagct | ggaatctctc | 1980 |

-continued

```
gtgagagtaa ggagaacggt tccttctgac agaactgatg cgctggaatt aaaatgcatg    2040
ctcaaagcct aacctcacaa ccttggctgg ggctttggga ctgtaagctt cagccataat    2100
tttaactgcc tcaaacttaa atagtataaa agaacttttt tttatgcttc ccatcttttt    2160 tcttttcct tttaacagat ttgtatttaa ttgttttttt aaaaaaatct taaaatctat     2220
ccaattttcc catgtaaata gggccttgaa atgtaaataa ctttaataaa acgtttataa    2280
cagttacaaa agattttaag acatgtacca taatttttt tatttaaaga catttcatt     2340 tttaaagttg attttttct attgttttta gaaaaaata aataattgg aaaaaatac        2399
```

<210> SEQ ID NO 26
<211> LENGTH: 439
<212> TYPE: PRT
<213> ORGANISM: Mus musculus

<400> SEQUENCE: 26

```
Met Pro Leu Asn Val Asn Phe Thr Asn Arg Asn Tyr Asp Leu Asp Tyr
1               5                   10                  15

Asp Ser Val Gln Pro Tyr Phe Ile Cys Asp Glu Glu Glu Asn Phe Tyr
                20                  25                  30

His Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Ala Thr Ser
65                  70                  75                  80

Phe Ser Pro Arg Glu Asp Asp Asp Gly Gly Gly Gly Asn Phe Ser Thr
                85                  90                  95

Ala Asp Gln Leu Glu Met Met Thr Glu Leu Leu Gly Gly Asp Met Val
            100                 105                 110

Asn Gln Ser Phe Ile Cys Asp Pro Asp Asp Glu Thr Phe Ile Lys Asn
        115                 120                 125

Ile Ile Ile Gln Asp Cys Met Trp Ser Gly Phe Ser Ala Ala Ala Lys
    130                 135                 140

Leu Val Ser Glu Lys Leu Ala Ser Tyr Gln Ala Ala Arg Lys Asp Ser
145                 150                 155                 160

Thr Ser Leu Ser Pro Ala Arg Gly His Ser Val Cys Ser Thr Ser Ser
                165                 170                 175

Leu Tyr Leu Gln Asp Leu Thr Ala Ala Ala Ser Glu Cys Ile Asp Pro
            180                 185                 190

Ser Val Val Phe Pro Tyr Pro Leu Asn Asp Ser Ser Ser Pro Lys Ser
        195                 200                 205

Cys Thr Ser Ser Asp Ser Thr Ala Phe Ser Pro Ser Ser Asp Ser Leu
    210                 215                 220

Leu Ser Ser Glu Ser Ser Pro Arg Ala Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Thr
            260                 265                 270

Pro Ala Lys Arg Ser Glu Ser Gly Ser Ser Pro Ser Arg Gly His Ser
        275                 280                 285

Lys Pro Pro His Ser Pro Leu Val Leu Lys Arg Cys His Val Ser Thr
    290                 295                 300
```

| | | | | | | | | | | | |
|---|---|---|---|---|---|---|---|---|---|---|---|
|His|Gln|His|Asn|Tyr|Ala|Ala|Pro|Ser|Thr|Arg|Lys|Asp|Tyr|Pro|
|305| | | |310| | | |315| | | |320|

His Gln His Asn Tyr Ala Ala Pro Ser Thr Arg Lys Asp Tyr Pro
305                 310                 315                 320

Ala Ala Lys Arg Ala Lys Leu Asp Ser Gly Arg Val Leu Lys Gln Ile
            325                 330                 335

Ser Asn Asn Arg Lys Cys Ser Ser Pro Arg Ser Ser Asp Thr Glu Glu
            340                 345                 350

Asn Asp Lys Arg Arg Thr His Asn Val Leu Glu Arg Gln Arg Arg Asn
            355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Ile Gln Ala Asp Glu His Lys Leu Thr Ser Glu
                405                 410                 415

Lys Asp Leu Leu Arg Lys Arg Arg Glu Gln Leu Lys His Lys Leu Glu
                420                 425                 430

Gln Leu Arg Asn Ser Gly Ala
            435

<210> SEQ ID NO 27
<211> LENGTH: 2396
<212> TYPE: DNA
<213> ORGANISM: Mus musculus

<400> SEQUENCE: 27

```
cccgcccacc cgcccttat  attccggggg tctgcgcggc cgaggacccc tgggctgcgc    60
tgctctcagc tgccgggtcc gactcgcctc actcagctcc cctcctgcct cctgaagggc   120
agggcttcgc cgacgcttgg cgggaaaaag aagggagggg agggatcctg agtcgcagta   180
taaagaagc ttttcgggcg ttttttctg  actcgctgta gtaattccag cgagagacag    240
agggagtgag cggacggttg gaagagccgt gtgtgcagag ccgcgctccg ggcgaccta    300
agaaggcagc tctggagtga gagggcttt  gcctccgagc ctgccgccca ctctccccaa   360
ccctgcgact gacccaacat cagcggccgc aaccctcgcc gccgctggga aactttgccc   420
attgcagcgg gcagacactt ctcactggaa cttacaatct gcgagccagg acaggactcc   480
ccaggctccg gggagggaat ttttgtctat ttggggacag tgttctctgc ctctgcccgc   540
gatcagctct cctgaaaaga gctcctcgag ctgtttgaag gctggatttc ctttgggcgt   600
tggaaacccc gacagccacg acgatgcccc tcaacgtgaa cttcaccaac aggaactatg   660
acctcgacta cgactccgta cagcccatt  tcatctgcga cgaggaagag aatttctatc   720
accagcaaca gcagagcgag ctgcagccgc ccgcgcccag tgaggatatc tggaagaaat   780
tcgagctgct tcccaccccg cccctgtccc cgagccgccg ctcccgggctc tgctctccat   840
cctatgttgc ggtcgctacg tccttctccc caagggaaga cgatgacggc ggcggtggca   900
acttctccac cgccgatcag ctggagatga tgaccgagtt acttggagga gacatggtga   960
accagagctt catctgcgat cctgacgacg agaccttcat caagaacatc atcatccagg  1020
actgtatgtg gagcggtttc tcagccgctg ccaagctggt ctcggagaag ctggcctcct  1080
accaggctgc gcgcaaagac agcaccagcc tgagccccgc ccgcgggcac agcgtctgct  1140
ccacctccag cctgtacctg caggacctca ccgccgccgc gtccgagtgc attgaccct   1200
cagtggtctt tcctacccg  ctcaacgaca gcagctcgcc caaatcctgt acctcgtccg  1260
attccacggc cttctctcct tcctcggact cgctgctgtc ctccgagtcc tccccacggg  1320
```

-continued

```
ccagccctga gccccctagtg ctgcatgagg agacaccgcc caccaccagc agcgactctg    1380
aagaagagca agaagatgag gaagaaattg atgtggtgtc tgtggagaag aggcaaaccc    1440
ctgccaagag gtcggagtcg ggctcatctc catcccgagg ccacagcaaa cctccgcaca    1500
gcccactggt cctcaagagg tgccacgtct ccactcacca gcacaactac gccgcacccc    1560
cctccacaag gaaggactat ccagctgcca agagggccaa gttggacagt ggcagggtcc    1620
tgaagcagat cagcaacaac cgcaagtgct ccagccccag gtcctcagac acggaggaaa    1680
acgacaagag gcggacacac aacgtcttgg aacgtcagag gaggaacgag ctgaagcgca    1740
gcttttttgc cctgcgtgac cagatccctg aattggaaaa caacgaaaag gcccccaagg    1800
tagtgatcct caaaaaagcc accgcctaca tcctgtccat tcaagcagac gagcacaagc    1860
tcacctctga aaaggactta ttgaggaaac gacgagaaca gttgaaacac aaactcgaac    1920
agcttcgaaa ctctggtgca taaactgacc taactcgagg aggagctgga atctctcgtg    1980
agagtaagga gaacggttcc ttctgacaga actgatgcgc tggaattaaa atgcatgctc    2040
aaagcctaac ctcacaacct tggctgdggc tttgggactg taagcttcag ccataatttt    2100
aactgcctca aacttaaata gtataaaaga actttttttt atgcttccca tctttttttct    2160
ttttcctttt aacagatttg tatttaattg ttttttttaaa aaaatcttaa aatctatcca    2220
attttcccat gtaaataggg ccttgaaatg taaataactt taataaaacg tttataacag    2280
ttacaaaaga ttttaagaca tgtaccataa ttttttttat ttaaagacat tttcattttt    2340
aaagttgatt ttttttctatt gttttttagaa aaaaataaaa taattggaaa aaatac       2396
```

<210> SEQ ID NO 28
<211> LENGTH: 439
<212> TYPE: PRT
<213> ORGANISM: Mus musculus

<400> SEQUENCE: 28

```
Met Pro Leu Asn Val Asn Phe Thr Asn Arg Asn Tyr Asp Leu Asp Tyr
1               5                   10                  15

Asp Ser Val Gln Pro Tyr Phe Ile Cys Asp Glu Glu Asn Phe Tyr
                20                  25                  30

His Gln Gln Gln Ser Glu Leu Gln Pro Ala Pro Ser Glu Asp
            35                  40                  45

Ile Trp Lys Lys Phe Glu Leu Leu Pro Thr Pro Leu Ser Pro Ser
        50                  55                  60

Arg Arg Ser Gly Leu Cys Ser Pro Ser Tyr Val Ala Val Ala Thr Ser
65                  70                  75                  80

Phe Ser Pro Arg Glu Asp Asp Gly Gly Gly Asn Phe Ser Thr
                85                  90                  95

Ala Asp Gln Leu Glu Met Met Thr Glu Leu Leu Gly Gly Asp Met Val
                100                 105                 110

Asn Gln Ser Phe Ile Cys Asp Pro Asp Asp Glu Thr Phe Ile Lys Asn
            115                 120                 125

Ile Ile Ile Gln Asp Cys Met Trp Ser Gly Phe Ser Ala Ala Ala Lys
        130                 135                 140

Leu Val Ser Glu Lys Leu Ala Ser Tyr Gln Ala Ala Arg Lys Asp Ser
145                 150                 155                 160

Thr Ser Leu Ser Pro Ala Arg Gly His Ser Val Cys Ser Thr Ser Ser
                165                 170                 175

Leu Tyr Leu Gln Asp Leu Thr Ala Ala Ala Ser Glu Cys Ile Asp Pro
            180                 185                 190
```

Ser Val Val Phe Pro Tyr Pro Leu Asn Asp Ser Ser Pro Lys Ser
    195                 200                 205

Cys Thr Ser Ser Asp Ser Thr Ala Phe Ser Pro Ser Ser Asp Ser Leu
    210                 215                 220

Leu Ser Ser Glu Ser Ser Pro Arg Ala Ser Pro Glu Pro Leu Val Leu
225                 230                 235                 240

His Glu Glu Thr Pro Pro Thr Thr Ser Ser Asp Ser Glu Glu Gln
                245                 250                 255

Glu Asp Glu Glu Glu Ile Asp Val Val Ser Val Glu Lys Arg Gln Thr
                260                 265                 270

Pro Ala Lys Arg Ser Glu Ser Gly Ser Ser Pro Ser Arg Gly His Ser
            275                 280                 285

Lys Pro Pro His Ser Pro Leu Val Leu Lys Arg Cys His Val Ser Thr
        290                 295                 300

His Gln His Asn Tyr Ala Ala Pro Pro Ser Thr Arg Lys Asp Tyr Pro
305                 310                 315                 320

Ala Ala Lys Arg Ala Lys Leu Asp Ser Gly Arg Val Leu Lys Gln Ile
                325                 330                 335

Ser Asn Asn Arg Lys Cys Ser Ser Pro Arg Ser Ser Asp Thr Glu Glu
            340                 345                 350

Asn Asp Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Ile Gln Ala Asp Glu His Lys Leu Thr Ser Glu
                405                 410                 415

Lys Asp Leu Leu Arg Lys Arg Glu Gln Leu Lys His Lys Leu Glu
            420                 425                 430

Gln Leu Arg Asn Ser Gly Ala
        435

<210> SEQ ID NO 29
<211> LENGTH: 2396
<212> TYPE: DNA
<213> ORGANISM: Mus musculus

<400> SEQUENCE: 29
cccgcccacc cgcccttat attccggggg tctgcgcggc cgaggacccc tgggctgcgc      60
tgctctcagc tgccgggtcc gactcgcctc actcagctcc cctcctgcct cctgaagggc    120
agggcttcgc cgacgcttgg cgggaaaaag aagggagggg agggatcctg agtcgcagta    180
taaaagaagc ttttcgggcg tttttttctg actcgctgta gtaattccag cgagagacag    240
agggagtgag cggacggttg gaagagccgt gtgtgcagag ccgcgctccg ggcgaccta     300 agaaggcagc tctggagtga gaggggcttt gcctccgagc ctgccgccca ctctccccaa    360
ccctgcgact gacccaacat cagcggccgc aaccctcgcc gccgctggga aactttgccc    420
attgcagcgg gcagacactt ctcactggaa cttacaatct gcgagccagg acaggactcc    480
ccaggctccg ggagggaat ttttgtctat ttggggacag tgttctctgc ctctgcccgc     540
gatcagctct cctgaaaaga gctcctcgag ctgtttgaag gctggatttc ctttgggcgt    600
tggaaacccc gacagccacg acgatgcccc tcaacgtgaa cttcaccaac aggaactatg    660

```
acctcgacta cgactccgta cagccctatt tcatctgcga cgaggaagag aatttctatc    720
accagcaaca gcagagcgag ctgcagccgc ccgcgcccag tgaggatatc tggaagaaat    780
tcgagctgct tcccaccccg cccctgtccc cgagccgccg ctccgggctc tgctctccat    840
cctatgttgc ggtcgctacg tccttctccc caagggaaga cgatgacggc ggcggtggca    900
acttctccac cgccgatcag ctggagatga tgaccgagtt acttggagga gacatggtga    960
accagagctt catctgcgat cctgacgacg agaccttcat caagaacatc atcatccagg   1020
actgtatgtg gagcggtttc tcagccgctg ccaagctggt ctcggagaag ctggcctcct   1080
accaggctgc cgcgcaaagac agcaccagcc tgagccccgc ccgcgggcac agcgtctgct   1140
ccacctccag cctgtacctg caggacctca ccgccgccgc gtccgagtgc attgacccct   1200
cagtggtctt tccctacccg ctcaacgaca gcagctcgcc caaatcctgt acctcgtccg   1260
attccacggc cttctctcct tcctcggact cgctgctgtc ctccgagtcc tccccacggg   1320
ccagccctga gccccctagtg ctgcatgagg agacaccgcc caccaccagc agcgactctg   1380
aagaagagca agaagatgag gaagaaattg atgtggtgtc tgtggagaag aggcaaaccc   1440
ctgccaagag gtcggagtcg ggctcatctc catcccgagg ccacagcaaa cctccgcaca   1500
gcccactggt cctcaagagg tgccacgtct ccactcacca gcacaactac gccgcacccc   1560
cctccacaag gaaggactat ccagctgcca gagggccaa gttggacagt ggcagggtcc   1620
tgaagcagat cagcaacaac cgcaagtgct ccagccccag gtcctcagac acggaggaaa   1680
acgacaagag gcggacacac aacgtcttgg aacgtcagag gaggaacgag ctgaagcgca   1740
gcttttttgc cctgcgtgac cagatccctg aattggaaaa caacgaaaag ccccccaagg   1800
tagtgatcct caaaaaagcc accgcctaca tcctgtccat tcaagcagac gagcacaagc   1860
tcacctctga aaaggactta ttgaggaaac gacgagaaca gttgaaacac aaactcgaac   1920
agcttcgaaa ctctggtgca taaactgacc taactcgagg aggagctgga atctctcgtg   1980
agagtaagga gaacggttcc ttctgacaga actgatgcgc tggaattaaa atgcatgctc   2040
aaagcctaac ctcacaacct tggctggggc tttgggactg taagcttcag ccataatttt   2100
aactgcctca aacttaaata gtataaaaga acttttttttt atgcttccca tcttttttct   2160
ttttcctttt aacagatttg tatttaattg ttttttttaaa aaaatcttaa aatctatcca   2220
atttccccat gtaaataggg ccttgaaatg taaataactt taataaaacg tttataacag   2280
ttacaaaaga ttttaagaca tgtaccataa tttttttttat ttaaagacat tttcattttt   2340
aaagttgatt tttttctatt gttttttagaa aaaaataaaa taattggaaa aaatac       2396
```

<210> SEQ ID NO 30
<211> LENGTH: 453
<212> TYPE: PRT
<213> ORGANISM: Mus musculus

<400> SEQUENCE: 30

Met Asp Phe Leu Trp Ala Leu Glu Thr Pro Thr Ala Thr Thr Met Pro
1               5                   10                  15

Leu Asn Val Asn Phe Thr Asn Arg Asn Tyr Asp Leu Asp Tyr Asp Ser
            20                  25                  30

Val Gln Pro Tyr Phe Ile Cys Asp Glu Glu Asn Phe Tyr His Gln
        35                  40                  45

Gln Gln Gln Ser Glu Leu Gln Pro Pro Ala Pro Ser Glu Asp Ile Trp
    50                  55                  60

Lys Lys Phe Glu Leu Leu Pro Thr Pro Pro Leu Ser Pro Ser Arg Arg

```
                65                  70                  75                  80
Ser Gly Leu Cys Ser Pro Ser Tyr Val Ala Val Ala Thr Ser Phe Ser
                    85                  90                  95

Pro Arg Glu Asp Asp Asp Gly Gly Gly Asn Phe Ser Thr Ala Asp
                100                 105                 110

Gln Leu Glu Met Met Thr Glu Leu Gly Gly Asp Met Val Asn Gln
                115                 120                 125

Ser Phe Ile Cys Asp Pro Asp Glu Thr Phe Ile Lys Asn Ile Ile
            130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Thr Ser
                165                 170                 175

Leu Ser Pro Ala Arg Gly His Ser Val Cys Ser Thr Ser Leu Tyr
                180                 185                 190

Leu Gln Asp Leu Thr Ala Ala Ala Ser Glu Cys Ile Asp Pro Ser Val
            195                 200                 205

Val Phe Pro Tyr Pro Leu Asn Asp Ser Ser Pro Lys Ser Cys Thr
            210                 215                 220

Ser Ser Asp Ser Thr Ala Phe Ser Pro Ser Ser Asp Ser Leu Leu Ser
225                 230                 235                 240

Ser Glu Ser Ser Pro Arg Ala Ser Pro Glu Pro Leu Val Leu His Glu
                245                 250                 255

Glu Thr Pro Pro Thr Thr Ser Ser Asp Ser Glu Glu Gln Glu Asp
                260                 265                 270

Glu Glu Glu Ile Asp Val Val Ser Val Glu Lys Arg Gln Thr Pro Ala
            275                 280                 285

Lys Arg Ser Glu Ser Gly Ser Ser Pro Ser Arg Gly His Ser Lys Pro
            290                 295                 300

Pro His Ser Pro Leu Val Leu Lys Arg Cys His Val Ser Thr His Gln
305                 310                 315                 320

His Asn Tyr Ala Ala Pro Pro Ser Thr Arg Lys Asp Tyr Pro Ala Ala
                325                 330                 335

Lys Arg Ala Lys Leu Asp Ser Gly Arg Val Leu Lys Gln Ile Ser Asn
                340                 345                 350

Asn Arg Lys Cys Ser Ser Pro Arg Ser Ser Asp Thr Glu Glu Asn Asp
            355                 360                 365

Lys Arg Arg Thr His Asn Val Leu Glu Arg Gln Arg Arg Asn Glu Leu
            370                 375                 380

Lys Arg Ser Phe Phe Ala Leu Arg Asp Gln Ile Pro Glu Leu Glu Asn
385                 390                 395                 400

Asn Glu Lys Ala Pro Lys Val Val Ile Leu Lys Lys Ala Thr Ala Tyr
                405                 410                 415

Ile Leu Ser Ile Gln Ala Asp Glu His Lys Leu Thr Ser Glu Lys Asp
            420                 425                 430

Leu Leu Arg Lys Arg Arg Glu Gln Leu Lys His Lys Leu Glu Gln Leu
            435                 440                 445

Arg Asn Ser Gly Ala
        450

<210> SEQ ID NO 31
<211> LENGTH: 2355
<212> TYPE: DNA
<213> ORGANISM: Rattus norvegicus
```

<400> SEQUENCE: 31

```
accccccgggc tgcgctgctc tccgctgccg cctccgccgc gcccactccg ctcgcctcct      60
gcctccaaaa gggcagggct tcgccgaggc ttggcgggaa aaagaagcga ggggagggat     120
ccggagtcgc agtataaaag aagcttttcg ggcgttttttt ttctgactcg ctgtagtaat     180
tccagcgaga gacagaggga gtgagcgggc gggttggaag agcccagtgt gcagagcccc     240
actccgggct tcctaggaag gcagctctgg agtgagaagg gctttgcctc caggcttgct     300
gcctcctcga cccaatcctc ccgctgaccc aacatcagcg gtcgcaaccc tcgccgcctc     360
tgggaaactt tgcccattgc aacgggcaga cacttctcac tggaacttac aatctgcgag     420
ccaggacagg actccccagg cgcaggggag ggaattttttg tctatttggg gacagtgttc     480
tctgcctctg cccgcgatcg gctcccctga aaagagctcc tcgcgttatt tgaagcctga     540
atttcctttg ggaggtggaa acccgacag tcacgacgat gcccctcaac gtgagcttcg      600
ctaacaggaa ctatgacctc gactacgact cggtgcagcc ctatttcatc tgcgacgagg     660
aagagaattt ctatcaccag caacagcaga gcgagctgca gccgcccgca cccagtgagg     720
atatctggaa gaaattcgag ctgctgccca ccccgcccct gtcccccagc cgccgctccg     780
ggctctgctc tccgtcctat gttgcggtcg ctacgtcctt ctccccaagg gaggacgatg     840
acggtggcgg tggcaacttc tccaccgccg atcagctgga gatgatgacc gagctacttg     900
gaggagacat ggtgaatcag agcttcatct gcgatcctga cgatgagacc ttcatcaaga     960
acatcatcat ccaggactgt atgtggagcg gcttctcggc cgctgccaaa ctggtctccg    1020
agaagctggc ctcttaccag gctgcgcgca agacagcac cagcctgagc cccgcccgcg    1080
ggcacagcgt ctgctccacc tccagcctgt acctgcagga cctcaccgcc gcagcgtccg    1140
agtgcatcga ccccctcagtg gtcttcccct acccgctcaa cgacagcagc tcgcccaaat    1200
cctgtacctc gtccgattcc acggccttct cttcttcctc ggactcgctg ctgtcctccg    1260
agtcctcccc acgggccacc cctgagcccc tagtgctgca tgaagagaca ccgcccacca    1320
ccagcagcga ctctgaagaa gaacaagatg atgaggaaga aattgatgtg gtgtctgtgg    1380
aaaagaggca accccctgcc aagaggtccg agtcagggtc atccccatca agaggccaca    1440
gcaaacctcc acacagccca ctggtcctca agaggtgcca tgtctctact caccagcaca    1500
attatgcagc accccctcc acaaggaagg actatccagc tgccaagagg gccaagttgg    1560
acagtggcag ggtcctgaaa cagatcagca caaccgcaa atgctccagc cccaggtcct    1620
cagacaccga ggaaaacgac aagaggcgga cacacaacgt cttggaacgt cagaggagaa    1680
acgagctgaa gcgtagcttt tttgccctgc gcgaccagat ccctgagttg gaaaacaacg    1740
aaaaggcccc caaggtagtt atcctcaaaa aagccaccgc ctacatcctg tccgttcaag    1800
cagatgagca caaactcatc tcagaaaagg acttactgag gaaacggcga gaacagttga    1860
aacacaaact cgaacagctt cgaaactctg gtgcataaac tgaccggaag tgaggaggag    1920
ctggaatctc gagtgtaagg agaacggttc cttctgacag aacttggact tcaaaaaatg    1980
catgctcaaa gcctaacctc acaaccttgg ctggggcttt gggacttcag ccataatgtt    2040
aactgcctca aagttaaggc ataaagaac tttttttat gcttcccatc ttctttcttt      2100
ttcctttaac agatttgtat ttaattgttt tttttaaaaa aatcttccgg tgtacatagg    2160
gcctttaaat gtaaataact ttaataaaac gttataaca gttatacaag attttaagac    2220
atgtatgata aaccataatt tttttatttt aaagaccttt tcatttttaa agttgatttt    2280
```

```
tttctattgt ttttagaaaa aataaaataa ttggaaaaaa tataattgag ccaactctta    2340
aaaaaaaaaa aaaaa                                                     2355
```

<210> SEQ ID NO 32
<211> LENGTH: 453
<212> TYPE: PRT
<213> ORGANISM: Rattus norvegicus

<400> SEQUENCE: 32

```
Met Asn Phe Leu Trp Glu Val Glu Asn Pro Thr Val Thr Thr Met Pro
1               5                   10                  15

Leu Asn Val Ser Phe Ala Asn Arg Asn Tyr Asp Leu Asp Tyr Asp Ser
            20                  25                  30

Val Gln Pro Tyr Phe Ile Cys Asp Glu Glu Asn Phe Tyr His Gln
        35                  40                  45

Gln Gln Gln Ser Glu Leu Gln Pro Pro Ala Pro Ser Glu Asp Ile Trp
    50                  55                  60

Lys Lys Phe Glu Leu Leu Pro Thr Pro Leu Ser Pro Ser Arg Arg
65                  70                  75                  80

Ser Gly Leu Cys Ser Pro Ser Tyr Val Ala Val Ala Thr Ser Phe Ser
                85                  90                  95

Pro Arg Glu Asp Asp Asp Gly Gly Gly Asn Phe Ser Thr Ala Asp
            100                 105                 110

Gln Leu Glu Met Met Thr Glu Leu Leu Gly Gly Asp Met Val Asn Gln
    115                 120                 125

Ser Phe Ile Cys Asp Pro Asp Asp Glu Thr Phe Ile Lys Asn Ile Ile
130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Thr Ser
                165                 170                 175

Leu Ser Pro Ala Arg Gly His Ser Val Cys Ser Thr Ser Ser Leu Tyr
            180                 185                 190

Leu Gln Asp Leu Thr Ala Ala Ala Ser Glu Cys Ile Asp Pro Ser Val
    195                 200                 205

Val Phe Pro Tyr Pro Leu Asn Asp Ser Ser Pro Lys Ser Cys Thr
210                 215                 220

Ser Ser Asp Ser Thr Ala Phe Ser Ser Ser Ser Asp Ser Leu Leu Ser
225                 230                 235                 240

Ser Glu Ser Ser Pro Arg Ala Thr Pro Glu Pro Leu Val Leu His Glu
                245                 250                 255

Glu Thr Pro Pro Thr Thr Ser Ser Asp Ser Glu Glu Glu Gln Asp Asp
            260                 265                 270

Glu Glu Glu Ile Asp Val Val Ser Val Glu Lys Arg Gln Pro Pro Ala
    275                 280                 285

Lys Arg Ser Glu Ser Gly Ser Pro Ser Arg Gly His Ser Lys Pro
        290                 295                 300

Pro His Ser Pro Leu Val Leu Lys Arg Cys His Val Ser Thr His Gln
305                 310                 315                 320

His Asn Tyr Ala Ala Pro Pro Ser Thr Arg Lys Asp Tyr Pro Ala Ala
                325                 330                 335

Lys Arg Ala Lys Leu Asp Ser Gly Arg Val Leu Lys Gln Ile Ser Asn
            340                 345                 350

Asn Arg Lys Cys Ser Ser Pro Arg Ser Ser Asp Thr Glu Glu Asn Asp
```

```
                355                 360                 365
Lys Arg Arg Thr His Asn Val Leu Glu Arg Gln Arg Asn Glu Leu
    370                 375                 380

Lys Arg Ser Phe Phe Ala Leu Arg Asp Gln Ile Pro Glu Leu Glu Asn
385                 390                 395                 400

Asn Glu Lys Ala Pro Lys Val Val Ile Leu Lys Ala Thr Ala Tyr
                405                 410                 415

Ile Leu Ser Val Gln Ala Asp Glu His Lys Leu Ile Ser Lys Asp
            420                 425                 430

Leu Leu Arg Lys Arg Glu Gln Leu Lys His Lys Leu Glu Gln Leu
        435                 440                 445

Arg Asn Ser Gly Ala
    450

<210> SEQ ID NO 33
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 33
taccaccatg tacccaggca                                                  20

<210> SEQ ID NO 34
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 34
ctcaggagga gcaatgatct tgat                                             24

<210> SEQ ID NO 35
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 35
acaccgacca ccgtatctca                                                  20

<210> SEQ ID NO 36
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 36
ctcaggataa tggtagccat gtc                                              23

<210> SEQ ID NO 37
<211> LENGTH: 23
<212> TYPE: DNA
<213> ORGANISM: Artificial Sequence
<220> FEATURE:
<223> OTHER INFORMATION: /note="Description of Artificial Sequence:
```

-continued

Synthetic primer"

<400> SEQUENCE: 37
gacagagagt caaactaacg tgg                                    23

<210> SEQ ID NO 38
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 38
gtccagcagg caagaaggt                                         19

<210> SEQ ID NO 39
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 39
aagaacacgc ttgggaatgg                                        20

<210> SEQ ID NO 40
<211> LENGTH: 17
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 40
ctgcacctgc tgcggac                                           17

<210> SEQ ID NO 41
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 41
gtgatagtgc agccggcat                                         19

<210> SEQ ID NO 42
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 42
aacggagcgt agcctttgg                                         19

<210> SEQ ID NO 43
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

```
<400> SEQUENCE: 43
caagatcaag ccccacctga t                                              21

<210> SEQ ID NO 44
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 44
agttcgcccc aaccagtact t                                              21

<210> SEQ ID NO 45
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 45
tcatcggacg cacttggaa                                                 19

<210> SEQ ID NO 46
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 46
caaccacctt gaatggcaag a                                              21

<210> SEQ ID NO 47
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 47
gtccctagct tggctgacag a                                              21

<210> SEQ ID NO 48
<211> LENGTH: 18
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 48
tggagagcga gggctttg                                                  18

<210> SEQ ID NO 49
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"
```

```
<400> SEQUENCE: 49
tccactctcc ccatggttta                                           20

<210> SEQ ID NO 50
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 50
gctatatccg ctgcactacg                                           20

<210> SEQ ID NO 51
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 51
ctggcggtag aatgcctct                                            19

<210> SEQ ID NO 52
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 52
tgagaccatt gtgtggaagg                                           20

<210> SEQ ID NO 53
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 53
gtggactaca gcgtttgcac a                                         21

<210> SEQ ID NO 54
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 54
catatcagcc ctcactgctg c                                         21

<210> SEQ ID NO 55
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 55
```

```
cccagtgtc aaactgtacc ag                                         22

<210> SEQ ID NO 56
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 56
agcgtttcca attttccata aatt                                      24

<210> SEQ ID NO 57
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 57
atccaaggca tcaaccagag                                           20

<210> SEQ ID NO 58
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 58
atgbacaact acatggcgca c                                         21

<210> SEQ ID NO 59
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 59
ctgtgtgctg tcagcttcca c                                         21

<210> SEQ ID NO 60
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 60
cctcctcccc agtgtgactc                                           20

<210> SEQ ID NO 61
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 61
```

-continued agtgacgcaa ggaccaaacg    20

<210> SEQ ID NO 62
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 62
ctacacgaaa cgcttcccca    20

<210> SEQ ID NO 63
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 63
ccaacaaatg caatgggagt    20

<210> SEQ ID NO 64
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 64
caagagtccc agggagagtg    20

<210> SEQ ID NO 65
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 65
tgagggttca tcaagctggt gtct    24

<210> SEQ ID NO 66
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 66
ttggagaggg cagtgcttaa ctca    24

<210> SEQ ID NO 67
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 67
ctcgtctgtc gactcacttc    20

```
<210> SEQ ID NO 68
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 68
tggaaaactg ttgttgctgc                                              20
```

USE OF IRE1α-XBP1 SIGNALING PATHWAY BIOMARKERS FOR MODULATING IMMUNE RESPONSES

CROSS-REFERENCE TO RELATED APPLICATIONS

This application is the U.S. national phase of International Patent Application No. PCT/US2019/060749, filed on 11 Nov. 2019, which claims the benefit of priority to U.S. Provisional Application No. 62/769,265, filed on 19 Nov. 2018, and U.S. Provisional Application No. 62/800,706, filed on 4 Feb. 2019; the entire contents of each of said applications are incorporated herein in their entirety by this reference.

GOVERNMENT FUNDING

This invention was made with government support under grant numbers T32GM007739 and F30 AI136239-01A1 awarded by The National Institutes of Health. The government has certain rights in the invention.

BACKGROUND OF THE INVENTION

NK cells are critical mediators of host immunity against malignancies and viral infection (Caligiuri et al. (2008) *Blood* 112:461-469). Although extrinsic regulators of NK cell development and function, including diverse ligands of key NK cell receptors and proinflammatory cytokines from the microenvironment have been identified (Cooper et al. (2009) *Proc. Natl. Acad. Sci. USA* 106:1915-1919; Madera et al. (2016) *J. Exp. Med.* 213:225-33; Zawislak et al. (2013) *Proc. Natl. Acad. Sci. USA* 110:6967-6972; Sun et al. (2012) *J. Exp. Med.* 209:947-954), relatively little is known about how NK cells mechanistically translate these signals into critical effector functions (Beaulieu et al. (2014) *Nat. Immunol.* 15:546-553; Rapp et al. (2017) *Sci. Immunol.* 2(18)). Furthermore, new features of NK cells have been uncovered in recent years, including their ability to undergo clonal proliferation and generate long-lived memory; however, the molecular mechanisms underlying these "adaptive" properties require further characterization. The emerging interest in developing NK cell-based cancer immunotherapy (Morvan and Lanier (2016) *Nat. Rev. Cancer* 16:7-19; Vivier et al. (2012) *Nat. Rev. Immunol.* 12:239-252) and new vaccine strategies for controlling lethal infectious diseases highlights an urgent need for identifying new intrinsic regulators of NK cell-mediated immunity.

The activation of ER stress sensor IRE1α and its substrate transcription factor XBP1 (Yoshida et al. (2001) *Cell* 107: 881-891; Lee et al. (2003) *Mol. Cell. Biol.* 23:7448-7459) is a hallmark of "professional" secretory cells that must constitutively deal with a high demand for protein synthesis, folding, and secretion (Hess et al. (2011) *Gastroenterol.* 141:1463-1472; Lee et al. (2011) *Proc. Natl. Acad. Sci. USA* 108:8885-8890; Lee et al. (2008) *Science* 320:1492-1496; Kaser et al. (2008) *Cell* 134:743-756). This highly evolutionarily conserved signaling pathway is also activated in tumor cells (Chen et al. (2014) *Nature* 508:103-107) and in myeloid-derived suppressor cells (Condamine et al. (2014) *J. Clin. Invest.* 124:2626-2639), macrophages (Yan et al. (2016) *Cell Rep.* 16:2914-2927), T cells (Song et al. (2018) *Nature* 562:423-428) and dendritic cells (Cubillos-Ruiz et al. (2015) *Cell* 161:1527-1538) in response to external stimuli such as hypoxia, nutrient-deprivation and low pH. However, it is unknown whether NK cell function is driven by IRE1α-XBP1 signaling, and if so, what specific activities it controls.

Thus, there is a great need in the art to elucidate the intrinsic pathways that regulate NK cell responses in order to develop new NK cell-based immunotherapy.

SUMMARY OF THE INVENTION

The present invention is based, at least in part, on the discovery that the ER stress sensor inositol-requiring enzyme 1 (IRE1α) and its substrate transcription factor X-box-binding protein 1 (XBP1) critically drive NK cell-mediated responses against viral infection and tumors in vivo, and accelerate homeostatic proliferation. It was found that IRE1α and XBP1 were important for the robust expansion of activated mouse and human NK cells and are situated downstream of the mTOR signaling pathway. In addition, transcriptome and chromatin immunoprecipitation analysis revealed c-Myc as a novel and direct downstream target of XBP1 for downstream regulation of NK cell proliferation. Genetic ablation or pharmaceutical blockade of IRE1α downregulated c-Myc, whereas overexpression of XBP1 resulted in c-Myc hyperactivation. NK cells with haploinsufficiency in c-Myc demonstrated a functional deficit comparable to IRE1α or XBP1 deficiency. Genetic overexpression of c-Myc largely rescued the proliferation defect in IRE1α-deficient NK cells. Consistent with the linkage to c-Myc, IRE1α/XBP1 also promotes oxidative phosphorylation in NK cells. This study identifies the IRE1α-XBP1-cMyc axis in NK cell immunity, providing new insight into the host protection against infection and cancer.

In one aspect, a composition comprising natural killer (NK) cells modified to upregulate the IRE1α-XBP1 pathway, is provided.

Numerous embodiments are further provided that can be applied to any aspect of the present invention described herein. For example, in one embodiment, the IRE1α-XBP1 pathway is upregulated by increasing the copy number, amount, and/or activity of at least one biomarker listed in Table 1 in the NK cells. In another embodiment, the copy number, amount, and/or activity of at least one biomarker listed in Table 1 is increased by contacting the NK cells with a nucleic acid molecule encoding at least one biomarker listed in Table 1 or fragment thereof, a polypeptide of at least one biomarker listed in Table 1 or fragment thereof, a small molecule that binds to at least one biomarker listed in Table 1, or a pro-inflammatory cytokine. In still another embodiment, the pro-inflammatory cytokine is IL-2, IL-15, IL-12 and/or IL-18. In yet another embodiment, the NK cells have increased splicing of XBP1 to XBP1s transcript. In another embodiment, the expression of XBP1 target genes are upregulated in the NK cells. In still another embodiment, the XBP1 target gene is c-Myc or a canonical XBP1 target gene selected from the group consisting of Hspa5, Dnajb9, Sec24d, Sec63, Hyou1, Sec61a, and P4hb. In yet another embodiment, the expression of c-Myc target genes are upregulated in the NK cells. In another embodiment, the oxidative phosphorylation (OXPHOS) is upregulated in the NK cells. In still another embodiment, the NK cells are activated NK cells and/or memory NK cells, optionally wherein the memory NK cells are cytokine-induced, memory-like NK cells (CIML). In yet another embodiment, the NK cells are Ly49H-expressing NK cells or CD56$^{bright}$ NK cells. In another embodiment, the NK cells are derived from peripheral blood mononuclear cells (PBMCs) or umbilical cord blood (UCB). In still another embodiment, the composition is derived from a NK cell line.

In another aspect, a method of treating a subject having a condition that would benefit from upregulation of an immune response comprising administering to the subject a therapeutically effective amount of a composition described herein, is provided.

As described above, certain embodiments are applicable to any method described herein. For example, in one embodiment, the NK cells are derived from the subject who is treated with the composition. In another embodiment, the NK cells are derived from a different subject who is not treated with the composition. In still another embodiment, the condition is an infection. In yet another embodiment, the infection is a viral infection, bacterial infection, protozoan infection, parasite infection, fungal infection, or helminth infection. In another embodiment, the viral infection is caused by a virus selected from the group consisting of CMV, human immunodeficiency virus (HIV), hepatitis B virus (HBV), hepatitis C virus (HCV), influenza A virus, Epstein-Barr virus (EBV), human herpes simplex virus (HSV) type 1 and type 2, respiratory syncytial virus (RSV), human papilloma virus (HPV), lymphocytic choriomeningitis virus (LCMV), Zika virus, Rift Valley fever virus (RVFV), dengue virus (DENV), chikungunya virus (CHIKV), enterovirus (EV), and human adenovirus (HAdV). In still another embodiment, the composition promotes antiviral immunity in the subject. In yet another embodiment, the composition decreases viral titers in the subject. In another embodiment, the composition increases overall survival rate. In another embodiment, the bacterial infection is caused by *Listeria monocytogenes, Mycobacterium tuberculosis*, or *Salmonella typhimurium*. In still another embodiment, the parasite infection is caused by *Plasmodium* or *Cryptosporidium*, optionally wherein the *Plasmodium* is malaria parasite. In yet another embodiment, the fungal infection is caused by *Aspergillus*, optionally wherein the *Aspergillus* is *Aspergillus fumigatus*. In another embodiment, the condition is lymphopenia. In still another embodiment, the subject has undergone hematopoietic cell transplantation (HCT). In yet another embodiment, the condition is cancer. In another embodiment, the cancer is a NK cell-sensitive cancer. In still another embodiment, the cancer is selected from the group consisting of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, thyroid cancer, and cervical cancer. In yet another embodiment, the composition promotes antitumor immunity in the subject. In another embodiment, the composition increases the amount of NK cells infiltrating a tumor. In still another embodiment, the composition increases the amount of type 1 conventional dendritic cells and/or CD8+ T cells infiltrating a tumor. In yet another embodiment, the composition reduces the number of proliferating cells in the cancer and/or reduces the volume or size of a tumor comprising the cancer cells. In another embodiment, the methods described herein further comprise administering to the subject an immunotherapy and/or cancer therapy, optionally wherein the immunotherapy and/or cancer therapy is administered before, after, or concurrently with the composition. The still another embodiment, the immunotherapy is cell-based. The yet another embodiment, the immunotherapy comprises a cancer composition and/or virus. In another embodiment, the immunotherapy inhibits an immune checkpoint. In still another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In yet another embodiment, the cancer therapy is selected from the group consisting of radiation, a radiosensitizer, and a chemotherapy.

In still another aspect, a method of treating a subject having a condition that would benefit from upregulation of an immune response comprising administering to the subject a therapeutically effective amount of an agent that upregulates the IRE1α-XBP1 pathway such that the condition that would benefit from upregulation of an immune response is treated, is provided.

As described above, certain embodiments are applicable to any method described herein. For example, in one embodiment, the agent upregulates the IRE1α-XBP1 pathway in NK cells. In another embodiment, the NK cells are activated NK cells and/or memory NK cells, optionally wherein the memory NK cells are cytokine-induced, memory-like NK cells (CIML). In still another embodiment, the NK cells are Ly49H-expressing NK cells or CD56$^{bright}$ NK cells. In yet another embodiment, the agent upregulates the IRE1α-XBP1 pathway by increasing the copy number, amount, and/or activity of at least one biomarker listed in Table 1. In another embodiment, the agent is a nucleic acid molecule encoding at least one biomarker listed in Table 1 or fragment thereof, a polypeptide of at least one biomarker listed in Table 1 or fragment thereof, a small molecule that binds to at least one biomarker listed in Table 1, or a pro-inflammatory cytokine. In still another embodiment, the pro-inflammatory cytokine is IL-2, IL-15, IL-12 and/or IL-18. In yet another embodiment, the agent promotes the splicing of XBP1 to XBP1s transcript. In another embodiment, the agent upregulates XBP1 target genes. In still another embodiment, the XBP1 target gene is c-Myc or a canonical XBP1 target gene selected from the group consisting of Hspa5, Dnajb9, Sec24d, Sec63, Hyou1, Sec61a, and P4hb. In another embodiment, the agent upregulates the expression of c-Myc target genes. In another embodiment, the agent upregulates the oxidative phosphorylation (OXPHOS) in the NK cells. In still another embodiment, the agent promotes NK cell proliferation. In yet another embodiment, the condition is an infection. In another embodiment, the infection is a viral infection, bacterial infection, protozoan infection, or helminth infection. In still another embodiment, the viral infection is caused by a virus selected from the group consisting of CMV, human immunodeficiency virus (HIV), hepatitis B virus (HBV), hepatitis C virus (HCV), influenza A virus, Epstein-Barr virus (EBV), human herpes simplex virus (HSV) type 1 and type 2, respiratory syncytial virus (RSV), human papilloma virus (HPV), lymphocytic choriomeningitis virus (LCMV), Zika virus, Rift Valley fever virus (RVFV), dengue virus (DENV), chikungunya virus (CHIKV), enterovirus (EV), and human adenovirus (HAdV). In yet another embodiment, the agent promotes antiviral immunity in the subject. In another embodiment, the agent promotes clonal expansion of NK cells upon viral infection. In still another embodiment, the agent decreases viral titers in the subject. In yet another embodiment, the agent increases overall survival rate. In another embodiment, the bacterial infection is caused by *Listeria monocytogenes, Mycobacterium tuberculosis*, or *Salmonella typhimurium*. In still another embodiment, the parasite infection is caused by *Plasmodium* or *Cryptosporidium*, optionally wherein the *Plasmodium* is malaria parasite. In yet another embodiment, the fungal infection is caused by *Aspergillus*, optionally wherein the *Aspergillus* is *Aspergillus fumigatus*. In another embodiment, the condition is lymphopenia. In still another embodiment, the subject has undergone HCT or NK cell adoptive transfer immunotherapy, optionally wherein the NK cells are genetically modified. In yet another embodiment, the agent promotes homeostatic proliferation of NK cells in vivo. In another embodiment, the condition is cancer. In still another embodiment, the cancer is a NK cell-sensitive cancer. In yet another embodiment, the cancer is selected from the group consisting of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, thyroid cancer, and cervical cancer. In another embodiment, the agent promotes NK cell-mediated antitumor immunity. In still another embodiment, the agent increases the number of NK cells infiltrating a tumor. In yet another embodiment, the agent increases the number of tumor-infiltrating type 1 conventional dendritic cells and/or CD8+ T cells infiltrating a tumor. In another embodiment, the agent reduces the number of proliferating cells in the cancer and/or reduces the volume or size of a tumor comprising the cancer cells. In still another embodiment, the methods described herein further comprise administering to the subject an immunotherapy and/or cancer therapy, optionally wherein the immunotherapy and/or cancer therapy is administered before, after, or concurrently with the composition. In yet another embodiment, the immunotherapy is cell-based. In another embodiment, the immunotherapy comprises a cancer vaccine and/or virus. In still another embodiment, the immunotherapy inhibits an immune checkpoint. In yet another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In another embodiment, the cancer therapy is selected from the group consisting of radiation, a radiosensitizer, and a chemotherapy.

In yet another aspect, a method of treating a subject having a condition that would benefit from downregulation of an immune response comprising administering to the subject a therapeutically effective amount of an agent that downregulates the IRE1α-XBP1 pathway such that the condition that would benefit from downregulation of an immune response is treated, is provided.

As described above, certain embodiments are applicable to any method described herein. For example, in one embodiment, the agent downregulates the IRE1α-XBP1 pathway in NK cells. In another embodiment, the NK cells are activated NK cells and/or memory NK cells, optionally wherein the memory NK cells are cytokine-induced, memory-like NK cells (CIML). In still another embodiment, the NK cells are Ly49H-expressing NK cells or CD56$^{bright}$ NK cells. In yet another embodiment, the agent downregulates the IRE1α-XBP1 pathway by decreasing the copy number, amount, and/or activity of at least one biomarker listed in Table 1. In another embodiment, the agent is a small molecule inhibitor, CRISPR guide RNA (gRNA), RNA interfering agent, antisense oligonucleotide, peptide or peptidomimetic inhibitor, aptamer, antibody, or intrabody. In still another embodiment, the RNA interfering agent is a small interfering RNA (siRNA), a CRISPR RNA (crRNA), a small hairpin RNA (shRNA), a microRNA (miRNA), or a piwi-interacting RNA (piRNA). In yet another embodiment, the agent comprises an antibody and/or intrabody, or an antigen binding fragment thereof, which specifically binds to the at least one biomarker listed in Table 1. In another embodiment, the antibody and/or intrabody, or antigen binding fragment thereof, is murine, chimeric, humanized, composite, or human. In still another embodiment, the antibody and/or intrabody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In yet another embodiment, the agent is a small molecule inhibitor of the IRE1α RNase domain. In another embodiment, the small molecule inhibitor is 4μ8c (also known as 8-formyl-7-hydroxy-4-methylcoumarin or 7-hydroxy-4-methyl-2-oxo-2H-chromene-8-carbaldehyde or CAS 14003-96-4). In still another embodiment, the agent reduces the splicing of XBP1 to XBP1s transcript. In yet another embodiment, the agent downregulates XBP1 target genes. In another embodiment, the XBP1 target gene is c-Myc or a canonical XBP1 target gene selected from the group consisting of Hspa5, Dnajb9, Sec24d, Sec63, Hyou1, Sec61a, and P4hb. In still another embodiment, the agent downregulates the expression of c-Myc target genes. In yet another embodiment, the agent downregulates the oxidative phosphorylation (OXPHOS) in the NK cells. In another embodiment, the agent inhibits NK cell proliferation. In still another embodiment, the agent inhibits proliferation of primary NK cells cultured in vitro with IL-2 and IL-15. In yet another embodiment, the condition is an inflammatory disease, optionally wherein the inflammatory disease is an autoimmune disease.

In another aspect, a method of assessing the efficacy of an agent that modulates the IRE1α-XBP1 pathway for treating a condition that would benefit from modulating an immune response in a subject is provided, the method comprising: a) detecting in a subject sample at a first point in time the copy number, amount, and/or or activity of at least one biomarker listed in Table 1 in NK cells; b) repeating step a) during at least one subsequent point in time after administration of the agent; and c) comparing the copy number, amount, and/or activity detected in steps a) and b), wherein the presence of, or a significant increase in the copy number, amount, and/or activity of at least one biomarker listed in Table 1 in the subsequent sample as compared to the copy number, amount, and/or activity in the sample at the first point in time, indicates that the agent treats a condition that would benefit from upregulating an immune response in the subject; wherein the absence of, or a significant decrease in the copy number, amount, and/or activity of at least one biomarkers listed in Table 1 in the subsequence sample as compared to the copy number, amount, and/or activity in the sample at the first point in time, indicates that the agent treats a condition that would benefit from downregulating an immune response in the subject.

As described above, certain embodiments are applicable to any method described herein. For example, in one embodiment, the first and/or at least one subsequent sample is selected from the group consisting of ex vivo and in vivo samples. In another embodiment, the first and/or at least one subsequent sample is a portion of a single sample or pooled samples obtained from the subject. In still another embodiment, agent upregulates the IRE1α-XBP1 pathway for treating a condition that would benefit from upregulating an immune response in a subject. In yet another embodiment, the condition that would benefit from upregulating an immune response is a cancer or infection. In another embodiment, the cancer is selected from the group consisting of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, thyroid cancer, and cervical cancer. In still another embodiment, between the first point in time and the subsequent point in time, the subject has undergone treatment, completed treatment, and/or is in remission for the cancer. In yet another embodiment, the cancer treatment is selected from the group consisting of immunotherapy, targeted therapy, chemotherapy, radiation therapy, hormonal therapy, an anti-cancer vaccine, an anti-cancer virus, and a checkpoint inhibitor. In another embodiment, the sample comprises cells, serum, peritumoral tissue, and/or intratumoral tissue obtained from the subject. In still another embodiment, the agent downregulates the IRE1α-XBP1 pathway for treating a condition that would benefit from downregulating an immune response in a subject. In yet another embodiment, the condition that would benefit from downregulating an immune response is an inflammatory disease. In another embodiment, the agent is administered in a pharmaceutically acceptable formulation. In still another embodiment, the subject is an animal model of the condition. In yet another embodiment, the animal model is a mouse model. In another embodiment, the subject is a mammal. In still another embodiment, the mammal is a mouse or a human. In yet another embodiment, the mammal is a human.

In still another aspect, a method of promoting proliferation of NK cells comprising contacting the NK cells with a therapeutically effective amount of an agent that upregulates the IRE1α-XBP1 pathway in the NK cells, is provided.

As described above, certain embodiments are applicable to any method described herein. For example, in one embodiment, the NK cells are activated NK cells and/or memory NK cells, optionally wherein the memory NK cells are cytokine-induced, memory-like NK cells (CIML). In another embodiment, the NK cells are Ly49H-expressing NK cells or CD56$^{bright}$ NK cells. In still another embodiment, the agent upregulates the IRE1α-XBP1 pathway by increasing the copy number, amount, and/or activity of at least one biomarker listed in Table 1. In yet another embodiment, the agent is a nucleic acid molecule encoding at least one biomarker listed in Table 1 or fragment thereof, a polypeptide of at least one biomarker listed in Table 1 or fragment thereof, a small molecule that binds to at least one biomarker listed in Table 1, or a pro-inflammatory cytokine. In another embodiment, the pro-inflammatory cytokine is IL-2, IL-15, IL-12, and/or IL-18. In still another embodiment, the agent promotes the splicing of XBP1 to XBP1s transcript. In yet another embodiment, the agent upregulates XBP1 target genes. In another embodiment, the XBP1 target gene is c-Myc or a canonical XBP1 target gene selected from the group consisting of Hspa5, Dnajb9, Sec24d, Sec63, Hyou1, Sec61a, and P4hb. In still another embodiment, the agent upregulates the expression of c-Myc target genes. In yet another embodiment, the agent upregulates the oxidative phosphorylation (OXPHOS) in the NK cells. In another embodiment, the agent increased the levels of the proliferation marker Ki-67 in the NK cells. In still another embodiment, the agent promotes NK cell proliferation in response to an infection. In yet another embodiment, the infection is a viral infection, bacterial infection, protozoan infection, parasite infection, fungal infection, or helminth infection. In another embodiment, the viral infection is caused by a virus selected from the group consisting of CMV, human immunodeficiency virus (HIV), hepatitis B virus (HBV), hepatitis C virus (HCV), influenza A virus, Epstein-Barr virus (EBV), human herpes simplex virus (HSV) type 1 and type 2, respiratory syncytial virus (RSV), human papilloma virus (HPV), lymphocytic choriomeningitis virus (LCMV), Zika virus, Rift Valley fever virus (RVFV), dengue virus (DENV), chikungunya virus (CHIKV), enterovirus (EV), and human adenovirus (HAdV). In still another embodiment, the bacterial infection is caused by *Listeria monocytogenes*, *Mycobacterium tuberculosis*, or *Salmonella typhimurium*. In yet another embodiment, the parasite infection is caused by *Plasmodium* or *Cryptosporidium*, optionally wherein the *Plasmodium* is malaria parasite. In another embodiment, the fungal infection is caused by *Aspergillus*, optionally wherein the *Aspergillus* is *Aspergillus fumigatus*. In still another embodiment, the agent promotes NK cell proliferation in response to lymphopenia. In yet another embodiment, the agent promotes NK cell proliferation in response to cancer. In another embodiment, the cancer is a NK cell-sensitive cancer. In still another embodiment, the cancer is selected from the group consisting of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, thyroid cancer, and cervical cancer.

In yet another aspect, a method of decreasing proliferation of NK cells comprising contacting the NK cells with a therapeutically effective amount of an agent that downregulates the IRE1α-XBP1 pathway in the NK cells.

As described above, certain embodiments are applicable to any method described herein. For example, in one embodiment, the NK cells are activated NK cells and/or memory NK cells, optionally wherein the memory NK cells are cytokine-induced, memory-like NK cells (CIML). In another embodiment, the NK cells are Ly49H-expressing NK cells or CD56$^{bright}$ NK cells. In still another embodiment, the agent downregulates the IRE1α-XBP1 pathway by decreasing the copy number, amount, and/or activity of at least one biomarker listed in Table 1. In yet another embodiment, the agent is a small molecule inhibitor, CRISPR guide RNA (gRNA), RNA interfering agent, antisense oligonucleotide, peptide or peptidomimetic inhibitor, aptamer, antibody, or intrabody. In another embodiment, the RNA interfering agent is a small interfering RNA (siRNA), a CRISPR RNA (crRNA), a small hairpin RNA (shRNA), a microRNA (miRNA), or a piwi-interacting RNA (piRNA). In still another embodiment, the agent comprises an antibody and/or intrabody, or an antigen binding fragment thereof, which specifically binds to the at least one biomarker listed in Table 1. In yet another embodiment, the antibody and/or intrabody, or antigen binding fragment thereof, is murine, chimeric, humanized, composite, or human. In another embodiment, the antibody and/or intrabody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In still another embodiment, the agent is a small molecule inhibitor of the IRE1α RNase domain. In yet another embodiment, the small molecule inhibitor is 4µ8c. In another embodiment, the agent reduces the splicing of XBP1 to XBP1s transcript. In still another embodiment, the agent downregulates XBP1 target genes. In yet another embodiment, the XBP1 target gene is c-Myc or a canonical XBP1 target gene selected from the group consisting of Hspa5, Dnajb9, Sec24d, Sec63, Hyou1, Sec61a, and P4hb. In another embodiment, the agent downregulates the expression of c-Myc target genes. In still another embodiment, the agent downregulates the oxidative phosphorylation (OX-PHOS) in the NK cells. In yet another embodiment, the agent decreased the levels of the proliferation marker Ki-67 in the NK cells. In another embodiment, the agent decreases the proliferation of NK cells in an NK cell-driven cancer. In still another embodiment, the NK cell-driven cancer is aggressive NK-cell leukemia (ANKL).

BRIEF DESCRIPTION OF THE DRAWINGS

FIG. 1A shows the gene ontology (GO) analysis of the top 500 differentially expressed genes in Ly49H$^+$ wild-type splenic NK cells harvested from either naïve or MCMV-infected mice day 1.5 post infection (PI). Top 10 enriched GO clusters with the key word "stimulus" are shown. FIG. 1B shows the heat map of RNA-seq analysis showing the expression of canonical IRE1α/XBP1 target genes during a time course after MCMV infection. FIG. 1C shows the flow cytometric analysis of Venus reporter expression in splenic NK cells from ERAI transgenic reporter mice at day 2 post infection (PI). FIG. 1D shows the heat map of the RNA-seq analysis showing the expression of canonical IRE1α/XBP1 target genes in splenic NK cells harvested from wild-type mice and cultured either in the presence or absence of IL-12 and IL-18 for 16 hours (GSE106138). FIG. 1E shows the flow cytometric analysis of Venus reporter expression in the sorting-purified splenic NK cells from ERAI transgenic reporter mice following 16 hours culture in the presence or absence of IL-12 and IL-18. Representative histogram plot (left) and quantification (right) are shown. FIG. 1F shows the quantitative real time PCR analysis of XBP1 splicing activity in sorted-purified human primary NK cells from PBMCs after 16 hours culture in the presence or absence of human recombinant IL-12 and IL-18, or IL-15. β-ACTIN was used as reference, and data are shown as fold change normalized to the unstimulated levels. FIG. 1G shows the flow cytometric analysis of Venus reporter expression in sorting-purified splenic and BM Nk cells from ERAI transgenic reporter mice following 16 hr culture in the present or absence of mouse recombinant IL-12 (20 ng/ml) and IL-18 (10 ng/ml), or IL-15 (100 ng/ml). Representative histogram plots (upper) and quantifications (bottom). p values are as indicated; ns indicates "not significant". One-way analysis of variance (ANOVA) with the Tukey post-test was performed on FIG. 1C and FIG. 1E. One sample t-test was performed on FIG. 1F. Error bars show standard deviation in FIG. 1C and FIG. 1E, and minimal to maximal value in FIG. 1F, from biological replicates. Each column in FIG. 1B and FIG. 1D is a different mouse. The experiment in FIG. 1C and FIG. 1E contained 2-3 mice/group, and was repeated independently three times. N equals 6 PBMC donors in FIG. 1F, and the experiment was repeated independently two times.

FIG. 2A-FIG. 2D show the qPCR validation of upregulation of the IRE1α/XBP1 pathway and ER stress markers in activated NK cells, and requirement of STAT4 and mTOR signaling pathways in driving IRE1α/XBP1. FIG. 2A shows the quantitative real time PCR analysis of indicated UPR genes in sorting-purified splenic NK cells from wild-type mice at day 1 post MCMV infection. β-ACTIN was used as reference, and data were normalized to the uninfected control expression levels. FIG. 2B shows the quantitative real time PCR analysis of indicated UPR genes in sorting-purified splenic NK cells from wild-type mice after 16 hours culture in the presence or absence of IL-12 and IL-18. FIG. 2C shows the heat map of RNA-seq analysis (GSE106138) showing the expression of canonical IRE1α/XBP1 target genes in WT and STAT4-deficient Ly49H$^+$ NK cells sorted from the spleens of mixed BM chimeric mice at day 2 PI. FIG. 2D shows the flow cytometric analysis of IRE1α activation in cytokine-activated NK cells after pharmaceutical inhibition of mTOR. NK cells from ERAI reporter mice were stimulated with mouse recombinant IL-12 (20 ng/ml) and IL-18 (10 ng/ml) for 6 hrs in the presence of mTOR inhibitor rapamycin (Rapa, 5 nM and 10 nM for low and high dose, respectively), Ku-0063794 (Ku, 1.5 µM and 3 µM for low and high dose, respectively), PP242 (PP, 0.5 µM and 1 µM for low and high dose, respectively), or IRE1 inhibitor 4µ8C (2.5 µM and 5 µM for low and high dose, respectively), or DMSO control. Representative flow cytometric plot (upper) and quantifications of relative inhibition efficiency (bottom) are shown. Ns indicates "not significant"; * indicates p<0.05,  indicates p<0.01, * indicates p<0.0001 and **** indicates p<0.0001. Two-way analysis of variance (ANOVA) with the Sidak post-test performed on FIG. 2A. Two tailed unpaired Student's t-test performed on FIG. 2B. All error bars show standard deviation from biological replicates. Data are representative of three independent experiments. N equals 3 mice/group in FIG. 2A. N equals 3 mice in FIG. 2B; with technical triplicates for ex vivo culture. Each column is a different mouse in FIG. 2C. N equals 3 ERAI mice in FIG. 2D. Experiments were independently repeated three (FIG. 2A and FIG. 2B) and two (FIG. 2D) times.

FIG. 3A-FIG. 3F show that IRE1α/XBP1 is dispensable in NK cell development & maturation. FIG. 3A shows the validation of IRE1$^{NK}$ knockout efficiency: XBP1 splicing assay (upper panel) and quantitative real time PCR analysis (bottom panel) of indicated UPR genes in sorting-purified splenic NK cells from IRE1$^{NK}$ and IRE1$^{f/f}$ littermate mice after 4 hours ex vivo incubation in the presence or absence of tunicamycin, a pharmacologic inducer of ER stress. The quantitative real time PCR data were presented as relative expression to β-Actin. FIG. 3B shows the flow cytometric analysis of NK cell development in bone marrow of IRE1$^{NK}$ and XBP1$^{NK}$ naïve mice: percentage of NK cells that are NK progenitors (NKP, DX5$^-$ NK1.1$^-$), immature NK cells (iNK, DX5$^-$ NK1.1$^+$) or mature NK (mNK, DX5$^-$NK1.1$^+$) are shown. FIG. 3C shows the flow cytometric analysis of NK cell maturation in spleen of IRE1$^{NK}$ and XBP1$^{NK}$ mice: absolute numbers and percentage of NK cells (Lin$^-$ NK1.1$^+$), and percentage of Ly49H or KLRG1 expression in splenic NK cells of naïve IRE1$^{NK}$ and IRE1$^{f/f}$ littermate control mice are shown (upper panel); percentage of NK cells that are immature (CD27$^+$ CD11b$^-$), mature (CD27$^-$ CD11b$^+$) or intermediate stage (CD27$^+$CD11b$^+$) are shown (bottom panel). FIG. 3D shows the representative histogram plots showing surface expression of cytokine receptors and activating receptors in splenic NK cells from naïve IRE1$^{NK}$ and IRE1$^{f/f}$ littermate control mice. FIG. 3E shows the flow cytometric analysis of NK cell repopulation in mixed bone marrow chimera mice: WT (CD45.1): IRE1$^{NK}$ (CD45.2), and WT (CD45.1):IRE1$^{vav1}$ (CD45.2) bone marrow chimeras were generated as in the schematic (left); NK cell repopulation in the irradiated recipient mice was assessed in the peripheral blood at week 8 after the bone marrow transfer (right). FIG. 3F shows the flow cytometric analysis of NK cell percentages and absolute numbers in BM, spleen and lung of IRE1$^{NK}$ and XBP1$^{NK}$ naïve mice, in comparison to their Cre-littermate controls. BM NK cells were identified by Lin$^-$CD122 and splenic NK cells were identified by Lin$^-$NK1.1$^+$. Ns indicates "not significant", * indicates p<0.05,  indicates p<0.01, * indicates p<0.001 and **** indicates p<0.0001. Two tailed unpaired Student's t-test performed on FIG. 3A. All error bars show standard deviation. N equals 3 mice/group in FIG. 3A and FIG. 3D. N equals 5 mice/group in FIGS. 3B-3C and FIG. 3F. N equals 10 mice in FIG. 3E. Experiments were independently repeated three (FIGS. 3A-3C and 3E-3F) and two (FIG. 3A and FIG. 3D) times.

FIG. 4A-FIG. 4H show that IRE1α is required for optimal protective antiviral NK cell responses. IRE1$^{NK}$ and littermate control mice were infected with a lethal dose of MCMV. FIG. 4A shows the viral titers in the blood at 4 days PI. FIG. 4B shows the survival curve. FIG. 4C shows the schematic of co-transfer experiments in FIG. 4D-FIG. 4H: equal numbers of Ly49H$^+$ NK cells from wild type and knockout donors were co-transferred into recipient Ly49H$^-$-deficient mice 1 day before infection with MCMV. FIG. 4D shows the quantification of the percentage of transferred wild-type and IRE1$^{NK}$ Ly49H$^+$ NK cells in peripheral blood at specified time points after infection with MCMV. FIG. 4E shows as in FIG. 4D except showing the relative percentage within the transferred Ly49H$^+$ NK cells. FIG. 4F shows the relative percentages of transferred wild-type and IRE1$^{NK}$ Ly49H$^+$ NK cells in various organs on day 8 (LN) or day 10 (all other tissues) after infection with MCMV. BM indicates bone marrow; LN indicates lymph nodes. FIG. 4G shows as in FIG. 4D except the knockout donors were XBP1$^{NK}$. FIG. 4H shows as in FIG. 4E, except the knockout donors were XBP1$^{NK}$. Two tailed unpaired Student's t-test performed on FIG. 4A, and Gehan-Breslow-Wilcoxon test performed on FIG. 4B. Two-way analysis of variance (ANOVA) with the Sidak post-test performed on FIG. 4D-FIG. 4H. p values are as indicated; ns indicates "not significant". Error bars show the standard error of the mean for FIG. 4A or standard deviation for FIGS. 4E, 4F, and 4H. Experiments were independently repeated three (FIGS. 4A, 4F, 4G, and 4H) and four (FIGS. 4D-4E) times. Data are cumulative of three experiments (FIG. 4B). N equals or >4 mice/group for all experiments.

FIG. 5A shows the gating strategy applied in analysis of co-transfer and mixed bone marrow chimera experiments. FIG. 5B shows the flow cytometric analysis of intracellular IFN-γ in splenic WT or IRE1$^{NK}$ Ly49H$^+$ NK cells from mixed bone marrow chimeric mice as indicated in FIG. 3E at day 2 after infection with MCMV. FIG. 5C shows the flow cytometric analysis of CD69 and intracellular Granzyme B in splenic WT or IRE1$^{NK}$ Ly49H$^+$ NK cells from mixed bone marrow chimeric mice at day 2 after infection with MCMV. FIG. 5D shows the flow cytometric analysis of co-transferred WT or IRE1$^{NK}$ Ly49H$^+$NK cells from the spllen of Ly49H-deficient recipients at day 2 PI: pan-Akt, p-Akt, and p-S6 with quantification normalized to WT expression levels as 100%. Two tailed unpaired Student's t-test performed on FIGS. 5B and 5C. All error bars show standard deviation. Data were independently repeated three times. N equals 6 mice in FIG. 5B. N equals 4 mice in FIG. 5C. N equals 3 mice in FIG. 5D.

FIG. 6A-FIG. 6F show IRE1α/XBP1 controls infection-induced NK cell proliferation but not survival. FIG. 6A shows the schematic of assays evaluating infection-driven NK cell proliferation and apoptosis in FIG. 6B-FIG. 6F. Equal numbers of Ly49H$^+$ NK cells from wild-type and IRE1$^{NK}$ donors were labelled with cell proliferation tracing dye CTV, and then co-transferred into recipient Ly49H-deficient mice 1 day before infection with MCMV. FIG. 6B shows the relative percentages of transferred wild-type and IRE1$^{NK}$ Ly49H$^+$ NK cells in the spleen of recipient Ly49H-deficient mice at specified time points after infection with MCMV. FIG. 6C show representative plots (left) and quantifications (right) of flow cytometric analysis showing CTV dilution of transferred wild-type and IRE1$^{NK}$ Ly49H$^+$ (responsive) and Ly49H$^-$ (bystander) NK cells in the spleen at day 4 after infection with MCMV. Flow cytometric analysis of EdU (FIG. 6D) and Annexin V (FIG. 6E) in co-transferred Ly49H$^+$ NK cells at day 3.5 after infection with MCMV. EdU was injected intraperitoneally into mice 12 hours before measurement. FIG. 6F shows the representative flow cytometric plots (left) and quantifications (right) of percentage of FLICA$^+$ cells in co-transferred Ly49H$^+$ NK cells as in FIG. 6D. p values are as indicated; ns indicates "not significant". Two-way analysis of variance (ANOVA) with the Sidak post-test performed on FIG. 6B. One-way analysis of variance (ANOVA) with the Tukey post-test performed on FIG. 6C. Two tailed unpaired Student's t-test performed on FIGS. 6D-6F. All error bars show standard deviation. Data were independently repeated three (FIGS. 6B, 6C, and 6F) and two (FIGS. 6D and 6E) times. N equals 4 mice/group for all experiments except n equals 3 mice/group in FIG. 6C.

FIG. 7A-FIG. 7J show that IRE1α/XBP1 supports NK homeostatic proliferation. FIG. 7A shows the schematic of lymphopenia-induced homeostatic proliferation experiments in FIGS. 7B-7D. Equal numbers of NK cells from wild-type and IRE1$^{NK}$ donors were labelled with cell proliferation tracing dye CTV, and then co-transferred into lymphocyte-lacking recipient Rag2–/–Il2rg–/– mice. Flow cytometric evaluation of NK cell expansion and proliferation was performed in the spleen of recipient mice at day 3-5 after transfer. FIG. 7B shows the relative percentage of transferred wild type and IRE1$^{NK}$ NK cells in the spleen of recipient Rag2–/–Il2rg–/– mice at specified time points after transfer. FIG. 7C shows the representative flow cytometric plots (left) and quantifications (middle) of CTV dilution, and Ki-67 levels (right) of transferred wild-type and IRE1$^{NK}$ NK cells in the spleen of recipient Rag2–/–Il2rg–/– mice at day 4 after transfer. FIG. 7D shows the relative percentages (left) and absolute number (right) of wild type and IRE1$^{NK}$ NK cells after co-incubation ex vivo with IL-2 and IL-15 for the indicated number of days. FIG. 7E shows the representative flow cytometric plots (upper) and quantifications (bottom) of FSC and SSC of cells in FIG. 7D at specified time points in culture. The left panel of FIG. 7F shows the quantitative real time PCR analysis of XBP1 splicing activity in sorting-purified human primary NK cells from PBMCs after 16 hours incubation ex vivo with IL-2 and IL-15, in the presence or absence of the IRE1 inhibitor (IRE1i) 4μ8c. β-ACTIN was used as reference, and data are shown as the ratio of XBP1s to XBP1 total. The middle panel of FIG. 7F shows the flow cytometric analysis of CTV dilution of human primary NK cells at specified time points in culture with IL-2 and IL-15, in the presence or absence of IRE1i. Plots showed representative data derived from three PBMC donors. The right panel of FIG. 7F shows the quantification of percentages of proliferated cells at day 6 in culture. FIG.

7G shows the representative flow cytometric plots and quantification of CTV dilution, and FIG. 7H shows the representative flow plots of Ki-67 levels at specified time points. IRE1$^{NK}$ and IRE1$^{f/f}$ NK cells from littermate animals were pre-labeled with CTV and cultured ex vivo with IL-2 and IL-15 for the indicated number of days. FIG. 7I shows, as in FIG. 7F, the representative flow cytometric plots and quantification of CTV dilution at day 6 in ex vivo culture with IL-2 and IL-15, except CD56$^{bright}$ and CD56$^{dim}$ NK cells were plotted separately. FIG. 7J shows the representative flow cytometric plots and quantification of XBP1s protein levels in CD56$^{bright}$ and CD56$^{dim}$ NK cells before and after 16 hrs of cytokine stimulation. p values are as indicated. Two-way analysis of variance (ANOVA) with the Sidak post-test performed on FIGS. 7B and 7D. Two tailed unpaired Student's t-test performed on FIG. 7C. One-way analysis of variance (ANOVA) with the Tukey post-test performed on FIG. 7G. Two tailed paired Student's t-test performed on FIGS. 7F, 7I and 7J. All error bars show the standard deviation. Data are representative of three (FIGS. 7B and 7C) and two (FIGS. 7D-7E and 7G-7H) independent repeats. Data in FIGS. 7F, 7I and 7J are pooled from two independent repeats. N equals 2 mice/group in FIG. 7B. N equals 4 mice/group in FIGS. 7C, 7G and 7H. N equals 3 mice/group (and technical duplicates for ex vivo culture) in FIGS. 7D and 7E. N equals 6, 5 and 5 PBMC donors in FIGS. 7F, 7I and 7J.

FIG. 8A shows the Venn diagram of differentially expressed genes in Ly49H$^+$ IRE1$^{NK}$ NK cells compared to WT NK cells during infection with MCMV. Cells were harvested from IRE1$^{NK}$ (CD45.2): WT (CD45.1) mixed BM chimeras at three time points: day 0, 1.5 and 7 after infection. FIG. 8B shows IPA upstream analysis derived from RNA-seq (day 1.5) as indicated in FIG. 8A: prediction of Myc regulation in IRE1$^{NK}$ NK cells. FIG. 8C shows the IPA analysis: functional overlap between IRE1- and c-Myc-regulated genes derived from RNA-seq analysis of Ly49H$^+$ IRE1$^{NK}$ NK cells at day 1.5 after infection with MCMV. FIG. 8D shows the quantitative real time PCR analysis of canonical c-Myc target genes in either transferred Ly49H$^+$ WT or IRE1$^{NK}$ NK cells that were sorting-purified from the spleen of recipient Ly49H-deficient mice at day 1.5 after infection with MCMV. β-Actin was used as reference, and data are shown as the relative expression normalized to transferred WT NK cells. FIG. 8E shows the schematic of the putative XBP1 binding site in the Myc promoter region (based on SABiosciences' proprietary database ENCODE). FIG. 8F shows the quantitative real time PCR and flow cytometric analysis of the basal levels of c-Myc mRNA and protein in naïve NK cells from IRE1$^{NK}$ and IRE1$^{f/f}$ littermate control mice. FIG. 8G shows the flow cytometric analysis of the kinetics of XBP1s, p-S6, p-Akt and pan-Akt expression in primary human NK cells after stimulation with IL-12 (20 ng/ml) and IL-18 (10 ng/ml) for the indicated time. FIG. 8H shows the purified splenic NK cells from IRE1$^{NK}$ and IRE1$^{f/f}$ littermate control mice stimulated with mouse recombinant IL-12 (20 ng/ml) and IL-18 (10 ng/ml) for 1 hr and 16 hrs in the presence or absence of mTOR inhibitor rapamycin (10 nM). c-Myc levels were quantified by flow cytometry. Ns indicates "not significant", * indicates p<0.05, ** indicates p<0.01. One sample t-test performed on FIG. 8D data (FIG. 8D) are cumulative from three experiments. All error bars, standard deviation, from biological replicates. N equals 3~5 mice/group for all experiments and data were independently repeated two (FIGS. 8G and 8H) or three times (FIGS. 8D and 8F).

FIG. 9A-FIG. 9J show that XBP1 promotes NK proliferation at least partially via direct regulation of c-Myc. FIG. 9A shows the top 10 enriched GSEA gene clusters in RNA-seq analysis of IRE1$^{NK}$ versus wild-type Ly49H$^+$ splenic NK cells harvested from IRE1$^{NK}$: WT bone marrow chimera mice day 1.5 PI. FIG. 9B shows the heat map of differentially expressed Myc target genes in IRE1$^{NK}$ versus wild-type NK cells. Genes were clustered by functional annotation. FIG. 9C shows the flow cytometric analysis of c-Myc induction at the levels of transcription (upper row) and translation (middle row) in splenic NK cells from wild type mice either naïve or at day 1 after infection with MCMV. The bottom row of FIG. 9C shows the representative flow cytometric plots indicating the concomitant induction of c-Myc protein and Venus reporter expression in NK cells from indicated organs of ERAI transgenic mice at day 2 after infection with MCMV. FIG. 9D shows the quantitative real time PCR and flow cytometric analysis of c-Myc expression in transferred wild type and IRE1$^{NK}$ Ly49H$^+$ NK cells in the spleen of recipient Ly49H-deficient mice at day 1 after infection with MCMV. Equal numbers of Ly49H$^+$ NK cells from wild type and knockout donors were co-transferred into recipient Ly49H-deficient mice 1 day before infection. FIG. 9E shows the flow cytometric analysis of c-Myc expression in transferred wild type and IRE1$^{NK}$ NK cells in the spleen of recipient Rag2-/- Il2rg-/- mice at specified time points after transfer. FIG. 9F shows the representative flow cytometric histogram of c-Myc expression in splenic NK cells of either XBP1$^{tg}$ mice or wild-type littermates. FIG. 9G shows the chromatin immunoprecipitation assays using NK cell lines MNK-1 (mouse, left graph), NKL and KHYG-1 (human, right graph) to assess XBP1 binding to the c-Myc locus. Anti-XBP1s Ab was used and IgG was used as mock control. FIG. 9H show the representative flow cytometric plots (left) and quantification of c-Myc reporter expression. Before assessment, splenic NK cells from c-Myc reporter mice (Myc$^{GFP}$) were treated with indicated cytokines for 16 hours, either in the presence or absence of the IRE1 inhibitor (IRE1i) 4μ8c. The upper panel of FIG. 9I shows the percentages of transferred wild type and Myc$^{NK}$ Ly49H$^+$ NK cells in peripheral blood (except the endpoint using spleen) at specified time points after infection with MCMV. Equal numbers of Ly49H$^+$ NK cells from wild type and Myc$^{NK}$ donors were co-transferred into recipient Ly49H- deficient mice 1 day before infection. The bottom panel of FIG. 9I shows the relative percentages within the transferred Ly49H$^+$ NK cells. FIG. 9J shows the representative immunoblot and quantification of c-Myc protein in IRE1$^{NK}$ and WT NK cells sorted from the same mixed BM chimera mice at day 1.5 PI; quantification shows cumulative data from four mixed BM chimeras. p values are as indicated; ns indicates "not significant". One sample t-test performed on FIG. 9J. Two tailed unpaired Student's t-test performed on FIG. 9D and FIG. 9G. Two-way analysis of variance (ANOVA) with the Sidak post-test performed on FIGS. 9E, and 9I. All error bars shows the standard deviation. Each column in FIG. 9B is a different mouse. Data are representative of three (FIGS. 9C-9E and FIG. 9G) and two independent repeats (FIGS. 9F, 9H, 9I and 9J). Data were independently repeated three (FIGS. 9D and 9H) and two (FIGS. 9G-9J). N equals 3 or 4 mice/group in FIG. 9D and FIG. 9J; n equals 3 technical replicates/group in FIG. 9G; n equals 3 replicates/treatment in ex vivo culture in FIG. 9H; n equals 5 mice/group in FIG. 9I.

FIG. 10A shows the gross morphology of lungs and individual lung lobes from IRE$^{f/f}$ and IRE1$^{NK}$ mice at day 10 following intravenous injection of B16F10 melanoma. Quantification of total extrapulmonary metastatic nodules is shown on the right. FIG. 10B shows the H&E microscopic analysis of lungs from IRE$^{f/f}$ and IRE1$^{NK}$ mice described in FIG. 10A. FIG. 10C shows the survival curve of B16F10-innoculated IRE1$^{f/f}$ and IRE1$^{NK}$ mice described in FIG. 10A. FIG. 10D is similar as in FIG. 10A, which shows the quantification of total extrapulmonary metastatic nodules from IRE1$^{f/f}$ and XBP1$^{NK}$ mice at day 20 following intravenous injection of B16F10 melanoma. FIGS. 10E-10G shows the flow cytometry analysis of lungs from B16F10 tumor-inoculated mice described in FIG. 10A. Graphs shown are (FIG. 10E) percentage of NK cells in total lymphocyte population and the absolute numbers, (FIG. 10F) Ki-67 and (FIG. 10G) c-Myc expression in lung-infiltrated NK cells. p values are as indicated. Two tailed unpaired Student's t-test was performed on FIGS. 10A and 10D-10G. Gehan-Breslow-Wilcoxon test was performed on FIG. 10C. All error bars show the standard error of mean (s.e.m.). Each dot is a different mouse. Data are pooled from three (FIG. 10A) and two independent experiments (FIGS. 10C-10E), or representative of two independent repeats (FIGS. 10B, 10F, and 10G). FIG. 10H shows gross morphology results of lungs and individual lung lobes from Myc$^{+/-}$Ncr1$^{Cre+}$ (Myc$^{NK}$) and Myc$^{+/-}$Ncr1$^{Cre-}$ (Cre-Ctrl) littermate mice at day 12 following intravenous injection of B16F10 melanoma. Quantification of total extrapulmonary metastatic nodules is shown in the histogram. FIG. 10I shows flow cytometry analysis results of lungs from B16F10 tumor-inoculated mice described in FIG. 10H, and graphs shown are representative flow cytometry plots (upper panel) and quantification (histogram) of the percentage of NK cells in total lymphocyte population in lung. p values are as indicated. Two tailed unpaired Student's t-test was performed. All error bars show the standard error of mean (s.e.m.). Each dot is a different mouse. Data are representative of two independent repeats.

FIG. 11A shows the gating strategy. FIG. 11B shows the percentage of conventional type 1 dendritic cells (cDC1) (left), CD8$^+$ T cells (middle), and CD4$^+$ T cells (right) in the lung and spleen of IRE1$^{NK}$ and IRE1$^{f/f}$ littermate control mice at day 20 following intravenous injection of B16F10 melanoma cells. FIG. 11C shows the representative flow cytometric plots and quantification of basal levels of NK cell numbers and relative percentage and Ki-67 and c-Myc expression in the lungs of naïve IRE1$^{NK}$ and IRE1$^{f/f}$ littermate control mice. * indicates p<0.05, ** indicates p<0.01. Two tailed unpaired Student's t-test was performed on FIG. 11B. All error bars show the standard error of mean (s.e.m.). n=4-5 mice/group and for all experiments, and date were independently repeated three times. FIG. 11D shows that IRE1α in NK cells promote IFN-γ production in tumor infiltrated lymphocytes. Bar graphs show the percentage of IFN-γ producing cells in NK cells, CD4$^+$ T cells, and CD8$^+$ T cells in the lung (upper panel) and spleen (lower panel) of IRE1$^{NK}$ and IRE1$^{f/f}$ littermate control mice at day 20 following intravenous injection of B16F10 melanoma cells. * indicates p<0.05, ** indicates p<0.01. Two tailed unpaired Student's t-test was performed. All error bars show the standard error of mean (s.e.m.). n=4-6 mice/group, and date were independently repeated three times.

FIG. 14A shows the top 10 enriched GSEA hallmark gene sets in RNA-seq analysis at day 1.5 PI as indicated in FIG. 8A. FIG. 14B shows the heat map of differentially expressed OXPHOS target genes in IRE1$^{NK}$ versus WT NK cells at day 1.5 PI. Genes were clustered by functional annotation. c-Myc-regulated genes (Morrish and Hockenbery (2014) Cold Spring Harb. Perspect. Med. 4:a014225) are shown in black text on the right. FIG. 14C shows the analysis of NK cell oxygen consumption rate (OCR) to assess rates of OXPHOS and maximal respiration. Primary human NK cells isolated from PBMC were incubated with IL-12 and IL-18 for 16 hr, in the presence or absence of the IRE1α inhibitor 4μ8C (5 uM). Approximately 600,000 cells were plated per well, and the data were normalized to total protein quantification. Oligo (Oligomycin, 1 μM), FCCP (carbonyl cyanide-p-(trifluoromethoxy) phenylhydrazone, 1 μM), R (rotenone, 0.5 μM) and A (antimycin, 0.5 μM). Representative plot in FIG. 14C shows data from one PBMC donor with three technical controls. Quantification in FIG. 14B shows the combined data of mean values from three PBMC donors and two independent experiments; two tailed unpaired Student's t-test was performed, and p values are as indicated.

FIG. 15A shows the real-time PCR analysis of c-Myc mRNA in naïve NK cells from Myc$^{OE}$ (Myc$^{fsf/+}$ Ncr1$^{Cre+}$) and littermate control (Myc$^{fsf/+}$ Ncr1$^{Cre-}$) mice. FIG. 15B shows the representative flow cytometric plots of CTV dilution after ex vivo culture of NK cells as in FIG. 15A with IL-2 and IL-15 for 3 days, in the presence or absence of IRE1α inhibitor 4μ8C (5 μM). FIG. 15C-FIG. 15E show WT (Myc$^{fsf/+}$ IRE1$^{f/f}$ Ncr1$^{Cre-}$), IRE1$^{NK}$ (Myc$^{+/+}$ IRE1$^{f/f}$ Ncr1$^{Cre+}$) Myc$^{OE}$ (Myc$^{fsf/+}$ IRE1$^{+/+}$ Ncr1$^{Cre+}$) and Myc$^{OE}$ IRE1$^{NK}$ (Myc$^{fsf/+}$ IRE1$^{f/f}$ Ncr1$^{Cre+}$) NK cells pre-labeled with CTV and cultured ex vivo with IL-2 and IL-15. FIG. 15C shows the representative flow cytometric plots and quantification of CTV dilution at day 3, and FIG. 15D shows the representative flow cytometric plots of Ki-67 levels and quantification of percentage of proliferating cells (defined as Ki-67$^+$ CTV$^{lo}$) at day 3. FIG. 15E shows the absolute numbers of NK cells at day 6. P values are as indicated; ns=not significant. One sample t-test is performed on FIG. 15A. One-way analysis of variance (ANOVA) with the Tukey post-test is performed on FIGS. 15C-15E. All error bars are s.e.m. N=5 mice/group in FIG. 15A, n=2 mice/group in FIG. 15B and n=4 mice/group in FIGS. 15C-15E. Technical duplicates in culture per mouse are shown in FIGS. 15B-15E. FIG. 15A shows cumulative data from two independent experiments. Experiments in FIGS. 15B-15E were independently repeated three times.

FIG. 16A-FIG. 16G show characterization of NK cell development and maturation in Myc$^{+/-}$ heterozygous mice (Het, referred to as "Myc$^{NK}$" in Main Text) and Myc$^{-/-}$ (KO) mice. FIG. 16A shows quantitative real time PCR validation of c-Myc expression in Het and KO NK cells before and after IL-12 and IL-18 stimulation ex vivo. FIG. 16B shows results of flow cytometric analysis of NK cell percentages and absolute numbers in BM and spleen of Myc$^{Het}$ mice, in comparison to their Cre littermate controls. BM NK cells were identified by Lin$^-$CD122 and splenic NK cells were identified by Lin$^-$NK1.1$^+$. FIG. 16C shows results as in FIG. 16B, except that data for Myc KO animals are shown. FIG. 16D shows results of flow cytometric analysis of NK cell development in BM and NK cell maturation in spleen of MycHet mice. For BM (upper panel), percentages of NK cells that are NK progenitors (NKP, DX5$^-$ NK1.1$^-$), immature NK cells (iNK, DX5$^-$ NK1.1$^+$) or mature NK (mNK, DX5$^-$ NK1.1$^+$) are shown; for spleen (bottom panel), percentages of NK cells that are immature (CD27$^+$ CD11b$^-$), mature (CD27$^-$ CD11b$^+$) or intermediate stage (CD27$^+$ CD11b$^+$) are shown. FIG. 16E shows results of flow cytometric analysis as in FIG. 16D, except that data for Myc KO animals are shown. FIG. 16F shows representative histogram plots showing surface expression of cytokine receptors and activating receptors in splenic NK cells from Myc Het mice in comparison to their Cre-littermate controls. FIG. 16G shows results as in FIG. 16F, except that data for Myc KO animals are shown. P values are as indicated. Two tailed unpaired Student's t-test is performed on FIGS. 16A-16E. All error bars are s.e.m. Data are representative of three (FIGS. 16A-16E) and two (FIGS. 16F and 16G) independent experiments. N=3 mice/group for FIGS. 16A, 16F, and 16G. N=4-5 mice/group for all experiments in FIGS. 16B-16E. Data were independently repeated three (FIGS. 16B-16E) or two (FIGS. 16F and 16G) times.

FIG. 17A provides a schematic describing the experimental approach. Briefly, NK cells are purified from human PBMC and preactivated for 16 hours with rhIL-12+rhIL-18+rhIL-15, or control conditions (rhIL-15), in the presence or absence of IRE1 inhibitor (IRE1i) named MKC8866; cells are then washed 3 times to remove cytokines and cultured in complete medium supplemented with rhIL-15 to support survival for 7 days; cells are restimulated with rhIL-12+rhIL-18 for 6 hours; and the readout is IFN-γ by flow cytometry. FIG. 17B shows the gating strategy used in flow cytometry analyses. FIG. 17C is a heatmap that shows after restimulation the percentage of IFN-γ-producing CIML NK cells, generated in the presence or absence of IRE1 inhibitor MKC8866 during preativation.

Figure 1A:
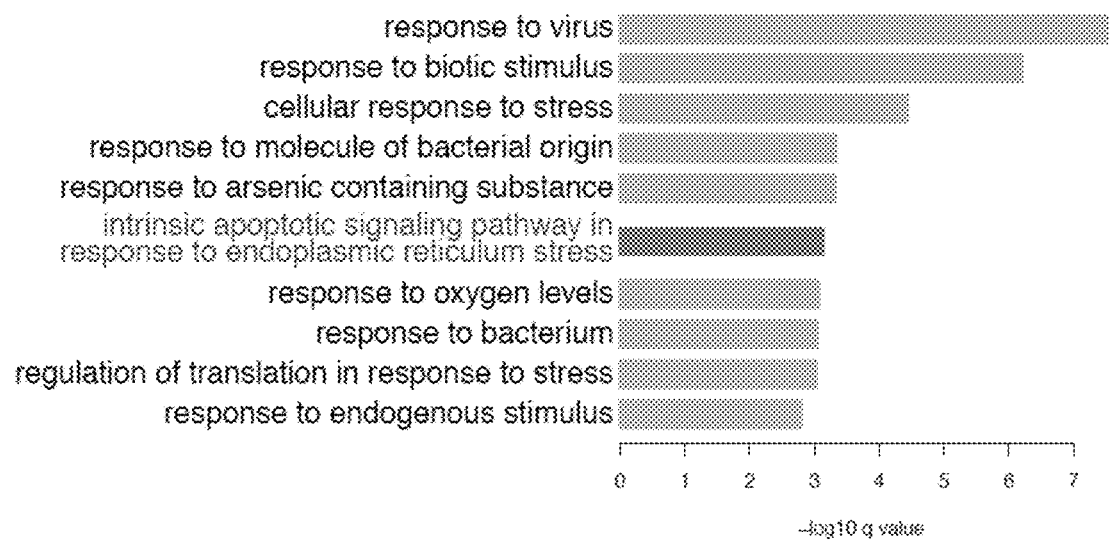
FIG. 1A-FIG. 1G show the induction of IRE1α/XBP1 UPR in mouse and human activated NK cells in vitro and in vivo.

Note that for every figure containing a histogram, the bars from left to right for each discreet measurement correspond to the figure boxes from top to bottom in the figure legend as indicated.

DETAILED DESCRIPTION OF THE INVENTION

The present invention is based, at least in part, on the discovery that the ER stress sensor inositol-requiring enzyme 1 (IRE1α) and its substrate transcription factor X-box-binding protein 1 (XBP1) critically drive NK cell-mediated responses against viral infection, homeostatic proliferation and tumors in vivo. An IRE1 activation reporter mouse strain was used to demonstrate that activated NK cells upregulate the IRE1α/XBP1 pathway following exposure to pro-inflammatory cytokines in vitro and to viral infection in vivo. Using a newly-engineered genetic mouse model, it was demonstrated that the IRE1α/XBP1 pathway is a positive cell-intrinsic regulator of NK cell proliferation and expansion during viral infection or lymphopenia, and of NK cell-mediated antitumor protection. It was also shown that IRE1α/XBP1 is induced by mTOR and Stat4 signaling pathways in activated NK cells. In addition, it was found that XBP1 facilitates NK cell expansion in part by directly binding to and activating the c-Myc promoter to upregulate key c-Myc target genes required for NK cell expansion as well as by controlling mitochondrial respiration. Moreover, it was determined that IRE1α/XBP1 regulates NK cell memory, especially generation of cytokine-induced, memory-like NK cells (CIML). This study reveals the role for the IRE1α/XBP1 pathway and for the transcriptional regulator c-Myc in NK cell-mediated immunity.

Accordingly, the present invention relates, in part, to compositions and methods for treating conditions that would benefit from modulating immune responses using compositions, such as modified NK cells, or an agent that modulates the IRE1α/XBP1 pathway.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a disease sample, as compared to the expression level or copy number of the biomarker nucleic acid in a control sample. The term "altered amount" of a biomarker also includes an increased or decreased protein level of a biomarker protein in a sample, e.g., a disease sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal amount if the amount is at least about two, and preferably at least about three, four, or five times, higher or lower, respectively, than the normal amount of the biomarker.

The term "altered level of expression" of a biomarker refers to an expression level or copy number of the biomarker in a test sample, e.g., a sample derived from a patient suffering from a condition that would benefit from modulating an immune response (e.g., cancer or viral infection), that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a disease sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, *Nature Biotechnology* 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, and vomit).

The term "a condition that would benefit from an increased immune response" refers to conditions in which upregulation of an immune response is desired. Such conditions are well-known in the art and include, without limitation, disorders requiring increased NK cell production or function, such as combating cancer, infections (e.g., parasitic, bacterial, helminthic, fungal, or viral infections), and the like. The term "a condition that would benefit from a decreased immune response" refers to conditions in which downregulation of an immune response is desired. Such conditions are also well-known in the art and include, without limitation, inflammatory diseases, such as autoimmune diseases. The term "a condition that would benefit from a modulation of immune response" refers to conditions in which upregulation or downregulation of an immune response is desired.

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The term "NK cell-driven cancer" or "NK cell cancer" refers to a cancer that comprises NK cells which proliferate in an uncontrolled manner. NK cell cancers are well-known in the art and includes, without limitation, aggressive NK cell leukemia (also called aggressive NK-cell lymphoma, or ANKL).

The term "NK cell-sensitive cancer" refers to a cancer that is responsive to NK cell-mediated tumor immunity. For example, NK cell-mediated tumor immunity may lead to a decreased cancer cell proliferation or metastasis and/or an increased cancer cell apoptosis.

The terms "lymphopenia" or "lymphocytopenia" or "lymphocytic leucopenia" interchangeably refer to an abnormally small number of lymphocytes in the circulating blood or in peripheral circulation. Lymphocytopenia has a wide range of possible causes, including viral (e.g., HIV infection), bacterial (e.g., active tuberculosis infection), and fungal infections; chronic failure of the right ventricle of the heart, Hodgkin's disease and cancers of the lymphatic system, leukemia, a leak or rupture in the thoracic duct, side effects of prescription medications including anticancer agents, antiviral agents, and glucocorticoids, malnutrition resulting from diets that are low in protein, radiation therapy, uremia, autoimmune disorders, immune deficiency syndromes, high stress levels, and trauma. Lymphopenia may also be of unknown etiology (i.e., idiopathic lymphopenia). Peripheral circulation of all types of lymphocytes or subpopulations of lymphocytes (e.g., CD4+ T cells) may be depleted or abnormally low in a patient suffering from lymphopenia. See, e.g., The Merck Manual, 18th Edition, 2006, Merck & Co.

The term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient (can be stored sample or previous sample measurement) with a known outcome; normal tissue or cells isolated from a subject, such as a normal patient or the patient having a condition of interest (cancer is used below as a representative condition), cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods encompassed by the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid, or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with a condition that would benefit from a modulation of immune response, or from a corresponding non-cancerous tissue in the same subject who has a condition that would benefit from a modulation of immune response, The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

Immune cells can be obtained from a single source or a plurality of sources (e.g., a single subject or a plurality of subjects). A plurality refers to at least two (e.g., more than one). In still another embodiment, the non-human mammal is a mouse. The animals from which cell types of interest are obtained may be adult, newborn (e.g., less than 48 hours old), immature, or in utero. Cell types of interest may be primary cells, stem cells, established cancer cell lines, immortalized primary cells, and the like.

Natural killer cells are large granular lymphocytes and differentiated from the common lymphoid progenitor-generating B and T lymphocytes. NK cells are known to differentiate and mature in the bone marrow, lymph nodes, spleen, tonsils, and thymus, where they then enter into the circulation. Natural killer cells are critical to the innate immune system. NK cells provide rapid responses to viral-infected cells, and respond to tumor formation. Typically, immune cells detect major histocompatibility complex (MHC) presented on infected cell surfaces, triggering cytokine release, causing lysis or apoptosis. NK cells are unique, however, as they have the ability to recognize stressed cells in the absence of antibodies and MHC, allowing for a much faster immune reaction. NK cells also play a role in the adaptive immune response: numerous experiments have demonstrated their ability to readily adjust to the immediate environment and formulate antigen-specific immunological memory, fundamental for responding to secondary infections with the same antigen. The role of NK cells in both the innate and adaptive immune responses is becoming increasingly important in research using NK cell activity as a potential cancer therapy.

Macrophages (and their precursors, monocytes) are the 'big eaters' of the immune system. These cells reside in every tissue of the body, albeit in different guises, such as microglia, Kupffer cells and osteoclasts, where they engulf apoptotic cells and pathogens and produce immune effector molecules. Upon tissue damage or infection, monocytes are rapidly recruited to the tissue, where they differentiate into tissue macrophages. Macrophages are remarkably plastic and can change their functional phenotype depending on the environmental cues they receive. Through their ability to clear pathogens and instruct other immune cells, these cells have a central role in protecting the host but also contribute to the pathogenesis of inflammatory and degenerative diseases. Macrophages that encourage inflammation are called M1 macrophages, whereas those that decrease inflammation and encourage tissue repair are called M2 macrophages. M1 macrophages are activated by LPS and IFN-gamma, and secrete high levels of IL-12 and low levels of IL-10. M2 is the phenotype of resident tissue macrophages, and can be further elevated by IL-4. M2 macrophages produce high levels of IL-10, TGF-beta and low levels of IL-12. Tumor-associated macrophages are mainly of the M2 phenotype, and seem to actively promote tumor growth.

Myeloid derived suppressor cells (MDSCs) are an intrinsic part of the myeloid cell lineage and are a heterogeneous population comprised of myeloid cell progenitors and precursors of granulocytes, macrophages and dendritic cells. MDSCs are defined by their myeloid origin, immature state and ability to potently suppress T cell responses. They regulate immune responses and tissue repair in healthy individuals and the population rapidly expands during inflammation, infection and cancer. MDSC are one of the major components of the tumor microenvironment. The main feature of these cells is their potent immune suppressive activity. MDSC are generated in the bone marrow and, in tumor-bearing hosts, migrate to peripheral lymphoid organs and the tumor to contribute to the formation of the tumor microenvironment. This process is controlled by a set of defined chemokines, many of which are upregulated in cancer. Hypoxia appears to have a critical role in the regulation of MDSC differentiation and function in tumors. Therapeutic strategies are now being developed to target MDSCs to promote antitumour immune responses or to inhibit immune responses in the setting of autoimmune disease or transplant rejection.

Dendritic cells (DCs) are professional antigen-presenting cells located in the skin, mucosa and lymphoid tissues. Their main function is to process antigens and present them to T cells to promote immunity to foreign antigens and tolerance to self antigens. They also secrete cytokines to regulate immune responses.

The term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes).

Conventional T cells, also known as Tconv or Teffs, have effector functions (e.g., cytokine secretion, cytotoxic activity, anti-self-recognition, and the like) to increase immune responses by virtue of their expression of one or more T cell receptors. Tcons or Teffs are generally defined as any T cell population that is not a Treg and include, for example, naïve T cells, activated T cells, memory T cells, resting Tcons, or Tcons that have differentiated toward, for example, the Th1 or Th2 lineages. In some embodiments, Teffs are a subset of non-Treg T cells. In some embodiments, Teffs are CD4+ Teffs or CD8+ Teffs, such as CD4+ helper T lymphocytes (e.g., Th0, Th1, Tfh, or Th17) and CD8+ cytotoxic T lymphocytes. As described further herein, cytotoxic T cells are CD8+ T lymphocytes. "Naïve Tcons" are CD4$^+$ T cells that have differentiated in bone marrow, and successfully underwent a positive and negative processes of central selection in a thymus, but have not yet been activated by exposure to an antigen. Naïve Tcons are commonly characterized by surface expression of L-selectin (CD62L), absence of activation markers such as CD25, CD44 or CD69, and absence of memory markers such as CD45RO. Naïve Tcons are therefore believed to be quiescent and non-dividing, requiring interleukin-7 (IL-7) and interleukin-15 (IL-15) for homeostatic survival (see, at least WO 2010/101870). The presence and activity of such cells are undesired in the context of suppressing immune responses. Unlike Tregs, Tcons are not anergic and can proliferate in response to antigen-based T cell receptor activation (Lechler et al. (2001) *Philos. Trans. R. Soc. Lond. Biol. Sci.* 356:625-637). In tumors, exhausted cells can present hallmarks of anergy.

The term "immunotherapy" or "immunotherapies" refer to any treatment that uses certain parts of a subject's immune system to fight diseases such as cancer. The subject's own immune system is stimulated (or suppressed), with or without administration of one or more agent for that purpose. Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

In some embodiments, immunotherapy comprises inhibitors of one or more immune checkpoints. The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein. In one embodiment, the immune checkpoint is PD-1.

"Anti-immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "immune response" refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus. Exemplary immune responses include T cell responses or NK-cell mediated immune responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

As used herein, the term "immunotherapeutic agent" can include any molecule, peptide, antibody or other agent which can stimulate a host immune system to promote immunomodulation in the subject. Various immunotherapeutic agents are useful in the compositions and methods described herein.

The term "determining a suitable treatment regimen for the subject" is taken to mean the determination of a treatment regimen (i.e., a single therapy or a combination of different therapies that are used for the prevention and/or treatment of a condition that would benefit from modulating an immune response(e.g., cancer or viral infection) in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "expression signature" or "signature" refers to a group of two or more coordinately expressed biomarkers. For example, the genes, proteins, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "homologous" refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "inhibit" or "downregulate" includes the decrease, limitation, or blockage, of, for example a particular action, function, or interaction. In some embodiments, a condition that would benefit from modulating an immune response is "inhibited" if at least one symptom of the condition is alleviated, terminated, slowed, or prevented. As used herein, the condition is also "inhibited" if recurrence or spread of the condition is reduced, slowed, delayed, or prevented. Similarly, a biological function, such as the function of a protein, is inhibited if it is decreased as compared to a reference state, such as a control like a wild-type state. Such inhibition or deficiency can be induced, such as by application of agent at a particular time and/or place, or can be constitutive, such as by a heritable mutation. Such inhibition or deficiency can also be partial or complete (e.g., essentially no measurable activity in comparison to a reference state, such as a control like a wild-type state). Essentially complete inhibition or deficiency is referred to as blocked. The term "promote" or "upregulate" has the opposite meaning.

The term "interaction," when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting costimulation). To inhibit such an interaction results in the disruption of the activity of one or more molecules involved in the interaction. To enhance such an interaction is to prolong or increase the likelihood of said physical contact, and prolong or increase the likelihood of said activity.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

The term "isotype" refers to the antibody class (e.g., IgM or IgG1) that is encoded by heavy chain constant region genes.

The term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

The term "modulate" includes up-regulation and down-regulation, e.g., enhancing or inhibiting a response.

The term "naturally-occurring" nucleic acid polypeptide refers to an RNA or DNA polypeptide having a nucleotide sequence that occurs in nature (e.g., encodes a natural protein).

A "kit" is any manufacture (e.g. a package or container) comprising at least one reagent, e.g. a probe or small molecule, for specifically detecting and/or affecting the expression of a marker of the invention. The kit may be promoted, distributed, or sold as a unit for performing the methods encompassed by the present invention. The kit may comprise one or more reagents necessary to express a composition useful in the methods encompassed by the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy.

The "normal" level of expression of a biomarker is the level of expression of the biomarker in cells of a subject, e.g., a human patient, not afflicted with a condition that would benefit from a modulation of immune response. An "over-expression" or "significantly higher level of expression" of a biomarker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples. Such "significance" levels can also be applied to any other measured parameter described herein, such as for expression, inhibition, cytotoxicity, cell growth, and the like.

The term "IRE1α-XBP1 signaling pathway" refers to one branch of the unfolded protein response (UPR) signaling pathway. The unfolded protein response (UPR) signaling pathway plays an important role in maintaining endoplasmic reticulum (ER) homeostasis under various environmental conditions that cause ER stress in eukaryotic cells. In mammalian cells, the UPR is mediated by three ER-localized transmembrane protein sensors: Inositol-requiring transmembrane kinase/endonuclease-1 (IRE1), PKR-like ER kinase (PERK) and activating transcription factor 6 (ATF6) (Walter, P., et al. 2011. *Science* 334, 1081-1086). Of these, IRE1 is the most evolutionarily conserved branch. An increase in the load of folding proteins in the ER activates IRE1α, an ER-resident kinase and endoribonuclease that acts as an ER-stress sensor (Walter, P., et al. 2011. *Science* 334, 1081-1086). Activated IRE1α removes a 26 bp intron from XBP1 mRNA and results in a frame shift in the coding sequence, with the spliced form encoding a 226 amino acid transcriptional activation domain (Calfon, M., et al. 2002. *Nature* 415, 92-96; Yoshida, H., et al. 2001. *Cell* 107, 881-891). In contrast to the unspliced XBP1 (XBP1u), which is unstable and quickly degraded, spliced XBP1 (XBP1s) is stable and is a potent inducer of target genes that orchestrate the cellular response to ER stress (Hetz, C., et al. 2011. *Physiol Rev* 91, 1219-1243). For example, the XBP1s protein translocates into the nucleus to initiate transcriptional programs that upregulate a broad spectrum of UPR-associated genes involved in protein entry into the ER, protein folding, ER-associated degradation (ERAD), and ER biogenesis. In one embodiment, XBP1s upregulates transcription of c-Myc. IRE1α-XBP1 pathway activation can be assessed by analyzing, for example, IRE1α activation (e.g., using ERAI reporter mouse), XBP1 splicing into the XBP1s transcript, and/or the expression levels of the XBP1 target genes. Molecular targets of IRE1α-XBP1 pathway include, but are not limited to, Hspa5, Dnajb9, Sec24d, Sec63, Hyou1, Sec61a1, P4hb, Ddit3, and the like. Other molecular targets are well known in the art.

The IRE1α-XBP1 signaling pathway is highly conserved from yeast to humans. This signaling pathway can be regulated at the level of XBP1 and IRE1α. Exemplary agents useful for activating IRE1α-XBP1 signaling pathway, or other biomarkers described herein, include small molecules, peptides, and nucleic acids, etc. that can upregulate the expression and/or activity of one or more biomarkers listed in Table 1, or fragments thereof. Exemplary agents useful for activating IRE1α-XBP1 signaling pathway, or other biomarkers described herein, also include proinflammatory cytokines such as IL-12, IL-15, and IL-18. Exemplary agents that promote IRE1 activity may include, but are not limited to Apigenin (Choi et al. (2009) *J. Clin. Biochem. Nutr.* 44:260-265), APY 29 (Wang et al. (2012) *Nat. Chem. Biol.* 8:982-989), Kaempferol (Montero et al. (2004) *Biochem. J.* 384:19-24), and Quercetin (Cermak et al. (2002) *Br. J. Pharmacol.* 135:1183-1190).

Exemplary agents useful for inhibiting IRE1α-XBP1 signaling pathway, or other biomarkers described herein, include antibodies, small molecules, peptides, peptidomimetics, natural ligands, and derivatives of natural ligands, that can either bind and/or inactivate or inhibit one or more biomarkers listed in Table 1, or fragments thereof; as well as RNA interference, antisense, nucleic acid aptamers, etc. that can downregulate the expression and/or activity of one or more biomarkers listed in Table 1, or fragments thereof.

Exemplary inhibitors of the IRE1α-XBP1 signaling pathway signaling pathway are also well known in the art and include, but are not limited to: IREα inhibitors, such as 4µ8C (Cross et al. (2012) *Proc. Natl. Acad. Sci. USA* 109:E869), AMG 18 hydrochloride (Harrington et al. (2014) *ACS Med. Chem. Lett.* 6:68-72), B I09 (Tang et al. (2014) *J. Clin. Invest.* 124:2585-2598), STF 083010 (Papandreou et al (2011) *Blood.* 117: 1311-1314), MKC-3946 (Mimura et al. (2012) *Blood* 119:5772-5781), and many more; XBP1 inhibitors, such as Trierixin (Tashiro et al. (2007) *J. Antibiot.* 60:547-553) and Doxorubicin (Jiang et al. (2016) *Sci. Rep.* 6:33353); and c-Myc inhibitors, such as 10058-F4 (Yin et al. (2003) *Oncogene* 22:6151) and KJ Pyr 9 (Hart et al. (2014) *Proc. Natl. Acad. Sci. U.S.A.* 111:12556).

The term "IRE1α" or "ERN1" refers to endoplasmic reticulum to nucleus signaling 1, a transmembrane protein kinase inositol-requiring enzyme 1. IRE1α protein contains two functional catalytic domains, a serine/threonine-protein kinase domain and an endoribonuclease domain. This protein functions as a sensor of unfolded proteins in the endoplasmic reticulum (ER) and triggers an intracellular signaling pathway termed the unfolded protein response (UPR). The UPR is an ER stress response that is conserved from yeast to mammals and activates genes involved in degrading misfolded proteins, regulating protein synthesis and activating molecular chaperones. This protein specifically mediates the splicing and activation of the stress response transcription factor X-box binding protein 1. IRE1α acts as a key sensor for the endoplasmic reticulum unfolded protein response (UPR). In unstressed cells, the endoplasmic reticulum luminal domain is maintained in its inactive monomeric state by binding to the endoplasmic reticulum chaperone HSPA5/BiP. Accumulation of misfolded protein in the endoplasmic reticulum causes release of HSPA5/BiP, allowing the luminal domain to homodimerize, promoting autophosphorylation of the kinase domain and subsequent activation of the endoribonuclease activity. The endoribonuclease activity is specific for XBP1 mRNA and excises 26 nucleotides from XBP1 mRNA. The resulting spliced transcript of XBP1 encodes a transcriptional activator protein that up-regulates expression of UPR target genes. Inositol-requiring enzyme 1 (IRE1) is a resident transmembrane ER protein with both kinase and endonuclease domains. Both yeast (IRE) and mammalian (IRE1α) homologs are involved in the degradation of misfolded proteins, as part of the unfolded protein response (UPR). In one embodiment, the human IRE1α protein has 977 amino acids and a molecular mass of 109735 Da.

The term "IRE1α" or "ERN1" is intended to include fragments, variants (e.g., allelic variants), and derivatives thereof. Representative human IRE1α cDNA and human IRE1α protein sequences are well-known in the art and are publicly available from the National Center for Biotechnology Information (NCBI). For example, one human IRE1α isoform is known. Human IRE1α (NP_001424.3) is encodable by the transcript (NM_001433.4). Nucleic acid and polypeptide sequences of IRE1α orthologs in organisms other than humans are well known and include, for example, chimpanzee IRE1α (XM_511585.7 and XP_511585.4; XM_016932752.2 and XP_016788241.1; XM_016932751.2 and XP_016788240.1; XM_016932749.2 and XP_016788238.1; and XM_016932753.2 and XP_016788242.1); monkey IRE1α (XM_015120098.1 and) CP 014975584.1; XM_015120099.1 and XP_014975585.1; XM_001109583.3 and XP_001109583.2); dog IRE1α (XM_848316.4 and XP_853409.3, XM_005624256.1 and XP_005624313.1; XM_022422839.1 and XP_022278547.1; XM_022422837.1 and XP_022278545.1; XM_022422838.1 and XP_022278546.1; XM_022422835.1 and XP_022278543.1; XM_005624255.2 and XP_005624312.1; XM_022422836.1 and XP_022278544.1), cattle IRE1α (NM_001099115.2 and NP_001092585.1), mouse IRE1α (NM_023913.2 and NP_076402.1), rat IRE1α (NM_001191926.1 and NP_001178855.1), and chicken IRE1α (NM_001285499.1 and NP_001272428.1). Representative sequences of IRE1α orthologs are presented below in Table 1.

Anti-IRE1α antibodies suitable for detecting IRE1α protein are well-known in the art and include, for example, antibodies AM06424SU-N and AM31059PU-N(OriGene Technologies, Rockville, MD), NB100-2323, NB100-2324, NB110-59971, and H00002081-M02 (antibodies from Novus Biologicals, Littleton, CO), ab48187, ab37073, and ab124945, (antibodies from AbCam, Cambridge, MA), etc. In addition, reagents are well-known for detecting IRE1α expression. Moreover, multiple siRNA, shRNA, CRISPR constructs for reducing IRE1α Expression can be found in the commercial product lists of the above-referenced companies, such as siRNA products #sc-40705 and #sc-40706 and CRISPR product #sc-400576 from Santa Cruz Biotechnology, RNAi products TR320345, SR320074, TG320345, and TF320345, and CRISPR product KN215023 (Origene), and multiple CRISPR products from GenScript (Piscataway, NJ). It is to be noted that the term can further be used to refer to any combination of features described herein regarding IRE1α molecules. For example, any combination of sequence composition, percentage identify, sequence length, domain structure, functional activity, etc. can be used to describe an IRE1α molecule encompassed by the present invention.

The term "XBP1" refers to a transcription factor whose gene product is a bZIP protein, which is also identified as a cellular transcription factor that binds to an enhancer in the promoter of the T cell leukemia virus type 1 promoter. It increases expression of viral proteins by acting as the DNA binding partner of a viral transactivator. It has been found that upon accumulation of unfolded proteins in the endoplasmic reticulum (ER), the mRNA of this gene is processed to an active form by an unconventional splicing mechanism that is mediated by the endonuclease inositol-requiring enzyme 1 (IRE1α). The resulting loss of 26 nt from the spliced mRNA causes a frame-shift and an isoform XBP1(S), which is the functionally active transcription factor. The isoform encoded by the unspliced mRNA, XBP1 (U), is constitutively expressed, and thought to function as a negative feedback regulator of XBP1(S), which shuts off transcription of target genes during the recovery phase of ER stress. A pseudogene of XBP1 has been identified and localized to chromosome 5. XBP1 functions as a transcription factor during endoplasmic reticulum (ER) stress by regulating the unfolded protein response (UPR). XBP1 is required for cardiac myogenesis and hepatogenesis during embryonic development, and the development of secretory tissues such as exocrine pancreas and salivary gland. XBP1 is involved in terminal differentiation of B lymphocytes to plasma cells and production of immunoglobulins. XBP1 modulates the cellular response to ER stress in a PIK3R-dependent manner. XBP1 binds to the cis-acting X box present in the promoter regions of major histocompatibility complex class II genes. XBP1 is involved in VEGF-induced endothelial cell (EC) proliferation and retinal blood vessel formation during embryonic development but also for angiogenesis in adult tissues under ischemic conditions. XBP1 also functions as a major regulator of the UPR in obesity-induced insulin resistance and type 2 diabetes for the management of obesity and diabetes prevention.

XBP1 is generally known as XBP1(S) and functions as a stress-inducible potent transcriptional activator during endoplasmic reticulum (ER) stress by inducing unfolded protein response (UPR) target genes via binding to the UPR element (UPRE). XBP1(S) up-regulates target genes encoding ER chaperones and ER-associated degradation (ERAD) components to enhance the capacity of productive folding and degradation mechanism, respectively, in order to maintain the homeostasis of the ER under ER stress. It plays a role in the production of immunoglobulins and interleukin-6 in the presence of stimuli required for plasma cell differentiation. XBP1(S) induces phospholipid biosynthesis and ER expansion. It contributes to the VEGF-induced endothelial cell (EC) growth and proliferation in a Akt/GSK-dependent and/or -independent signaling pathway, respectively, leading to beta-catenin nuclear translocation and E2F2 gene expression. XBP1(S) also promotes umbilical vein EC apoptosis and atherosclerotisis development in a caspase-dependent signaling pathway, and contributes to VEGF-induced EC proliferation and angiogenesis in adult tissues under ischemic conditions. It is involved in the regulation of endostatin-induced autophagy in EC through BECN1 transcriptional activation. XBP1(S) plays a role as an oncogene by promoting tumor progression: stimulates zinc finger protein SNAI1 transcription to induce epithelial-to-mesenchymal (EMT) transition, cell migration and invasion of breast cancer cells. It is involved in adipocyte differentiation by regulating lipogenic gene expression during lactation. XBP1(S) plays a role in the survival of both dopaminergic neurons of the substantia nigra pars compacta (SNpc), by maintaining protein homeostasis and of myeloma cells. It increases insulin sensitivity in the liver as a response to a high carbohydrate diet, resulting in improved glucose tolerance. It also improves glucose homeostasis in an ER stress- and/or insulin-independent manner through both binding and proteasome-induced degradation of the transcription factor FOXO1, hence resulting in suppression of gluconeogenic genes expression and in a reduction of blood glucose levels. XBP1(S) controls the induction of de novo fatty acid synthesis in hepatocytes by regulating the expression of a subset of lipogenic genes in an ER stress- and UPR-independent manner. It associates preferentially to the HDAC3 gene promoter region in a disturbed flow-dependent manner. It also binds to the BECN1 gene promoter region and the CDH5/VE-cadherin gene promoter region. XBP1(S) also binds to the ER stress response element (ERSE) upon ER stress, and to the 5-CCACG-3 motif in the PPARG promoter.

In addition, a minor form of XBP1, which has a very short half-life and is a very weak transcriptional activator, is known. This minor form of XBP1, also referred to as XBP1(U), plays a role in the unconventional cytoplasmic splicing processing of its own mRNA triggered by the endoplasmic reticulum (ER) transmembrane endoribonuclease ENR1: upon ER stress, the emerging XBP1 polypeptide chain, as part of a mRNA-ribosome-nascent chain (R-RNC) complex, cotranslationally recruits its own unprocessed mRNA through transient docking to the ER membrane and translational pausing, therefore facilitating efficient IRE1-mediated XBP1(S) production. In endothelial cells (EC), XBP1(U) associates with KDR (Kinase Insert Domain Receptor, also known as VEGFR2 or FLK1), and promotes IRE1-mediated XBP1(S) production in a vascular endothelial growth factor (VEGF)-dependent manner, leading to EC proliferation and angiogenesis. It also functions as a negative feed-back regulator of the potent transcription factor XBP1(S) protein levels through proteasome-mediated degradation, thus preventing the constitutive activation of the ER stress response signaling pathway. It inhibits the transactivation activity of XBP1(S) in myeloma cells when these cells are treated with proteasome inhibitors. Together with HDAC3, XBP1(U) contributes to the activation of NFE2L2-mediated HMOX1 transcription factor gene expression in a PI(3)K/mTORC2/Akt-dependent signaling pathway leading to EC survival under disturbed flow/oxidative stress. XBP1(U) binds to the ER stress response element (ERSE) upon ER stress. It also binds to the consensus 5-GATGACGTG[TG]N(3)[AT]T-3 sequence related to cAMP responsive element (CRE)-like sequences (Clauss et al. (1996) *Nucleic Acids Res.* 24:1855-1864). XBP1(U) also binds to the Tax-responsive element (TRE) present in the long terminal repeat (LTR) of T-cell leukemia virus type 1 (HTLV-I) and to the TPA response elements (TRE). XBP1(U) associates preferentially to the HDAC3 gene promoter region in a static flow-dependent manner, and binds to the CDH5/VE-cadherin gene promoter region.

In one embodiment, the human XBP1 protein has 261 amino acids with a molecular mass of 28695 Da. The known binding partners of XBP1(S) include, for example, SIRT1, PIK3R1, PIK3R2, ATF6. The known binding partners of XBP1(U) include, for example, HM13, RNF139, DERL1, HDAC3, AKT1, and FOS.

The term "XBP1" is intended to include fragments, variants (e.g., allelic variants), and derivatives thereof. Representative human XBP1 cDNA and human XBP1 protein sequences are well-known in the art and are publicly available from the National Center for Biotechnology Information (NCBI). For example, two human XBP1 isoforms are known. The XBP1 transcript variant 1 (NM_005080.3) represents the longer transcript but encodes the shorter isoform, XBP1(U) (NP_005071.2). The XBP1 transcript variant 2 (NM_001079539.1) lacks a 26 nt segment in the CDS compared to variant 1, that causes a frameshift. The resulting isoform, XBP1(S) (NP_001073007.1), has the same N-terminus, but a longer and distinct C-terminus compared to isoform XBP1 (U). Nucleic acid and polypeptide sequences of XBP1 orthologs in organisms other than humans are well known and include, for example, dog XBP1 (XM_849540.5 and XP_854633.3); cattle XBP1 (NM_001034727.3 and NP_001029899.1; and NM_001271737.1 and NP_001258666.1); mouse IRE1α (NM_001271730.1 and NP_001258659.1; NM_013842.3 and NP_038870.2), and rat XBP1 (NM_001004210.2 and NP_001004210.1; NM_001271731.1 and NP_001258660.1). Representative sequences of XBP1 orthologs are presented below in Table 1.

Anti-XBP1 antibodies suitable for detecting XBP1 protein are well-known in the art and include, for example, antibodies AM06434SU-N and AP07389PU-N(OriGene Technologies, Rockville, MD), NBP1-77681, NB100-80861, NBP1-77253, and NBP1-77252 (antibodies from Novus Biologicals, Littleton, CO), ab37152, ab109221, and ab37151, (antibodies from AbCam, Cambridge, MA), etc. In addition, reagents are well-known for detecting XBP1 expression. Moreover, multiple siRNA, shRNA, CRISPR constructs for reducing XBP1 Expression can be found in the commercial product lists of the above-referenced companies, such as siRNA products #sc-38627 and #sc-38628 and CRISPR product #sc-400131-KO-2 from Santa Cruz Biotechnology, RNAi products TR316780, SR305120, TF316780, and TL316780, and CRISPR products KN201959 and KN319483 (Origene), and multiple CRISPR products from GenScript (Piscataway, NJ). It is to be noted that the term can further be used to refer to any combination of features described herein regarding XBP1 molecules. For example, any combination of sequence composition, percentage identify, sequence length, domain structure, functional activity, etc. can be used to describe an XBP1 molecule encompassed by the present invention.

The term "c-Myc" or "MYC" refers to a proto-oncogene and encodes a nuclear phosphoprotein that plays a role in cell cycle progression, apoptosis and cellular transformation. The encoded protein forms a heterodimer with the related transcription factor MAX. This complex binds to the E box DNA consensus sequence and regulates the transcription of specific target genes. Amplification of this gene is frequently observed in numerous human cancers. Translocations involving this gene are associated with Burkitt lymphoma and multiple myeloma in human patients. There is evidence to show that translation initiates both from an upstream, in-frame non-AUG (CUG) and a downstream AUG start site, resulting in the production of two isoforms with distinct N-termini. C-Myc binds DNA in a non-specific manner, yet also specifically recognizes the core sequence 5-CAC[GA]TG-3. C-Myc activates the transcription of growth-related genes. C-Myc binds to the VEGFA promoter, promoting VEGFA production and subsequent sprouting angiogenesis (PubMed:24940000). In one embodiment, human c-Myc protein has 439 amino acids and a molecular mass of 48804 Da. The known binding partners of c-Myc include, for example, MAX, TAF1C, SPAG9, PARP10, KDM5A, KDM5B, FBXW7, PIM2, RIOX1, ABI1, TRIM6, NPM1, CIP2A, etc.

The term "c-Myc" or "MYC" is intended to include fragments, variants (e.g., allelic variants), and derivatives thereof. Representative human c-Myc cDNA and human c-Myc protein sequences are well-known in the art and are publicly available from the National Center for Biotechnology Information (NCBI). For example, two human c-Myc isoforms are known. Human c-Myc isoform 1 (NP_002458.2) is encodable by the transcript variant 1 (NM_002467.5). Human c-Myc isoform 2 (NP_001341799.1) is encodable by the transcript variant 2 (NM_001354870.1). Nucleic acid and polypeptide sequences of c-Myc orthologs in organisms other than humans are well known and include, for example, chimpanzee c-Myc (NM_001142794.1 and NP_001136266.1); monkey c-Myc (NM_001142873.1 and NP_001136345.1); dog c-Myc (NM_001003246.2 and NP_001003246.2), cattle c-Myc (NM_001046074.2 and NP_001039539.1), mouse c-Myc (NM_001177352.1 and NP_001170823.1; NM_001177353.1 and NP_001170824.1; NM_001177354.1 and NP_001170825.1; NM_010849.4 and NP_034979.3), rat c-Myc (NM_012603.2 and NP_036735.2), and chicken c-Myc (NM_001030952.1 and NP_001026123.1). Representative sequences of c-Myc orthologs are presented below in Table 1.

Anti-c-Myc antibodies suitable for detecting c-Myc protein are well-known in the art and include, for example, antibodies AM05252PU-N and AM05253PU-N(OriGene Technologies, Rockville, MD), NB600-302, NB600-335, NB600-336, and NB200-108 (antibodies from Novus Biologicals, Littleton, CO), ab32072, ab185656, and ab39688, (antibodies from AbCam, Cambridge, MA), etc. In addition, reagents are well-known for detecting c-Myc expression. Moreover, multiple siRNA, shRNA, CRISPR constructs for reducing c-Myc Expression can be found in the commercial product lists of the above-referenced companies, such as siRNA products #sc-29226 and #sc-44248 and CRISPR product #sc-400001-KO-2 from Santa Cruz Biotechnology, RNAi products TR311323, TG311323, TL311323, and TF311323, and CRISPR products KN201611 and KN310576 (Origene), and multiple CRISPR products from GenScript (Piscataway, NJ). It is to be noted that the term can further be used to refer to any combination of features described herein regarding c-Myc molecules. For example, any combination of sequence composition, percentage identify, sequence length, domain structure, functional activity, etc. can be used to describe a c-Myc molecule encompassed by the present invention.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a condition that would benefit from modulating an immune response(e.g., cancer or viral infection), such as modulators of the IRE1α-XBP1 pathway (e.g., modulators of the copy number, the expression level, and/or the activity of one or more biomarkers listed in Table 1, either alone or in combination with additional treatments). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC) and/or biomarker target, or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with a condition that would benefit from a modulation of immune response; (3) its absolute or relatively modulated presence or absence in clinical subset of patients with a condition that would benefit from modulating an immune response(e.g., those responding to modulators of the IRE1α-XBP1 pathway or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of a condition that would benefit from modulating an immune response or the likelihood of recovery from the disease. In some embodiments, the use of statistical algorithms provides a prognosis of the condition that would benefit from modulating an immune response in an individual. For example, the prognosis can be surgery, development of a clinical subtype of the condition that would benefit from modulating an immune response(e.g., cancer or viral infection), development of one or more clinical factors, or recovery from the disease.

The term "response to therapy" relates to any response of a condition that would benefit from modulating an immune response(e.g., IRE1α-XBP1 pathway modulator therapy (e.g., modulator of the copy number, the expression level, and/or the activity of one or more biomarkers listed in Table 1, either alone or in combination with additional treatments), preferably to a change in symptoms, such as reduced infection or viral load, tumor mass and/or volume after initiation of neoadjuvant or adjuvant chemotherapy, and the like. T cell function, such as CD4+ and/or CD8+ effector function, as well as antigen-specific function thereof, can be assessed according to numerous assays well-known in the art and/or described herein. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any immunomodulatory therapy. The outcome measurement may be pathologic response to therapy given in the neoadjuvant setting. Alternatively, outcome measures, such as overall survival and disease-free survival can be monitored over a period of time for subjects following immunomodulatory therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months.

The term "resistance" refers to an acquired or natural resistance of a sample or a mammal with a condition that would benefit from modulating an immune response(e.g., cancer or viral infection) to a modulator of IREα/XBP1 pathway therapy (i.e., being nonresponsive to or having reduced or limited response to the therapeutic treatment), such as having a reduced response to a therapeutic treatment by 5% or more, for example, 10%, 15%, 20%, 25%, 30%, 35%, 40%, 45%, 50%, 55%, 60%, 65%, 70%, 75%, 80%, 85%, 90%, 95%, 100%, or more, to 2-fold, 3-fold, 4-fold, 5-fold, 10-fold, 15-fold, 20-fold or more. The reduction in response can be measured by comparing with the same disease sample or mammal before the resistance is acquired, or by comparing with a different disease sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to response to therapy. For example, an anti-cancer response includes reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

The term "tolerance" or "unresponsiveness" includes refractivity of cells, such as immune cells, to stimulation, e.g., stimulation via an activating receptor or a cytokine. Unresponsiveness can occur, e.g., because of exposure to immunosuppressants or exposure to high doses of antigen. Several independent methods can induce tolerance. One mechanism is referred to as "anergy," which is defined as a state where cells persist in vivo as unresponsive cells rather than differentiating into cells having effector functions. Such refractivity is generally antigen-specific and persists after exposure to the tolerizing antigen has ceased. For example, anergy in T cells is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134). Another mechanism is referred to as "exhaustion." T cell exhaustion is a state of T cell dysfunction that arises during many chronic infections and cancer. It is defined by poor effector function, sustained expression of inhibitory receptors and a transcriptional state distinct from that of functional effector or memory T cells.

The term "peripheral blood cell subtypes" refers to cell types normally found in the peripheral blood including, but is not limited to, eosinophils, neutrophils, T cells, monocytes, NK cells, granulocytes, and B cells. The term "peripheral blood mononuclear cell (PBMC)" refers to any peripheral blood cell having a round nucleuc. PBMCs include lymphocytes (T cells, B cells, NK cells) and monocytes. PBMCs can be extracted from whole blood using ficoll, a hydrophilic polysaccharide, and gradient centrifugation, which separates the blood into a top layer of plasma, followed by a layer of PBMCs and a bottom fraction of polymorphonuclear cells (such as neutrophils and eosinophils) and erythrocytes.

The term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method encompassed by the present invention further comprises obtaining the sample from the individual prior to detecting or determining the presence or level of at least one marker in the sample.

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

"Piwi-interacting RNA (piRNA)" is the largest class of small non-coding RNA molecules. piRNAs form RNA-protein complexes through interactions with piwi proteins. These piRNA complexes have been linked to both epigenetic and post-transcriptional gene silencing of retrotransposons and other genetic elements in germ line cells, particularly those in spermatogenesis. They are distinct from microRNA (miRNA) in size (26-31 nt rather than 21-24 nt), lack of sequence conservation, and increased complexity. However, like other small RNAs, piRNAs are thought to be involved in gene silencing, specifically the silencing of transposons. The majority of piRNAs are antisense to transposon sequences, suggesting that transposons are the piRNA target. In mammals it appears that the activity of piRNAs in transposon silencing is most important during the development of the embryo, and in both *C. elegans* and humans, piRNAs are necessary for spermatogenesis. piRNA has a role in RNA silencing via the formation of an RNA-induced silencing complex (RISC).

"Aptamers" are oligonucleotide or peptide molecules that bind to a specific target molecule. "Nucleic acid aptamers" are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. "Peptide aptamers" are artificial proteins selected or engineered to bind specific target molecules. These proteins consist of one or more peptide loops of variable sequence displayed by a protein scaffold. They are typically isolated from combinatorial libraries and often subsequently improved by directed mutation or rounds of variable region mutagenesis and selection. The "Affimer protein", an evolution of peptide aptamers, is a small, highly stable protein engineered to display peptide loops which provides a high affinity binding surface for a specific target protein. It is a protein of low molecular weight, 12-14 kDa, derived from the cysteine protease inhibitor family of cystatins. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, a siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having a condition that would benefit from a modulation of immune response, to modulate the IRE1α-XBP1 pathway and thereby treat, prevent, or inhibit the condition in the subject.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

As used herein, the term "intracellular immunoglobulin molecule" is a complete immunoglobulin which is the same as a naturally-occurring secreted immunoglobulin, but which remains inside of the cell following synthesis. An "intracellular immunoglobulin fragment" refers to any fragment, including single-chain fragments of an intracellular immunoglobulin molecule. Thus, an intracellular immunoglobulin molecule or fragment thereof is not secreted or expressed on the outer surface of the cell. Single-chain intracellular immunoglobulin fragments are referred to herein as "single-chain immunoglobulins." As used herein, the term "intracellular immunoglobulin molecule or fragment thereof" is understood to encompass an "intracellular immunoglobulin," a "single-chain intracellular immunoglobulin" (or fragment thereof), an "intracellular immunoglobulin fragment," an "intracellular antibody" (or fragment thereof), and an "intrabody" (or fragment thereof). As such, the terms "intracellular immunoglobulin," "intracellular Ig," "intracellular antibody," and "intrabody" may be used interchangeably herein, and are all encompassed by the generic definition of an "intracellular immunoglobulin molecule, or fragment thereof." An intracellular immunoglobulin molecule, or fragment thereof encompassed by the present invention may, in some embodiments, comprise two or more subunit polypeptides, e.g., a "first intracellular immunoglobulin subunit polypeptide" and a "second intracellular immunoglobulin subunit polypeptide." However, in other embodiments, an intracellular immunoglobulin may be a "single-chain intracellular immunoglobulin" including only a single polypeptide. As used herein, a "single-chain intracellular immunoglobulin" is defined as any unitary fragment that has a desired activity, for example, intracellular binding to an antigen. Thus, single-chain intracellular immunoglobulins encompass those which comprise both heavy and light chain variable regions which act together to bind antigen, as well as single-chain intracellular immunoglobulins which only have a single variable region which binds antigen, for example, a "camelized" heavy chain variable region as described herein. An intracellular immunoglobulin or Ig fragment may be expressed anywhere substantially within the cell, such as in the cytoplasm, on the inner surface of the cell membrane, or in a subcellular compartment (also referred to as cell subcompartment or cell compartment) such as the nucleus, Golgi, endoplasmic reticulum, endosome, mitochondria, etc. Additional cell subcompartments include those that are described herein and well known in the art.

The term "sensitize" means to alter disease cells, such as infected or cancer cells, in a way that allows for more effective treatment of the associated condition with a therapy (e.g., IRE1α-XBP1 pathway modulator therapy (e.g., modulator of the copy number, the expression level, and/or the activity of one or more biomarkers listed in Table 1), either alone or in combination with additional treatments). In some embodiments, normal cells are not affected to an extent that causes the normal cells to be unduly injured by the therapy (e.g., IRE1α-XBP1 pathway modulator therapy (e.g., modulator of the copy number, the expression level, and/or the activity of one or more biomarkers listed in Table 1), either alone or in combination with additional treatments). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 months for human and 4-6 weeks for mouse. A composition or a method sensitizes response to a therapeutic treatment if the increase in treatment sensitivity or the reduction in resistance is 5% or more, for example, 10%, 15%, 20%, 25%, 30%, 35%, 40%, 45%, 50%, 55%, 60%, 65%, 70%, 75%, 80%, 85%, 90%, 95%, 100%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of an immunomodulatory can be equally applied to methods for sensitizing hyperproliferative or otherwise cancerous cells (e.g., resistant cells) to the therapy.

The term "subject" refers to any healthy animal, mammal or human, or any animal, mammal or human afflicted with a condition of interest (e.g., a condition that would benefit from modulating an immune response(e.g., cancer or viral infection)). The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include a condition that would benefit from modulating an immune response (e.g., cancer or viral infection) and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to therapy, probability of survival, probability of recurrence within a given time period, and the like.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods encompassed by the present invention may be administered in a sufficient amount to produce a reasonable benefit/risk ratio applicable to such treatment.

The terms "therapeutically-effective amount" and "effective amount" as used herein means that amount of a compound, material, or composition comprising a compound encompassed by the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, similarly, the $IC_{50}$ (i.e., the concentration which achieves a half-maximal effect, such as cytotoxic or cytostatic effect on cancer cells or inhibition of viral replication or load) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, an effect in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a malignancy or viral load can be achieved.

The term "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

The term "host cell" is intended to refer to a cell into which a nucleic acid encompassed by the present invention, such as a recombinant expression vector encompassed by the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
| --- | --- |
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers encompassed by the present invention and related biomarkers (e.g., biomarkers listed in Tables 1 and 2) are well known in the art and readily available on publicly available databases, such as the National Center for Biotechnology Information (NCBI). For example, exemplary nucleic acid and amino acid sequences derived from publicly available sequence databases are provided below.

TABLE 1

| SEQ ID NO: 1 Human IRE1α cDNASequence (NM_001433.4, CDS:114-3047) |
| --- |
| 1 tgcctagtca gttctgcgtc cgctgaggct cggtcaccgc ctcgctgtcg tcgcggcgcc |
| 61 cccgccccgt cctctgtccg taccgccccc ggagccaggg ccgagtcctc gccatgccgg |
| 121 cccggcggct gctgctgctg ctgacgctgc tgctgcccgg cctcgggatt tttggaagta |
| 181 ccagcacagt gacgcttcct gaaaccttgt tgtttgtgtc aacgctggat ggaagtttgc |
| 241 atgctgtcag caagaggaca ggctcaatca aatggacttt aaaagaagat ccagtcctgc |
| 301 aggtcccaac acatgtggaa gagcctgcct ttctcccaga tcctaatgat ggcagcctgt |
| 361 atacgcttgg aagcaagaat aatgaaggcc tgacgaaact tccttttacc atcccagaat |
| 421 tggtgcaggc atccccatgc cgaagttcag atggaatcct ctacatgggt aaaaagcagg |
| 481 acatctggta tgttattgac ctcctgaccg gagagaagca gcagactttg tcatcggcct |
| 541 ttgcagatag tctctgccca tcaacctctc ttctgtatct tgggcgaaca gaatacacca |
| 601 tcaccatgta cgacaccaaa acccgagagc tccgtggaa tgccacctac tttgactatg |
| 661 cggcctcact gcctgaggac gacgtggact acaagatgtc ccactttgtg tccaatggtg |
| 721 atgggctggt ggtgactgtg acagtgaat ctggggacgt cctgtggatc caaaactacg |
| 781 cctcccctgt ggtggccttt tatgtctggc agcgggaggg tctgaggaag gtgatgcaca |
| 841 tcaatgtcgc tgtggagacc ctgcgctatc tgaccttcat gtctggggag gtggggcgca |
| 901 tcacaaagtg gaagtacccg ttccccaagg agacagaggc aagagcaag ctgacgccca |
| 961 ctctgtatgt tgggaaatac tctaccagcc tctatgcctc ccctcaatg gtacacgagg |
| 1021 gggttgctgt cgtgccccgc ggcagcacac ttcctttgct ggaagggccc cagactgatg |
| 1081 gcgtcaccat tggggacaag ggggagtgtg tgatcacgcc cagcacggac gtcaagtttg |
| 1141 atcccggact caaaagcaag aacaagctca actacttgag gaattactgg cttctgatag |
| 1201 gacaccatga aaccccactg tctgcgtcta ccaagatgct ggagagattt cccaacaatc |
| 1261 tacccaaaca tcgggaaaat gtgattcctg ctgattcaga gaaaaagagc tttgaggaag |
| 1321 ttatcaacct ggttgaccag acttcagaaa acgcacctac caccgtgtct cgggatgtgg |
| 1381 aggagaagcc cgcccatgcc cctgcccggc cgaggcccc cgtggactcc atgcttaagg |
| 1441 acatggctac catcatcctg agcaccttcc tgctgattgg ctgggtggcc ttcatcatca |
| 1501 cctatccccct gagcatgcat cagcagcagc agctccagca ccagcagttc cagaaggaac |
| 1561 tggagaagat ccagctcctg cagcagcagc agcagcagct gccttccac ccacctggag |
| 1621 acacggctca ggacgcgag ctcctggaca cgtctggccc gtactcagag agctcgggca |
| 1681 ccagcagccc cagcacgtcc cccagggcct caaccactc gctctgctcc ggcagctctg |
| 1741 cctccaaggc tggcagcagc ccctccctgg aacaagacga tggagatgag gaaaccagcg |
| 1801 tggtgatagt tgggaaaatt tccttctgtc caaggatgt cctgggccat ggagctgagg |
| 1861 gcacaattgt gtacgggggc atgtttgaca accgcgacgt ggccgtgaag aggatcctcc |
| 1921 ccgagtgttt tagcttcgca gaccgtgagg tccagctgtt gcgagaatcg gatgagcacc |
| 1981 cgaacgtgat ccgctacttc tgcacggaga aggaccggga attccagtac attgccatcg |
| 2041 agctgtgtgc agccaccctg caagagtatg tggagcagaa ggactttgcg catctcggcc |
| 2101 tggagcccat caccttgctg cagcagacca cctcgggcct ggcccacctc cactccctca |
| 2161 acatcgttca cagagaccta aagccacaca acatcctcat atccatgccc aatgcacacg |
| 2221 gcaagatcaa ggccatgatc tccgacttg gcctctgcaa gaagctggca gtgggcagac |
| 2281 acagtttcag ccgccgatct ggggtgcctg gcacagaagg ctggatcgct ccagagatgc |

TABLE 1-continued

```
2341 tgagcgaaga ctgtaaggag aaccctacct acacggtgga catcttttct gcaggctgcg
2401 tcttttacta cgtaatctct gagggcagcc acccttttgg caagtccctg cagcggcagg
2461 ccaacatcct cctgggtgcc tgcagccttg actgcttgca cccagagaag cacgaagacg
2521 tcattgcacg tgaattgata gagaagatga ttgcgatgga tcctcagaaa cgcccctcag
2581 cgaagcatgt gctcaaacac ccgttcttct ggagcctaga gaagcagctc cagttcttcc
2641 aggacgtgag cgacagaata gaaaaggaat ccctggatgg cccgatcgtg aagcagttag
2701 agagaggcgg gagagccgtg gtgaagatgg actggcggga gaacatcact gtcccctcc
2761 agacagacct gcgtaaattc aggacctata aaggtggttc tgtcagagat ctcctccgag
2821 ccatgagaaa taagaagcac cactaccggg agctgcctgc agaggtgcgg gagacgctgg
2881 ggtccctccc cgacgacttc gtgtgctact tcacatctcg cttcccccac ctcctcgcac
2941 acacctaccg ggccatggag ctgtgcagcc acgagagact cttccagccc tactacttcc
3001 acgagccccc agagccccag cccccagtga ctccagacgc cctctgagcg agggcggccc
3061 ctctgttctg gtggcccag ctgtgactga gggcctggtc accacaatta gagcttgatg
3121 cctcccggct ttgcagggag accaggcttc caaaccaag tgccttgagc tgcctgctct
3181 gcagcccaca gaggacagtg ctgaccccag gaagtgggag aagtggcccc tcgtgaccta
3241 cagggaactg ggaagatgct ggccccaaaa gccttacggt catgatgtct gcaaaggagg
3301 gcctcagaga cagcgcgagt agcacccca gccatctact ggataaactt gcttcagact
3361 ttttaaattc ctgcttaatg tcagtctaca ggcctttcag gaagggagag gagggaatcg
3421 tacattttgc ttgcgtgctg ggacagctag gctgagatgc accaagtaca gccttcactg
3481 gagaccggaa ttgagaggtg ggggatgctg aggaggggga ggacggagtt cagagggtgt
3541 cgtcctgcag tgtgagattt ctcattgatc acagatgtgc ccagagtagc ccaggtcact
3601 gttaactagt gtttctgcag aggcagcagg agccatgagc atgaggtgtg cattaggga
3661 ctggtcagct atgcatgctg gcaggtgggg ttgtgtctgc aggtctcaga aatgaagagg
3721 ctgctctgtt ctggaggcag ccgtggccca gtgccagtgg ccagaacagt ggcctttggt
3781 gggtgtgtcc cgggccatct cggggtggtg ctcaggagcg cctggggcaa gaggtaaaga
3841 gttccctggc cttcaaggag agcagcgaag acccagacag gggccagcct tcaggaccag
3901 agggaggccg ccgaatggga ccctcctggt caccaggaga aagccctggg ccagcgagta
3961 ggcagtcaaa ctccttcgtc cccaaggccg gtggaacaag aggctcgtgg tgagtcaggg
4021 ccagggtggg tggccaaggc cagggtcacc gtgtgcttca tgggccagct ttttgtttt
4081 tcttggcaaa ttttaataac tatattttga ttatactgta gaatgctatg tcagcataag
4141 taagctaaac ttgaagcttt cttgtgaaga ataaatgcaa gatagaatac atcttctatt
4201 ttttgtggta ccaaaaatca ccatcccctc aagagtgttc atgtatagaa cattctctaa
4261 tgctgaagag taaaacatta tagcaacact atgtaaatgt attgaacagt atcaaagaaa
4321 tagtctctaa attgtttgta ccatattttt ttttctaaac ttaacataat ttttagcttt
4381 agtttcagtc aaaactttgt cttttctctc ccgagagcct tagaggttaa aatgcaatca
4441 gcctaccgtg taaggagatg ttgtccatgt actttctcca gccagttggg ggatcattgc
4501 agctcaggcc tggtgaactc agagattcca ttcagtatta agaatgggat tgttgaattt
4561 tactcacaga gaaatcactg tttcttcatg ttgtaagatg ttttctgttt gtgtatttgt
4621 atcatggtta ctcatcaaaa gctctcattc tgcctttgta gaattcagtt cccttccttt
4681 catcatagct aaagtgactt ttttccctac tattaacgtg atcctacatc cttaaatctc
```

TABLE 1-continued

```
4741 atcgattacc tcacttaggc cttggaacct tggcccttgg tcggtgtcct tggcgtcttc
4801 taagcaaggc tgtgcgttgt tcagaaacgt ggccagaccg catttcctgc tgctcccatg
4861 ccgcatgcca ggtggcctga gacagagctc cccatacggc tgcaaggtgc tttacctgtg
4921 ggctttggca gtaacccaag agaggatcag aaggtggaga aggtgccacg agtgatttaa
4981 caggcctgcc acagggagtg cccccagccc agctcgttct cagcacaggt tttctctttg
5041 ggagtaccca ggtgatttct agtgacccaa ttttgtgtca tctccctgtt ttagccccac
5101 ttgcctagag acaactgttt ccgatgcctt ttctgcttat catactagtt tctaaccacg
5161 cagatttctc aaaatcattt attcaatgta ttttatttga gcacttagtg tattgagcta
5221 ggcaggatat agggtgccgg agatacagcg atgaacaaga caggcaaaac ttctgctttc
5281 ctaaaacttg tgatgagaga gaacaataaa aaagtgttgc tgccacaaag aaaccaaagt
5341 gtgtggggaa gggcgcgtgt ttgcggttta catctcttct gtcccagaat cacagggatc
5401 tggtccggtc acctctggtc tttcctctta gtcgccttta ggagccctgg ttccgtcca
5461 tcctctgggg ggtttgtttg aagagatctc gtgtgggtac ttgtcatgaa aacaccttgg
5521 gcatcatctg gtgtatccag ttctagtctc gagaattctg gtttcccact gtgctcagca
5581 agtggaaagt tcttttcagg ccagaacagc tctgcaccat cacatatcgt gttgcggctt
5641 agctgtttgg tctgtagttc aggttatggg acttctccaa tcctggaagg ctgttgagct
5701 ttttagaagt actgtacgct atcttcaaga tggagcttgg tcacatctgt taggaatcca
5761 aaggacacta tgacttattt aaatcttgtc ttactaaacc tctcttgggc acgtgtgcca
5821 gaatttctct tgttgcttct tgagtctttt taatttcagt gttttttcgt ttgttttttg
5881 ttttttttgag acagagtctc gctctgtcac ccaggctgga gtgcagtggc acgacctcag
5941 ctcactgcaa cctccgcctc cttggttcaa gcaattctcc tgcctcagcc tcccgagtag
6001 ctgggattac aggtgtgtgc caccacgctc ggctaatttt ttatattttt tttagtagag
6061 acggggtttc cccatgttag gcaggatggt ctcgatctcc taacctcgtg atccgcctgc
6121 ctcagcctcc caaagtgctg ggattacagg cttgagccac cgcacccggc ctaatctcag
6181 tttttgaagt gctccacaag tcattaggca ccaaaacatt ttcacctggg gaacactggc
6241 atttccctga ttagctgtga agcaatctag tggctaagtg tgaaatcctg ggtgcgcagg
6301 tgttctcact cccgccgtgt tctcagtgca gtggtggtca gaggcccttc caggagaca
6361 tcactctgat cagttacaga tagatgttct ggaagatctg caggtgagta gatccagcag
6421 agtttcttcc caccaactct agaagaaagg gccttatcag agttgaccct gagcctttgg
6481 taaggttttg tgtgcatgcg attcagttat ctttggcaat tcttttcttg ctgcagtgag
6541 agattaattg gttgctgatc aaaccgttca tgcagatggg gggacctttg gattgtacgg
6601 ctttctcctc ttggctgctt tcttttcagg aagttggact ttggccaggt ttggcttttcc
6661 cagagccgtt cctttctctg tcctttcctt gggtcctcat ggtgtgccca ttggatcctt
6721 ggccttgtga tcctctggga actggggcc agttccactt ttgcagcctt ctgtgctgga
6781 agagaagccc agcgccctgg aaggagcctc tttaagtccc ccatgtcgct ttctctctct
6841 gctctttag tgtctgagat tgcctttctt tgaatttccc agtgtttctt ttccttgtcc
6901 cttccctcac caacctggag ttattttggt tgactatgtc ctggctttgg cttctcctgg
6961 caggaagtca tcaggcatcc tctccaggtg agccgaaatt ccaccctccc aggttggaca
7021 tcatctttta aacccaatgg tctactcccc tccttcttta tgaaacagtg atttcccgtg
7081 agtaactctg gttctgattt tttgtaccgg cgcttaaatt cttttctgtag acgttggaaa
```

TABLE 1-continued

```
7141 gccacaaaga acgtgactgc agtgagcctc ccactggagc agccttaacc aacactttgg
7201 ccaaagcccc cccacctccc ctgtgtactg tgtgtgtgtt tggtggatac agtattcctt
7261 ttcagtgtcc ctaaagctgt gatggggagt ccccacttac ctagaaagca ttaccagtca
7321 cctactctgc attctcagat gtaaaccttg tgtagtgttc ttttttgcaat gacctattta
7381 tttaacctat ttatatttat ttaatttta ctctgaaatg tatccagtta caattgtact
7441 tgcttaaagc acatcagatt tgttttggac aacaccttg accatttaa aactggaaaa
7501 gtgatactgt atccttccat gggatggatg ctttacagta gtcttattat taaagggtga
7561 ttaatttggt cggggtaaaa tgttaatttt taggtgattt ttaagaattc tgtgccatta
7621 tgtcttctgt gtggatggtt aattgtttaa ttagtacgtg ttaattgtgt gatacagtct
7681 tctttgtgga acccaaaatc ctcttttag ctttatattt tataaactgc cagattgtac
7741 aactttatg tgcattttta aagcttgaag acatgagggt cattatctaa gttaaacagc
7801 ctattttgt gcctcctgta cagttttata attctgctga tggcggcatc ttatgtcgag
7861 ccaaccacaa taaaggtagt tttagatttt ggaaaaaaaa aaaaaaaaa
```

SEQ ID NO: 2 Human IRE1α Amino Acid Sequence (NP_001424.3)

```
  1 mparrlllll tlllpglgif gststvtlpe tllfvstldg slhayskrtg sikwtlkedp
 61 vlqvpthvee paflpdpndg slytlgsknn egltklpfti pelvgaspor ssdgilymgk
121 kgdiwyvidl ltgekqqtls safadslcps tsllylgrte ytitmydtkt relrwnatyf
181 dyaaslpedd vdykmshfvs ngdglvvtvd sesgdvlwiq nyaspvvafy vwqreglrkv
241 mhinvavetl ryltfmsgev gritkwkypf pketeakskl tptlyvgkys tslyaspsmv
301 hegvavvprg stlpllegpq tdgvtigdkg ecvitpstdv kfdpglkskn klnylrnywl
361 lighhetpls astkmlerfp nnlpkhrenv ipadsekksf eevinlvdqt senapttvsr
421 dveekpahap arpeapvdsm lkdmatiils tflligwvaf iityplsmhq qqqlqhqqfq
481 kelekiqllq qqqqqlpfhp pgdtaqdgel ldtsgpyses sgtsspstsp rasnhslcsg
541 ssaskagssp sleqddgdee tsvvivgkis fcpkdvlghg aegtivyrgm fdnrdvavkr
601 ilpecfsfad revqllresd ehpnviryfc tekdrqfqyi aielcaatlq eyveqkdfah
661 lglepitllq qttsglahlh slnivhrdlk phnilismpn ahgkikamis dfglckklav
721 grhsfsrrsg vpgtegwiap emlsedcken ptytvdifsa gcvfyyvise gshpfgkslq
781 rqanillgac sldclhpekh edviarelie kmiamdpqkr psakhvlkhp ffwslekqlq
841 ffqdvsdrie kesldgpivk qlerggravv kmdwrenitv plqtdlrkfr tykggsvrdl
901 lramrnkkhh yrelpaevre tlgslpddfv cyftsrfphl lahtyramel csherlfqpy
961 yfheppepqp pvtpdal
```

SEQ ID NO: 3 Mouse IRE1α cDNA Sequence (NM_023913.2, CDS:121-3054)

```
  1 tccgtgtcca ccgatcctcc gccggtgccg cgctgtcgtt gcggcgcccc cgtccagccc
 61 tctgttcgcg cgggctccag aaccggccgg cggggcccgg agtcagggcc acgtcctgcc
121 atgccggccc ggtggctgtt gctcctgctg gcgctgctgc taccgccgcc ggcccggg
181 agttttggaa gaaccagcac agttacactg cctgagacct tgttgtttgt ctcgaccctg
241 gatggaagct tgcatgctgt tagcaagagg acgggctcca tcaagtggac tttaaaagaa
301 gatccagtcc tgcaggtccc aacacacgtg aagagccgg ctttcctccc agatcccaat
361 gatggcagtc tgtacacact tggaggcaag aacaacgaag gcctgacgaa acttcccttt
421 accatcccag aattggttca ggcctcccca tgccgaagtt cagatggaat cctctacatg
```

TABLE 1-continued

```
 481 ggtaaaaagc aagatatttg gtatgttatc gacctcctga ctggcgagaa gcagcagact
 541 ttgtcatcgg cctttgctga tagtctctgc ccatcaactt cccttctata tcttggacgg
 601 acagaataca ccatcaccat gtatgacacc aagacccggg agctccgctg aatgccacc
 661 tattttgact atgcagcctc actgccggaa gacgacgtgg actacaagat gtcccacttt
 721 gtgtccaatg gcgatggact ggtggtaact gtggacagtg aatctgggga tgtcctgtgg
 781 atccaaaact atgcctctcc tgtggtggcc ttctacgtct gcaggggga ggtcctgaga
 841 aaggtggtgc acatcaacgt tgctgtggag actctacgct acttgacctt catgtctggg
 901 gaagtggggc gcatcaccaa gtggaagtat ccattcccca aggagacaga ggccaagagc
 961 aagctaacgc ctactctgta tgttgggaag tattccacca gcctctatgc ctctccctca
1021 atggtgcatg agggggttgc tgtcgtgcct cgaggcagca ctcttccttt gctggaaggc
1081 ccccagacag atggcgtcac cattggagac aaaggagagt gtgtgatcac tcccagcaca
1141 gacctcaagt ttgaccctgg actcaaaggg aagagcaagc tgaactactt gaggaattac
1201 tggcttctca taggacacca tgaaactcct ctgtctgcat ccaccaagat gctggagaga
1261 tttcctaaca acctgcccaa acatcgagaa aatgtgattc ctgctgattc agaaaaaagg
1321 agctttgagg aagttatcaa catagttggc cagacttcag acaacacacc gaccaccgta
1381 tctcaggatg tggaggagaa gctcgctcgc gcccctgcca agcctgaggc ccccgtggac
1441 tccatgctca aggacatggc taccattatc ctgagcacct tcctgctggt tggatgggtg
1501 gcgttcatca tcacttaccc cctgagcgtg catcagcagc gtcagctcca gcaccaacag
1561 ttccagaagg agctggagaa gattcagctc ctgcagcagc agcagctgcc cttccaccca
1621 cacggagacc ttacccagga ccctgagttc ctggattcat ctggcccctt ctcagagagc
1681 tctggcacca gcagccccag cccatccccc agagcctcca accactccct ccacccagc
1741 agctctgcct ccagggccgg caccagcccc tctctggagc aggatgatga ggatgaggaa
1801 accagaatgg tgattgttgg gaaaatttca ttctgcccca aggatgtcct gggtcatgga
1861 gctgagggca caattgtata caaaggtatg tttgacaacc gagatgtggc cgtgaagagg
1921 atcctccctg agtgttttag ctttgccgac cgtgaggtcc agctgcttcg agaatcagac
1981 gagcacccaa atgtgatccg ctacttttgc acagagaagg accggcagtt ccagtacatt
2041 gctatcgagc tgtgtgcagc caccctacaa gagtatgtgg agcagaagga ctttgcccac
2101 cttggcctcg agcccatcac cctgcttcat cagaccacct caggcctggc acacctgcat
2161 tctctcaaca ttgttcacag agacctgaag ccccacaaca ttctcctctc catgcccaac
2221 gcacatggca ggatcaaggc gatgatctct gactttggcc tctgcaagaa gctggcagtg
2281 ggcaggcaca gtttcagccg ccgttcaggg gtacctggca ctgaagggtg gatcgcccca
2341 gagatgctga gtgaagactg taaggacaac cctacctaca cggtggacat cttttctgca
2401 ggctgtgtct tttactatgt catctctgag ggcaaccatc cttttggcaa atccttgcag
2461 cggcaggcca acatcctcct gggcgcctgc aaccttgact gtttccactc agacaagcat
2521 gaggacgtca ttgctcgtga attgatagag aaaatgattg ctatggatcc ccagcagcgt
2581 ccctctgcaa agcacgtgct gaaacacccc ttcttctgga gcctggagaa gcagctccag
2641 tttttccagg atgtaagtga ccgaatagaa aaggaggcct tggacggtcc aatcgtacgg
2701 cagttggaga gaggcgggag agctgtggtc aagatggact ggcgggagaa catcactgtc
2761 cccctgcaga cagatctgcg caaattcaga acctacaaag gtggctctgt gagagacctc
2821 ctccgagcca tgagaaacaa gaaacaccac taccgggagc tccccgtgga ggttcaggag
```

TABLE 1-continued

```
2881 acgctgggct ccatcccgga tgactttgtg cgctacttca cttcccgctt cccccacctc
2941 ctctctcaca cctaccaagc catggagctg tgcagacatg agagactctt tcagacctac
3001 tactggcacg agcccacaga accccagcct ccagtgattc catatgccct ctgagctagg
3061 gcagccctct ggtctggtgg ccccaataat gaccatgggc ccgatctctg cagtcatagt
3121 ttgttgcctc tgggattagc aggaagacta agcttcgcaa atcaagtgcc ttgagctgct
3181 gatctgcagc cagaagagga taacgctgat cctaggacgc aggggaagat ggtccctcat
3241 gactacagag acctgaggag atgtggccct gaaaccttgt agtgaaggac gtctacgaag
3301 gcagcctgtc ccagaggctg caaggaaac agcatcagcc tttcaccgga tgagcttgct
3361 cccacttctc tttctttcta aaattcctgt gggatggcat tttgggggc ctttcagtga
3421 gagtagagga atctggtttt gcctgcatgg tggaagcagc ctggttgggg tattgcatgt
3481 gcagcctctg atagaaatgg tttgagagat gtggggtgct aaggaagaga tgttcagagg
3541 tgttgccatg gggataggag gcacctccaa gttactgata gcccgtgttg cctcatgcag
3601 caagttgtga gagtgggttg tggagactcg ttagcaatgc tgtggacact gacatgtgct
3661 gtgggtctgg aagatgaagc agacactcag ttctggatgt ggtgctggcc cagcacagtg
3721 gcctaaaatag tggcccctga taggttgaat cctggctatg tgggccagag atgagtttcc
3781 tggccaccag gtggcagcta agaccagaca gggacagaga cagattgtca gggccagaga
3841 ggagcaacta gagggagctt cccagtcact caaagatgct aagaactaga aggtgagtga
3901 tatggtccct ctaccccaga ggccagcaga ttagcgcata gattatgaat caaggccctg
3961 ggggtagaga gccaag
```

SEQ ID NO: 4 Mouse IRE1α Amino Acid Sequence (NP_076402.1)

```
  1 mparwlllll alllpppgpg sfgrtstvtl petllfvstl dgslhayskr tgsikwtlke
 61 dpvlqvpthv eepaflpdpn dgslytlggk nnegltklpf tipelvqasp crssdgilym
121 gkkgdiwyvi dlltgekqqt lssafadslc pstsllylgr teytitmydt ktrelrwnat
181 yfdyaaslpe ddvdykmshf vsngdglvvt vdsesgdvlw iqnyaspvva fyvwqgevlr
241 kvvhinvave tlryltfmsg evgritkwky pfpketeaks kltptlyvgk ystslyasps
301 mvhegvavvp rgstlplleg pqtdgvtigd kgecvitpst dlkfdpglkg ksklnylrny
361 wllighhetp lsastkmler fpnnlpkhre nvipadsekr sfeevinivg qtsdntpttv
421 sqdveeklar apakpeapvd smlkdmatii lstfllvgwv afiityplsv hqqrqlqhqq
481 fqkelekiql lqqqqlpfhp hgdltqdpef ldssgpfses sgtsspspsp rasnhslhps
541 ssasragtsp sleqddedee trmvivgkis fcpkdvlghg aegtivykgm fdnrdvavkr
601 ilpecfsfad revqllresd ehpnviryfc tekdrqfqyi aielcaatlq eyveqkdfah
661 lglepitllh qttsglahlh slnivhrdlk phnillsmpn ahgrikamis dfglckklav
721 grhsfsrrsg vpgtegwiap emlsedckdn ptytvdifsa gcvfyyvise gnhpfgkslq
781 rqanillgac nldcfhsdkh edviarelie kmiamdpqqr psakhvlkhp ffwslekqlq
841 ffqdvsdrie kealdgpivr qlerggravv kmdwrenitv plqtdlrkfr tykggsvrdl
901 lramrnkkhh yrelpvevqe tlgsipddfv ryftsrfphl lshtyqamel crherlfqty
961 ywheptepqp pvipyal
```

SEQ ID NO: 5 Rat IRE1α cDNA Sequence (NM_001191926.1, CDS:1-2898)

```
  1 atgcgcaggt gcaatgacat acaaagtttt ggaagagcca gcacagtaac actgcctgaa
 61 gccttgttat ttgtttccac cctggacgga agtttgcatg ctgtcagcaa gaggacaggc
```

TABLE 1-continued

```
 121 tccatcaagt ggactttaaa agaagatcca gtcctgcagg tcccaacaca cgtggaagag
 181 cctgctttcc tcccagaccc caatgatggc agtctgtaca cacttggagg caagaacaat
 241 gaaggcctga cgaaacttcc ctttaccatc ccggaattgg ttcaggcatc cccatgccga
 301 agttcagatg gaattctcta catgggtaag aagcaagaca tttggtatgt catcgacctc
 361 ctgactggcg agaagcagca gactttgtca tcagccttcg cagacagtct gtgcccgtca
 421 acttcccttc tgtatcttgg acggacagaa tacaccatca ccatgtatga caccaagacc
 481 cgggagctcc gctggaatgc cacctatttt gactatgcag cctcacttcc cgaggatgac
 541 gtggactaca agatgtccca ctttgtgtcc aatggcgatg gactggtggt aactgtggac
 601 agtgaatctg gggatgtctt gtggatccaa aactatgcct ctcctgtggt ggccttctac
 661 atctggcagc gggagggcct gagaaaggtg gtgcacatca cgttgctgt ggagacccta
 721 cgctatttga ccttcatgtc tggggaagtg gggcgcatca ccaagtggaa atatccattc
 781 cccaaggaga cagaggccaa gagcaaactg acgcccactc tgtatgtggg gaagtactcc
 841 accagcctct atgcctcgcc ctcgatggtg cacgaggggg tcgctgttgt gcctcgaggc
 901 agcactcttc ctttgctcga aggacccag acagatggtg tcaccattgg agacaaagga
 961 gaatgtgtga tcactcccag cacagacctc aagtttgacc ctggactcaa aggcaagagc
1021 aagctgaact acctgaggaa ttactggctt ctcataggac accatgaaac tcctctgtct
1081 gcatccacca agatgctgga gagatttcct aacaatcttc ccaaacatcg agaaaacgtg
1141 attcctgctg attcggagaa aaggagcttt gaggaggtta tcaacctagt tggccagact
1201 tcagaaaaca caccaaccac tgtgtctcag gatgtagaag agaagctgcc ccgtgccccc
1261 gccaagccag aggcccccgt ggactccatg ctcaaggaca tggctactat tatcctgagc
1321 accttcctgc tggtcggatg ggtggcgttc atcatcactt accccctgag catgcatcag
1381 cagcgccagc tccagcacca gcagttccag aaggaactgg agaaaattca gctccttcag
1441 caacagcagc tgcccttcca cccacacgga gaccttaccc aggaccctga cttcctggat
1501 tcatctggcc tcttctcgga gagctcaggc accagcagcc ccagcccatc ccccagagcc
1561 tccaaccact cactcaactc tagcagctct gcctccaagg ctggcaccag tcctcccctg
1621 gagccagatg acgaggatga ggaaaccaga atggtgattg ttgggaaaat ctcattctgc
1681 cccaaggatg tcctgggcca tggagctgag ggcacaattg tatacaaagg tatgtttgac
1741 aaccgtgatg tggccgtgaa gaggatcctc cctgagtgtt ttagctttgc agaccgagag
1801 gtccagctgc ttcgagaatc agacgagcat ccgaatgtga tccgctactt ttgcacagag
1861 aaggaccggc agttccagta cattgccatt gagctgtgtg cagctaccct gcaggagtat
1921 gtggagcaga aggacttcgc ccaccttggc ctagagccca tcaccttgct tcatcagacc
1981 acctcaggcc tggcgcacct gcattccctc aacattgttc acagagacct gaagccccac
2041 aacattctcc tctccatgcc caacgcacat ggcaggatca aggcgatgat ctcagacttt
2101 ggcctctgca gaagctggc agtgggcagg catagtttca gccgccgttc agggggtgcct
2161 ggcactgaag gttggatcgc cccagagatg ctgagtgaag actgcaagga acccctacc
2221 tacacagtgg acatcttctc tgcaggctgt gtcttttact atgtcatctc tgagggcaac
2281 catccttttg gcaaatcctt gcagcggcag gccaacatcc tcctgggcgc ctgcagcctt
2341 gactgcttcc actcagacaa gcacgaggac gtcattgctc gtgagttgat agagaaaatg
2401 attgcaatgg atccgcagca gcgacccctcg gcaaagcacg tgctaaaaca cccattcttc
2461 tggagcctgg aaaagcagct ccagttcttc caggatgtga gtgaccgaat agaaaaggag
```

TABLE 1-continued

```
2521 tccttggatg gcccgatcgt gcggcagttg agagaggcg ggagagctgt ggttaagatg 2581 gactggcggg agaacatcac tgtccccctg cagacagatc tgcgcaaatt cagaacctat 2641 aaaggtggct ccgtccggga tctcctccga gccatgagga ataagagaca ccactaccgg 2701 gagctccctc tggaggttca ggagacgctg ggctccatcc ctgatgactt cgtgcgctac 2761 ttcacatcac gtttccccca cctcctctct cacacctacc gagccatgga actgtgcaga 2821 catgagagac ttttccagac ctactactgg cacgagccca cagaagccca gcctccaggg 2881 attccagatg ccctctgagc gagggcagcc ctctggtctg gtggccccaa caaggaccat 2941 gggcctgatc tctg
```

SEQ ID NO: 6 Rat IRE1α Amino Acid Sequence (NP_001178855.1)

```
  1 mrrondigsf grastvtlpe allfvstldg slhayskrtg sikwtlkedp vlqvpthvee 61 paflpdpndg slytlggknn egltklpfti pelvgaspor ssdgilymgk kgdiwyvidl 121 ltgekqqtls safadslcps tsllylgrte ytitmydtkt relrwnatyf dyaaslpedd 181 vdykmshfvs ngdglvvtvd sesgdvlwiq nyaspvvafy iwqreglrkv vhinvavetl 241 ryltfmsgev gritkwkypf pketeakskl tptlyvgkys tslyaspsmv hegvavvprg 301 stlpllegpq tdgvtigdkg ecvitpstdl kfdpglkgks klnylrnywl lighhetpls 361 astkmlerfp nnlpkhrenv ipadsekrsf eevinlvgqt sentpttvsq dveeklprap 421 akpeapvdsm lkdmatiils tfllvgwvaf iityplsmhq qrqlqhqqfq kelekiqllq 481 qqqlpfhphg dltqdpdfld ssglfsessg tsspspspra snhslnssss askagtspsl 541 epddedeetr mvivgkisfc pkdvlghgae gtivykgmfd nrdvavkril pecfsfadre 601 vqllresdeh pnviryfcte kdrqfqyiai elcaatlqey veqkdfahlg lepitllhqt 661 tsglahlhsl nivhrdlkph nillsmpnah grikamisdf glckklavgr hsfsrrsgvp 721 gtegwiapem lsedckenpt ytvdifsagc vfyyvisegn hpfgkslqrq anillgacsl 781 dcfhsdkhed viareliekm iamdpqqrps akhvlkhpff wslekqlqff qdvsdrieke 841 sldgpivrql erggravvkm dwrenitvpl qtdlrkfrty kggsvrdllr amrnkrhhyr 901 elplevgetl gsipddfvry ftsrfphlls htyramelcr herlfqtyyw hepteaqppg 961 ipdal
```

SEQ ID NO: 7 Human XBP1 transcript variant 2
Sequence (NM_001079539.1; CDS: 49-1179)

```
  1 ggcgctgggc ggctgcggcg cgcggtgcgc ggtgcgtagt ctggagctat ggtggtggtg 61 gcagccgcgc cgaacccggc cgacgggacc cctaaagttc tgcttctgtc ggggcagccc 121 gcctccgccg ccggagcccc ggccggccag gccctgccgc tcatggtgcc agcccagaga 181 ggggccagcc cggaggcagc gagcgggggg ctgcccagg cgcgcaagcg acagcgcctc 241 acgcacctga gccccgagga aaggcgctg aggaggaaac tgaaaaacag agtagcagct 301 cagactgcca gagatcgaaa gaaggctcga atgagtgagc tggaacagca gtggtagat 361 ttagaagaag agaaccaaaa acttttgcta gaaaatcagc ttttacgaga gaaaactcat 421 ggccttgtag ttgagaacca ggagttaaga cagcgcttgg ggatggatgc cctggttgct 481 gaagaggagg cggaagccaa ggggaatgaa gtgaggccag tggccgggtc tgctgagtcc 541 gcagcaggtg caggcccagt tgtcaccct ccagaacatc tccccatgga ttctggcggt 601 attgactctt cagattcaga gtctgatatc ctgttgggca ttctggacaa cttggacccc 661 gtcatgttct tcaaatgccc ttccccagag cctgccagcc tggaggagct cccagaggtc 721 tacccagaag gacccagttc cttaccagcc tccctttctc tgtcagtggg gacgtcatca
```

TABLE 1-continued

```
 781 gccaagctgg aagccattaa tgaactaatt cgttttgacc acatatatac caagcccta
 841 gtcttagaga taccctctga cacagagagc caagctaatg tggtagtgaa aatcgaggaa
 901 gcacctctca gccctcaga gaatgatcac cctgaattca ttgtctcagt gaaggaagaa
 961 cctgtagaag atgacctcgt tccggagctg gtatctcaa atctgctttc atccagccac
1021 tgcccaaagc catcttcctg cctactggat gcttacagtg actgtggata cgggggttcc
1081 ctttccccat tcagtgacat gtcctctctg cttggtgtaa accattcttg ggaggacact
1141 tttgccaatg aactctttcc ccagctgatt agtgtctaag gaatgatcca atactgttgc
1201 cctttccctt gactattaca ctgcctggag gatagcagag aagcctgtct gtacttcatt
1261 caaaaagcca aaatagagag tatacagtcc tagagaattc ctctatttgt tcagatctca
1321 tagatgaccc ccaggtattg tcttttgaca tccagcagtc caaggtattg agacatatta
1381 ctggaagtaa gaaatattac tataattgag aactacagct tttaagattg tacttttatc
1441 ttaaaagggt ggtagttttc cctaaaatac ttattatgta agggtcatta dacaaatgtc
1501 ttgaagtaga catggaattt atgaatggtt ctttatcatt tctcttcccc cttttttggca
1561 tcctggcttg cctccagttt taggtccttt agtttgcttc tgtaagcaac gggaacacct
1621 gctgagggg ctcttttccct catgtatact tcaagtaaga tcaagaatct tttgtgaaat
1681 tatagaaatt tactatgtaa atgcttgatg gaattttttc ctgctagtgt agcttctgaa
1741 aggtgctttc tccatttatt taaaactacc catgcaatta aaaggtacaa tgcaaaaaaa
1801 aaaaaaaaaa
```

SEQ ID NO: 8 Human XBP1 Isoform S Amino Acid Sequence (NP_001073007.1)

```
  1 mvvvaaapnp adgtpkvlll sguasaaga paggalplmv paqrgaspea asgglpqark
 61 rqrlthlspe ekalrrklkn rvaaqtardr kkarmseleq qvvdleeenq klllengllr
121 ekthglvven gelrgrlgmd alvaeeeaea kgnevrpvag saesaagagp vvtppehlpm
181 dsggidssds esdillgild nldpvmffkc pspepaslee lpevypegps slpaslslsv
241 gtssakleai nelirfdhiy tkplvleips etesganvvv kieeaplsps endhpefivs
301 vkeepveddl vpelgisnll ssshcpkpss clldaysdcg yggslspfsd mssllgvnhs
361 wedtfanelf pqlisv
```

SEQ ID NO: 9 Human XBP1 transcript variant 1 Sequence (NM_005080.3, CDS:49-834)

```
  1 ggcgctgggc ggctgcggcg cgcggtgcgc ggtgcgtagt ctggagctat ggtggtggtg
 61 gcagccgcgc cgaaccccgg cgacgggacc cctaaagttc tgcttctgtc ggggcagccc
121 gcctccgccg ccggagcccc ggccggccag gccctgccgc tcatggtgcc agcccagaga
181 ggggccagcc cggaggcagc gagcgggggg ctgccccagg cgcgcaagcg acagcgcctc
241 acgcacctga gccccgagga aaaggcgctg aggaggaaac tgaaaaacag agtagcagct
301 cagactgcca gagatcgaaa gaaggctcga atgagtgagc tggaacagca agtggtagat
361 ttagaagaag agaaccaaaa acttttgcta gaaaatcagc ttttacgaga gaaaactcat
421 ggccttgtag ttgagaacca ggagttaaga cagcgcttgg ggatggatgc cctggttgct
481 gaagaggagg cggaagccaa ggggaatgaa gtgaggccag tggccgggtc tgctgagtcc
541 gcagcactca gactacgtgc acctctgcag caggtgcagg cccagttgtc accctccag
601 aacatctccc catggattct ggcggtattg actcttcaga ttcagagtct gatatcctgt
661 tgggcattct ggacaacttg gacccagtca tgttcttcaa atgcccttcc ccagagcctg
```

TABLE 1-continued

```
 721 ccagcctgga ggagctccca gaggtctacc cagaaggacc cagttcctta ccagcctccc
 781 tttctctgtc agtggggacg tcatcagcca agctggaagc cattaatgaa ctaattcgtt
 841 ttgaccacat ataccaagc ccctagtct tagagatacc ctctgagaca gagagccaag
 901 ctaatgtggt agtgaaaatc gaggaagcac ctctcagccc ctcagagaat gatcaccctg
 961 aattcattgt ctcagtgaag gaagaacctg tagaagatga cctcgttccg gagctgggta
1021 tctcaaatct gctttcatcc agccactgcc caaagccatc ttcctgccta ctggatgctt
1081 acagtgactg tggatacggg ggttcccttt ccccattcag tgacatgtcc tctctgcttg
1141 gtgtaaacca ttcttgggag acacttttg ccaatgaact ctttccccag ctgattagtg
1201 tctaaggaat gatccaatac tgttgcccct tccttgact attacactgc ctggaggata
1261 gcagagaagc ctgtctgtac ttcattcaaa agccaaaat agagagtata cagtcctaga
1321 gaattcctct atttgttcag atctcataga tgacccccag gtattgtctt ttgacatcca
1381 gcagtccaag gtattgagac atattactgg aagtaagaaa tattactata attgagaact
1441 acagcttta agattgtact tttatcttaa aagggtggta gttttcccta aaatacttat
1501 tatgtaaggg tcattagaca aatgtcttga agtagacatg gaatttatga atggttcttt
1561 atcatttctc ttccccctt ttggcatcct ggcttgcctc cagttttagg tcctttagtt
1621 tgcttctgta agcaacggga acacctgctg aggggctct ttccctcatg tatacttcaa
1681 gtaagatcaa gaatcttttg tgaaattata gaaatttact atgtaaatgc ttgatggaat
1741 ttttcctgc tagtgtagct tctgaaaggt gctttctcca tttatttaaa actacccatg
1801 caattaaaag gtacaatgca
```

SEQ ID NO: 10 Human XBP1 Isoform U Amino Acid
Sequence (NP_005071.2)

```
  1 mvvvaaapnp adgtpkvlll sgqpasaaga paggalplmv paqrgaspea asgglpqark
 61 rqrlthlspe ekalrrklkn rvaaqtardr kkarmseleq qvvdleeenq klllengllr
121 ekthglvven gelrgrlgmd alvaeeeaea kgnevrpvag saesaalrlr aplqqvgaql
181 splqnispwi lavltlqiqs liscwafwtt wtqscssnal pgslpawrss qrstqkdpvp
241 yqppflcqwg rhqpswkplm n
```

SEQ ID NO: 11 Mouse XBP1 transcript variant 1
Sequence (NM_013842.3, CDS:355-1158)

```
  1 ctagggtaaa accgtgagac tcggtctgga aatctggcct gagaggacag cctggcaatc
 61 ctcagccggg gtggggacgt ctgccgaaga tccttggact ccagcaacca gtggtcgcca
121 ccgtccatcc accctaaggc ccagtttgca cggcggagaa cagctgtgca gccacgctgg
181 acactcaccc cgcccgagtt gagcccgccc ccgggactac aggaccaata agtgatgaat
241 atcccgcgc gtcacggagc accggccaat cgcggacggc cacgacccta gaaaggctgg
301 gcgcggcagg aggccacggg gcggtggcgg cgctggcgta gacgtttcct ggctatggtg
361 gtggtggcag cggcgccgag gcgggccacg gcggcccca aagtgctact cttatctggc
421 cagcccgcct ccggcggccg ggcgctgccg ctcatggtac ccggtccgcg ggcagcaggg
481 tcggaggcga gcgggacacc gcaggctcgc aagcggcagc ggctcacgca cctgagcccg
541 gaggagaaag cgctgcggag gaaactgaaa acagagtag cagcgcagac tgctcgagat
601 agaaagaaag cccggatgag cgagctggag cagcaagtgg tggatttgga agaagagaac
661 cacaaactcc agctagaaaa tcagcttta cgggagaaaa ctcacggcct tgtggttgag
721 aaccaggagt taagaacacg cttgggaatg gacacgctgg atcctgacga ggttccagag
```

TABLE 1-continued

```
 781 gtggaggcca aggggagtgg agtaaggctg gtggccgggt ctgctgagtc cgcagcactc
 841 agactatgtg cacctctgca gcaggtgcag gcccagttgt cacctcccca gaacatcttc
 901 ccatggactc tgacactgtt gcctcttcag attctgagtc tgatatcctt ttgggcattc
 961 tggacaagtt ggaccctgtc atgttttca aatgtccttc cccagagtct gctagtctgg
1021 aggaactccc agaggtctac ccagaaggac ctagttcctt accagcctcc ctttctctgt
1081 cagtggggac ctcatcagcc aagctggaag ccattaatga actcattcgt tttgaccatg
1141 tataccaa gcctctagtt ttagagatcc cctctgagac agagagtcaa actaacgtgg
1201 tagtgaaaat tgaggaagca cctctaagct cttcagaaga ggatcaccct gaattcattg
1261 tctcagtgaa gaaagagcct ttggaagatg acttcatccc agagctgggc atctcaaacc
1321 tgctttcatc cagccattgt ctgagaccac cttcttgcct gctggacgct cacagtgact
1381 gtggatatga gggctcccct ctcccttca gtgacatgtc ttctccactt ggtacagacc
1441 actcctggga ggatactttt gccaatgaac ttttcccca gctgattagt gtctaaagag
1501 ccacataaca ctgggcccct ttccctgacc atcacattgc ctagaggata gcataggcct
1561 gtctctttcg ttaaaagcca aagtagaggc tgtctggcct tagaagaatt cctctaaagt
1621 atttcaaatc tcatagatga cttccaagta ttgtcgtttg acactcagct gtctaaggta
1681 ttcaaaggta ttccagtact acagcttttg agattctagt ttatcttaaa ggtggtagta
1741 tactctaaat cgcagggagg gtcatttgac agttttttcc cagcctggct tcaaactatg
1801 tagccgaggc taggcagaaa cttctgaccc tcttgacccc acctcccaag tgctgggctt
1861 caccaggtgt gcacctccac acctgcccc ccgacatgtc aggtggacat gggattcatg
1921 aatggccctt agcatttctt tctccactct ctgcttccca ggtttcgtaa cctgaggggg
1981 cttgttttcc cttatgtgca ttttaaatga agatcaagaa tctttgtaaa atgatgaaaa
2041 tttactatgt aaatgcttga tggatcttct tgctagtgta gcttctagaa ggtgctttct
2101 ccatttattt aaaactaccc ttgcaattaa aaaaaaagca acacagcgtc ctgttctgtg
2161 atttctaggg ctgttgtaat ttctctttat tgttggctaa aggagtaatt tatccaacta
2221 aagtgagcat accactttt aaagtcaaaa aaaaaaaaaa aaaa
```

SEQ ID NO: 12 Mouse XBP1 Isoform U Amino Acid
Sequence (NP_038870.2)

```
  1 mvvvaaapsa ataapkvlll sgqpasggra lplmvpgpra agseasgtpq arkrqrlthl
 61 speekalrrk lknrvaaqta rdrkkarmse leqqvvdlee enhklqlenq llrekthglv
121 vengelrtrl gmdtldpdev peveakgsgv rlvagsaesa alrlcaplqq vgaglsppqn
181 ifpwtltllp lqilslisfw afwtswtlsc fsnvlpqsll vwrnsqrstq kdlvpyqppf
241 lcqwgphqps wkplmnsfvl tmytpsl
```

SEQ ID NO: 13 Mouse XBP1 transcript variant 2
Sequence (NM_001271730.1, CDS:355-1470)

```
  1 ctagggtaaa accgtgagac tcggtctgga aatctggcct gagaggacag cctggcaatc
 61 ctcagccggg gtggggacgt ctgccgaaga tccttggact ccagcaacca gtggtcgcca
121 ccgtccatcc accctaaggc ccagtttgca cggcggagaa cagctgtgca gccacgctgg
181 acactcaccc cgcccgagtt gagcccgccc cgggactac aggaccaata agtgatgaat
241 atacccgcgc gtcacggagc accggccaat cgcggacggc cacgaccta gaaaggctgg
301 gcgcggcagg aggccacggg gcggtggcgg cgctggcgta cgtttcct ggctatggtg
361 gtggtggcag cggcgccgag cgcggccacg gcggccccca aagtgctact cttatctggc
```

TABLE 1-continued

```
 421 cagcccgcct ccggcggccg ggcgctgccg ctcatggtac ccgtccgcg ggcagcaggg
 481 tcggaggcga gcgggacacc gcaggctcgc aagcggcagc ggctcacgca cctgagcccg
 541 gaggagaaag cgctgcggag gaaactgaaa aacagagtag cagcgcagac tgctcgagat
 601 agaaagaaag cccggatgag cgagctggag cagcaagtgg tggatttgga agaagagaac
 661 cacaaactcc agctagaaaa tcagctttta cgggagaaaa ctcacggcct tgtggttgag
 721 aaccaggagt taagaacacg cttgggaatg gacacgctgg atcctgacga ggttccagag
 781 gtggaggcca aggggagtgg agtaaggctg gtggccgggt ctgctgagtc cgcagcaggt
 841 gcaggcccag ttgtcacctc cccagaacat cttcccatgg actctgacac tgttgcctct
 901 tcagattctg agtctgatat ccttttgggc attctggaca agttggaccc tgtcatgttt
 961 ttcaaatgtc cttccccaga gtctgctagt ctggaggaac tcccagaggt ctacccagaa
1021 ggacctagtt ccttaccagc ctcccttttct ctgtcagtgg ggacctcatc agccaagctg
1081 gaagccatta atgaactcat tcgttttgac catgtataca ccaagcctct agttttagag
1141 atcccctctg agacagagag tcaaactaac gtggtagtga aaattgagga agcacctcta
1201 agctcttcag aagaggatca ccctgaattc attgtctcag tgaagaaaga gccttttggaa
1261 gatgacttca tcccagagct gggcatctca aacctgcttt catccagcca ttgtctgaga
1321 ccaccttctt gcctgctgga cgctcacagt gactgtggat atgagggctc cccttctccc
1381 ttcagtgaca tgtcttctcc acttggtaca gaccactcct gggaggatac ttttgccaat
1441 gaacttttcc cccagctgat tagtgtctaa agagccacat aacactgggc ccctttccct
1501 gaccatcaca ttgcctagag gatagcatag gcctgtctct ttcgttaaaa gccaaagtag
1561 aggctgtctg gccttagaag aattcctcta agtatttca aatctcatag atgacttcca
1621 agtattgtcg tttgacactc agctgtctaa ggtattcaaa ggtattccag tactacagct
1681 tttgagattc tagtttatct taaaggtggt agtatactct aaatcgcagg agggtcatt
1741 tgacagtttt ttcccagcct ggcttcaaac tatgtagccg aggctaggca gaaacttctg
1801 accctcttga ccccacctcc caagtgctgg gcttcaccag gtgtgcacct ccacacctgc
1861 cccccgaca tgtcaggtgg acatgggatt catgaatggc ccttagcatt tctttctcca
1921 ctctctgctt cccaggtttc gtaacctgag ggggcttgtt ttcccttatg tgcattttaa
1981 atgaagatca agaatctttg taaaatgatg aaaatttact atgtaaatgc ttgatggatc
2041 ttcttgctag tgtagcttct agaaggtgct ttctccattt atttaaaact acccttgcaa
2101 ttaaaaaaaa agcaacacag cgtcctgttc tgtgatttct agggctgttg taatttctct
2161 ttattgttgg ctaaaggagt aatttatcca actaaagtga gcataccact ttttaaagtc
2221 aaaaaaaaaa aaaaaaa
```

SEQ ID NO: 14 Mouse XBP1 Isoform S Amino Acid Sequence (NP_001258659.1)

```
  1 mvvvaaapsa ataapkvlll sgqpasggra lplmvpgpra agseasgtpq arkrqrlthl
 61 speekalrrk lknrvaaqta rdrkkarmse leqqvvdlee enhklqlenq llrekthglv
121 vengelrtrl gmdtldpdev peveakgsgv rlvagsaesa agagpvvtsp ehlpmdsdtv
181 assdsesdil lgildkldpv mffkcpspes asleelpevy pegpsslpas lslsvgtssa
241 kleainelir fdhvytkplv leipsetesq tnvvvkieea plssseedhp efivsvkkep
301 leddfipelg isnllsssshc lrppscllda hsdcgyegsp spfsdmsspl gtdhswedtf
361 anelfpqlis v
```

TABLE 1-continued

SEQ ID NO: 15 Rat XBP1 transcript variant 1
Sequence (NM_001004210.2, CDS:25-828)

```
   1 cgctggcgta gacgtttcct ggctatggtg gtggtggcag cggcgccgag cgcggcctcg
  61 gcggccccca aagtgctact cctatctggt cagcccgcct ccggcggccg agcgctgccg
 121 ctcatggttc cgggcccgcg agccgcaggg tcggaggcga gcgggacacc gcaggctcgc
 181 aagcggcagc gcctcacgca cctgagcccg gaggagaaag cgctgcggag gaaactgaaa
 241 aacagagtag cagcacagac tgcgcgagat agaaagaaag cccggatgag cgagctggag
 301 cagcaagtgg tggatttgga agaagagaac cagaaactcc agctagaaaa tcagctttta
 361 cgagagaaaa ctcatgggct tgtgattgag aaccaggagt taaggacacg cttggggatg
 421 aatgccctgg ttactgaaga ggtctcagag gcagagtcca aggggaatgg agtaaggctg
 481 gtggccgggt ctgctgagtc cgcagcactc agactacgtg cgcctctgca gcaggtgcag
 541 gcccagttgt cacctcccca gaacatcttc catggattc tgacgctgtt gcctcttcag
 601 attctgagtc tgatatcctt ttgggcattc tggacaagtt ggaccctgtc atgttttttca
 661 aatgtccttc cccagagtct gctaatctgg aggaactccc agaggtctac ccagaaggac
 721 ctagttcctt accagcctcc ctttctctgt cagtggggac ctcatcagcc aagctggaag
 781 ccattaatga actcattcgt tttgaccatg tatacaccaa gcctctagtc ttagagatcc
 841 cctctgagac agagagccaa actaatgtgg tagtgaaaat tgaggaagca cctctaagct
 901 cttcagaaga ggatcaccct gaattcattg tctcagtgaa gaaagaacct tggatgatg
 961 acttcattcc cgagctgggc atctcaaacc tgctttcatc cagccattgt ctgagaccac
1021 cttcctgcct gctggatgct cacagtgact gtggatatga gggctcccct tctcccttca
1081 gcgacatgtc ttctccactt ggtacagacc actcctggga ggacactttt gccaacgaac
1141 ttttccccca gctgattagt gtctaaagcc acccaccact gggctccttc cctgatcatc
1201 acactgccta gaggatagca taggcctgtc tgcttcacta aaagccaaag tagaggctat
1261 ctggccttat aagaattcct ctaaagtatt tcaaacctct tagatgactt ccaagtattg
1321 tcttttgaca ctcagctgtc tgaggtcttc aaaggtattc caatactaca gcttttgaga
1381 ttctcattat cttaaaggtg gtagcatgct ctaaatcata gggaaagtca tctgacagtt
1441 atcgttcagc ctggctatgt agccgaggct aagctgaaac ttgtgaccct cttgacccca
1501 ctcccaagtg ctggacttta ccaggtgtgc agctccacac cggcctcttc acatgtcctg
1561 aagtagacat gagagtcacc agttctttct ctcctcccg ccccacaggt ttcttttgtt
1621 tccttctaca agcagagaaa cagcaacctg aggggcctgt ccttccttat gtccagttca
1681 agtgaagatc aagaatcttt gtaaaattat tggaaattta ctgtgtaaat gcttgatgga
1741 atcttcttgc tagtgtagct tctagaaggt gctttctcca tttatttaaa actacccatg
1801 caattaaaaa agcaacgcag catccccgtt gaatgatttt aaaaaaaaaa aaaaaaaaaa
1861 aaaaaaaaaa
```

SEQ ID NO: 16 Rat XBP1 Isoform U Amino Acid
Sequence (NP_001004210.1)

```
   1 mvvvaaapsa asaapkvlll sgqpasggra lplmvpgpra agseasgtpq arkrqrlthl
  61 speekalrrk lknrvaaqta rdrkkarmse leqqvvdlee enqklqlenq llrekthglv
 121 iengelrtrl gmnalvteev seaeskgngv rlvagsaesa alrlraplqq vgaglsppqn
 181 ifpwiltllp lqilslisfw afwtswtlsc fsnvlpqsll iwrnsqrstq kdlvpyqppf
 241 lcqwgphqps wkplmnsfvl tmytpsl
```

TABLE 1-continued

SEQ ID NO: 17 Rat XBP1 transcript variant 2
Sequence (NM_001271731.1, CDS:25-1140)

```
   1 cgctggcgta gacgtttcct ggctatggtg gtggtggcag cggcgccgag cgcggcctcg
  61 gcggccccca aagtgctact cctatctggt cagcccgcct ccggcggccg agcgctgccg
 121 ctcatggttc cgggcccgcg agccgcaggg tcggaggcga gcgggacacc gcaggctcgc
 181 aagcggcagc gcctcacgca cctgagcccg gaggagaaag cgctgcggag gaaactgaaa
 241 aacagagtag cagcacagac tgcgcgagat agaaagaaag cccggatgag cgagctggag
 301 cagcaagtgg tggatttgga agaagagaac cagaaactcc agctagaaaa tcagcttta
 361 cgagagaaaa ctcatgggct tgtgattgag aaccaggagt taaggacacg cttggggatg
 421 aatgccctgg ttactgaaga ggtctcagag gcagagtcca aggggaatgg agtaaggctg
 481 gtggccgggt ctgctgagtc cgcagcaggt gcaggcccag ttgtcacctc cccagaacat
 541 cttcccatgg attctgacgc tgttgcctct tcagattctg agtctgatat ccttttgggc
 601 attctggaca gttggacccc tgtcatgttt ttcaaatgtc cttccccaga gtctgctaat
 661 ctggaggaac tcccagaggt ctacccagaa ggacctagtt ccttaccagc ctccctttct
 721 ctgtcagtgg ggacctcatc agccaagctg aagccatta atgaactcat tcgttttgac
 781 catgtataca ccaagcctct agtcttagag atcccctctg acacagagag ccaaactaat
 841 gtggtagtga aaattgagga agcacctcta agctcttcag aagaggatca ccctgaattc
 901 attgtctcag tgaagaaaga acctttggat gatgacttca ttcccgagct gggcatctca
 961 aacctgcttt catccagcca ttgtctgaga ccaccttcct gcctgctgga tgctcacagt
1021 gactgtggat atgagggctc cccttctccc ttcagcgaca tgtcttctcc acttggtaca
1081 gaccactcct gggaggacac ttttgccaac gaacttttcc cccagctgat tagtgtctaa
1141 agccacccac cactgggctc cttccctgat catcacactg cctagaggat agcataggcc
1201 tgtctgcttc actaaaagcc aaagtagagg ctatctggcc ttataagaat tcctctaaag
1261 tatttcaaac ctcttagatg acttccaagt attgtctttt gacactcagc tgtctgaggt
1321 cttcaaaggt attccaatac tacagctttt gagattctca ttatcttaaa ggtggtagca
1381 tgctctaaat catagggaaa gtcatctgac agttatcgtt cagcctggct atgtagccga
1441 ggctaagctg aaacttgtga ccctcttgac cccactccca agtgctggac tttaccaggt
1501 gtgcagctcc acaccggcct cttcacatgt cctgaagtag acatgagagt caccagttct
1561 ttctctcctc cccgccccac aggtttcttt tgtttccttc tacaagcaga gaaacagcaa
1621 cctgaggggc ctgtccttcc ttatgtccag ttcaagtgaa gatcaagaat ctttgtaaaa
1681 ttattggaaa tttactgtgt aaatgcttga tggaatcttc ttgctagtgt agcttctaga
1741 aggtgctttc tccatttatt taaaactacc catgcaatta aaaagcaac gcagcatccc
1801 cgttgaatga ttttaaaaaa aaaaaaaaa aaaaaaaaa aaaa
```

SEQ ID NO: 18 Human XBP1 Isoform S Amino Acid
Sequence (NP_001258660.1)

```
  1 mvvvaaapsa asaapkvlll sgqpasggra lplmvpgpra agseasgtpq arkrqrlthl
 61 speekalrrk lknrvaaqta rdrkkarmse leqqvvdlee enqklqlenq llrekthglv
121 iengelrtrl gmnalvteev seaeskgngv rlvagsaesa agagpvvtsp ehlpmdsdav
181 assdsesdil lgildkldpv mffkcpspes anleelpevy pegpsslpas lslsvgtssa
```

TABLE 1-continued

```
241 kleainelir fdhvytkplv leipsetesq tnvvvkieea plssseedhp efivsvkkep 301 ldddfipelg isnllssshc lrppscllda hsdcgyegsp spfsdmsspl gtdhswedtf 361 anelfpqlis v
```

SEQ ID NO: 19 Human c-Myc transcript variant 1
Sequence (NM_002467.5, CDS:1161-2525)

```
   1 ggagtttatt cataacgcgc tctccaagta tacgtggcaa tgcgttgctg ggttattta
  61 atcattctag gcatcgtttt cctccttatg cctctatcat tcctccctat ctacactaac
 121 atcccacgct ctgaacgcgc gcccattaat accttctttt cctccactct ccctgggact
 181 cttgatcaaa gcgcggccct ttccccagcc ttagcgaggc gccctgcagc tggtacgcg
 241 cgtggcgtgg cggtgggcgc gcagtgcgtt ctcggtgtgg agggcagctg ttccgcctgc
 301 gatgatttat actcacagga caaggatgcg gtttgtcaaa cagtactgct acggaggagc
 361 agcagagaaa gggagagggt tgagaggga gcaaaagaaa atggtaggcg cgcgtagtta
 421 attcatgcgg ctctcttact ctgtttacat cctagagcta gagtgctcgg ctgcccggct
 481 gagtctcctc cccaccttcc caccctccc caccctcccc ataagcgccc ctcccgggtt
 541 cccaaagcag agggcgtggg ggaaaagaaa aaagatcctc tctcgctaat ctccgcccac
 601 cggcccttta taatgcgagg gtctggacgg ctgaggaccc ccgagctgtg ctgctcgcgg
 661 ccgccaccgc cgggccccgg ccgtccctgg ctccctcct gcctcgagaa gggcagggct
 721 tctcagaggc ttggcgggaa aaagaacgga gggagggatc gcgctgagta taaaagccgg
 781 ttttcggggc tttatctaac tcgctgtagt aattccagcg agaggcagag ggagcgagcg
 841 ggcggccggc tagggtggaa gagccgggcg agcagagctg cgctgcgggc gtcctgggaa
 901 gggagatccg gagcgaatag ggggcttcgc ctctggccca gccctcccgc tgatccccca
 961 gccagcggtc cgcaacccct gccgcatcca cgaaactttg cccatagcag cgggcgggca
1021 ctttgcactg gaacttacaa cacccgagca aggacgcgac tctcccgacg cggggaggct
1081 attctgccca tttggggaca cttccccgcc gctgccagga cccgcttctc tgaaaggctc
1141 tccttgcagc tgcttagacg ctggattttt ttcgggtagt ggaaaaccag cagcctcccg
1201 cgacgatgcc cctcaacgtt agcttcacca acaggaacta tgacctcgac tacgactcgg
1261 tgcagccgta tttctactgc gacgaggagg agaacttcta ccagcagcag cagcagagcg
1321 agctgcagcc cccggcgccc agcgaggata tctggaagaa attcgagctg ctgcccaccc
1381 cgcccctgtc ccctagccgc cgctccgggc tctgctcgcc ctcctacgtt gcggtcacac
1441 ccttctccct cgggagac aacgacggcg gtggcgggag cttctccacg gccgaccagc
1501 tggagatggt gaccgagctg ctgggaggag acatggtgaa ccagagtttc atctgcgacc
1561 cggacgacga gaccttcatc aaaaacatca tcatccagga ctgtatgtgg agcggcttct
1621 cggccgccgc caagctcgtc tcagagaagc tggcctccta ccaggctgcg cgcaaagaca
1681 gcggcagccc gaaccccgcc cgcggccaca gcgtctgctc cacctccagc ttgtacctgc
1741 aggatctgag cgccgccgcc tcagagtgca tcgaccctc ggtggtcttc cctacccctc
1801 tcaacgacag cagctcgccc aagtcctgcg cctcgcaaga ctccagcgcc ttctctccgt
1861 cctcggattc tctgctctcc tcgacggagt cctccccgca gggcagcccc gagcccctgg
1921 tgctccatga ggagacaccg cccaccacca gcagcgactc tgaggaggaa caagaagatg
1981 aggaagaaat cgatgttgtt tctgtggaaa agaggcaggc tcctggcaaa aggtcagagt
2041 ctggatcacc ttctgctgga ggccacagca aacctcctca cagcccactg gtcctcaaga
```

TABLE 1-continued

```
2101 ggtgccacgt ctccacacat cagcacaact acgcagcgcc tccctccact cggaaggact 2161 atcctgctgc caagagggtc aagttggaca gtgtcagagt cctgagacag atcagcaaca 2221 accgaaaatg caccagcccc aggtcctcgg acaccgagga gaatgtcaag aggcgaacac 2281 acaacgtctt ggagcgccag aggaggaacg agctaaaacg gagctttttt gccctgcgtg 2341 accagatccc ggagttggaa acaatgaaa aggcccccaa ggtagttatc cttaaaaaag 2401 ccacagcata catcctgtcc gtccaagcag aggagcaaaa gctcatttct gaagaggact 2461 tgttgcggaa acgacgagaa cagttgaaac acaaacttga acagctacgg aactcttgtg 2521 cgtaaggaaa agtaaggaaa acgattcctt ctaacagaaa tgtcctgagc aatcacctat 2581 gaacttgttt caaatgcatg atcaaatgca acctcacaac cttggctgag tcttgagact 2641 gaaagattta gccataatgt aaactgcctc aaattggact ttgggcataa aagaactttt 2701 ttatgcttac catcttttttt ttttctttaa cagatttgta tttaagaatt gttttttaaaa 2761 aattttaaga tttacacaat gtttctctgt aaatattgcc attaaatgta aataacttta 2821 ataaaacgtt tatagcagtt acacagaatt tcaatcctag tatatagtac ctagtattat 2881 aggtactata aaccctaatt ttttttattt aagtacattt tgcttttttaa agttgatttt 2941 tttctattgt tttttagaaaa aataaaataa ctggcaaata tatcattgag ccaaatctta 3001 agttgtgaat gttttgtttc gtttcttccc cctcccaacc accaccatcc ctgtttgttt 3061 tcatcaattg ccccttcaga gggtggtctt aagaaaggca agagttttcc tctgttgaaa 3121 tgggtctggg ggccttaagg tctttaagtt cttggaggtt ctaagatgct tcctggagac 3181 tatgataaca gccagagttg acagttagaa ggaatggcag aaggcaggtg agaaggtgag 3241 aggtaggcaa aggagataca agaggtcaaa ggtagcagtt aagtacacaa agaggcataa 3301 ggactgggga gttgggagga aggtgaggaa gaaactcctg ttactttagt taaccagtgc 3361 cagtcccctg ctcactccaa acccaggaat tctgcccagt tgatggggac acggtgggaa 3421 ccagcttctg ctgccttcac aaccaggcgc cagtcctgtc catgggttat ctcgcaaacc 3481 ccagaggatc tctgggagga atgctactat taaccctatt tcacaaacaa ggaaatagaa 3541 gagctcaaag aggttatgta acttatctgt agccacgcag ataatacaaa gcagcaatct 3601 ggacccattc tgttcaaaac acttaaccct tcgctatcat gccttggttc atctgggtct 3661 aatgtgctga gatcaagaag gtttaggacc taatggacag actcaagtca taacaatgct 3721 aagctctatt tgtgtcccaa gcactcctaa gcatttttatc cctaactcta catcaacccc 3781 atgaaggaga tactgttgat ttccccatat tagaagtaga gagggaagct gaggcacaca 3841 aagactcatc cacatgccca agattcactg atagggaaaa gtggaagcga gatttgaacc 3901 caggctgttt actcctaacc tgtccaagcc acctctcaga cgacggtagg aatcagctgg 3961 ctgcttgtga gtacaggagt tacagtccag tgggttatgt ttttttaagtc tcaacatcta 4021 agcctggtca ggcatcagtt ccccttttttt tgtgatttat tttgttttta ttttgttgtt 4081 cattgtttaa tttttccttt tacaatgaga aggtcaccat cttgactcct accttagcca 4141 tttgttgaat cagactcatg acggctcctg ggaagaagcc agttcagatc ataaaataaa 4201 acatatttat tctttgtcat gggagtcatt atttagaaaa ctacaaactc tccttgcttc 4261 catccttttt tacatactca tgacacatgc tcatcctgag tccttgaaaa ggtatttttg 4321 aacatgtgta ttaattataa gcctctgaaa acctatggcc caaaccagaa atgatgttga
```

TABLE 1-continued

```
4381 ttatataggt aaatgaagga tgctattgct gttctaatta cctcattgtc tcagtctcaa
4441 agtaggtctt cagctccctg tactttggga ttttaatcta ccaccaccca taaatcaata
4501 aataattact ttctttga
```

SEQ ID NO: 20 Human c-Myc Isoform 1 Amino Acid
Sequence (NP_002458.2)

```
  1 mdffrvvenq qppatmpinv sftnrnydld ydsvqpyfyc deeenfyqqg qqselqppap
 61 sediwkkfel lptpplspsr rsglcspsyv avtpfslrgd ndggggsfst adqlemvtel
121 lggdmvngsf icdpddetfi kniiiqdcmw sgfsaaaklv seklasyqaa rkdsgspnpa
181 rghsvcstss lylqdlsaaa secidpsvvf pypindsssp kscasqdssa fspssdslls
241 stesspqgsp eplvlheetp pttssdseee qedeeeidvv svekrqapgk rsesgspsag
301 ghskpphspl vlkrchvsth qhnyaappst rkdypaakry kldsvrvlrq isnnrkctsp
361 rssdteenvk rrthnvlerq rrnelkrsff alrdqipele nnekapkvvi lkkatayils
421 vgaeeqklis eedllrkrre qlkhkleglr nsca
```

SEQ ID NO: 21 Human c-Myc transcript variant 2
Sequence (NM_001354870.1, CDS:1161-2522)

```
   1 ggagtttatt cataacgcgc tctccaagta tacgtggcaa tgcgttgctg ggttatttta
  61 atcattctag gcatcgtttt cctccttatg cctctatcat tcctccctat ctacactaac
 121 atcccacgct ctgaacgcgc gcccattaat accttctttt cctccactct ccctgggact
 181 cttgatcaaa gcgcggccct ttccccagcc ttagcgaggc gccctgcagc tggtacgcgc
 241 cgtggcgtgg cggtgggcgc gcagtgcgtt ctcggtgtgg agggcagctg ttccgcctgc
 301 gatgatttat actcacagga caaggatgcg gtttgtcaaa cagtactgct acggaggagc
 361 agcagagaaa gggagagggt ttgagaggga gcaaaagaaa atggtaggcg cgcgtagtta
 421 attcatgcgg ctctcttact ctgtttacat cctagagcta gagtgctcgg ctgcccggct
 481 gagtctcctc cccaccttcc ccaccctccc caccctcccc ataagcgccc ctcccgggtt
 541 cccaaagcag agggcgtggg ggaaaagaaa aaagatcctc tctcgctaat ctccgcccac
 601 cggcccttta taatgcgagg gtctggacgg ctgaggaccc ccgagctgtg ctgctcgcgg
 661 ccgccaccgc cgggccccgg ccgtccctgg ctcccctcct gcctcgagaa gggcagggct
 721 tctcagaggc ttggcgggaa aaagaacgga gggagggatc gcgctgagta taaaagccgg
 781 ttttcggggc tttatctaac tcgctgtagt aattccagcg agaggcagag ggagcgagcg
 841 ggcggccggc tagggtggaa gagccgggcg agcagagctg cgctgcgggc gtcctgggaa
 901 gggagatccg gagcgaatag ggggcttcgc ctctggccca gccctcccgc tgatccccca
 961 gccagcggtc cgcaacccct gccgcatcca cgaaactttg cccatagcag cgggcgggca
1021 ctttgcactg gaacttacaa cacccgagca aggacgcgac tctcccgacg cggggaggct
1081 attctgccca tttggggaca cttccccgcc gctgccagga cccgcttctc tgaaaggctc
1141 tccttgcagc tgcttagacg ctggattttt tcgggtagt ggaaaaccag cctcccgcga
1201 cgatgcccct caacgttagc ttcaccaaca ggaactatga cctcgactac gactcggtgc
1261 agccgtattt ctactgcgac gaggaggaga acttctacca gcagcagcag cagagcgagc
1321 tgcagccccc ggcgccagc gaggatatct ggaagaaatt cgagctgctg cccacccgc
1381 ccctgtcccc tagccgccgc tccgggctct gctcgccctc ctacgttgcg gtcacaccct
1441 tctcccttcg gggagacaac gacggcggtg gcggagctt ctccacgcc gaccagctgg
1501 agatggtgac cgagctgctg ggaggagaca tggtgaacca gagtttcatc tgcgacccgg
```

TABLE 1-continued

```
1561 acgacgagac cttcatcaaa aacatcatca tccaggactg tatgtggagc ggcttctcgg
1621 ccgccgccaa gctcgtctca gagaagctgg cctcctacca ggctgcgcgc aaagacagcg
1681 gcagcccgaa ccccgcccgc ggccacagcg tctgctccac ctccagcttg tacctgcagg
1741 atctgagcgc cgccgcctca gagtgcatcg acccctcggt ggtcttcccc taccctctca
1801 acgacagcag ctcgcccaag tcctgcgcct cgcaagactc cagcgccttc tctccgtcct
1861 cggattctct gctctcctcg acggagtcct ccccgcaggg cagccccgag ccctggtgc
1921 tccatgagga gacaccgccc accaccagca gcgactctga ggaggaacaa gaagatgagg
1981 aagaaatcga tgttgtttct gtggaaaaga ggcaggctcc tggcaaaagg tcagagtctg
2041 gatcaccttc tgctggaggc cacagcaaac ctcctcacag cccactggtc ctcaagaggt
2101 gccacgtctc cacacatcag cacaactacg cagcgcctcc ctccactcgg aaggactatc
2161 ctgctgccaa gagggtcaag ttggacagtg tcagagtcct gagacagatc agcaacaacc
2221 gaaaatgcac cagccccagg tcctcggaca ccgaggagaa tgtcaagagg cgaacacaca
2281 acgtcttgga gcgccagagg aggaacgagc taaaacggag cttttttgcc ctgcgtgacc
2341 agatcccgga gttggaaaac aatgaaaagg cccccaaggt agttatcctt aaaaaagcca
2401 cagcatacat cctgtccgtc caagcagagg agcaaaagct catttctgaa gaggacttgt
2461 tgcggaaacg acgagaacag ttgaaacaca aacttgaaca gctacggaac tcttgtgcgt
2521 aaggaaaagt aaggaaaacg attccttcta acagaaatgt cctgagcaat cacctatgaa
2581 cttgtttcaa atgcatgatc aaatgcaacc tcacaacctt ggctgagtct tgagactgaa
2641 agatttagcc ataatgtaaa ctgcctcaaa ttggactttg ggcataaaag aacttttta
2701 tgcttaccat cttttttttt tctttaacag atttgtattt aagaattgtt tttaaaaaat
2761 tttaagattt acacaatgtt tctctgtaaa tattgccatt aaatgtaaat aactttaata
2821 aaacgtttat agcagttaca cagaatttca atcctagtat atagtaccta gtattatagg
2881 tactataaac cctaatttt tttatttaag tacattttgc tttttaaagt tgattttttt
2941 ctattgtttt tagaaaaaat aaaataactg gcaaatatat cattgagcca atcttaagt
3001 tgtgaatgtt ttgtttcgtt tcttcccct cccaaccacc accatccctg tttgttttca
3061 tcaattgccc cttcagaggg tggtcttaag aaaggcaaga gttttcctct gttgaaatgg
3121 gtctgggggc cttaaggtct ttaagttctt ggaggttcta agatgcttcc tggagactat
3181 gataacagcc agagttgaca gttagaagga atggcagaag gcaggtgaga aggtgagagg
3241 taggcaaagg agatacaaga ggtcaaaggt agcagttaag tacacaaaga ggcataagga
3301 ctggggagtt gggaggaagg tgaggaagaa actcctgtta ctttagttaa ccagtgccag
3361 tccctgctc actccaaacc caggaattct gcccagttga tggggacacg gtgggaacca
3421 gcttctgctg ccttcacaac caggcgccag tcctgtccat gggttatctc gcaaaccca
3481 gaggatctct gggaggaatg ctactattaa ccctatttca caaacaagga aatagaagag
3541 ctcaaagagg ttatgtaact tatctgtagc cacgcagata atacaaagca gcaatctgga
3601 cccattctgt tcaaaacact taacccttcg ctatcatgcc ttggttcatc tgggtctaat
3661 gtgctgagat caagaaggtt taggacctaa tggacagact caagtcataa caatgctaag
3721 ctctatttgt gtcccaagca ctcctaagca ttttatccct aactctacat caaccccatg
3781 aaggagatac tgttgatttc cccatattag aagtagagag ggaagctgag gcacacaaag
3841 actcatccac atgcccaaga ttcactgata gggaaaagtg gaagcgagat ttgaacccag
3901 gctgtttact cctaaccctgt ccaagccacc tctcagacga cggtaggaat cagctggctg
```

TABLE 1-continued

```
3961 cttgtgagta caggagttac agtccagtgg gttatgtttt ttaagtctca acatctaagc
4021 ctggtcaggc atcagttccc cttttttttgt gatttatttt gtttttattt tgttgttcat
4081 tgtttaattt ttcctttttac aatgagaagg tcaccatctt gactcctacc ttagccattt
4141 gttgaatcag actcatgacg gctcctggga agaagccagt tcagatcata aaataaaaca
4201 tatttattct ttgtcatggg agtcattatt ttagaaacta caaactctcc ttgcttccat
4261 ccttttttac atactcatga cacatgctca tcctgagtcc ttgaaaaggt attttttgaac
4321 atgtgtatta attataagcc tctgaaaacc tatggcccaa accagaaatg atgttgatta
4381 tataggtaaa tgaaggatgc tattgctgtt ctaattacct cattgtctca gtctcaaagt
4441 aggtcttcag ctccctgtac tttgggattt taatctacca ccacccataa atcaataaat
4501 aattactttc tttga
```

SEQ ID NO: 22 Human c-Myc Isoform 2 Amino Acid
Sequence (NP_001341799.1)

```
  1 mdffrvvenq ppatmpinvs ftnrnydldy dsvqpyfycd eeenfyqqqq qselqppaps
 61 ediwkkfell ptpplspsrr sglcspsyva vtpfslrgdn dggggsfsta dqlemvtell
121 ggdmvnqsfi cdpddetfik niiiqdcmws gfsaaaklvs eklasyqaar kdsgspnpar
181 ghsvcstssl ylqdlsaaas ecidpsvvfp ypindssspk scasqdssaf spssdsllss
241 tesspqgspe plvlheetpp ttssdseeeq edeeeidvvs vekrqapgkr sesgspsagg
301 hskpphsplv lkrchvsthq hnyaappstr kdypaakrvk ldsvrvlrqi snnrkctspr
361 ssdteenvkr rthnvlerqr rnelkrsffa lrdqipelen nekapkvvil kkatayilsv
421 qaeeqklise edllrkrreq lkhkleqlrn sca
```

SEQ ID NO: 23 Mouse c-Myc transcript variant 1
Sequence (NM_010849.4, CDS:582-1946)

```
   1 cccgcccacc cgcccttat attccggggg tctgcgcggc cgaggacccc tgggctgcgc
  61 tgctctcagc tgccgggtcc gactcgcctc actcagctcc cctcctgcct cctgaagggc
 121 agggcttcgc cgacgcttgg cgggaaaaag aagggagggg agggatcctg agtcgcagta
 181 taaaagaagc ttttcgggcg ttttttttctg actcgctgta gtaattccag cgagagacag
 241 agggagtgag cggacggttg gaagagccgt gtgtgcagag ccgcgctccg gggcgaccta
 301 agaaggcagc tctggagtga gaggggcttt gcctccgagc ctgccgccca ctctccccaa
 361 ccctgcgact gacccaacat cagcggccgc aaccctcgcc gccgctggga aactttgccc
 421 attgcagcgg gcagacactt ctcactggaa cttacaatct gcgagccagg acaggactcc
 481 ccaggctccg ggagggaat ttttgtctat ttggggacag tgttctctgc ctctgcccgc
 541 gatcagctct cctgaaaaga gctcctcgag ctgtttgaag gctggatttc ctttgggcgt
 601 tggaaacccc gcagacagcc acgacgatgc ccctcaacgt gaacttcacc aacaggaact
 661 atgacctcga ctacgactcc gtacagccct atttcatctg cgacgaggaa gagaatttct
 721 atcaccagca acagcagagc gagctgcagc cgccccgcgcc cagtgaggat atctggaaga
 781 aattcgagct gcttcccacc ccgccccctgt ccccgagccg ccgctccggg ctctgctctc
 841 catcctatgt tgcggtcgct acgtccttct ccccaaggga agacgatgac ggcggcggtg
 901 gcaacttctc caccgccgat cagctggaga tgatgaccga gttacttgga ggagacatgg
 961 tgaaccagag cttcatctgc gatcctgacg acgagacctt catcaagaac atcatcatcc
1021 aggactgtat gtggagcggt ttctcagccg ctgccaagct ggtctcggag aagctggcct
1081 cctaccaggc tgcgcgcaaa gacagcacca gcctgagccc cgcccgcggg cacagcgtct
```

TABLE 1-continued

```
1141 gctccacctc cagcctgtac ctgcaggacc tcaccgccgc cgcgtccgag tgcattgacc
1201 cctcagtggt ctttccctac ccgctcaacg acagcagctc gcccaaatcc tgtacctcgt
1261 ccgattccac ggccttctct ccttcctcgg actcgctgct gtcctccgag tcctccccac
1321 gggccagccc tgagcccta gtgctgcatg aggagacacc gccaccacc agcagcgact
1381 ctgaagaaga gcaagaagat gaggaagaaa ttgatgtggt gtctgtggag aagaggcaaa
1441 cccctgccaa gaggtcggag tcgggctcat ctccatcccg aggccacagc aaacctccgc
1501 acagcccact ggtcctcaag aggtgccacg tctccactca ccagcacaac tacgccgcac
1561 cccctccac aaggaaggac tatccagctg ccaagagggc caagttggac agtggcaggg
1621 tcctgaagca gatcagcaac aaccgcaagt gctccagccc caggtcctca gacacggagg
1681 aaaacgacaa gaggcggaca cacaacgtct tggaacgtca gaggaggaac gagctgaagc
1741 gcagcttttt tgccctgcgt gaccagatcc ctgaattgga aaacaacgaa aaggccccca
1801 aggtagtgat cctcaaaaaa gccaccgcct acatcctgtc cattcaagca gacgagcaca
1861 agctcacctc tgaaaaggac ttattgagga acgacgaga acagttgaaa cacaaactcg
1921 aacagcttcg aaactctggt gcataaactg acctaactcg aggaggagct ggaatctctc
1981 gtgagagtaa ggagaacggt tccttctgac agaactgatg cgctggaatt aaaatgcatg
2041 ctcaaagcct aacctcacaa ccttggctgg ggctttggga ctgtaagctt cagccataat
2101 tttaactgcc tcaaacttaa atagtataaa agaacttttt tttatgcttc ccatctttt
2161 tcttttttcct tttaacagat ttgtatttaa ttgtttttt aaaaaaatct taaaatctat
2221 ccaattttcc catgtaaata gggccttgaa atgtaaataa ctttaataaa acgtttataa
2281 cagttacaaa agattttaag acatgtacca taattttttt tatttaaaga catttcatt
2341 tttaagttg atttttttct attgtttta gaaaaaaata aaataattgg aaaaaatac
```

SEQ ID NO: 24 Mouse c-Myc Isoform A Amino Acid
Sequence (NP_034979.3)

```
  1 mdflwaletp qtattmpinv nftnrnydld ydsvqpyfic deeenfyhqq qqselqppap
 61 sediwkkfel lptpplspsr rsglcspsyv avatsfspre dddggggnfs tadqlemmte
121 llggdmvngs ficdpddetf ikniiiqdcm wsgfsaaakl vseklasyqa arkdstslsp
181 arghsvcsts slylqdltaa asecidpsvv fpypindsss pksctssdst afspssdsll
241 ssesssprasp eplvlheetp pttssdseee qedeeeidvv svekrqtpak rsesgssspsr
301 ghskpphspl vlkrchvsth qhnyaappst rkdypaakra kldsgrvlkg isnnrkcssp
361 rssdteendk rrthnvlerq rrnelkrsff alrdqipele nnekapkvvi lkkatayils
421 iqadehklts ekdllrkrre qlkhkleglr nsga
```

SEQ ID NO: 25 Mouse c-Myc transcript variant 2
Sequence (NM_001177352.1, CDS:627-1946)

```
  1 cccgcccacc cgcccttat attccggggg tctgcgcggc cgaggacccc tgggctgcgc
 61 tgctctcagc tgccgggtcc gactcgcctc actcagctcc cctcctgcct cctgaagggc
121 agggcttcgc cgacgcttgg cgggaaaaag aagggagggg agggatcctg agtcgcagta
181 taaaagaagc ttttcgggcg ttttttttctg actcgctgta gtaattccag cgagagacag
241 agggagtgag cggacggttg gaagagccgt gtgtgcagag ccgcgctccg ggcgaccta
301 agaaggcagc tctggagtga gaggggcttt gcctccgagc ctgccgccca ctctccccaa
361 ccctgcgact gacccaacat cagcggccgc aaccctcgcc gccgctggga actttgccc
421 attgcagcgg gcagacactt ctcactggaa cttacaatct gcgagccagg acaggactcc
```

TABLE 1-continued

```
 481 ccaggctccg gggagggaat ttttgtctat ttggggacag tgttctctgc ctctgcccgc
 541 gatcagctct cctgaaaaga gctcctcgag ctgtttgaag gctggatttc ctttgggcgt
 601 tggaaacccc gcagacagcc acgacgatgc ccctcaacgt gaacttcacc aacaggaact
 661 atgacctcga ctacgactcc gtacagccct atttcatctg cgacgaggaa gagaatttct
 721 atcaccagca acagcagagc gagctgcagc cgcccgcgcc cagtgaggat atctggaaga
 781 aattcgagct gcttcccacc ccgcccctgt ccccgagccg ccgctccggg ctctgctctc
 841 catcctatgt tgcggtcgct acgtccttct ccccaaggga agacgatgac ggcggcggtg
 901 gcaacttctc caccgccgat cagctggaga tgatgaccga gttacttgga ggagacatgg
 961 tgaaccagag cttcatctgc gatcctgacg acgagacctt catcaagaac atcatcatcc
1021 aggactgtat gtggagcggt ttctcagccg ctgccaagct ggtctcggag aagctggcct
1081 cctaccaggc tgcgcgcaaa gacagcacca gcctgagccc cgcccgcggg cacagcgtct
1141 gctccacctc cagcctgtac ctgcaggacc tcaccgccgc cgcgtccgag tgcattgacc
1201 cctcagtggt ctttccctac ccgctcaacg acagcagctc gcccaaatcc tgtacctcgt
1261 ccgattccac ggccttctct ccttcctcgg actcgctgct gtcctccgag tcctccccac
1321 gggccagccc tgagcccctc gtgctgcatg aggagacacc gcccaccacc agcagcgact
1381 ctgaagaaga gcaagaagat gaggaagaaa ttgatgtggt gtctgtggag aagaggcaaa
1441 cccctgccaa gaggtcggag tcgggctcat ctccatcccg aggccacagc aaacctccgc
1501 acagcccact ggtcctcaag aggtgccacg tctccactca ccagcacaac tacgccgcac
1561 ccccctccac aaggaaggac tatccagctg ccaagagggc caagttggac agtggcaggg
1621 tcctgaagca gatcagcaac aaccgcaagt gctccagccc caggtcctca gacacggagg
1681 aaaacgacaa gaggcggaca cacaacgtct tggaacgtca gaggaggaac gagctgaagc
1741 gcagcttttt tgccctgcgt gaccagatcc ctgaattgga aaacaacgaa aaggccccca
1801 aggtagtgat cctcaaaaaa gccaccgcct acatcctgtc cattcaagca gacgagcaca
1861 agctcacctc tgaaaaggac ttattgagga acgacgaga acagttgaaa cacaaactcg
1921 aacagcttcg aaactctggt gcataaactg acctaactcg aggaggagct ggaatctctc
1981 gtgagagtaa ggaaacggt tccttctgac agaactgatg cgctggaatt aaaatgcatg
2041 ctcaaagcct aacctcacaa ccttggctgg ggctttggga ctgtaagctt cagccataat
2101 tttaactgcc tcaaacttaa atagtataaa agaactttt tttatgcttc ccatcttttt
2161 tcttttttcct tttaacagat ttgtatttaa ttgtttttt aaaaaaatct taaaatctat
2221 ccaattttcc catgtaaata gggccttgaa atgtaaataa ctttaataaa acgtttataa
2281 cagttacaaa agatttaag acatgtacca taatttttt tatttaaaga cattttcatt
2341 tttaagttg atttttttct attgttttta gaaaaaaata aaataattgg aaaaaatac
```

SEQ ID NO: 26 Mouse c-Myc Isoform B Amino Acid Sequence (NP_001170823.1)

```
  1 mpinvnftnr nydldydsvg pyficdeeen fyhqqqqsel qppapsediw kkfellptpp
 61 lspsrrsglc spsyvavats spredddgg ggnfstadql emmtellggd mvnqsficdp
121 ddetfiknii iqdcmwsgfs aaaklvsekl asyqaarkds tslsparghs vcstsslylq
181 dltaaaseci dpsvvfpypl ndssspksct ssdstafsps sdsllssess praspeplvl
241 heetppttss dseeeqedee eidvvsvekr qtpakrsesg sspsrghskp phsplvlkrc
301 hvsthqhnya appstrkdyp aakrakldsg rvlkgisnnr kcssprssdt eendkrrthn
```

TABLE 1-continued

```
361 vlerqrrnel krsffalrdq ipelenneka pkvvilkkat ayilsiqade hkltsekdll 421 rkrreqlkhk leqlrnsga
```

SEQ ID NO: 27 Mouse c-Myc transcript variant 3
Sequence (NM_001177354.1, CDS:624-1943)

```
   1 cccgcccacc cgcccttat attccggggg tctgcgcggc cgaggacccc tgggctgcgc
  61 tgctctcagc tgccgggtcc gactcgcctc actcagctcc cctcctgcct cctgaagggc
 121 agggcttcgc cgacgcttgg cgggaaaaag aagggagggg agggatcctg agtcgcagta
 181 taaaagaagc ttttcgggcg ttttttttctg actcgctgta gtaattccag cgagagacag
 241 agggagtgag cggacggttg aagagccgt gtgtgcagag ccgcgctccg gggcgaccta
 301 agaaggcagc tctggagtga gaggggcttt gcctccgagc ctgccgccca ctctccccaa
 361 ccctgcgact gacccaacat cagcggccgc aaccctcgcc gccgctggga aactttgccc
 421 attgcagcgg gcagacactt ctcactggaa cttacaatct gcgagccagg acaggactcc
 481 ccaggctccg ggagggaat ttttgtctat ttggggacag tgttctctgc ctctgcccgc
 541 gatcagctct cctgaaaaga gctcctcgag ctgtttgaag gctggatttc ctttgggcgt
 601 tggaaacccc gacagccacg acgatgcccc tcaacgtgaa cttcaccaac aggaactatg
 661 acctcgacta cgactccgta cagccctatt tcatctgcga cgaggaagag aatttctatc
 721 accagcaaca gcagagcgag ctgcagccgc ccgcgcccag tgaggatatc tggaagaaat
 781 tcgagctgct tcccaccccg cccctgtccc cgagccgccg ctccgggctc tgctctccat
 841 cctatgttgc ggtcgctacg tccttctccc caagggaaga cgatgacggc ggcggtggca
 901 acttctccac cgccgatcag ctggagatga tgaccgagtt acttggagga gacatggtga
 961 accagagctt catctgcgat cctgacgacg agaccttcat caagaacatc atcatccagg
1021 actgtatgtg gagcggtttc tcagccgctg ccaagctggt ctcggagaag ctggcctcct
1081 accaggctgc gcgcaaagac agcaccagcc tgagccccgc ccgcgggcac agcgtctgct
1141 ccacctccag cctgtacctg caggacctca ccgccgccgc gtccgagtgc attgaccct
1201 cagtggtctt tccctacccg ctcaacgaca gcagctcgcc caaatcctgt acctcgtccg
1261 attccacggc cttctctcct cctcggact cgctgctgtc ctccgagtcc tccccacggg
1321 ccagccctga gccctagtg ctgcatgagg agacaccgcc caccaccagc agcgactctg
1381 aagaagagca agaagatgag gaagaaattg atgtggtgtc tgtggagaag aggcaaaccc
1441 ctgccaagag gtcggagtcg ggctcatctc catcccgagg ccacagcaaa cctccgcaca
1501 gcccactggt cctcaagagg tgccacgtct ccactcacca gcacaactac gccgcacccc
1561 cctccacaag gaaggactat ccagctgcca gagggccaa gttggacagt ggcagggtcc
1621 tgaagcagat cagcaacaac cgcaagtgct ccagccccag gtcctcagac acggaggaaa
1681 acgacaagag gcggacacac aacgtcttgg aacgtcagag gaggaacgag ctgaagcgca
1741 gcttttttgc cctgcgtgac cagatccctg aattggaaaa caacgaaaag gcccccaagg
1801 tagtgatcct caaaaaagcc accgcctaca tcctgtccat tcaagcagac gagcacaagc
1861 tcacctctga aaaggactta ttgaggaaac gacgagaaca gttgaaacac aaactcgaac
1921 agcttcgaaa ctctggtgca taaactgacc taactcgagg aggagctgga atctctcgtg
1981 agagtaagga gaacggttcc ttctgacaga actgatgcgc tggaattaaa atgcatgctc
2041 aaagcctaac ctcacaacct ggctggggc tttgggactg taagcttcag ccataatttt
2101 aactgcctca aacttaaata gtataaaaga acttttttt atgcttccca tcttttttct
2161 ttttcctttt aacagatttg tatttaattg ttttttaaa aaaatcttaa aatctatcca
```

TABLE 1-continued

```
2221 attttcccat gtaaataggg ccttgaaatg taaataactt taataaaacg tttataacag 2281 ttacaaaaga ttttaagaca tgtaccataa ttttttttat ttaaagacat tttcattttt 2341 aaagttgatt tttttctatt gttttagaa aaaaataaaa taattggaaa aaatac
```

SEQ ID NO: 28 Mouse c-Myc Isoform C Amino Acid
Sequence (NP_001170825.1)

```
  1 mpinvnftnr nydldydsvg pyficdeeen fyhqqqqsel qppapsediw kkfellptpp 61 lspsrrsglc spsyvavats fspredddgg ggnfstadql emmtellggd mvnqsficdp 121 ddetfiknii iqdcmwsgfs aaaklvsekl asyqaarkds tslsparghs vcstsslylq 181 dltaaaseci dpsvvfpypl ndssspksct ssdstafsps sdsllssess praspeplvl 241 heetppttss dseeeqedee eidvvsvekr qtpakrsesg sspsrghskp phsplvlkrc 301 hvsthqhnya appstrkdyp aakrakldsg rvlkgisnnr kcssprssdt eendkrrthn 361 vlerqrrnel krsffalrdq ipelenneka pkvvilkkat ayilsiqade hkltsekdll 421 rkrreqlkhk leqlrnsga
```

SEQ ID NO: 29 Mouse c-Myc transcript variant 4
Sequence (NM_001177353.1, CDS:582-1943)

```
   1 cccgcccacc cgccctttat attccggggg tctgcgcggc cgaggacccc tgggctgcgc 61 tgctctcagc tgccgggtcc gactcgcctc actcagctcc cctcctgcct cctgaagggc 121 agggcttcgc cgacgcttgg cgggaaaaag aagggagggg agggatcctg agtcgcagta 181 taaaagaagc ttttcgggcg ttttttttctg actcgctgta gtaattccag cgagagacag 241 agggagtgag cggacggttg gaagagccgt gtgtgcagag ccgcgctccg ggcgaccta 301 agaaggcagc tctggagtga gaggggctttt gcctccgagc ctgccgccca ctctccccaa 361 ccctgcgact gacccaacat cagcggccgc aaccctcgcc gccgctggga aactttgccc 421 attgcagcgg gcagacactt ctcactggaa cttacaatct gcgagccagg acaggactcc 481 ccaggctccg ggagggaat ttttgtctat ttggggacag tgttctctgc ctctgcccgc 541 gatcagctct cctgaaaaga gctcctcgag ctgtttgaag gctggatttc ctttgggcgt 601 tggaaacccc gacagccacg acgatgcccc tcaacgtgaa cttcaccaac aggaactatg 661 acctcgacta cgactccgta cagcccctatt tcatctgcga cgaggaagag aatttctatc 721 accagcaaca gcagagcgag ctgcagccgc ccgcgcccag tgaggatatc tggaagaaat 781 tcgagctgct tccaccccg cccctgtccc cgagccgccg ctccgggctc tgctctccat 841 cctatgttgc ggtcgctacg tccttctccc caagggaaga cgatgacggc ggcggtggca 901 acttctccac cgccgatcag ctggagatga tgaccgagtt acttggagga gacatggtga 961 accagagctt catctgcgat cctgacgacg agaccttcat caagaacatc atcatccagg 1021 actgtatgtg gagcggtttc tcagccgctg ccaagctggt ctcggagaag ctggcctcct 1081 accaggctgc gcgcaaagac agcaccagcc tgagccccgc ccgcgggcac agcgtctgct 1141 ccacctccag cctgtacctg caggacctca ccgccgccgc gtccgagtgc attgaccct 1201 cagtggtctt tccctacccg ctcaacgaca gcagctcgcc caaatcctgt acctcgtccg 1261 attccacggc cttctctcct tcctcggact cgctgctgtc ctccgagtcc tccccacggg 1321 ccagccctga gccctagtg ctgcatgagg agacaccgcc caccaccagc agcgactctg 1381 aagaagagca agaagatgag gaagaaattg atgtggtgtc tgtggagaag aggcaaaccc 1441 ctgccaagag gtcggagtcg ggctcatctc catcccgagg ccacagcaaa cctccgcaca 1501 gcccactggt cctcaagagg tgccacgtct ccactcacca gcacaactac gccgcacccc
```

TABLE 1-continued

```
1561 cctccacaag gaaggactat ccagctgcca agagggccaa gttggacagt ggcagggtcc 1621 tgaagcagat cagcaacaac cgcaagtgct ccagcccag gtcctcagac acggaggaaa 1681 acgacaagag gcggacacac aacgtcttgg aacgtcagag gaggaacgag ctgaagcgca 1741 gcttttttgc cctgcgtgac cagatccctg aattggaaaa caacgaaaag cccccaagg 1801 tagtgatcct caaaaaagcc accgcctaca tcctgtccat tcaagcagac gagcacaagc 1861 tcacctctga aaaggactta ttgaggaaac gacgagaaca gttgaaacac aaactcgaac 1921 agcttcgaaa ctctggtgca taaactgacc taactcgagg aggagctgga atctctcgtg 1981 agagtaagga gaacggttcc ttctgacaga actgatgcgc tggaattaaa atgcatgctc 2041 aaagcctaac ctcacaacct ggctgggggc tttgggactg taagcttcag ccataatttt 2101 aactgcctca aacttaaata gtataaaaga acttttttt atgcttccca tctttttct 2161 ttttcctttt aacagatttg tatttaattg tttttttaaa aaaatcttaa aatctatcca 2221 attttcccat gtaaataggg ccttgaaatg taaataactt taataaaacg tttataacag 2281 ttacaaaaga ttttaagaca tgtaccataa ttttttttat ttaaagacat tttcattttt 2341 aaagttgatt tttttctatt gtttttagaa aaaaataaaa taattggaaa aaatac
```

SEQ ID NO: 30 Mouse c-Myc Isoform D Amino Acid
Sequence (NP_001170824.1)

```
  1 mdflwaletp tattmpinvn ftnrnydldy dsvqpyficd eeenfyhqqq qselqppaps 61 ediwkkfell ptpplspsrr sglcspsyva vatsfspred ddggggnfst adqlemmtel 121 lggdmvngsf icdpddetfi kniiiqdcmw sgfsaaaklv seklasyqaa rkdstslspa 181 rghsvcstss lylqdltaaa secidpsvvf pypindsssp ksctssdsta fspssdslls 241 sesspraspe plvlheetpp ttssdseeeq edeeeidvvs vekrqtpakr sesgsspsrg 301 hskpphsplv lkrchvsthq hnyaappstr kdypaakrak ldsgrvlkqi snnrkcsspr 361 ssdteendkr rthnvlerqr rnelkrsffa lrdqipelen nekapkvvil kkatayilsi 421 qadehkltse kdllrkrreq lkhkleqlrn sga
```

SEQ ID NO: 31 Rat c-Myc cDNA
Sequence (NM_012603.2, CDS:537-1898)

```
  1 acccccgggc tgcgctgctc tccgctgccg cctccgccgc gcccactccg ctcgcctcct 61 gcctccaaaa gggcagggct tcgccgaggc ttggcgggaa aaagaagcga ggggagggat 121 ccggagtcgc agtataaaag aagcttttcg ggcgtttttt ttctgactcg ctgtagtaat 181 tccagcgaga gacagaggga gtgagcgggc gggttggaag agcccagtgt gcagagcccc 241 actccgggct tcctaggaag gcagctctgg agtgagaagg gctttgcctc caggcttgct 301 gcctcctcga cccaatcctc ccgctgaccc aacatcagcg gtcgcaaccc tcgccgcctc 361 tgggaaactt tgcccattgc aacgggcaga cacttctcac tggaacttac aatctgcgag 421 ccaggacagg actccccagg cgcaggggag ggaatttttg tctatttggg gacagtgttc 481 tctgcctctg cccgcgatcg gctcccctga aaagagctcc tcgcgttatt tgaagcctga 541 atttcctttg ggaggtggaa aacccgacag tcacgacgat gccctcaac gtgagcttcg 601 ctaacaggaa ctatgacctc gactacgact cggtgcagcc ctatttcatc tgcgacgagg 661 aagagaattt ctatcaccag caacagcaga gcgagctgca gccgcccgca cccagtgagg 721 atatctggaa gaaattcgag ctgctgccca cccgcccct gtccccagc cgccgctccg 781 ggctctgctc tccgtcctat gttgcggtcg ctacgtcctt ctccccaagg gaggacgatg 841 acggtggcgg tggcaacttc tccaccgccg atcagctgga gatgatgacc gagctacttg
```

TABLE 1-continued

```
 901 gaggagacat ggtgaatcag agcttcatct gcgatcctga cgatgagacc ttcatcaaga
 961 acatcatcat ccaggactgt atgtggagcg gcttctcggc cgctgccaaa ctggtctccg
1021 agaagctggc ctcttaccag gctgcgcgca aagacagcac cagcctgagc cccgcccgcg
1081 ggcacagcgt ctgctccacc tccagcctgt acctgcagga cctcaccgcc gcagcgtccg
1141 agtgcatcga ccccctcagtg gtcttcccct acccgctcaa cgacagcagc tcgcccaaat
1201 cctgtacctc gtccgattcc acggccttct cttcttcctc ggactcgctg ctgtcctccg
1261 agtcctcccc acgggccacc cctgagcccc tagtgctgca tgaagagaca ccgcccacca
1321 ccagcagcga ctctgaagaa gaacaagatg atgaggaaga aattgatgtg gtgtctgtgg
1381 aaaagaggca ccccctgcc aagaggtccg agtcagggtc atccccatca agaggccaca
1441 gcaaacctcc acacagccca ctggtcctca agaggtgcca tgtctctact caccagcaca
1501 attatgcagc accccctcc acaaggaagg actatccagc tgccaagagg gccaagttgg
1561 acagtggcag ggtcctgaaa cagatcagca caaccgcaa atgctccagc cccaggtcct
1621 cagacaccga ggaaaacgac aagaggcgga cacacaacgt cttggaacgt cagaggagaa
1681 acgagctgaa gcgtagcttt tttgccctgc gcgaccagat ccctgagttg gaaaacaacg
1741 aaaaggcccc caaggtagtt atcctcaaaa aagccaccgc ctacatcctg tccgttcaag
1801 cagatgagca caaactcatc tcagaaaagg acttactgag gaaacggcga gaacagttga
1861 aacacaaact cgaacagctt cgaaactctg gtgcataaac tgaccggaag tgaggaggag
1921 ctggaatctc gagtgtaagg agaacggttc cttctgacag aacttggact tcaaaaaatg
1981 catgctcaaa gcctaacctc acaaccttgg ctggggcttt gggacttcag ccataatgtt
2041 aactgcctca aagttaaggc ataaaagaac ttttttttat gcttcccatc ttctttcttt
2101 ttcctttaac agatttgtat ttaattgttt tttttaaaaa aatcttccgg tgtacatagg
2161 gcctttaaat gtaaataact ttaataaaac gtttataaca gttatacaag attttaagac
2221 atgtatgata aaccataatt ttttttattt aaagacctt tcattttaa agttgattt
2281 tttctattgt tttagaaaa aataaaataa ttggaaaaaa tataattgag ccaactctta
2341 aaaaaaaaaa aaaaa
```

SEQ ID NO: 32 Rat c-Myc Amino Acid Sequence (NP_036735.2)

```
  1 mnflwevenp tvttmpinvs fanrnydldy dsvqpyficd eeenfyhqqq qselqppaps
 61 ediwkkfell ptpplspsrr sglcspsyva vatsfspred ddggggnfst adqlemmtel
121 lggdmvngsf icdpddetfi kniiiqdcmw sgfsaaaklv seklasyqaa rkdstslspa
181 rghsvcstss lylqdltaaa secidpsvvf pypindsssp ksctssdsta fssssdslls
241 sesspratpe plvlheetpp ttssdseeeq ddeeeidvvs vekrqppakr sesgsspsrg
301 hskpphsplv lkrchvsthq hnyaappstr kdypaakrak ldsgrvlkqi snnrkcsspr
361 ssdteendkr rthnvlerqr rnelkrsffa lrdqipelen nekapkvvil kkatayilsv
421 qadehklise kdllrkrreq lkhkleqlrn sga
```

Included in Table 1 are nucleic acid molecules comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of any SEQ ID NO listed in Table 1. Such nucleic acid molecules can encode a polypeptide having a function of the full-length polypeptide as described further herein.

Included in Table 1 are polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1. Such polypeptides can have a function of the full-length polypeptide as described further herein.

II. Agents that Modulate Immune Responses

It is demonstrated herein that IRE1α-XBP1-cMyc axis plays an important role in NK cell-mediated immunity, such that modulating IRE1α-XBP1 pathway can modulate immune responses. Thus, the agents encompassed by the present invention described herein are IRE1α-XBP1 pathway modulators (e.g., modulator of the copy number, the expression, and/or the activity of one or more biomarkers listed in Table 1) that can modulate the immune responses and, thereby treating a subject with a condition that would benefit from a modulation of immune responses. In one embodiment, the agent increases the copy number, the expression, and/or the activity of one or more biomarkers listed in Table 1 and thereby treat a subject with a condition that would benefit from upregulation of an immune response. In another embodiment, the agent decreases the copy number, the expression, and/or the activity of one or more biomarkers listed in Table 1 and thereby treat a subject with a condition that would benefit from downregulation of an immune response. Agents that modulate (e.g., increase or decrease) the copy number, the expression, and/or the activity of one or more biomarkers listed in Table 1 can do so either directly or indirectly.

Agents useful in the methods encompassed by the present invention include antibodies, small molecules, peptides, peptidomimetics, natural ligands, derivatives of natural ligands, etc. that can bind and/or modulate one or more biomarkers listed in Table 1, or fragments thereof; RNA interference, antisense, nucleic acid aptamers, nucleic acid, polypeptide, etc. that can modulate the expression and/or activity of one or more biomarkers listed in Table 1, or fragments thereof.

In one embodiment, isolated nucleic acid molecules that specifically hybridize with or encode one or more biomarkers listed in Table 1 or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecules corresponding to one or more biomarkers listed in Table 1 can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a lymphoma cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule encompassed by the present invention, e.g., a nucleic acid molecule having the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence of one or more biomarkers listed in Table for a portion thereof (i.e., 100, 200, 300, 400, 450, 500, or more nucleotides), can be isolated using standard molecular biology techniques and the sequence information provided herein. For example, a human cDNA can be isolated from a human cell line (from Stratagene, LaJolla, CA, or Clontech, Palo Alto, CA) using all or portion of the nucleic acid molecule, or fragment thereof, as a hybridization probe and standard hybridization techniques (i.e., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, NY, 1989). Moreover, a nucleic acid molecule encompassing all or a portion of the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence, or fragment thereof, can be isolated by the polymerase chain reaction using oligonucleotide primers designed based upon one or more biomarkers listed in Table 1, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, MD; or AMV reverse transcriptase, available from Seikagaku America, Inc., St. Petersburg, FL). Synthetic oligonucleotide primers for PCR amplification can be designed according to well-known methods in the art. A nucleic acid encompassed by the present invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequence of one or more biomarkers listed in Table 1 can be prepared by standard synthetic techniques, i.e., using an automated DNA synthesizer.

Probes based on the nucleotide sequences of one or more biomarkers listed in Table 1 can be used to detect or confirm the desired transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express one or more biomarkers listed in Table 1, such as by measuring a level of nucleic acid of one or more biomarkers listed in Table 1 in a sample of cells from a subject, i.e., detecting mRNA levels of one or more biomarkers listed in Table 1.

Nucleic acid molecules encoding proteins corresponding to one or more biomarkers listed in Table 1 from different species are also contemplated. For example, rat or monkey cDNA can be identified based on the nucleotide sequence of a human and/or mouse sequence and such sequences are well-known in the art. In one embodiment, the nucleic acid molecule(s) encompassed by the present invention encodes a protein or portion thereof which includes an amino acid sequence which is sufficiently homologous to an amino acid sequence of one or more biomarkers listed in Table 1, such that the protein or portion thereof modulates (e.g., enhance), one or more of the following biological activities: a) binding to the biomarker; b) modulating the copy number of the biomarker; c) modulating the expression level of the biomarker; and d) modulating the activity level of the biomarker.

As used herein, the language "sufficiently homologous" refers to proteins or portions thereof which have amino acid sequences which include a minimum number of identical or equivalent (e.g., an amino acid residue which has a similar side chain as an amino acid residue in one or more biomarkers listed in Table 1, or fragment thereof) amino acid residues to an amino acid sequence of the biomarker, or fragment thereof, such that the protein or portion thereof modulates (e.g., enhance) one or more of the following biological activities: a) binding to the biomarker; b) modulating the copy number of the biomarker; c) modulating the expression level of the biomarker; and d) modulating the activity level of the biomarker.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of the biomarker, or a fragment thereof.

Portions of proteins encoded by nucleic acid molecules of one or more biomarkers listed in Table 1 are preferably biologically active portions of the protein. As used herein, the term "biologically active portion" of one or more biomarkers listed in Table 1 is intended to include a portion, e.g., a domain/motif, that has one or more of the biological activities of the full-length protein.

Standard binding assays, e.g., immunoprecipitations and yeast two-hybrid assays, as described herein, or functional assays, e.g., RNAi or overexpression experiments, can be performed to determine the ability of the protein or a biologically active fragment thereof to maintain a biological activity of the full-length protein.

The invention further encompasses nucleic acid molecules that differ from the nucleotide sequence of one or more biomarkers listed in Table 1, or fragment thereof due to degeneracy of the genetic code and thus encode the same protein as that encoded by the nucleotide sequence, or fragment thereof. In another embodiment, an isolated nucleic acid molecule encompassed by the present invention has a nucleotide sequence encoding a protein having an amino acid sequence of one or more biomarkers listed in Table 1, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of one or more biomarkers listed in Table 1, or fragment thereof. In another embodiment, a nucleic acid encoding a polypeptide consists of nucleic acid sequence encoding a portion of a full-length fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of one or more biomarkers listed in Table 1 may exist within a population (e.g., a mammalian and/or human population). Such genetic polymorphisms may exist among individuals within a population due to natural allelic variation. As used herein, the terms "gene" and "recombinant gene" refer to nucleic acid molecules comprising an open reading frame encoding one or more biomarkers listed in Table 1, preferably a mammalian, e.g., human, protein. Such natural allelic variations can typically result in 1-5% variance in the nucleotide sequence of one or more biomarkers listed in Table 1. Any and all such nucleotide variations and resulting amino acid polymorphisms in one or more biomarkers listed in Table 1 that are the result of natural allelic variation and that do not alter the functional activity of one or more biomarkers listed in Table 1 are intended to be within the scope encompassed by the present invention. Moreover, nucleic acid molecules encoding proteins of one or more biomarkers listed in Table 1 from other species.

In addition to naturally-occurring allelic variants of one or more biomarkers listed in Table 1 that may exist in the population, the skilled artisan will further appreciate that changes can be introduced by mutation into the nucleotide sequence, or fragment thereof, thereby leading to changes in the amino acid sequence of the encoded one or more biomarkers listed in Table 1, without altering the functional ability of one or more biomarkers listed in Table 1. For example, nucleotide substitutions leading to amino acid substitutions at "non-essential" amino acid residues can be made in the sequence, or fragment thereof. A "non-essential" amino acid residue is a residue that can be altered from the wild-type sequence of one or more biomarkers listed in Table 1 without altering the activity of one or more biomarkers listed in Table 1, whereas an "essential" amino acid residue is required for the activity of one or more biomarkers listed in Table 1. Other amino acid residues, however, (e.g., those that are not conserved or only semi-conserved between mouse and human) may not be essential for activity and thus are likely to be amenable to alteration without altering the activity of one or more biomarkers listed in Table 1.

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a protein homologous to one or more biomarkers listed in Table 1, or fragment thereof, can be created by introducing one or more nucleotide substitutions, additions or deletions into the nucleotide sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in one or more biomarkers listed in Table 1 is preferably replaced with another amino acid residue from the same side chain family. Alternatively, in another embodiment, mutations can be introduced randomly along all or part of the coding sequence of one or more biomarkers listed in Table 1, such as by saturation mutagenesis, and the resultant mutants can be screened for an activity described herein to identify mutants that retain desired activity. Following mutagenesis, the encoded protein can be expressed recombinantly according to well-known methods in the art and the activity of the protein can be determined using, for example, assays described herein.

The levels of one or more biomarkers listed in Table 1 may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, the levels of one or more biomarkers listed in Table 1 are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well-known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding one or more biomarkers listed in Table 1. Other suitable probes for use in the diagnostic assays encompassed by the present invention are described herein. Hybridization of an mRNA with the probe indicates that one or more biomarkers listed in Table 1 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of one or more biomarkers listed in Table 1 mRNA expression levels.

An alternative method for determining mRNA expression level in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or viceversa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to mRNA of one or more biomarkers listed in Table 1.

As an alternative to making determinations based on the absolute expression level, determinations may be based on the normalized expression level of one or more biomarkers listed in Table 1. Expression levels are normalized by correcting the absolute expression level by comparing its expression to the expression of a non-biomarker gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a protein corresponding to one or more biomarkers listed in Table 1 can also be detected and/or quantified by detecting or quantifying the expressed polypeptide. The polypeptide can be detected and quantified by any of a number of means well-known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (MA), enzyme-linked immunosorbent assays (ELISAs), immunofluorescent assays, Western blotting, and the like. A skilled artisan can readily adapt known protein/antibody detection methods for use in determining whether cells express the biomarker of interest.

The present invention further provides soluble, purified and/or isolated polypeptide forms of one or more biomarkers listed in Table 1, or fragments thereof. In addition, it is to be understood that any and all attributes of the polypeptides described herein, such as percentage identities, polypeptide lengths, polypeptide fragments, biological activities, antibodies, etc. can be combined in any order or combination with respect to one or more biomarkers listed in Table 1.

In one aspect, a polypeptide may comprise a full-length amino acid sequence corresponding to one or more biomarkers listed in Table 1 or a full-length amino acid sequence with 1 to about 20 conservative amino acid substitutions. An amino acid sequence of any described herein can also be at least 50, 55, 60, 65, 70, 75, 80, 85, 90, 91, 92, 93, 94, 95, 96, 97, 98, 99, or 99.5% identical to the full-length sequence of one or more biomarkers listed in Table 1, which is either described herein, well-known in the art, or a fragment thereof. In another aspect, the present invention contemplates a composition comprising an isolated polypeptide corresponding to polypeptide of one or more biomarkers listed in Table 1 and less than about 25%, or alternatively 15%, or alternatively 5%, contaminating biological macromolecules or polypeptides.

The present invention further provides compositions related to producing, detecting, or characterizing such polypeptides, or fragment thereof, such as nucleic acids, vectors, host cells, and the like. Such compositions may serve as compounds that modulate the expression and/or activity of one or more biomarkers listed in Table 1.

An isolated polypeptide or a fragment thereof (or a nucleic acid encoding such a polypeptide) corresponding to one or more biomarkers listed in Table 1, can be used as an immunogen to generate antibodies that bind to said immunogen, using standard techniques for polyclonal and monoclonal antibody preparation according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, an antibody, especially an interbody, binds substantially specifically to one or more biomarkers listed in Table 1, and inhibits or blocks its biological function. In another embodiment, an antibody, especially an interbody, binds substantially specifically to a binding partner of one or more biomarkers listed in Table 1, and inhibits or blocks its biological function, such as by interrupting its interaction to one or more biomarkers listed in Table 1.

Antibodies for use according to the present invention can be generated according to well-known methods in the art. For example, a polypeptide immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today*

4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well-known (see generally Kenneth, R. H. in *Monoclonal Antibodies: A New Dimension In Biological Analyses*, Plenum Publishing Corp., New York, NY (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well-known protocols used for fusing lymphocytes and immortalized cell lines can be applied for the purpose of generating a monoclonal antibody against one or more biomarkers listed in Table 1, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation encompassed by the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, MD Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody encompassed by the present invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology (NY)* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology (NY)* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Since it is well-known in the art that antibody heavy and light chain CDR3 domains play a particularly important role in the binding specificity/affinity of an antibody for an antigen, the recombinant monoclonal antibodies encompassed by the present invention prepared as set forth above preferably comprise the heavy and light chain CDR3s of variable regions of antibodies of interest. The antibodies further can comprise the CDR2s of variable regions encompassed by the present invention. The antibodies further can comprise the CDR1s of variable regions encompassed by the present invention. In other embodiments, the antibodies can comprise any combinations of the CDRs.

The CDR1, 2, and/or 3 regions of the engineered antibodies described above can comprise the exact amino acid sequence(s) as those of variable regions encompassed by the present invention. However, the ordinarily skilled artisan will appreciate that some deviation from the exact CDR sequences may be possible while still retaining the ability of the antibody to bind a target of interest, such as one or more biomarkers listed in Table 1 and/or one or more natural binding partners effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs encompassed by the present invention.

For example, the structural features of non-human or human antibodies (e.g., a rat anti-mouse/anti-human antibody) can be used to create structurally related human antibodies, especially introbodies, that retain at least one functional property of the antibodies encompassed by the present invention, such as binding to one or more biomarkers listed in Table 1, binding partners/substrates of one or more biomarkers listed in Table 1, and/or an immune checkpoint. Another functional property includes inhibiting binding of the original known, non-human or human antibodies in a competition ELISA assay.

A skilled artisan will note that such percentage homology is equivalent to and can be achieved by introducing 1, 2, 3, 4, 5, 6, 7, 8, 9, 10, or more conservative amino acid substitutions within a given CDR.

The monoclonal antibodies encompassed by the present invention can comprise a heavy chain, wherein the variable domain comprises at least a CDR having a sequence selected from the group consisting of the heavy chain variable domain CDRs described herein, and a light chain, wherein the variable domain comprises at least a CDR having a sequence selected from the group consisting of the light chain variable domain CDRs described herein.

Such monoclonal antibodies can comprise a light chain, wherein the variable domain comprises at least a CDR having a sequence selected from the group consisting of CDR-L1, CDR-L2, and CDR-L3, as described herein; and/ or a heavy chain, wherein the variable domain comprises at least a CDR having a sequence selected from the group consisting of CDR-H1, CDR-H2, and CDR-H3, as described herein. In some embodiments, the monoclonal antibodies capable of binding one or more biomarkers listed in Table 1, comprises or consists of CDR-L1, CDR-L2, CDR-L3, CDR-H1, CDR-H2, and CDR-H3, as described herein.

The heavy chain variable domain of the monoclonal antibodies encompassed by the present invention can comprise or consist of the vH amino acid sequence set forth herein and/or the light chain variable domain of the monoclonal antibodies encompassed by the present invention can comprise or consist of the vκ amino acid sequence set forth herein.

The present invention further provides fragments of said monoclonal antibodies which include, but are not limited to, Fv, Fab, F(ab')2, Fab', dsFv, scFv, sc(Fv)2 and diabodies; and multispecific antibodies formed from antibody fragments. For example, a number of immunoinhibitory molecules, such as PD-L1, PD-1, CTLA-4, and the like, can be bound in a bispecific or multispecific manner.

Other fragments of the monoclonal antibodies encompassed by the present invention are also contemplated. For example, individual immunoglobulin heavy and/or light chains are provided, wherein the variable domains thereof comprise at least a CDR described herein. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs described herein. In another embodiment, an immunoglobulin light chain comprises at least a CDR having a sequence that is at least 80%, 85%, 90%, 91%, 92%, 93%, 94%, 95%, 96%, 97%, 98%, 99%, 99.5% or 100% identical from the group of light chain or heavy chain variable domain CDRs described herein, are also provided.

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1, CDR-L2, and CDR-L3.

In other embodiments, an immunoglobulin heavy and/or light chain according to the present invention comprises or consists of a vH or vκ variable domain sequence, respectively, described herein.

The present invention further provides polypeptides which have a sequence selected from the group consisting of vH variable domain, vκ variable domain, CDR-L1, CDR-L2, CDR-L3, CDR-H1, CDR-H2, and CDR-H3 sequences described herein.

Antibodies, immunoglobulins, and polypeptides encompassed by the present invention can be use in an isolated (e.g., purified) form or contained in a vector, such as a membrane or lipid vesicle (e.g. a liposome).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies encompassed by the present invention, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences encompassed by the present invention, or corresponding DNA sequences which encode said polypeptides, without appreciable loss of their biological activity.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well-known to those of skill in the art and include: arginine and lysine; glutamate and aspartate; serine and threonine; glutamine and asparagine; and valine, leucine and isoleucine.

Another type of amino acid modification of the antibody encompassed by the present invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins encompassed by the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, carbon labeled 1-isothiocyanatobenzyl methyldiethylene triamine-pentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody encompassed by the present invention can be conjugated to a radioisotope, e.g., radioactive iodine, to generate cytotoxic radiopharmaceuticals for treating a related disorder, such as a cancer.

Conjugated antibodies can be used diagnostically or prognostically to monitor polypeptide levels in tissue as part of a clinical testing procedure, e.g., to determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$I, $^{131}$I, $^{35}$S, or $^{3}$H. [0134] As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable sub stance.

The antibody conjugates encompassed by the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well-known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985);

Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

Additionally, recombinant polypeptide antibodies, such as chimeric and humanized monoclonal antibodies, comprising both human and non-human portions, which can be made using standard recombinant DNA techniques, are within the scope encompassed by the present invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology (NY)* 12:396-399; Chen, S-Y. et al. (1994) *Hum. Gene Ther.* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

Additionally, fully human antibodies could be made against one or more biomarkers listed in Table 1, or fragments thereof. Fully human antibodies can be made in mice that are transgenic for human immunoglobulin genes, e.g. according to Hogan et al., "Manipulating the Mouse Embryo: A Laboratory Manuel," Cold Spring Harbor Laboratory. Briefly, transgenic mice are immunized with purified immunogen. Spleen cells are harvested and fused to myeloma cells to produce hybridomas. Hybridomas are selected based on their ability to produce antibodies which bind to the immunogen. Fully human antibodies would reduce the immunogenicity of such antibodies in a human.

In one embodiment, an antibody for use in the instant invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers encompassed by the present invention, including one or more biomarkers listed in Table 1, or a fragment thereof. In one embodiment, the bispecific antibody could specifically bind to both a polypeptide or a fragment thereof and its natural binding partner(s) or a fragment(s) thereof.

In another aspect encompassed by the present invention, peptides or peptide mimetics can be used to antagonize or agonize the activity of one or more biomarkers encompassed by the present invention, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. USA* 89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers encompassed by the present invention, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well-known in the art and are described further in Maniatis et al. *Molecular Cloning: A Laboratory Manual* (1989), 2nd Ed., Cold Spring Harbor, NY; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments encompassed by the present invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere, J. (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH2S—, —CH2-CH2-, —CH═CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982)(—CH(OH) CH2-; Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

Also encompassed by the present invention are small molecules which can modulate (inhibit) interactions, e.g., between one or more biomarkers listed in Table 1 and their natural binding partners. The small molecules encompassed by the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

The invention also relates to chimeric or fusion proteins of the biomarkers encompassed by the present invention, including one or more biomarkers listed in Table 1, or fragments thereof. As used herein, a "chimeric protein" or "fusion protein" comprises one or more biomarkers encompassed by the present invention, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers encompassed by the present invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ 1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well-known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein encompassed by the present invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992).

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins encompassed by the present invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers encompassed by the present invention, including one or more biomarkers listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well-known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences encompassed by the present invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin. In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296: 550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to nucleic acids of one or more biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, R. (1994) *Nature* 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxyethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well-known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug et al. (1984) Science 224:574-578; Zaug et al. (1986) Science 231:470-475; Zaug et al. (1986) Nature 324:429-433; published International patent application No. WO88/04300 by University Patents Inc.; Been et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well-known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein. It is believed that certain combinations work synergistically in the treatment of conditions that would benefit from the mouldation of immune responses. Second active agents can be large molecules (e.g., proteins) or small molecules (e.g., synthetic inorganic, organometallic, or organic molecules).

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well-known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well-known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335, 167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.). In another embodiment, the hybridization protocol of Pinkel et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). Measurement of DNA copy number at microsatellite loci using quantitative PCR analysis is described in Ginzonger et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods encompassed by the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren et al. (1988) *Science* 241:1077, and Barringer et al. (1990) *Gene* 89: 117), transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C. et al. (2004) *Cancer Res* 64(1):64-71; Seymour, A. B. et al. (1994) *Cancer Res* 54, 2761-4; Hahn, S. A. et al. (1995) *Cancer Res* 55, 4670-5; Kimura, M. et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) *Science* 278: 1481; Emmert-Buck et al. (1996) *Science* 274:998; Fend et al. (1999) *Am. J. Path.* 154: 61 and Murakami et al. (2000) *Kidney Int.* 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, *Biochemistry* 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) *Proc. Natl. Acad. Sci. U.S.A.* 86: 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope encompassed by the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos. 6,618,796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a condition that would benefit from modulating an immune response to modulators of IRE1α-XBP1 pathway. Any method known in the art for detecting polypeptides can be used. Such methods include, but are not limited to, immunodiffusion, immunoelectrophoresis, radioimmunoassay (MA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and MA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99m}$Tc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MM. For X-radiographic techniques, suitable markers include any radioisotope that emits detectable radiation but that is not overtly harmful to the subject, such as barium or cesium, for example. Suitable markers for NMR and MM generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$ M, $10^{-7}$ M, $10^{-8}$ M, $10^{-9}$ M, $10^{-10}$ M, $10^{-11}$ M, $10^{-12}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify one or more biomarkers listed in Table 1, or other biomarkers used in the immunotherapies described herein.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397 and Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

III. Cellular Compositions

The present invention provides a composition comprising NK cells, such as a vaccine, wherein the IRE1α-XBP1 pathway is upregulated in the NK cells. The NK cells may be derived from peripheral blood mononuclear cells (PBMCs) or umbilical cord blood (UCB). In one embodiment, the NK cells are derived from a subject. In another embodiment, the NK cells are derived from a NK cell line, such as NK-92. The NK cells may be derived from the subject who is treated with the composition, such as a vaccine composition. The NK cells may also be derived from a different subject who is not treated with the composition.

Cell types of interest may be obtained from any animal having an immune system. In one embodiment, cell types of interest are obtained from a mammal, including humans. As used herein, the terms "mammal" and "mammalian" refer to any vertebrate animal, including monotremes, marsupials and placental, that suckle their young and either give birth to living young (eutharian or placental mammals) or are egg-laying (metatharian or nonplacental mammals). For example, cell types of interest having a defined genetic background or unknown genetic background may be obtained from a human for use in the methods encompassed by the present invention. In another embodiment, cell types of interest may be obtained from non-human mammals. Representative, non-limiting examples of non-human mammals include non-human primates (e.g., monkeys and chimpanzees), rodents (e.g., rats, mice, and guinea pigs), canines, felines, birds, fish, and ruminants (e.g., cows, sheep, pigs, and horses). In still another embodiment, the non-human mammal is a mouse. The animals from which cell types of interest are obtained may be adult, newborn (e.g., less than 48 hours old), immature, or in utero. Cell types of interest may be primary cells, stem cells, and zygotes. In yet another embodiment, human progenitor cells are used to reconstitute human immune systems in host animals such as mice. Such systems are well known in the art and include, for example, SCID:Hu models in which human cells are reconstituted in SCID mice (see, for example, McCune et al. (1988) *Science* 241:1632-1639).

As used herein, "obtained" from a biological material source means any conventional method of harvesting or partitioning a source of biological material from a donor. For example, biological material may obtained from a blood sample, such as a peripheral or cord blood sample, or harvested from bone marrow or amniotic fluid. Methods for obtaining such samples are well known to the artisan. In the present invention, the samples may be fresh (i.e., obtained from a donor without freezing). Moreover, the samples may be further manipulated to remove extraneous or unwanted components prior to expansion. The samples may also be obtained from a preserved stock. For example, in the case of peripheral or cord blood, the samples may be withdrawn from a cryogenically or otherwise preserved bank of such blood. Such samples may be obtained from any suitable donor.

"Marker phenotyping" refers to identification of markers or antigens on cells for determining their phenotype (e.g., differentiation state and/or cell type). This may be done by immunophenotyping, which uses antibodies that recognize antigens present on a cell. The antibodies may be monoclonal or polyclonal, but are generally chosen to have minimal cross reactivity with other cell markers. It is to be understood that certain cell differentiation or cell surface markers are unique to the animal species from which the cells are derived, while other cell markers will be common between species. These markers defining equivalent cell types between species are given the same marker identification even though there are species differences in structure (e.g., amino acid sequence). Cell markers include cell surfaces molecules, also referred to in certain situations as cell differentiation (CD) markers, and gene expression markers. The gene expression markers are those sets of expressed genes indicative of the cell type or differentiation state. In part, the gene expression profile will reflect the cell surface markers, although they may include non-cell surface molecules.

As used herein, "enriched" means that the percentage of marker phenotyped cells relative to other cells in a population is increased. In one embodiment, "purified" means that the percentage of marker phenotyped cells is substantially pure and excludes cells that are not marker phenotyped. A "substantially pure cell population" refers to a population of cells having a specified cell marker characteristic and differentiation potential that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or more, or any value or range in between, of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

In one embodiment, "isolated" refers to a product, compound, or composition which is separated from at least one other product, compound, or composition with which it is associated in its naturally occurring state, whether in nature or as made synthetically. In other embodiments, "isolated" means that desired marker phenotyped cells are physically separated from other cell populations. Methods for the enrichment, purification, and/or isolation of marker phenotyped cells are disclosed herein and are also well known in the art, such as by using fluorescence-activated cell scanning (FACS), magnetic cell sorting, and centrifugation (see, for example, U.S. Pat. Nos. 5,474,687, 5,677,136, and 6,004,743; and U.S. Pat. Publ. 2001/0039052).

In some embodiments, the NK cells are derived from a subject. Such cells may be obtained from a variety of sources, including bone marrow, peripheral blood, cord blood, amniotic fluid, and other sources known to harbor NK cells. Peripheral and cord blood is a rich source of NK cells. Isolation and purification of NK cell from PBMCs is a common process to obtain the purified NK cells. NK cells may be purified from fresh PBMC samples from heathy donors or animal models. The PBMC samples often contain a heterogeneous population of blood cells. Preferably, a purified NK cell composition can have greater than 70%, 75%, 80%, 85%, 90%, 95%, 99%, or more, or any range in between or any value in between, total viable NK cells. To purify NK cells from the heterogeneous population, a number of methods can be used.

In one embodiment, fluorescence activated cell sorting (FACS), also referred to as flow cytometry, is used to sort and analyze the different cell populations. Cells having a cellular marker or other specific marker of interest are tagged with an antibody, or typically a mixture of antibodies, that bind the cellular markers. Each antibody directed to a different marker is conjugated to a detectable molecule, particularly a fluorescent dye that may be distinguished from other fluorescent dyes coupled to other antibodies. A stream of tagged or "stained" cells is passed through a light source that excites the fluorochrome and the emission spectrum from the cells detected to determine the presence of a particular labeled antibody. By concurrent detection of different fluorochromes, also referred to in the art as multicolor fluorescence cell sorting, cells displaying different sets of cell markers may be identified and isolated from other cells in the population. Other FACS parameters, including, by way of example and not limitation, side scatter (SSC), forward scatter (FSC), and vital dye staining (e.g., with propidium iodide) allow selection of cells based on size and viability. FACS sorting and analysis of HSC and related lineage cells is well-known in the art and described in, for example, U.S. Pat. Nos. 5,137,809; 5,750,397; 5,840,580; 6,465,249; Manz et al. (202) *Proc. Natl. Acad. Sci. U.S.A.* 99:11872-11877; and Akashi et al. (200) *Nature* 404:193-197. General guidance on fluorescence activated cell sorting is described in, for example, Shapiro (2003) *Practical Flow Cytometry,* 4th Ed., Wiley-Liss (2003) and Ormerod (2000) *Flow Cytometry: A Practical Approach,* 3rd Ed., Oxford University Press.

Another method of isolating useful cell populations involves a solid or insoluble substrate to which is bound antibodies or ligands that interact with specific cell surface markers. In immunoadsorption techniques, cells are contacted with the substrate (e.g., column of beads, flasks, magnetic particles, etc.) containing the antibodies and any unbound cells removed. Immunoadsorption techniques may be scaled up to deal directly with the large numbers of cells in a clinical harvest. Suitable substrates include, by way of example and not limitation, plastic, cellulose, dextran, polyacrylamide, agarose, and others known in the art (e.g., Pharmacia Sepharose 6 MB macrobeads). When a solid substrate comprising magnetic or paramagnetic beads is used, cells bound to the beads may be readily isolated by a magnetic separator (see, e.g., Kato and Radbruch (1993) *Cytometry* 14:384-92). Affinity chromatographic cell separations typically involve passing a suspension of cells over a support bearing a selective ligand immobilized to its surface. The ligand interacts with its specific target molecule on the cell and is captured on the matrix. The bound cell is released by the addition of an elution agent to the running buffer of the column and the free cell is washed through the column and harvested as a homogeneous population. As apparent to the skilled artisan, adsorption techniques are not limited to those employing specific antibodies, and may use nonspecific adsorption. For example, adsorption to silica is a simple procedure for removing phagocytes from cell preparations. One of the most common uses of this technology is for isolating circulating tumor cells (CTCs) from the blood of breast, NSC lung cancer, prostate and colon cancer patients using an antibody against EpCAM, a cell surface glycoprotein that has been found to be highly expressed in epithelial cancers.

FACS and most batch wise immunoadsorption techniques may be adapted to both positive and negative selection procedures (see, e.g., U.S. Pat. No. 5,877,299). In positive selection, the desired cells are labeled with antibodies and removed away from the remaining unlabeled/unwanted cells. In negative selection, the unwanted cells are labeled and removed. Another type of negative selection that may be employed is use of antibody/complement treatment or immunotoxins to remove unwanted cells.

It is to be understood that the purification or isolation of cells also includes combinations of the methods described above. A typical combination may comprise an initial procedure that is effective in removing the bulk of unwanted cells and cellular material. A second step may include isolation of cells expressing a marker common to one or more of the progenitor cell populations by immunoadsorption on antibodies bound to a substrate. An additional step providing higher resolution of different cell types, such as FACS sorting with antibodies to a set of specific cellular markers, may be used to obtain substantially pure populations of the desired cells.

The IRE1α-XBP1 signaling pathway is upregulated in the NK cells. In some embodiments, the copy number, amount, and/or activity of at least one biomarker listed in Table 1 is increased in the NK cells, such as by genetic engineering means described herein. The copy number, amount, and/or activity of at least one biomarker listed in Table 1 may be increased by contacting the NK cells with a nucleic acid molecule encoding at least one biomarker listed in Table 1 or fragment thereof, a polypeptide of at least one biomarker listed in Table 1 or fragment thereof, or a small molecule that binds to at least one biomarker listed in Table 1.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well-known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Also encompassed by the present invention are small molecules which can increase activity of one or more biomarkers listed in Table 1 or their interactions with their natural binding partners. The small molecules encompassed by the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

Also provided herein are compositions comprising one or more nucleic acids capable of expressing at least one or more biomarkers listed in Table 1, or functional fragments thereof. Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides and nucleic acids can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The present invention also contemplates well-known methods for genetically modifying the genome of an organism or cell to modify the expression and/or activity of one or more biomarkers listed in Table 1 without contacting the organism or cell with agent once the genetic modification has been completed. For example, NK cells can be genetically modified using recombinant techniques in order to modulate the expression and/or activity of one or more biomarkers listed in Table 1, such that no agent needs to contact the NK cells in order for the expression and/or activity one or more biomarkers listed in Table 1 to be modulated. For example, targeted or untargeted gene knockout methods can be used, such as to recombinantly engineer subject cancer cell ex vivo prior to infusion into the subject. For example, the target DNA in the genome can be manipulated by deletion, insertion, and/or mutation using retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis. Such methods generally use host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

Similarly, the CRISPR-Cas system can be used for precise editing of genomic nucleic acids (e.g., for creating null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

IV. Methods of Selecting Agents that Modulate Immune Responses

Another aspect encompassed by the present invention relates to methods of selecting agents (e.g., antibodies, fusion proteins, peptides, or small molecules) which modulate an immune response by modulate the copy number, the expression, and/or the activity of one or more biomarkers listed in Table 1. Such methods utilize screening assays, including cell based and non-cell based assays. In one embodiment, the assays provide a method for identifying agents that inhibit the endonuclease activity and/or the substrate binding activity of one or more biomarkers listed in Table 1.

In one embodiment, the present invention relates to assays for screening test agents which bind to, or modulate the biological activity of, at least one biomarker described herein (e.g., in the tables, figures, examples, or otherwise in the specification). In one embodiment, a method for identifying such an agent entails determining the ability of the agent to modulate the at least one biomarker described herein.

In one embodiment, an assay is a cell-free or cell-based assay, comprising contacting at least one biomarker described herein, with a test agent, and determining the ability of the test agent to modulate the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies described herein can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) *Int. J. Tryptophan Res.* 2:1-19).

The present invention further pertains to novel agents identified by the above-described screening assays. Accordingly, it is within the scope of this invention to further use an agent identified as described herein, such as in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

V. Pharmaceutical Compositions

Agents that modulate IRE1α-XBP1 pathway (e.g., agents that modulate one or more biomarkers listed in Table 1), including, e.g., blocking antibodies, peptides, fusion proteins, or small molecules, can be incorporated into pharmaceutical compositions suitable for administration to a subject. Such compositions typically comprise the antibody, peptide, fusion protein or small molecule and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary active compounds can also be incorporated into the compositions.

A pharmaceutical composition encompassed by the present invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms encompassed by the present invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method encompassed by the present invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The above described modulating agents may be administered it he form of expressible nucleic acids which encode said agents. Such nucleic acids and compositions in which they are contained, are also encompassed by the present invention. For instance, the nucleic acid molecules encompassed by the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

VI. Uses and Methods of the Invention

The modulatory agents described herein can be used according to a number of methods related to the modulation of IRE1α-XBP1 pathway, and corresponding modulation of immune responses.

1. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect encompassed by the present invention relates to diagnostic assays for determining the amount and/or activity level of a biomarker described herein in the context of a biological sample (e.g., blood, serum, cells, or tissue) to thereby determine whether an individual afflicted with a condition that would benefit from modulating an immune response is likely to respond to modulators of IRE1α-XBP1 pathway, such as in a cancer. Such assays can be used for prognostic or predictive purpose alone, or can be coupled with a therapeutic intervention to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those in the tables, figures, examples, and otherwise described in the specification.

Another aspect encompassed by the present invention pertains to monitoring the influence of agents (e.g., drugs, compounds, and small nucleic acid-based molecules) on the expression or activity of a biomarker described herein. These and other agents are described in further detail in the following sections.

The skilled artisan will also appreciated that, in certain embodiments, the methods encompassed by the present invention implement a computer program and computer system. For example, a computer program can be used to perform the algorithms described herein. A computer system can also store and manipulate data generated by the methods encompassed by the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part encompassed by the present invention.

Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods encompassed by the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

2. Diagnostic Assays

The present invention provides, in part, methods, systems, and code for accurately classifying whether a biological sample is associated with a condition that would benefit from modulating an immune response that is likely to respond to modulators of IRE1α-XBP1 pathway. In some embodiments, the present invention is useful for classifying a sample (e.g., from a subject) as associated with or at risk for a condition that would benefit from modulating an immune response responding to or not responding to such modulator using a statistical algorithm and/or empirical data (e.g., the amount or activity of a biomarker described herein, such as in the tables, figures, examples, and otherwise described in the specification).

An exemplary method for detecting the amount or activity of a biomarker described herein, and thus useful for classifying whether a sample is likely or unlikely to respond to modulators of IRE1α-XBP1 pathway involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely immunotherapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method encompassed by the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a condition that would benefit from modulating an immune response or whose condition is susceptible to modulators of IRE1α-XBP1 pathway), a biological sample from the subject during remission, or a biological sample from the subject during treatment for developing a condition that would benefit from modulating an immune response progressing despite such modulators.

3. Prognostic Assays

The diagnostic methods described herein can furthermore be utilized to identify subjects having or at risk of developing a condition that would benefit from modulating an immune response (e.g., cancer or viral infection) that is likely or unlikely to be responsive to modulators of IRE1α-XBP1 pathway. The assays described herein, such as the preceding diagnostic assays or the following assays, can be utilized to identify a subject having or at risk of developing a disorder associated with a misregulation of the amount or activity of at least one biomarker described herein, such as in cancer. Alternatively, the prognostic assays can be utilized to identify a subject having or at risk for developing a disorder associated with a misregulation of the at least one biomarker described herein, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

4. Prophylactic Methods

In one aspect, the present invention provides a method for preventing in a subject, a disease or condition associated with less than desirable immune response. Subjects at risk for a disease that would benefit from treatment with the claimed agents or methods can be identified, for example, by any or a combination of diagnostic or prognostic assays known in the art. Administration of a prophylactic agent can occur prior to the manifestation of symptoms associated with less than desirable immune response. The appropriate agent used for treatment (e.g. antibodies, peptides, fusion proteins or small molecules) can be determined based on clinical indications and can be identified, e.g., using screening assays described herein.

5. Therapeutic Methods

Another aspect encompassed by the present invention pertains to therapeutic methods of modulating an immune response by modulating IREα/XBP1 pathway. In one embodiment, the methods relate to upregulating an immune response by upregulating IREα/XBP1 pathway (e.g., by increasing the copy number, the expression level, and/or the activity of one or more biomarkers listed in Table 1). In another embodiment, the methods related to downregulating an immune response by downregulating IREα/XBP1 pathway (e.g., by decreasing the copy number, the expression level, and/or the activity of one or more biomarkers listed in Table 1). The therapeutic compositions described herein, such as the modulators of IREα/XBP1 pathway, can be used in a variety of in vitro and in vivo therapeutic applications using the formulations and/or combinations described herein. In one embodiment, the therapeutic agents can be used to treat conditions determined to be responsive thereto.

Modulatory methods encompassed by the present invention involve contacting a cell, such as an immune cell (e.g., NK cells) with an agent that modulates the IREα/XBP1 pathway. Exemplary agents useful in such methods are described above. Such agents can be administered in vitro or ex vivo (e.g., by contacting the cell with the agent) or, alternatively, in vivo (e.g., by administering the agent to a subject). As such, the present invention provides methods useful for treating an individual afflicted with a condition that would benefit from a modulation of immune response, for example, an upregulation or downregulation of immune response.

Agents that upregulate immune responses can be in the form of enhancing an existing immune response or eliciting an initial immune response. Thus, enhancing an immune response using the subject compositions and methods is useful for treating cancer, but can also be useful for treating an infectious disease (e.g., bacteria, viruses, fungi or parasites), a parasitic infection, and an immunosuppressive disease. The infectious disorders include, for example, a viral infection (e.g., an infection caused by human immunodeficiency virus (HIV), hepatitis B virus (HBV), hepatitis C virus (HCV), influenza A virus (e.g., H1N1), Epstein-Barr virus (EBV), human herpes simplex virus (HSV) type 1 and type 2, respiratory syncytial virus (RSV), human papilloma virus (HPV), lymphocytic choriomeningitis virus (LCMV), Zika virus, Rift Valley fever virus (RVFV), dengue virus (DENV), chikungunya virus (CHIKV), enterovirus (EV), human adenovirus (HAdV)), a bacterial infection (e.g., an infection caused by *Listeria monocytogenes*, a lung bacterial infection caused by *Mycobacterium tuberculosis*, or a gastrointestinal tract infection by *Salmonella typhimurium*), a parasitic infection (e.g., an infection caused by *Plasmodium* (e.g., malaria parasite) or *Cryptosporidium*), and a fungal infection (e.g., an infection caused by *Aspergillus*, optionally wherein the *Aspergillus* is *Aspergillus fumigatus*).

Exemplary infectious disorders include viral skin diseases, such as Herpes or shingles, in which case such an agent can be delivered topically to the skin. In addition, systemic viral diseases, such as influenza, the common cold, and encephalitis might be alleviated by systemic administration of such agents. In one preferred embodiment, agents that upregulate the immune response described herein are useful for protect again CMV infection.

Immune responses can also be enhanced in an infected patient through an ex vivo approach, for instance, by removing NK cells from the patient, contacting NK cells in vitro with an agent described herein and reintroducing the in vitro stimulated NK cells into the patient.

In certain instances, it may be desirable to further administer other agents that upregulate immune responses, for example, forms of other B7 family members that transduce signals via costimulatory receptors, in order to further augment the immune response. Such additional agents and therapies are described further below.

Agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

In another embodiment, upregulation or enhancement of an immune response function, as described herein, is useful in the induction of tumor immunity.

In another embodiment, the immune response can be stimulated by the methods described herein alone or in combination with methods that are able to overcome pre-existing tolerance, clonal deletion, and/or exhaustion (e.g., T cell exhaustion). For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, the subject agents can be used as adjuvants to boost responses to foreign antigens in the process of active immunization.

Agents that downregulate immune responses can be in the form of decreasing an existing immune response or blocking an initiation of an immune response. Thus, decreasing an immune response using the subject compositions and methods is useful for treating inflammatory diseases, such as autoimmune diseases. In certain instances, it may be desirable to further administer other agents that downregulate immune responses.

In one embodiment, NK cells are obtained from a subject and cultured ex vivo in the presence of an agent as described herein, to expand the population of immune cells and/or to enhance immune cell activation. In a further embodiment, the NK cells are then administered to a subject. NK cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

The therapeutic agents encompassed by the present invention can be used alone or can be administered in combination therapy with, e.g., chemotherapeutic agents, hormones, anti-angiogens, radiolabelled, compounds, or with surgery, cryotherapy, and/or radiotherapy. The preceding treatment methods can be administered in conjunction with other forms of conventional therapy (e.g., standard-of-care treatments for cancer well-known to the skilled artisan), either consecutively with, pre- or post-conventional therapy. For example, agents encompassed by the present invention can be administered with a therapeutically effective dose of chemotherapeutic agent. In another embodiment, agents encompassed by the present invention are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular cancer being treated, the extent of the disease and other factors familiar to the physician of skill in the art, and can be determined by the physician.

Nutritional supplements that enhance immune responses, such as vitamin A, vitamin E, vitamin C, and the like, are well-known in the art (see, for example, U.S. Pat. Nos. 4,981,844 and 5,230,902 and PCT Publ. No. WO 2004/004483) can be used in the methods described herein.

Similarly, agents and therapies other than immunotherapy or in combination thereof can be used in combination with modulators of IRE1α-XBP1 pathway to modulate an immune response to thereby treat a condition that would benefit therefrom. For example, chemotherapy, radiation, epigenetic modifiers (e.g., histone deacetylase (HDAC) modifiers, methylation modifiers, phosphorylation modifiers, and the like), targeted therapy, and the like are well-known in the art.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E et al. (2005) Nature 434:913-917; Farmer H et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, surgical intervention can occur to physically remove cancerous cells and/or tissues.

In still another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In yet another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early non-small cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with therapies may vary according to the particular therapeutic agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods encompassed by the present invention is a factor in determining optimal treatment doses and schedules.

VII. Administration of Agents

The immune modulating agents encompassed by the present invention are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition encompassed by the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agents or the invention described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

As described in detail below, the pharmaceutical compositions encompassed by the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods encompassed by the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods encompassed by the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions encompassed by the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents encompassed by the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods encompassed by the present invention so as to obtain an amount of the active ingredient, which is effective to achieve the desired therapeutic response for a particular subject, composition, and mode of administration, without being toxic to the subject.

The nucleic acid molecules encompassed by the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent encompassed by the present invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well-known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms encompassed by the present invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent encompassed by the present invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

As described above, in some embodiments, agents for administration are cell-based. Cell-based agents have an immunocompatibility relationship to a subject host and any such relationship is contemplated for use according to the present invention. For example, the cells, such as adoptive T cells, can be syngeneic. The term "syngeneic" can refer to the state of deriving from, originating in, or being members of the same species that are genetically identical, particularly with respect to antigens or immunological reactions. These include identical twins having matching MEW types. Thus, a "syngeneic transplant" refers to transfer of cells from a donor to a recipient who is genetically identical to the donor or is sufficiently immunologically compatible as to allow for transplantation without an undesired adverse immunogenic response (e.g., such as one that would work against interpretation of immunological screen results described herein).

A syngeneic transplant can be "autologous" if the transferred cells are obtained from and transplanted to the same subject. An "autologous transplant" refers to the harvesting and reinfusion or transplant of a subject's own cells or organs. Exclusive or supplemental use of autologous cells may eliminate or reduce many adverse effects of administration of the cells back to the host, particular graft versus host reaction.

A syngeneic transplant can be "matched allogeneic" if the transferred cells are obtained from and transplanted to different members of the same species yet have sufficiently matched major histocompatibility complex (MEW) antigens to avoid an adverse immunogenic response. Determining the degree of MHC mismatch may be accomplished according to standard tests known and used in the art. For instance, there are at least six major categories of MEW genes in humans, identified as being important in transplant biology. HLA-A, HLA-B, HLA-C encode the HLA class I proteins while HLA-DR, HLA-DQ, and HLA-DP encode the HLA class II proteins. Genes within each of these groups are highly polymorphic, as reflected in the numerous HLA alleles or variants found in the human population, and differences in these groups between individuals is associated with the strength of the immune response against transplanted cells. Standard methods for determining the degree of MHC match examine alleles within HLA-B and HLA-DR, or HLA-A, HLA-B and HLA-DR groups. Thus, tests may be made of at least 4, and even 5 or 6 WIC antigens within the two or three HLA groups, respectively. In serological WIC tests, antibodies directed against each HLA antigen type are reacted with cells from one subject (e.g., donor) to determine the presence or absence of certain MHC antigens that react with the antibodies. This is compared to the reactivity profile of the other subject (e.g., recipient). Reaction of the antibody with an WIC antigen is typically determined by incubating the antibody with cells, and then adding complement to induce cell lysis (i.e., lymphocytotoxicity testing). The reaction is examined and graded according to the amount of cells lysed in the reaction (see, for example, Mickelson and Petersdorf (1999) *Hematopoietic Cell Transplantation*, Thomas, E. D. et al. eds., pg 28-37, Blackwell Scientific, Malden, Mass.). Other cell-based assays include flow cytometry using labeled antibodies or enzyme linked immunoassays (ELISA). Molecular methods for determining WIC type are well-known and generally employ synthetic probes and/or primers to detect specific gene sequences that encode the HLA protein. Synthetic oligonucleotides may be used as hybridization probes to detect restriction fragment length polymorphisms associated with particular HLA types (Vaughn (2002) *Method. Mol. Biol. MHC Protocol.* 210:45-60). Alternatively, primers may be used for amplifying the HLA sequences (e.g., by polymerase chain reaction or ligation chain reaction), the products of which may be further examined by direct DNA sequencing, restriction fragment polymorphism analysis (RFLP), or hybridization with a series of sequence specific oligonucleotide primers (SSOP) (Petersdorf et al. (1998) *Blood* 92:3515-3520; Morishima et al. (2002) *Blood* 99:4200-4206; and Middleton and Williams (2002) *Method. Mol. Biol. MHC Protocol.* 210:67-112).

A syngeneic transplant can be "congenic" if the transferred cells and cells of the subject differ in defined loci, such as a single locus, typically by inbreeding. The term "congenic" refers to deriving from, originating in, or being members of the same species, where the members are genetically identical except for a small genetic region, typically a single genetic locus (i.e., a single gene). A "congenic transplant" refers to transfer of cells or organs from a donor to a recipient, where the recipient is genetically identical to the donor except for a single genetic locus. For example, CD45 exists in several allelic forms and congenic mouse lines exist in which the mouse lines differ with respect to whether the CD45.1 or CD45.2 allelic versions are expressed.

By contrast, "mismatched allogeneic" refers to deriving from, originating in, or being members of the same species having non-identical major histocompatibility complex (MHC) antigens (i.e., proteins) as typically determined by standard assays used in the art, such as serological or molecular analysis of a defined number of MHC antigens, sufficient to elicit adverse immunogenic responses. A "partial mismatch" refers to partial match of the MHC antigens tested between members, typically between a donor and recipient. For instance, a "half mismatch" refers to 50% of the MHC antigens tested as showing different MHC antigen type between two members. A "full" or "complete" mismatch refers to all MHC antigens tested as being different between two members.

Similarly, in contrast, "xenogeneic" refers to deriving from, originating in, or being members of different species, e.g., human and rodent, human and swine, human and chimpanzee, etc. A "xenogeneic transplant" refers to transfer of cells or organs from a donor to a recipient where the recipient is a species different from that of the donor.

In addition, cells can be obtained from a single source or a plurality of sources (e.g., a single subject or a plurality of subjects). A plurality refers to at least two (e.g., more than one). In still another embodiment, the non-human mammal is a mouse. The animals from which cell types of interest are obtained may be adult, newborn (e.g., less than 48 hours old), immature, or in utero. Cell types of interest may be primary cancer cells, cancer stem cells, established cancer cell lines, immortalized primary cancer cells, and the like. In certain embodiments, the immune systems of host subjects can be engineered or otherwise elected to be immunological compatible with transplanted cancer cells. For example, in one embodiment, the subject may be "humanized" in order to be compatible with human cancer cells. The term "immune-system humanized" refers to an animal, such as a mouse, comprising human HSCs and/or cells derived therefrom and human acquired and innate immune cells, survive without being rejected from the host animal, thereby allowing human hematopoiesis and both acquired and innate immunity to be reconstituted in the host animal. Acquired immune cells include T cells and B cells. Innate immune cells include macrophages, granulocytes (basophils, eosinophils, neutrophils), DCs, NK cells and mast cells. Representative, non-limiting examples include SCID-hu, Hu-PBL-SCID, Hu-SRC-SCID, NSG (NOD-SCID IL2r-gamma(null) lack an innate immune system, B cells, T cells, and cytokine signaling), NOG (NOD-SCID IL2r-gamma (truncated)), BRG (BALB/c-Rag2(null)IL2r-gamma(null)), and H2dRG (Stock-H2d-Rag2(null)IL2r-gamma(null)) mice (see, for example, Shultz et al. (2007) *Nat. Rev. Immunol.* 7:118; Pearson et al. (2008) *Curr. Protocol. Immunol.* 15:21; Brehm et al. (2010) *Clin. Immunol.* 135:84-98; McCune et al. (1988) *Science* 241:1632-1639, U.S. Pat. No. 7,960,175, and U.S. Pat. Publ. 2006/0161996), as well as related null mutants of immune-related genes like Rag1 (lack B and T cells), Rag2 (lack B and T cells), TCR alpha (lack T cells), perforin (cD8+ T cells lack cytotoxic function), FoxP3 (lack functional CD4+ T regulatory cells), IL2rg, or Prfl, as well as mutants or knockouts of PD-1, PD-L1, Tim3, and/or 2B4, allow for efficient engraftment of human immune cells in and/or provide compartment-specific models of immunocompromised animals like mice (see, for example, PCT Publ. WO2013/062134). In addition, NSG-CD34+ (NOD-SCID IL2r-gamma(null) CD34+) humanized mice are useful for studying human gene and tumor activity in animal models like mice.

As used herein, "obtained" from a biological material source means any conventional method of harvesting or partitioning a source of biological material from a donor. For example, biological material may obtained from a solid tumor, a blood sample, such as a peripheral or cord blood sample, or harvested from another body fluid, such as bone marrow or amniotic fluid. Methods for obtaining such samples are well-known to the artisan. In the present invention, the samples may be fresh (i.e., obtained from a donor without freezing). Moreover, the samples may be further manipulated to remove extraneous or unwanted components prior to expansion. The samples may also be obtained from a preserved stock. For example, in the case of cell lines or fluids, such as peripheral or cord blood, the samples may be withdrawn from a cryogenically or otherwise preserved bank of such cell lines or fluid. Such samples may be obtained from any suitable donor.

The obtained populations of cells may be used directly or frozen for use at a later date. A variety of mediums and protocols for cryopreservation are known in the art. Generally, the freezing medium will comprise DMSO from about 5-10%, 10-90% serum albumin, and 50-90% culture medium. Other additives useful for preserving cells include, by way of example and not limitation, disaccharides such as trehalose (Scheinkonig et al. (2004) *Bone Marrow Transplant.* 34:531-536), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% dimethyl sulfoxide (DMSO), and 2% hetastarch. Other compositions and methods for cryopreservation are well-known and described in the art (see, e.g., Broxmeyer et al. (2003) *Proc. Natl. Acad. Sci. U.S.A.* 100:645-650). Cells are preserved at a final temperature of less than about −135° C.

Cells can be administered at $0.1\times10^6$, $0.2\times10^6$, $0.3\times10^6$, $0.4\times10^6$, $0.5\times10^6$, $0.6\times10^6$, $0.7\times10^6$, $0.8\times10^6$, $0.9\times10^6$, $1.0\times10^6$, $5.0\times10^6$, $1.0\times10^7$, $5.0\times10^7$, $1.0\times10^8$, $5.0\times10^8$, or more, or any range in between or any value in between, cells per kilogram of subject body weight. The number of cells transplanted may be adjusted based on the desired level of engraftment in a given amount of time. Generally, $1\times10^5$ to about $1\times10^9$ cells/kg of body weight, from about $1\times10^6$ to about $1\times10^8$ cells/kg of body weight, or about $1\times10^7$ cells/kg of body weight, or more cells, as necessary, may be transplanted. In some embodiment, transplantation of at least about $0.1\times10^6$, $0.5\times10^6$, $1.0\times10^6$, $2.0\times10^6$, $3.0\times10^6$, $4.0\times10^6$, or $5.0\times10^6$ total cells relative to an average size mouse is effective.

Cells can be administered in any suitable route as described herein, such as by infusion. Cells can also be administered before, concurrently with, or after, other anti-cancer agents.

Administration can be accomplished using methods generally known in the art. Agents, including cells, may be introduced to the desired site by direct injection, or by any other means used in the art including, but are not limited to, intravascular, intracerebral, parenteral, intraperitoneal, intravenous, epidural, intraspinal, intrasternal, intra-articular, intra-synovial, intrathecal, intra-arterial, intracardiac, or intramuscular administration. For example, subjects of interest may be engrafted with the transplanted cells by various routes. Such routes include, but are not limited to, intravenous administration, subcutaneous administration, administration to a specific tissue (e.g., focal transplantation), injection into the femur bone marrow cavity, injection into the spleen, administration under the renal capsule of fetal liver, and the like. In certain embodiment, the compositions encompassed by the present invention are injected to the subject intratumorally or subcutaneously. Cells may be administered in one infusion, or through successive infusions over a defined time period sufficient to generate a desired effect. Exemplary methods for transplantation, engraftment assessment, and marker phenotyping analysis of transplanted cells are well-known in the art (see, for example, Pearson et al. (2008) *Curr. Protoc. Immunol.* 81:15.21.1-15.21.21; Ito et al. (2002) *Blood* 100:3175-3182; Traggiai et al. (2004) *Science* 304:104-107; Ishikawa et al. *Blood* (2005) 106:1565-1573; Shultz et al. (2005) *J. Immunol.* 174:6477-6489; and Holyoake et al. (1999) *Exp. Hematol.* 27:1418-1427).

Two or more cell types can be combined and administered, such as cell-based therapy and adoptive cell transfer of stem cells, cancer vaccines and cell-based therapy, and the like. For example, adoptive cell-based immunotherapies can be combined with the cell-based therapies encompassed by the present invention. Well-known adoptive cell-based immunotherapeutic modalities, including, without limitation, irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, and the like. The ratio of cancer cells in the compositions described herein to other cell types can be 1:1, but can modulated in any amount desired (e.g., 1:1, 1.1:1, 1.2:1, 1.3:1, 1.4:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, or greater).

Engraftment of transplanted cells may be assessed by any of various methods, such as, but not limited to, tumor volume, cytokine levels, time of administration, flow cytometric analysis of cells of interest obtained from the subject at one or more time points following transplantation, and the like. For example, a time-based analysis of waiting 1, 2, 3, 4, 5, 6, 7, 8, 9, 10, 11, 12, 13, 14, 15, 16, 17, 18, 19, 20, 21, 22, 23, 24, 25, 26, 27, 28 days or can signal the time for tumor harvesting. Any such metrics are variables that can be adjusted according to well-known parameters in order to determine the effect of the variable on a response to anti-cancer immunotherapy. In addition, the transplanted cells can be co-transplanted with other agents, such as cytokines, extracellular matrices, cell culture supports, and the like.

The present invention is further illustrated by the following examples which should not be construed as limiting. The contents of all references, patents and published patent applications cited throughout this application, as well as the Figures, are incorporated herein by reference.

VIII. Kits

The present invention also encompasses kits for detecting and/or modulating biomarkers described herein. A kit encompassed by the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

EXAMPLES

Example 1: Materials and Methods for Examples 2-8 a. Mice

Mice were bred at Dana-Farber Cancer Institute in accordance with the guidelines of the Institutional Animal Care and Use Committee (IACUC). The following strains were used in this study, all on the C57BL/6 genetic background: C57BL/6 (CD45.2$^+$; the Jackson Laboratory), B6.SJL (CD45.1$^+$; the Jackson Laboratory), Rag2$^{-/-}$Il2rg$^{-/-}$ (Taconic), Klra8–/– (Ly49H– deficient) (Fodil-Cornu et al. (2008) *J. Immunol.* 181:6394-405), IRE1$^{f/f}$ (Iwawaki et al. (2009) *Proc. Natl. Acad. Sci. USA* 106:16657-16662), XBP1$^{f/f}$ (Lee et al. (2008) *Science* 320:1492-1496), Myc$^{f/f}$, Ncr1$^{iCre}$, ERAI (ER stress-activated indicator) (Iwawaki et al. (2004) *Nat. Med.* 10:98-102), GFP-c-Myc KI (here called Myc$^{GFP}$, the Jackson Laboratory), XBP1s$^{FSP}$ (Fedeles et al. (2015) *J. Clin. Invest.* 125:1955-1967) and Vav1$^{iCre}$ (the Jackson Laboratory) mice. Myc$^{fsf/fsf}$ on mixed B6.126 background was also used. IRE1$^{f/f}$Ncr1$^{iCre/WT}$ (here called IRE1$^{NK}$) XBP1$^{f/f}$Ncr1$^{iCre/WT}$ (XBP1$^{NK}$), Myc$^{f/+}$Ncr1$^{iCre/WT}$ (Myc$^{NK}$), Myc$^{fsf/+}$ Ncr1$^{iCre/WT}$ (Myc$^{OE}$), Myc$^{fsf/+}$ IRE1$^{f/f}$ Ncr1$^{iCre/WT}$ (Myc$^{OE}$ IRE1$^{NK}$) and XBP1s$^{FSP}$Vav1$^{iCre/WT}$ (here called XBP1$^{tg}$) animals and littermate controls were generated by breeding at Dana-Farber Cancer Institute. Recipient Klra8–/– (CD45.1$^+$CD45.2$^+$) mice were generated by crossing Klra8–/– (CD45.2$^+$) to B6.SJL (CD45.1$^+$). Experiments were conducted without blinding using age- and gender-matched mice in accordance with approved institutional protocols.

Figure 3A:
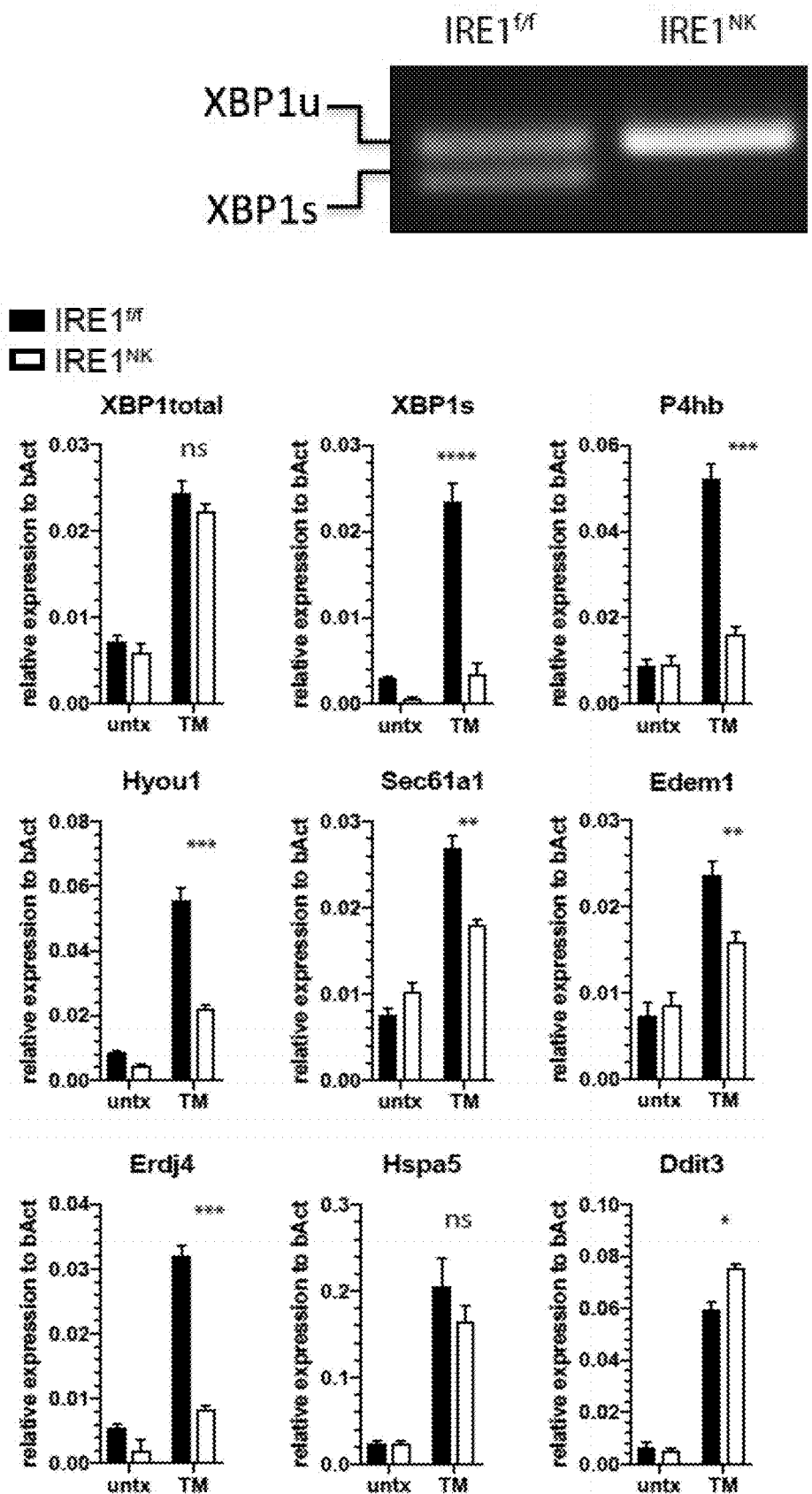
Figure 3B:
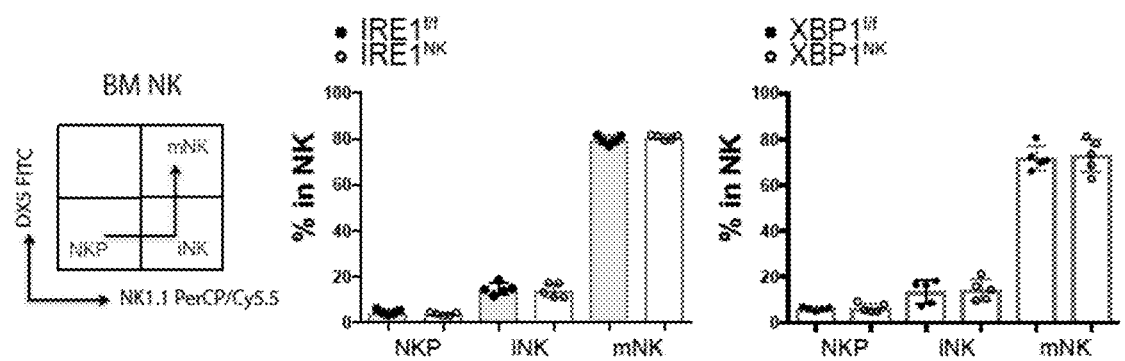
Figure 3C:
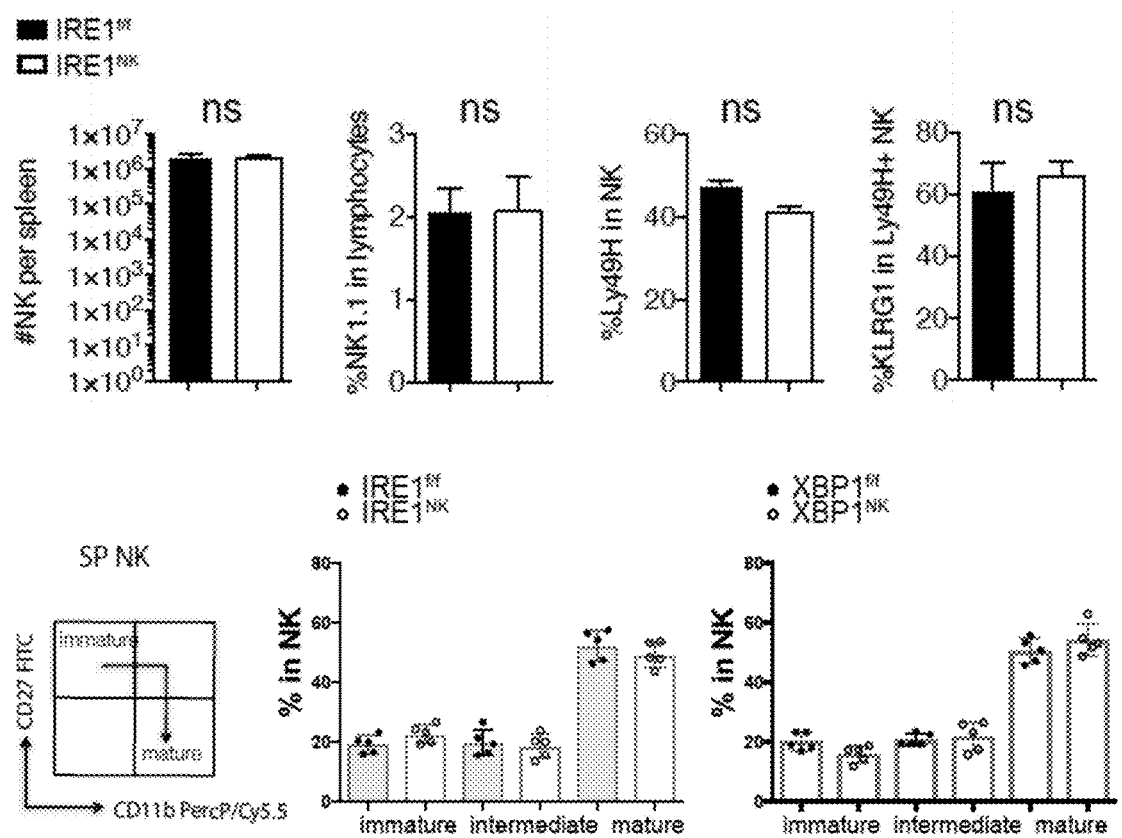
Figure 3E:
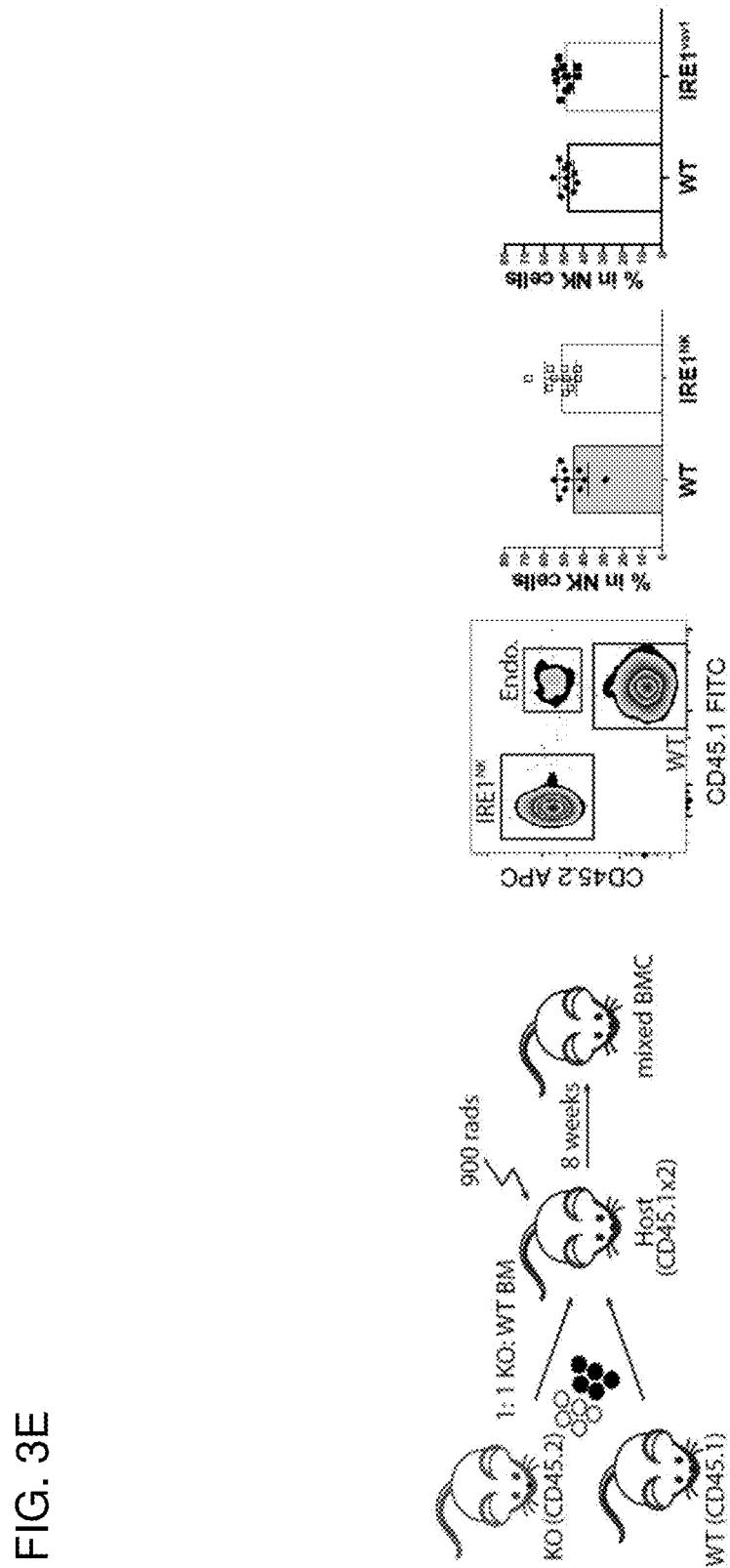

IRE1$^{vav1}$ mice (IRE1$^{f/f}$ Vav1$^{iCre/WT}$) were generated by crossing Vav1$^{iCre}$ (The Jackson Laboratory) and IRE1$^{f/f}$ mice, and then used as BM donors in FIG. 3E to make mixed WT (CD45.1): IRE1$^{vav1}$ (CD45.2) bone marrow (BM) chimeras.

b. Virus Infection

MCMV (Smith strain) was passaged serially through BALB/c hosts two times, then viral stocks were prepared using a dounce homogenizer to dissociate the salivary glands of infected mice 3 weeks after infection. For direct infection of C57BL/6 or ERAI mice, 7.5×10$^3$ plaque-forming units (PFU) of MCMV was injected by i.p. For the adoptive transfer studies, Ly49-deficient mice were infected by intraperitoneal (i.p.) injection of 7.5×10$^2$ PFU of MCMV one day after receiving approximately 2×10$^5$ Ly49H$^+$ NK cells by intravenous (i.v.) injection.

c. NK Cell Enrichment and Adoptive Transfer

Figure 9A:
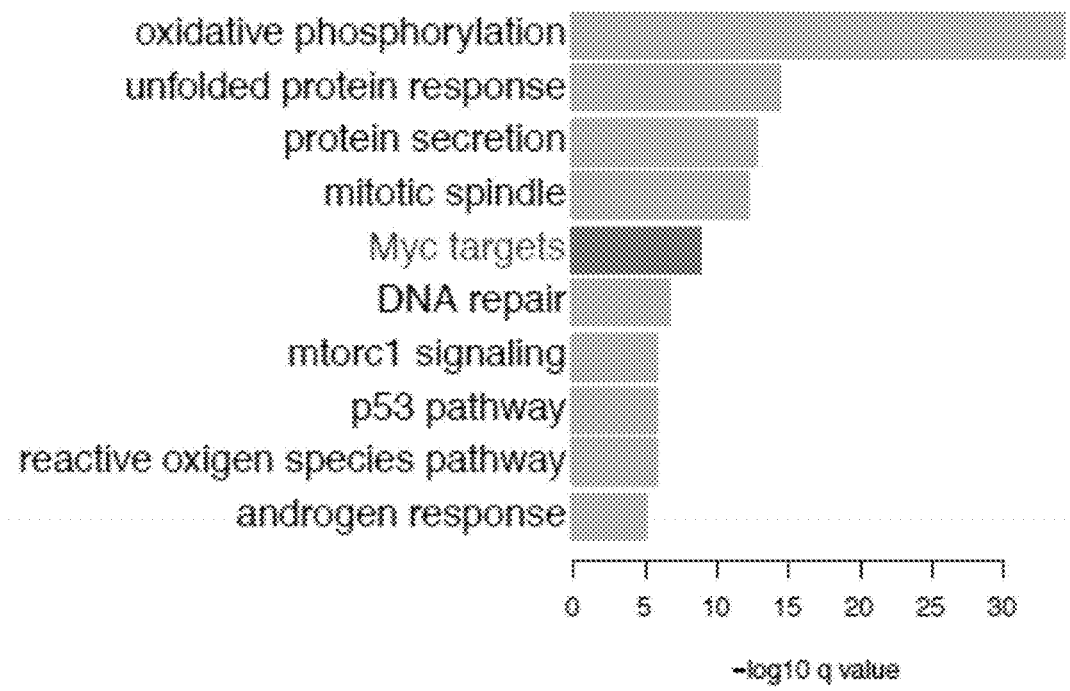
Figure 9B:
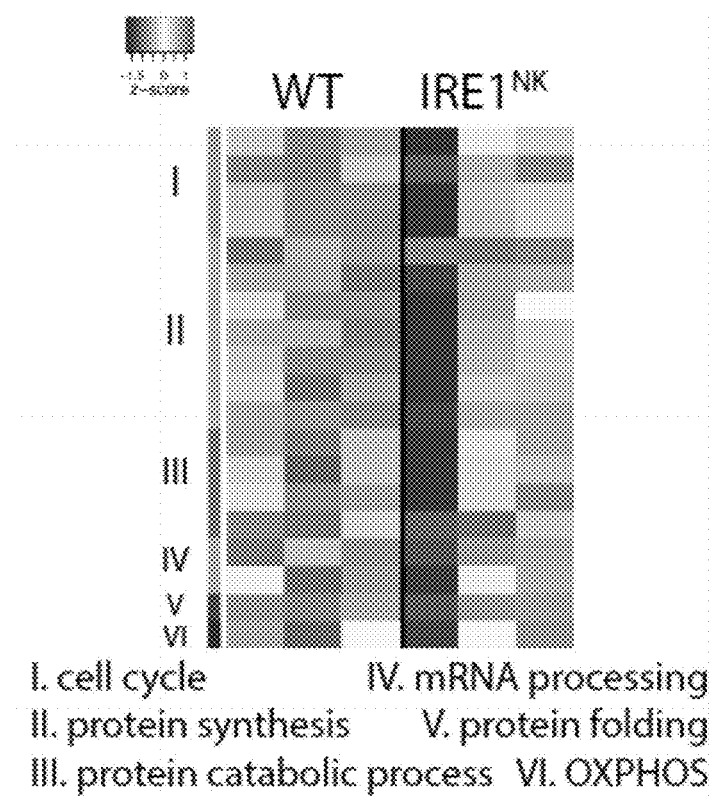
Figure 9D:
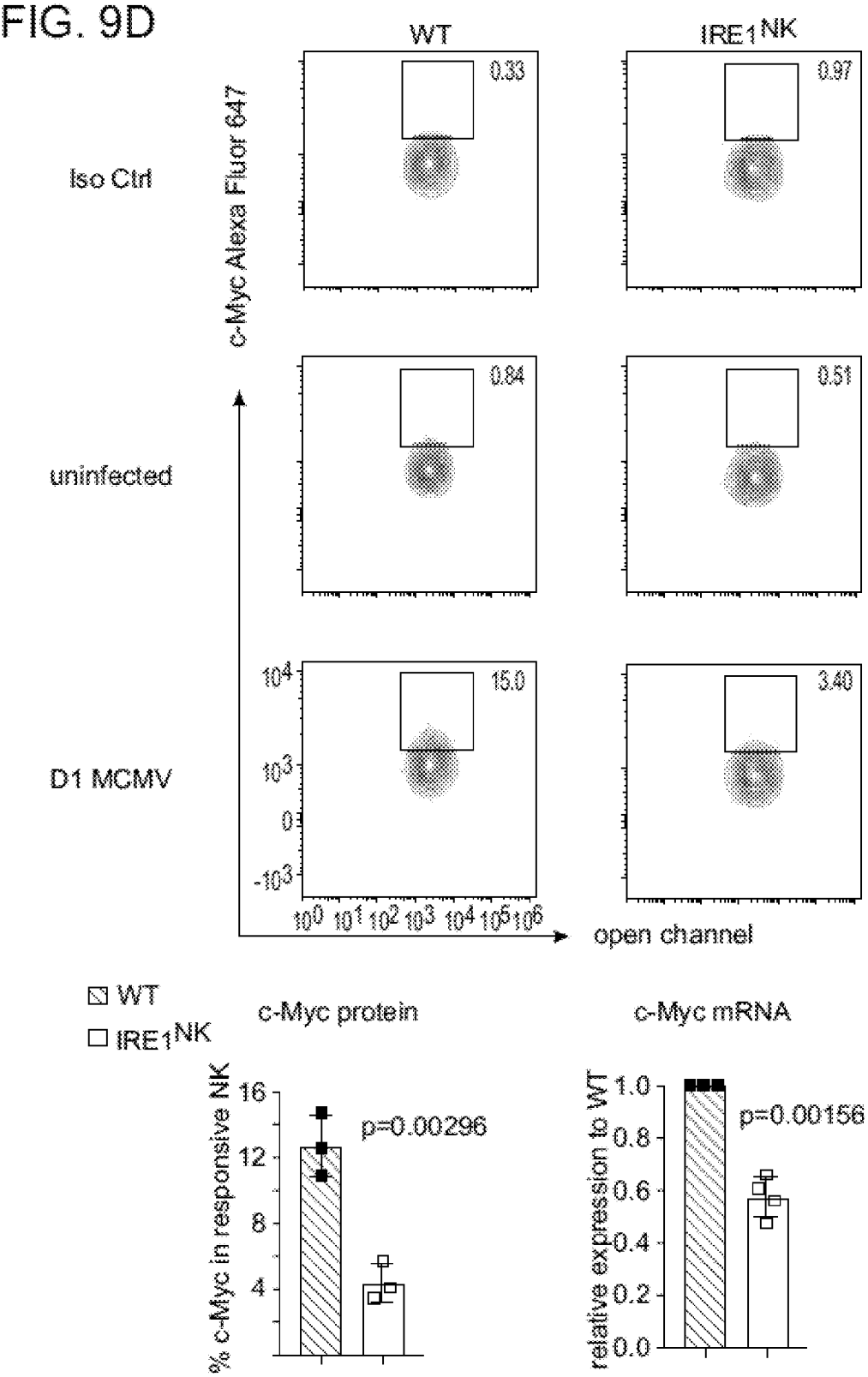
Figure 9E:
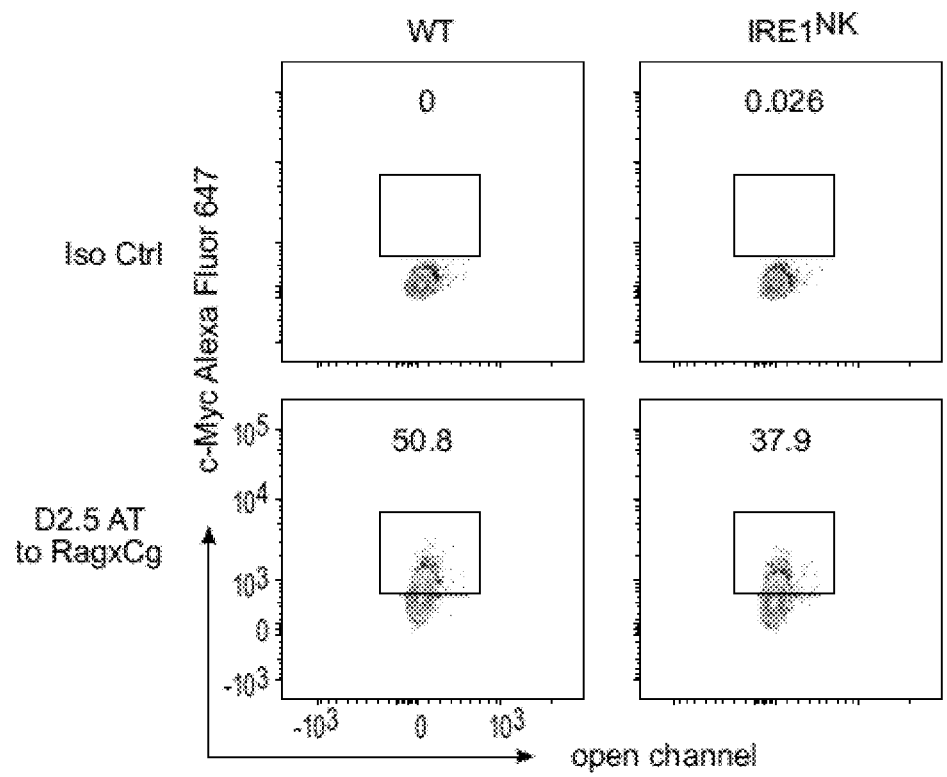
Figure 9E:
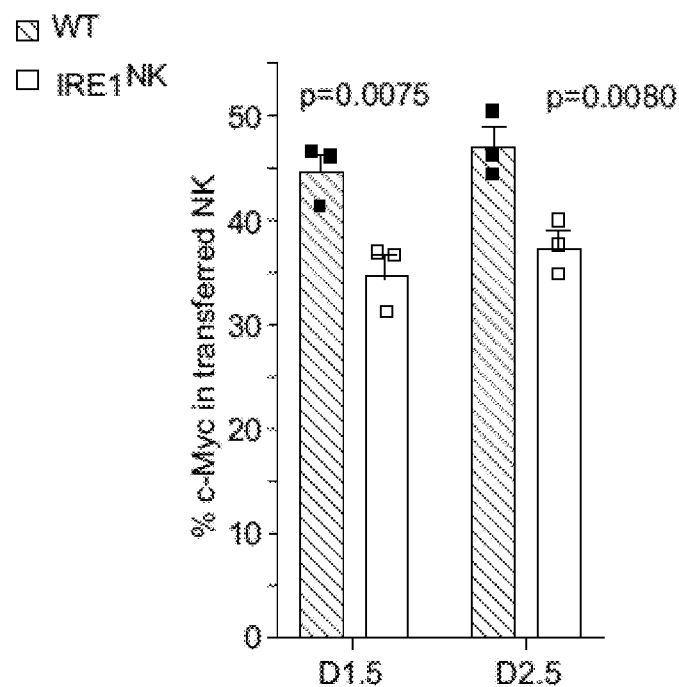

Enrichment of NK cells was performed using the magnetic bead-based negative selection kit (Miltenyi Biotec) per the manufacturer's protocol (typically 50-70% purity) before the flow cytometric analysis of the transferred NK cells in the spleen of recipients at early time points after infection of MCMV in some experiments (FIGS. 6C-6F; FIGS. 9D and 9E). As previously described (Sun et al. (2009) *Nature* 457:557-561), for experiments involving co-transfer of CD45.1$^+$ and CD45.2$^+$ populations, equal numbers of Ly49H$^+$ NK cells (normalized on KLRG1$^{Lo}$ population) from each population were co-transferred together by intravenous injection into the tail vein of adult Ly49H-deficient recipients 1 d before infection with MCMV, or equal numbers of NK cells from each population were co-transferred together into adult Rag2–/–xIl2r–/– recipients. Wildtype (WT) and knockout (KO) NK cells are transferred together into the same mouse and the numbers of cells are the same. Thus, the percentages shown are directly correlated with the absolute number of cells. In some experiments, cells were labeled before transferring with CellTrace™ Violet (CTV; Invitrogen) to trace cell proliferation.

d. Flow Cytometry and Cell Sorting

Cell surface staining of single-cell suspensions was performed using the following fluorophore-conjugated antibodies (purchased from BD Biosciences, eBioscience, BioLegend, Tonbo Biosciences, Cell Signaling Technology, and R&D Systems): NK1.1 (PK136), KLRG1 (2F1), Ly49H (3D10), CD45.1 (A20), CD45.2 (104), CD8α (53-6.7), TCRβ (H57-597), CD3ε (145-2C11), F4/80 (BM8), CD19 (eBio1D3), Ki-67 (SolA15), c-Myc (D84C12), and XBP1s (Q3-695). NK cells were CD19$^-$CD3$^-$ TCRβ$^-$ F4/80$^-$ NK1.1$^+$. All analysis was performed on viable populations by exclusion of the dead cells using a fixable viability dye (Thermo Fisher). For the evaluation of NK cell apoptosis, Pan-caspase (FLICA) staining was carried out using the FAM FLICA™ in vitro Poly Caspase Kit (Immunochemistry Technologies) per the manufacturer's protocol; Annexin V staining was carried out using the Invitrogen eBioscience Annexin V Apoptosis Detection Kit per the manufacturer's instructions. For the evaluation of NK cell proliferation, cells were labeled with 5 uM CTV (Invitrogen) according to the manufacturer's protocol before transferring into recipient mice; intracellular staining of Ki-67 and c-Myc was performed by fixing and permeabilizing with the Foxp3/ Transcription Factor Staining Kit (eBioscience); for the EdU labeling experiments, mice were subjected to i.p. injection of 1.5 mg of EdU in PBS on days 3.5 and 5.5 after infection with MCMV, and EdU labeling was determined ~16 h later using the Click-iT® EdU Assay Kit (Thermo Fisher Scientific). Flow cytomeric analysis of c-Myc mRNA was carried out using PrimeFlow™ RNA Assay Kit (Invitrogen) per the manufacturer's instructions. Flow cytometry was performed on the LSR II (BD Biosciences), LSR Fortessa™ X-20 and CytoFLEX LX (Beckman Coulter). Cell sorting was performed on Aria™ II cytometers (BD Biosciences). For experiments involving qRT-PCR, cell populations were sorted to >95% purity. Data were analyzed with FlowJo™ software (Tree Star).

The following fluorophore-conjugated antibodies were used (purchased from BD Biosciences, eBioscience, BioLegend, Cell Signaling Technology and Tonbo Biosciences): IFN-γ (XMG1.2), Granzyme B (16G6), CD69 (H1.2F3), CD11b (M1/70), CD27 (LG.3A10), CD49b/DX5 (DX5), CD25 (3C7), CD122 (TM-β1), CD132 (TUGm2), CD215 (DNT15Ra), CD212 (114), CD218a (BG/IL18RA), NKp46 (29A1.4), NKG2D (C7), Ly49D (4E5), pan-Akt (C67E7), p-Akt (Ser473, D9E), and p-S6 (Ser235/236, D57.2.2E). Intracellular staining of IFN-γ and Granzyme B was performed by fixing and permeabilizing with Cytofix/Cytoperm™ Plus (BD). Intracellular staining of pan-Akt, p-Akt and p-mTOR was performed by fixing with Phosflow Lyse/ Fix Buffer (BD) and permeabilizing with Phosflow Perm Buffer IV (BD) following the manufacturer's instructions.

e. Ex Vivo Stimulation of Primary Mouse and Human NK Cells

Figure 1B:
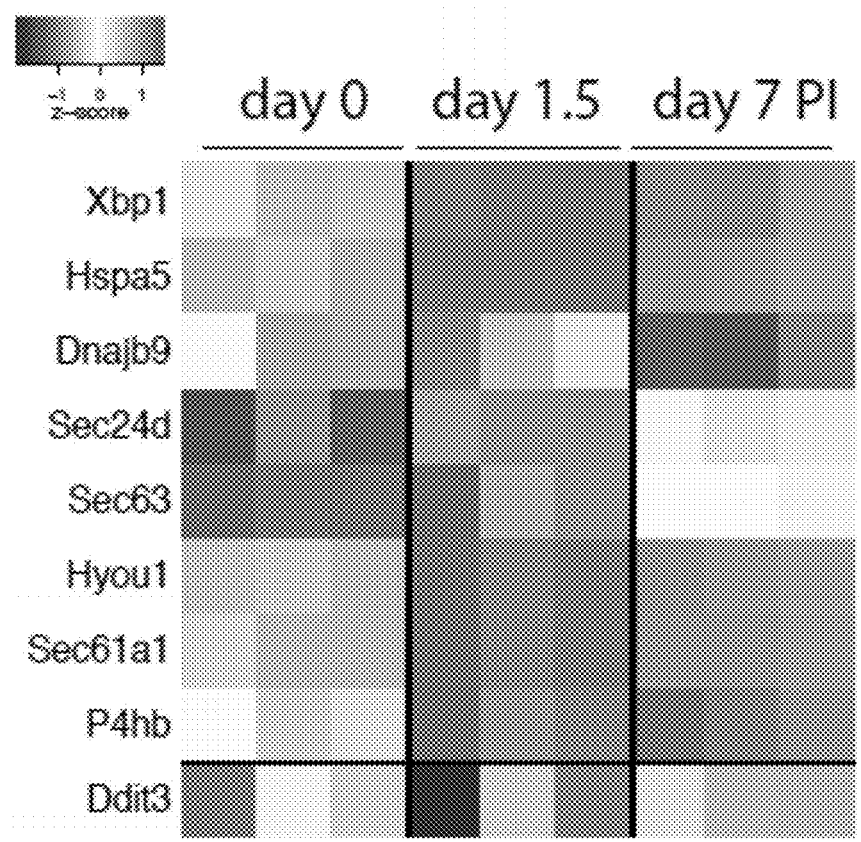
Figure 1C:
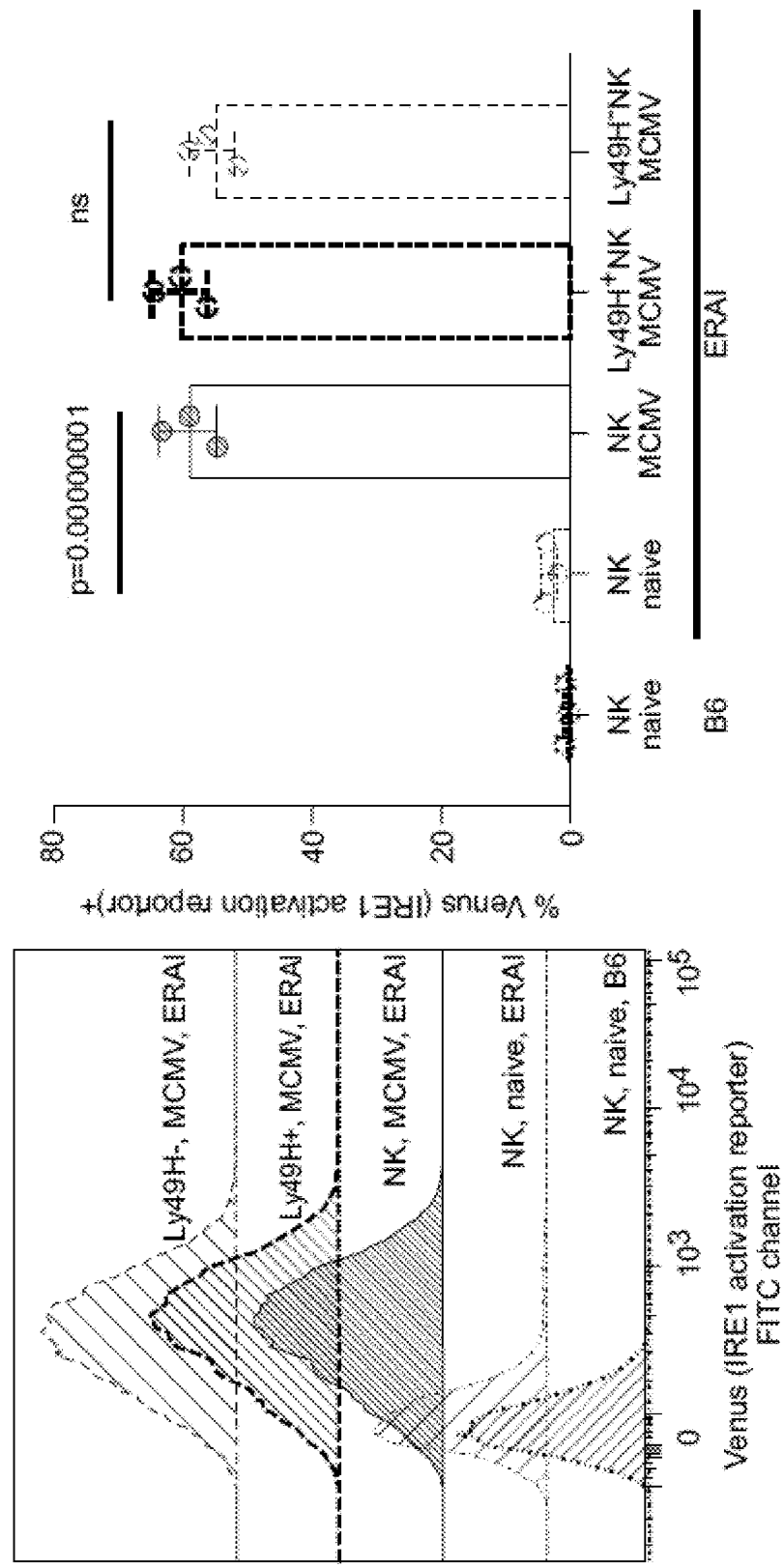
Figure 1D:
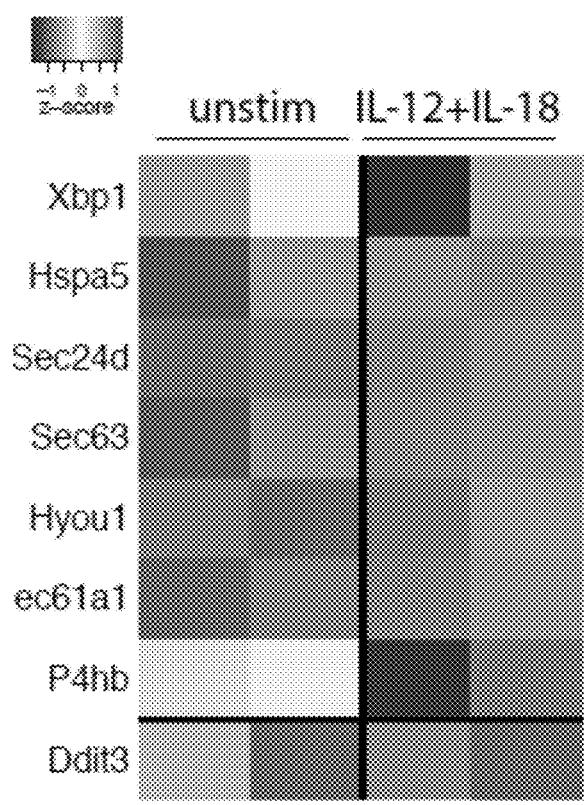
Figure 1E:
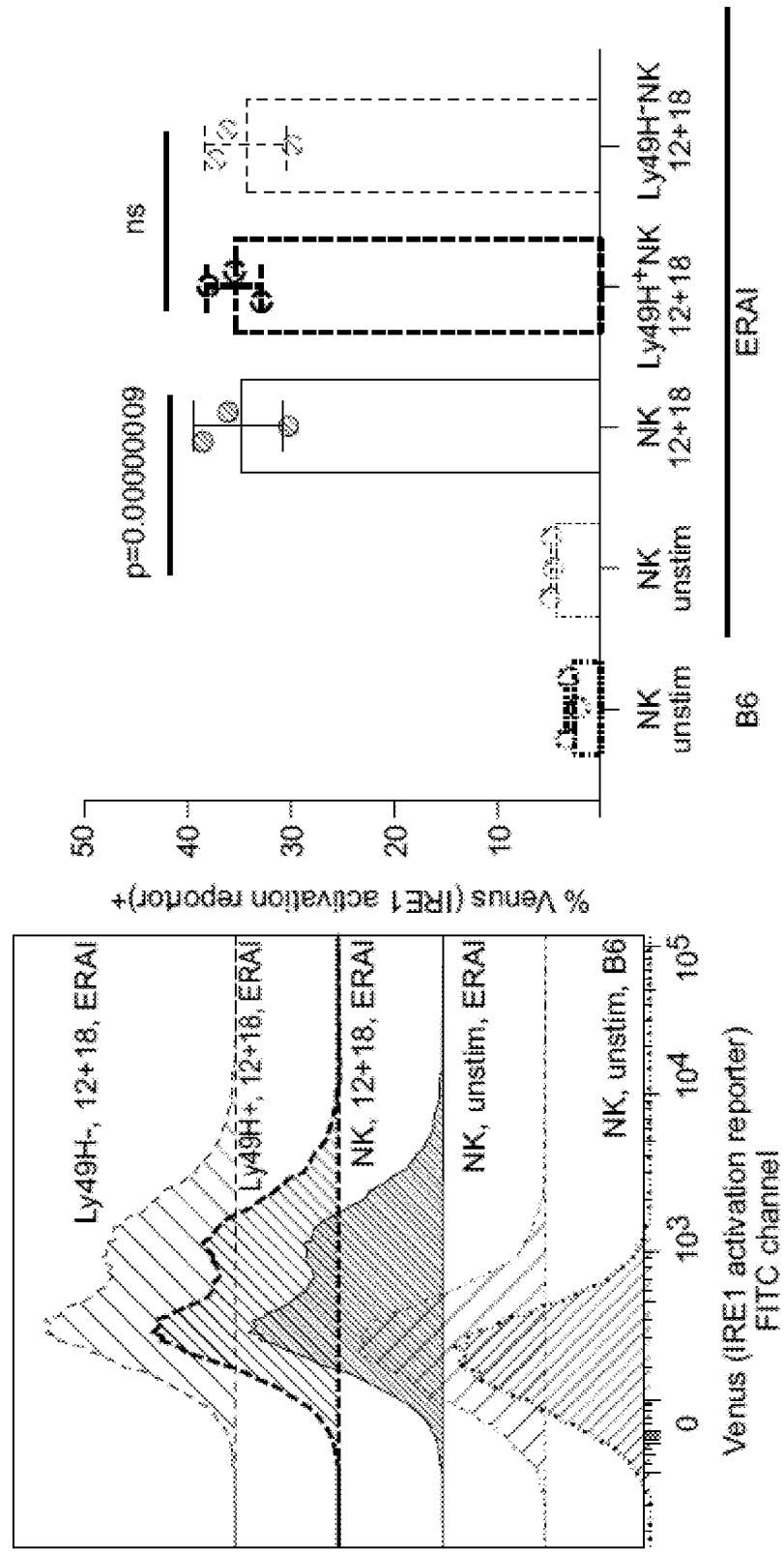

For FIG. 1E, ~2×10$^5$ sorted splenic NK cells were stimulated for 16 hr in complete RPMI containing 10% FBS with recombinant mouse IL-2 (10 μg/ml; BioLegend), either in the presence or absence of IL-12 (20 ng/ml; Peprotech) and IL-18 (10 ng/ml; R&D Systems). For ex vivo NK cell expansion experiments, 2.5×10$^5$ sorted NK cells (>97% purity) were stimulated in RPMI supplemented with 10% FBS, penicillin-streptomycin, L-glutamine and β-mercaptoethanol, and with recombinant mouse IL-2 (10 ng/ml; R&D Systems) and IL-15/15R (40 ng/ml; eBioscience) re-applied every other day. In some assays indicated, 5 µM of 4µ8c (IRE1 inhibitor; Sigma Aldrich) was added to the culture and DMSO was used as the control treatment.

Peripheral blood mononuclear cells (PBMCs) from healthy donors (New York Blood Center) were isolated by density gradient centrifugation with Ficoll (GE Healthcare). NK cells were enriched by negative selection using the human NK Cell Isolation Kit (Miltenyi Biotec; >90% purity). For ex vivo stimulation in FIG. 1F, ~$10^6$ sorted NK cells were stimulated for 16 hr in complete RPMI containing 10% FBS with recombinant human IL-2 (10 µg/ml; Sigma Aldrich), in combination with either IL-12 (20 ng/ml; StemCell) and IL-18 (10 ng/ml; Thermo Figher Scientific), or IL-15 (40 ng/ml, StemCell). For human NK ex vivo expansion in FIG. 7F, recombinant human IL-2 (100 U/ml, Roche) and IL-15 (10 ng/ml, StemCell) was applied. Fresh medium and cytokines were added on alternating days of culture. In some assays indicated, 5 µM of 4µ8c (IRE1 inhibitor) was added to the culture and DMSO was used as the control treatment. For flow cytometric analysis or cell sorting, human NK cells were CD3$^-$CD56$^+$.

f. Generation of Cytokine-Induced, Memory-Like (CIML) Human NK Cells

Figure 17A:
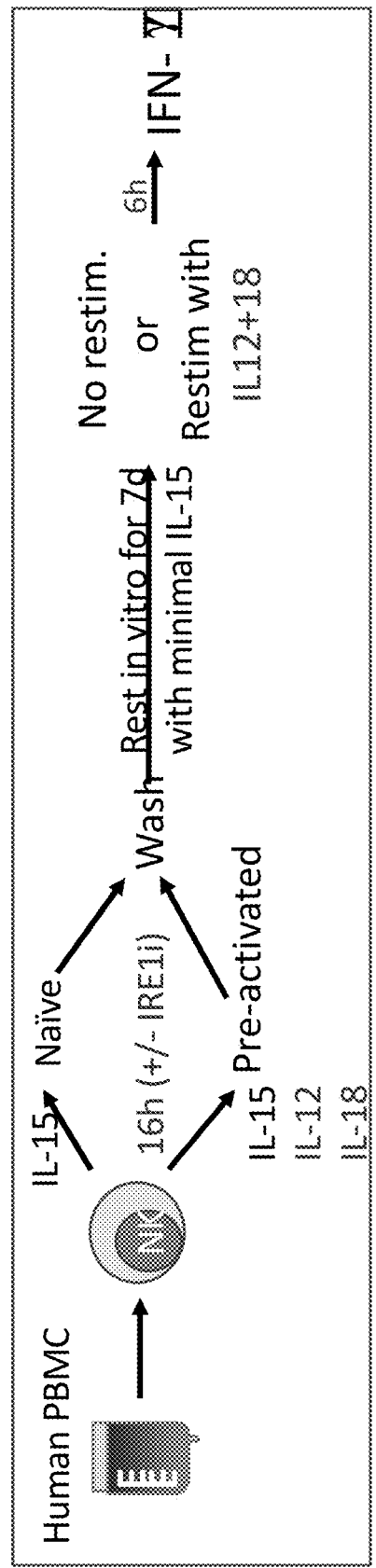
FIG. 17A-FIG. 17C show that IRE1α is important for IFN-γ production of cytokine-induced, memory like (CIML) human primary NK cells (such as cells described in Romee et al. (2012) *Blood* 120:4751-4760).
Figure 17B:
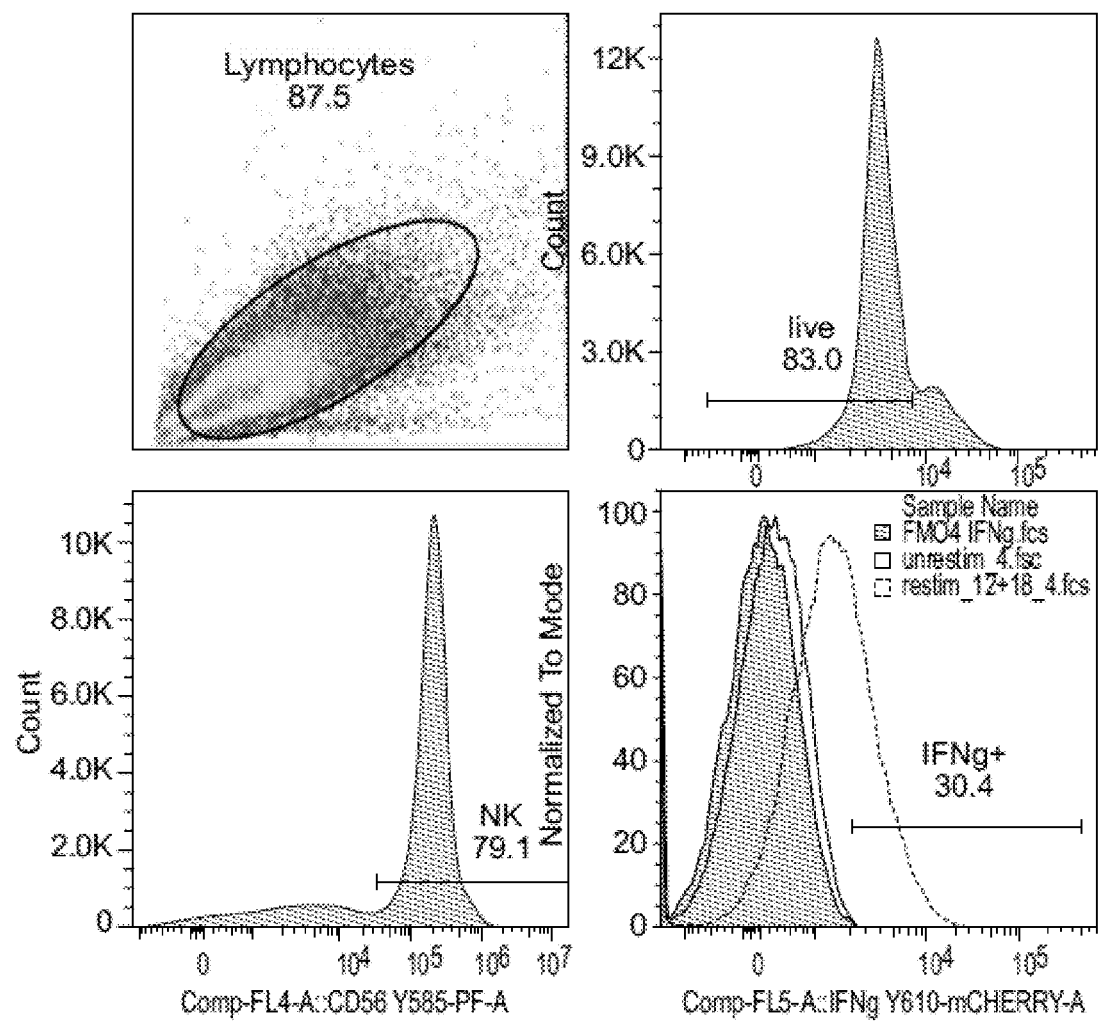
Figure 17C:
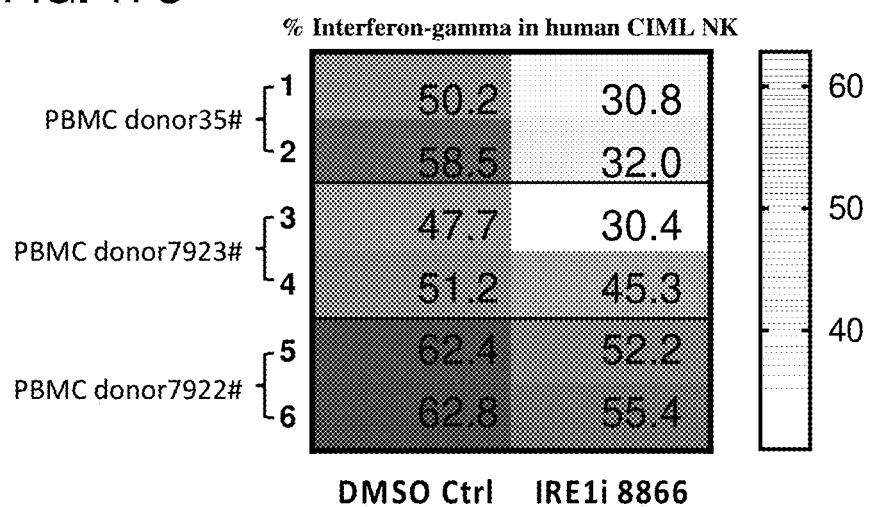

For data shown in FIG. 17A-17C, enriched primary human NK cells were plated at 5×$10^6$ cells/ml and preactivated for 16 hours using rhIL-12 (10 ng/mL)+rhIL-18 (50 ng/mL)+rhIL-15 (1 ng/mL) or control conditions (rhIL-15, 1 ng/mL). 5 µM of MKC8866 (IRE1 inhibitor) was added to the culture during the preactivation phase and DMSO was used as the control treatment. Cells were then washed 3 times to remove cytokines, and were cultured in complete RPMI supplemented with rhIL-15 (1 ng/mL) to support survival, with 50% of the medium being replaced every 2 days with fresh cytokines. At day 7, cells were restimulated with rhIL-12 (10 ng/mL)+IL-18 (50 ng/mL)+rhIL-15 (1 ng/mL) for 6 hours before the flow cytometric analysis for IFN-gamma production.

g. NK Cell Lines and Culture Conditions

MNK-1 cells (Allan et al. (2015) *Mucosal. Immunol.* 8:340-351) were cultured in DMEM supplemented with 10% FBS, 2 mM GlutaMAX, 1 mM sodium pyruvate, 55 µM 2-mercaptoethanol, 10 mM HEPES, 50 µg/ml gentamicin, 100 U/ml penicillin, and 100 µg/ml streptomycin (all from Corning or Gibco Life Technologies, except FBS from Atlanta Biologicals). To facilitate robust survival, 10 ng/ml recombinant mouse IL-2 (BioLegend) were re-applied daily. NKL cells (Robertson et al. (1996) *Exp. Hematol.* 24:406-415) and KHYG-1 cells (Frazier et al. (2013) *J. Immunol.* 190:6198-6208) were cultured in RPMI 1640 medium supplemented with 2 mM L-glutamine, 1 mM sodium pyruvate, 100 U/ml penicillin, 100 µg/ml streptomycin and 7.5% FCS plus 7.5% new born calf serum (all from Corning or Gibco Life Technologies, except FBS from Atlanta Biologicals). The cell concentration was maintained at ~5×$10^5$/ml in the presence of 50 U/ml of recombinant human IL-2 (Amgen).

h. Quantitative Real Time PCR

Cells were pre-enriched (Miltenyi Biotec) and then sorted to >95% purity and RNA was isolated using the RNeasy® RNA purification mini (for 5×$10^5$ cells or beyond) or micro (for <5×$10^5$ cells) kit (Qiagen) according to the manufacturer's protocol. From purified RNA, cDNA was synthesized using the reverse-transcriptase kit gScript™ cDNA synthesis kit (Quanta Biosciences). Quantitative real time PCR (qRT-PCR) was performed in triplicates in a 384-well plate using Taqman® Probes (Themo Fisher) or SYBR® Green (Quanta Biosciences)-based detection on an ABI QuantStudio™ 6 Flex qRT-PCR machine. For experiments in FIG. 9D, Cell-Direct™ One-Step qRT-PCR Kit with Rox (Life Technologies) was used according to the manufacturer's instruction. For the analysis of mRNA abundance, the derived values were normalized to those of β-Actin (β-ACTIN for human materials). Primer sequences are listed in Table 2 below and Taqman® probe information is provided in Table 3 below.

TABLE 2

Primers used for qRT-PCR

| Species | Gene Target | Forward Primer (5'-3') | Reverse Primer (5'-3') |
|---|---|---|---|
| Mouse | Actb | TACCACCATGTACC CAGGCA | CTCAGGAGGAGCAA TGATCTTGAT |
| Mouse | Ern1 | ACACCGACCACCGT ATCTCA | CTCAGGATAATCCT AGCCATGTC |
| Mouse | Xbp1 | GACAGAGAGTCAAA CTAACGTGG | GTGGAGCAGGCAAG AAGGT |
| Mouse | XBP1s | AAGAACACGCTTGG GAATGG | CTGCACCTGCTGCG GAC |
| Mouse | Hyou1 | GTGATAGTGCAGCC GGCAT | AACGGAGCGTAGCC TTTGG |
| Mouse | P4hb | CAAGATCAAGCCCC ACCTGAT | AGTTCGCCCCAACC AGTACTT |
| Mouse | Hspa5 | TCATCGGACGCACT TGGAA | CAACCACCTTGAAT GGCAAGA |
| Mouse | Ddit3 | GTCCCTAGCTTGGC TGACAGA | TGGAGAGCGAGGGC TTTG |
| Mouse | Sec24d | TCCACTCTCCCCAT GGTTTA | GCTATATCCGCTGC ACTACG |
| Mouse | Sec61a | CTGGCGGTAGAATG CCTCT | TGAGACCATTGTGT GGAAGG |
| Mouse | Sec63 | GTGGACTACAGCGT TTGCACA | CATATCAGCCCTCA CTGCTGC |
| Mouse | Erdj4 | CCCCAGTGCAAACT GTACCAG | AGCGTTTCCAATTT TCCATAAATT |
| Mouse | Edem1 | ATCCAAGGCATCAA CCAGAG | ATGACAACTACATG GCGCAC |

TABLE 3

Taqman® assays for qRT-PCR

| Species | Gene Target | Taqman assay name |
|---|---|---|
| Human | ACTB | Hs01060665_g1 |
| Human | XBP1 | Hs002319636_m1 |
| Human | XBP1S | Hs03929085_g1 |
| Human | ERDJ4 | Hs01052402_m1 |
| Human | MYC | Hs00153408_m1 |
| Mouse | Actb | Mm02619580_g1 |
| Mouse | Myc | Mm00487804_m1 |
| Mouse | Cdkn1a (p21) | Mm00432448 m1 |
| Mouse | Ddx18 | Mn03047856_g1 |
| Mouse | Hspd1 | Mm00849835 g1 |
| Mouse | Ncl | Mm01290600_g1 |
| Mouse | Odc1 | Mm02019269_g1 |
| Mouse | Cdk4 | Mm00726334_s1 | i. RNA-Seq Analysis

Mixed IRE1$^{\Delta NK}$ (CD45.2): WT (CD45.1) bone marrow chimeric mice were generated as previously described (Sun et al. (2009) *Nature* 457:557-561). Briefly, host C57BL/6× B6.SJL animals (CD45.1⁺CD45.2⁺) were lethally irradiated with 900 grays of radiation and reconstituted with a 1:1 mixture of bone marrow cells from B6. SJL WT (CD45.1⁺) and knockout or transgenic donor (CD45.2⁺) mice, co-injected with anti-NK1.1 (clone PK136) to deplete any residual donor or host mature NK cells. CD45.1⁺CD45.2⁺ host NK cells were excluded from all analyses.

Mice were infected with 7.5×10³ PFU of MCMV by i.p. injection and spleens were harvested at day 0, 1.5 and 7 after infection. Total RNA from sorting-purified Ly49H⁺ WT or IRE1$^{NK}$ NK cells was extracted with the RNeasy® RNA purification micro kit (Qiagen) according to the manufacturer's instructions. Poly (A)+ RNA-seq libraries (pair-end 100) were prepared with an Illumina TruSeq RNA Sample Preparation Kit V2 according to the manufacturer's instructions (Illumina). Sequence data from Illumina's HiSeq4000 sequencer were "de-multiplexed" to generate FASTQ files for each sample with Illumina's CASAVA pipeline (version 1.8.2).

The reads that passed Illumina's quality and purity filter (>90%) were aligned to the mouse genome (Illumina iGenomes mm9 build) with tophat2 (Wang et al. (2019) *Nat. Immunol.* 20:10-17) with default parameters. The resulting SAM alignment files were then converted to the BAM file format, then were sorted and indexed with SAMtools (version 0.1.14). The HTSeq (Anders and Huber (2015) *Bioinformatics* 31:166-169) was used for summarization of the aligned sequence reads into counts. Differential gene expression was analyzed with the DESeq2 (Anders and Huber (2010) *Genome Biol.* 11:R106). Transcripts with adjusted P value<0.01 were considered differentially expressed between genotypes (wild-type and IRE1$^{NK}$) and infection times (day 0, 1.5, 7). Gene ontology analysis of differentially expressed genes was performed in GSEA (gene sets enrichment analysis) (Subramanian et al. (2005) *Proc. Natl. Acad. Sci. USA* 102:15545-15550). Pathway analysis of predicted upstream regulators was performed with Ingenuity Pathway Analysis software (Qiagen). For heat maps, normalized data from DESeq RNA-seq analyses were exported, manually curated for specific genes in each category, and the gene-expression z-score was visualized with the Heatmap.2 function within the gplots R library.

j. Chromatin Immunoprecipitation (CHIP)

MNK-1, NKL and KHYG-1 cells were crosslinked with 1% formaldehyde for 10 min at room temperature. Reaction was quenched with 125 mM glycine. CHIP was performed as previously described (Chen et al. (2008) *Cell* 133:1106-17) with XBP1 antibody (Cat. 619502, Biolegend), or normal rabbit IgG control (Cat. #2729, CST). The sequences of all primers are listed in Table 4 below.

TABLE 4

Primers used for qPCR of XBP1 ChIP targets.

| Species | Gene Target | Primer sequence or Information |
|---|---|---|
| Mouse | c-Myc | Commercial primer assay: Qiagen Epitect ChIP qPCR Primer Assay for Mouse Myc, NM_010849.4(-)01Kb; Cat#GPM1032014(-)01A (linked to Supplementary FIG. 4e) |
| Mouse | Apoa4 (negative control) | Forward (5'-3'): CTGTGTGCTGTCAGCTTCCAC Reverse (5'-3'): CCTCCTCCCCAGTGTGACTC |
| Mouse | Erdj4 (positive control) | Forward (5'-3'): AGTGACGCAAGGACCAAACG Reverse (5'-3'): CTACACGAAACGCTTCCCCA |
| Human | c-MYC | Forward (5'-3'): CCAACAAATGCAATGGGAGT Reverse (5'-3'): CAAGAGTCCCAGGGAGAGTG |
| Human | VEGFA (negative control) | Forward (5'-3'): TGAGGGTTCATCAAGCTGGTGTCT Reverse (5'-3'): TTGGAGAGGGCAGTGCTTAACTCA |
| Human | ERDJ4 (positive control) | Forward (5'-3'): CTCGTCTGTCGACTCACTTC Reverse (5'-3'): TGGAAAACTGTTGTTGCTGC | k. Experimental Melanoma Lung Metastasis

B16F10 cells (Peinado et al. (2012) *Nat. Med.* 18:883-891) were cultured in DMEM supplemented with 10% FBS, 100 U/ml penicillin and 100 ug/ml streptomycin. 2.0×10⁵ B16F10 cells were injected intravenously through the tail vein. Mice were sacrificed and lungs were harvested on day 10-20 post inoculation. Lung tumor nodules were enumerated by gross count of visible sites of disease. Micrometastatic lesions were identified using H&E stained lung sections. All pulmonary tumor measurements were performed in a blinded manner. For the flow cytometric analysis, mice received an intravenous injection of fluorescence-conjugated anti-CD45.2 three minutes prior to euthanasia to label intravascular immune cells that would be excluded from downstream analysis. Lungs were harvested from tumor-bearing mice following euthanasia by $CO_2$ inhalation, and single-cell suspensions were obtained using a gentleMACS™ dissociator (Miltenyi Biotec) per manufacturer's instructions.

l. Statistics

For graphs, data are shown as mean±standard error of the mean (s.e.m.) or standard deviation (s.d.) as indicated. Unless otherwise indicated, statistical differences were evaluated using a two-tailed unpaired Student's t-test, assuming equal sample variance. P<0.05 was considered significant. Graphs were produced and statistical analyses were performed using GraphPad Prism or R. Sample size was not specifically predetermined, but the number of mice used was consistent with prior experience with similar experiments.

m. Data Availability

The RNA-seq data were deposited in the Gene Expression Omnibus under the accession number GSE 113214. The remaining data that support the findings of this study are available from the corresponding authors upon request. Materials will be provided with material transfer agreements in place as appropriate.

n. Xbp1 mRNA-Splicing Assay

The Xbp1 mRNA-splicing assay was performed as described (Martinon et al. (2010) *Nat. Immunol.* 11:411-418). Primers surrounding the splice site in the Xbp1 mRNA (5'-ACACGCTTGGGAATGGACAC-3' and 5'-CCATGG-GAAGATGTTCTGGG-3') were used for amplification by PCR, after which the products were separated by electrophoresis through a 2.5% agarose gel and visualized by staining with ethidium bromide.

o. Immunoblots

Sorted purified NK cells (purity>97%) from WT:IRE1$^{NK}$ mixed BM chimeras day 1.5 PI were collected directly into 20% TCA (trichloroacetic acid) buffer. After sorting, the concentration of TCA was adjusted to 10% before incubation on ice for 30 min to precipitate proteins. The homogenates were centrifuged at 13,000 r.p.m. for 10 min at 4° C., and the supernatant was carefully removed. The pellets with concentrated proteins were washed twice with acetone, and then solubilized in solubilization buffer (containing 9M Urea, 2% Triton X-100, and 1% DTT) mixed with LDS buffer (Invitrogen). The samples were heated at 70° C. for 10 min and protein concentrations determined using a BCA protein assay kit (Thermo Fisher Scientific). Equivalent amounts of protein for WT and KO cells from the same BM chimeras were separated by SDS-PAGE (Bis-Tris gel, Invitrogen) and transferred onto PVDF membranes following the standard protocol. Anti-cMyc (D84C12, Cell Signaling Technology) and goat anti-rabbit secondary antibodies conjugated with HRP (Thermo Fisher Scientific) were used. SuperSignal™ West Pico and Femto chemiluminescent substrates (Thermo Fisher Scientific) were used to image blots in a ChemiDoc™ MP Imaging System instrument (BioRad). Densitometric quantification was performed using Image J software (NIH).

p. Metabolic Flux Assays

Purified human primary NK cells from healthy PBMC donors were stimulated with human recombinant IL-12 and IL-18 for 16 hr in complete RPMI medium, in the presence or absence of IRE1 inhibitor 4μ8C (5 μM). After incubation, NK cells were collected, thoroughly washed and then subjected to Seahorse analyses using non-buffered XF base medium containing 25 mM glucose, 2 mM L-glutamine, and 1 mM sodium Pyruvate but lacking serum. XF96 cell-culture microplates were coated with CellTak™ (Corning) before analysis according to the manufacturer's instructions and washed twice with distilled water. $6 \times 10^5$ NK cells were plated and OCR measurements were analyzed on an XFe96 Extracellular Flux Analyzer (Agilent). After basal OCR measurements were obtained, an OCR trace was recorded in response to oligomycin (1 μM), carbonyl cyanide-p-(trifluoromethoxy) phenylhydrazone (FCCP, 1 μM), and rotenone and antimycin (0.5 μM each) following the XF Cell Mito Stress test kit (Agilent). Metabolic parameters were calculated as follows: basal OCR=last rate measurement before oligomycin injection–minimum rate measurement after rotenone and antimycin injection; maximal OCR=maximum rate measurement after FCCP injection–minimum rate measurement after rotenone and antimycin injection. Typically, 3-6 technical replicates per each sample were examined. OCR values were normalized by protein input amount accordingly.

q. Transmission Electron Microscopy

Sorting-purified IRE1$^{NK}$ and WT Ly49H$^+$ NK cells from the spleens of the mixed BM at day 7 PI were fixed, dehydrated, embedded and sectioned for electron microscopy analysis following a standard protocol at Weill Cornell CLC Imaging Core Facility. Sections were viewed on a JEM 1400 Transmission Electron Microscope (JEOL) operated at 100 kV and digital images were acquired with a Veleta 2K Å~2K charge-coupled device camera (Olympus-SIS).

Example 2: Upregulation of the IRE1α/XBP1 Pathway in Activated NK Cells

Figure 2A:
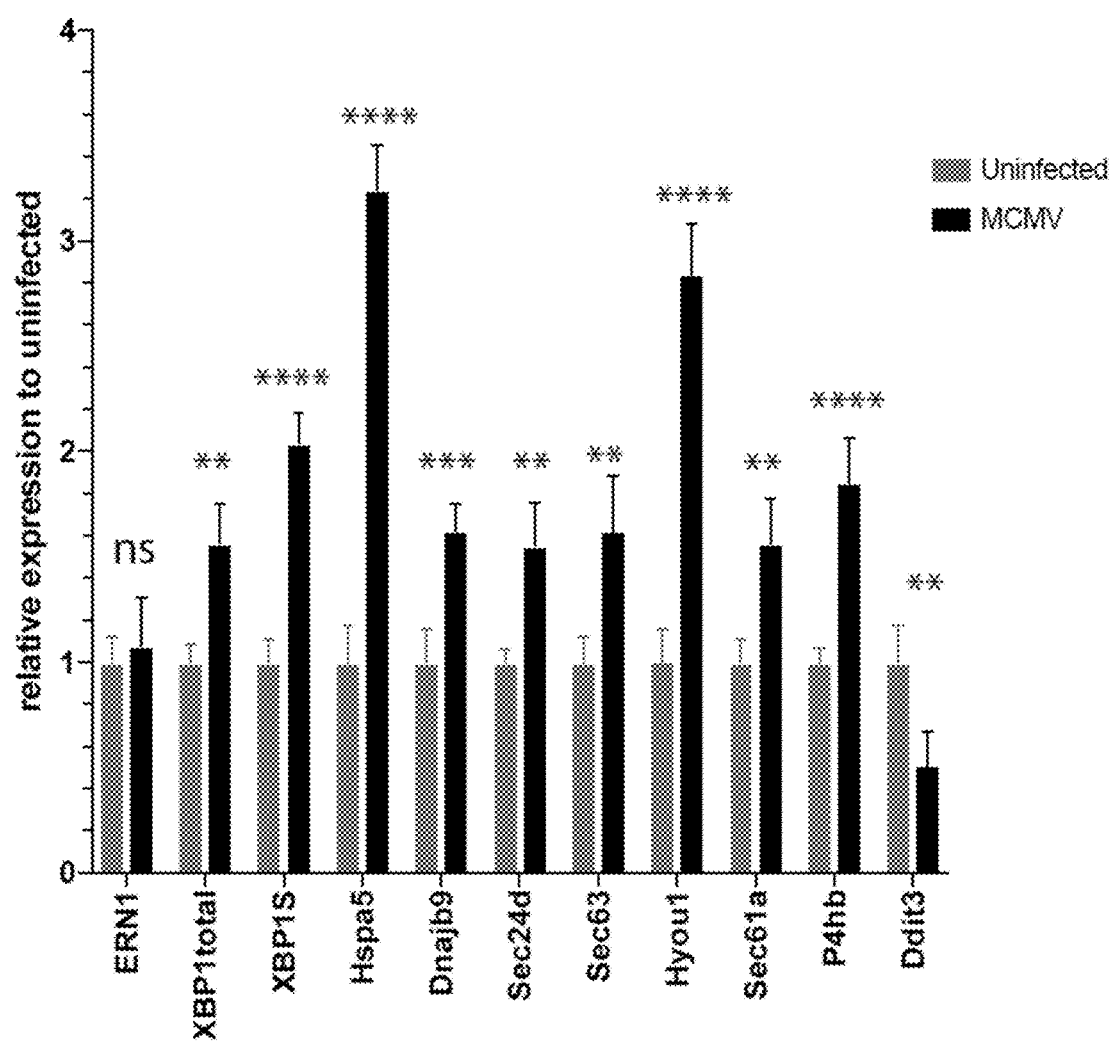

It was investigated whether the IRE1α/XBP1 ER stress response (also termed the Unfolded Protein Response, UPR) is induced in activated NK cells in vivo following mouse cytomegalovirus (MCMV) exposure, where NK cells are known to be critical for control of infection (Madera et al. (2016) *J. Exp. Med.* 213:225-33; Sun and Lanier (2009) *Viruses* 1:362; Schlub et al. (2011) *J. Immunol.* 187:1385-1392; Beaulieu and Sun (2016) *Methods Mol. Biol.* 1441: 1-12). An unbiased transcriptome analysis highlighted ER stress response as one of the top enriched gene ontology (GO) categories in MCMV-primed NK cells (FIG. 1A), as illustrated by a rapid upregulation of the IRE1α/XBP1 pathway at day 1.5 post infection (PI) (FIG. 1B). This was accompanied by the induction of XBP1 splicing leading to generation of the active spliced XBP1s RNA, along with the upregulation of canonical XBP1 target genes (FIG. 2A). Consistent with the transcriptomics, analysis of transgenic ER stress activated indicator (ERAI) reporter mice (Iwawaki et al. (2004) *Nat. Med.* 10:98-102) revealed minimal IRE1α activation in naïve NK cells, but significantly elevated levels in activated NK cells at day 2 PI (FIG. 1C). IRE1α signature levels returned to baseline by day 7 PI (FIG. 1B), indicating transient activation of this pathway in response to viral infection.

Figure 1F:
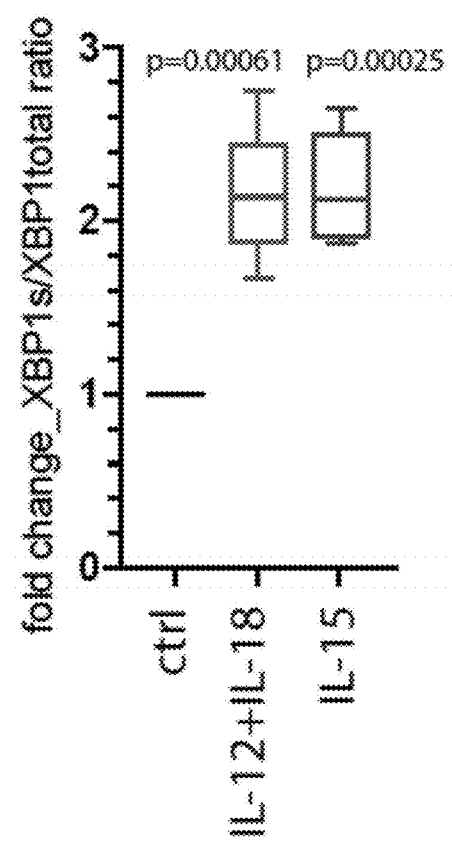
Figure 1G:
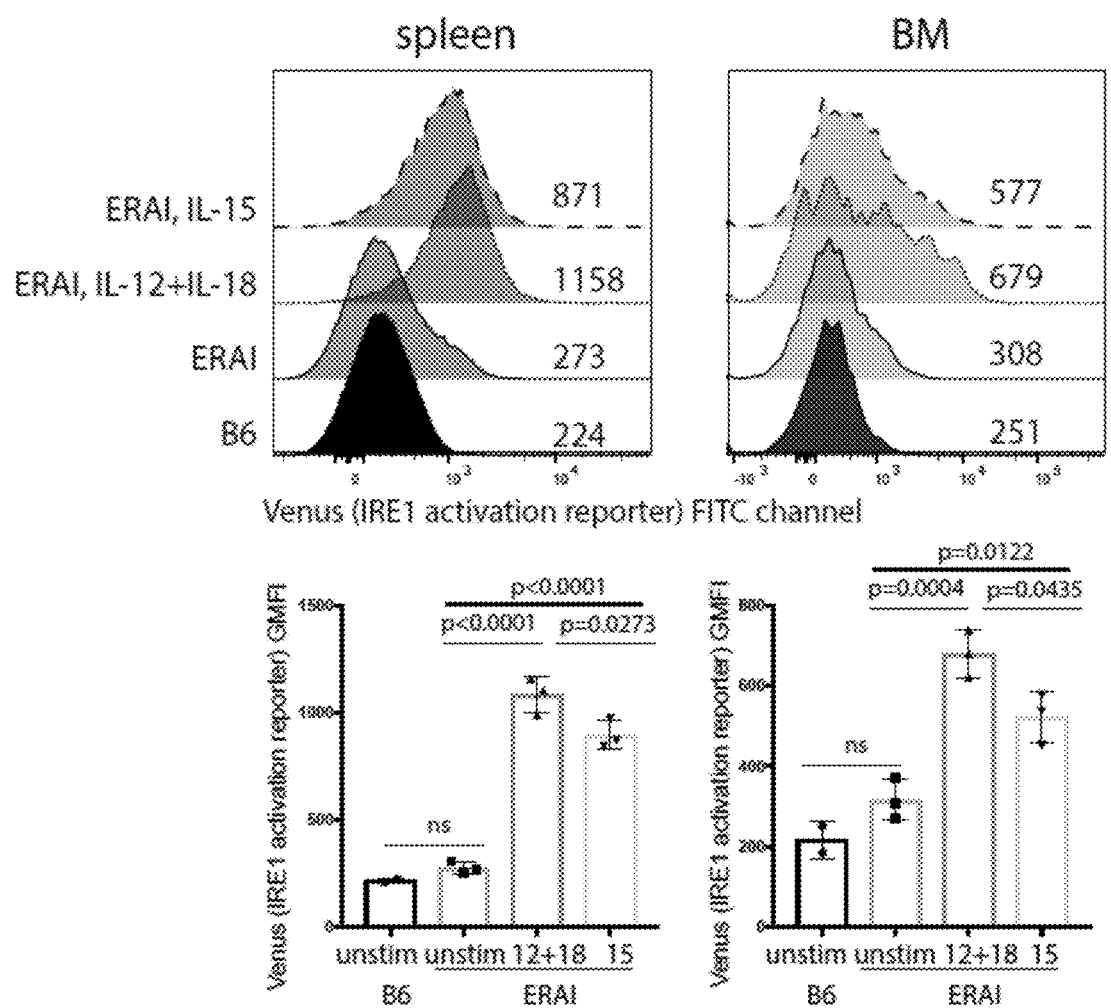
Figure 2B:
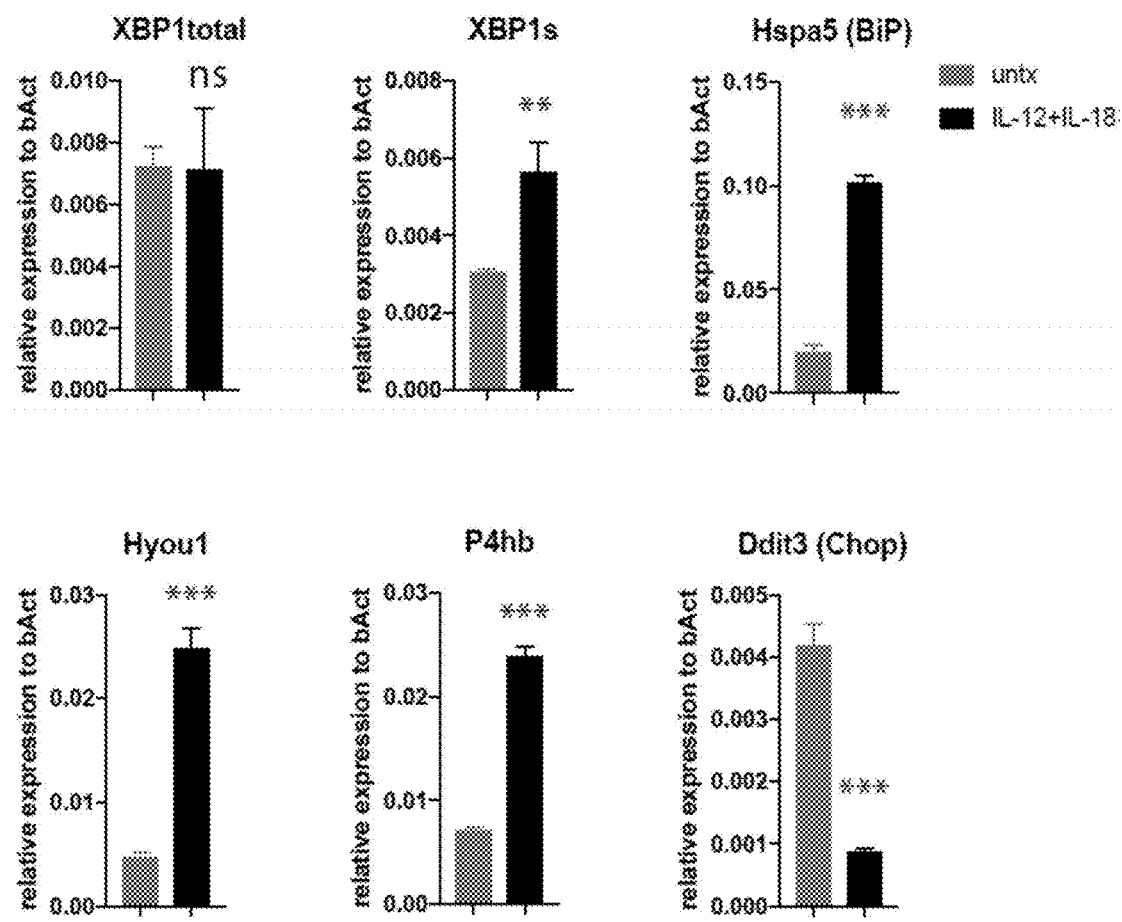

NK cell activation during viral infection occurs when exposed to proinflammatory cytokines including IL-12 and IL-18, and ligation of activating receptors (Sun et al. (2012) *J. Exp. Med.* 209:947-954, Rapp et al. (2017) *Sci. Immunol.* 2:eaan3796, Madera and Sun (2015) *J. Immunol.* 194:1408-1412; Orr et al. (2009) *J. Exp. Med.* 206:807-817; Sun et al. (2009) *J. Immunol.* 183:2911-2914). Consistent with the in vivo findings, RNA-seq analysis of IL-12 and IL-18 activated NK cells revealed a robust upregulation of the IRE1α/XBP1 ER stress/UPR signature compared to the unstimulated controls (FIG. 1D). The induction of spliced XBP1 along with activation of its canonical target genes in NK cells following cytokine stimulation was also observed by quantitative real-time PCR (FIG. 2B). The ERAI reporter mouse was utilized to confirm IRE1α activity in cytokine-activated NK cells from spleen and bone marrow (BM) (FIGS. 1E and 1G). Of note, consistent with the phenotype of mouse NK cells, induction of XBP1 splicing was also observed in primary human NK cells following IL-12 and IL-18 stimulation (FIG. 1F).

Figure 2D:
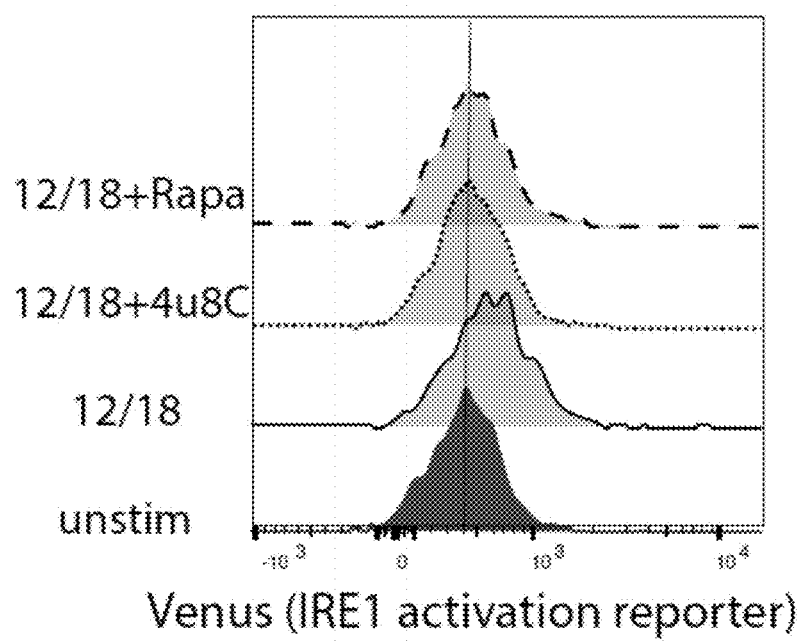
Figure 2D:
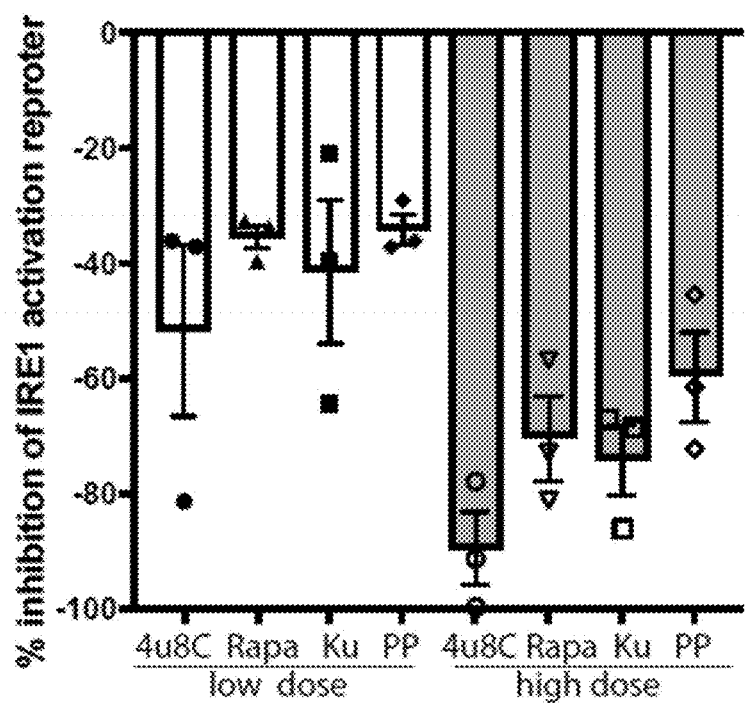

The potential upstream regulators of IRE1α/XBP1 function in infection and in cytokine-activated NK cells were identified. STAT4-deficient NK cells displayed compromised activation of IRE1α and its downstream target genes during MCMV infection (FIG. 2C), indicating an essential role of IL-12/STAT4 signaling in driving this branch of the ER stress response. The mammalian target of rapamycin (mTOR) signaling pathway has been demonstrated by others to activate IRE1α/XBP1 function in liver and other organs and cell types (Brandt et al. (2018) Cell 175:1321-1335; Hsu et al. (2017) Sci. Rep. 7:14272; Zheng et al. (2018) Sci. Rep. 8:8905). It was found that pharmaceutical blockade of mTOR in NK cells significantly reduced IRE1α activation in response to cytokine stimulation in vitro (FIG. 2D). Thus, induction of IRE1α/XBP1 in NK cells is at least partially driven by both STAT4 and mTOR signaling pathways.

The UPR also activates Chop (encoded by Ddit3), a canonical ER stress marker and a multifaceted transcriptional factor that mediates the response to ER stress. Interestingly, whereas MCMV infection in mice activated the IRE1α/XBP1 pathway in NK cells, the expression of Chop was found to be significantly repressed at day 1.5 PI compared to naïve NK cells (FIG. 1B and FIG. 2A). NK cells stimulated with IL-12 and IL-18 in vitro also showed Chop downregulation (FIG. 1D and FIG. 2B). In contrast to viral infection and proinflammatory cytokine exposure, treatment of NK cells with the pharmacologic ER stress inducer tunicamycin strongly triggered Chop expression along with the upregulation of the IRE1α/XBP1 pathway (FIG. 3A). Taken together, these findings indicated that viral infection-driven NK cell activation selectively induces a limited or "non-canonical" UPR restricted to the IRE1α/XBP1 branch.

Example 3: Intrinsic Requirement for IRE1α in NK Cell Antiviral Immunity

Figure 4A:
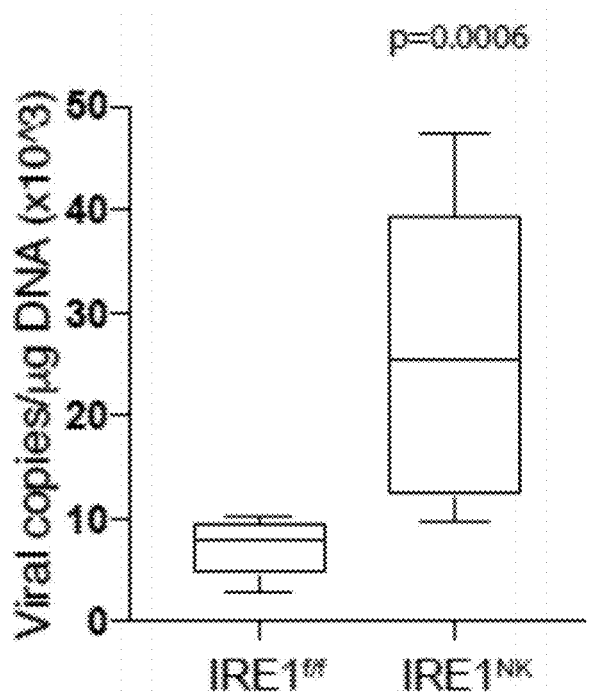
Figure 4B:
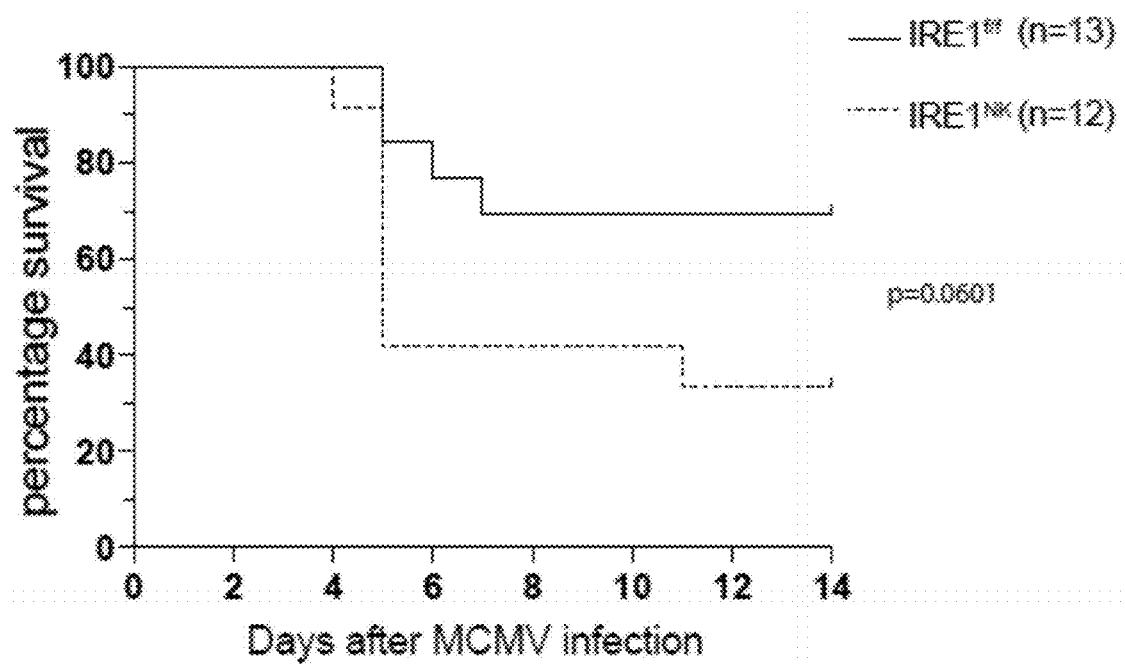

It was next determined whether the induction of the IRE1α/XBP1 pathway in NK cells contributes to host protection against lethal viral infection. To this end, mice in which IRE1α was specifically ablated in NK cells (denoted as IRE1$^{NK}$, and IRE1α-deficient NK cells henceforth denoted as IRE1$^{NK}$ cells, FIGS. 3A-3F) were generated. IRE1$^{NK}$ and littermate control (denoted as IRE1$^{f/f}$, FIGS. 3A-3D and 3F) mice were infected with MCMV. IRE1$^{NK}$ mice were found to be highly susceptible to MCMV infection, with significantly increased viral titers (FIG. 4A) and reduced overall survival (FIG. 4B) compared with IRE1$^{f/f}$ littermate controls. These data demonstrated that IRE1α is required for NK cell-mediated antiviral immunity.

Example 4: Intrinsic Requirement for IRE1α/XBP1 in NK Cell Expansion

Figure 4E:
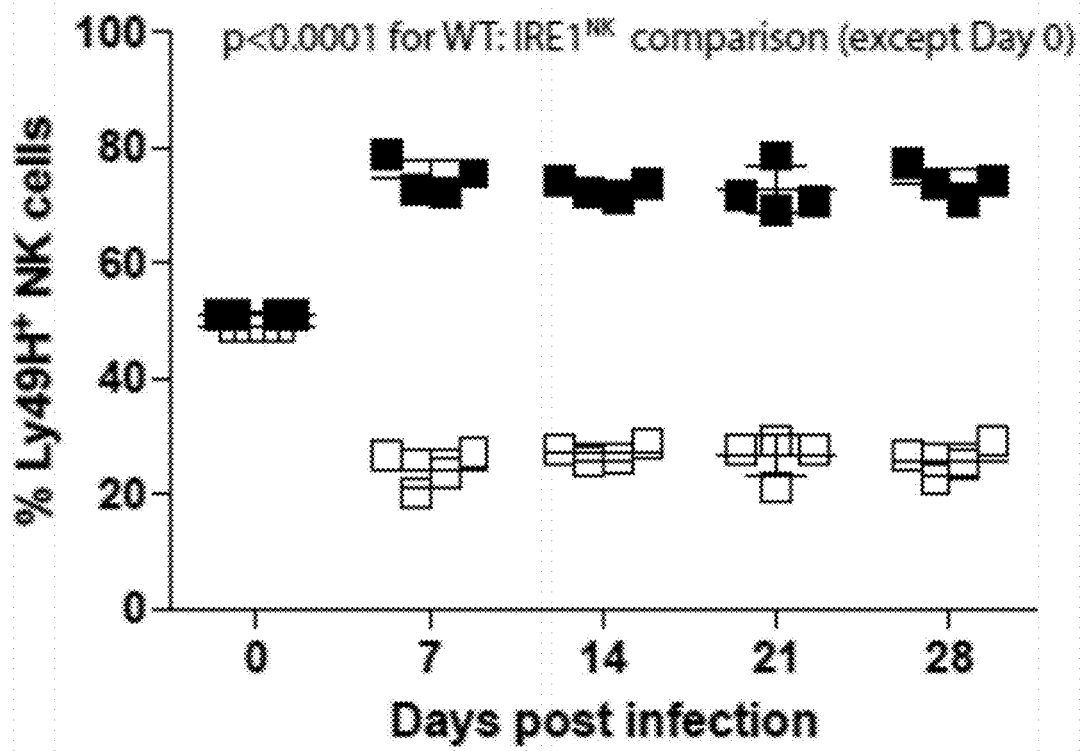
Figure 5A:
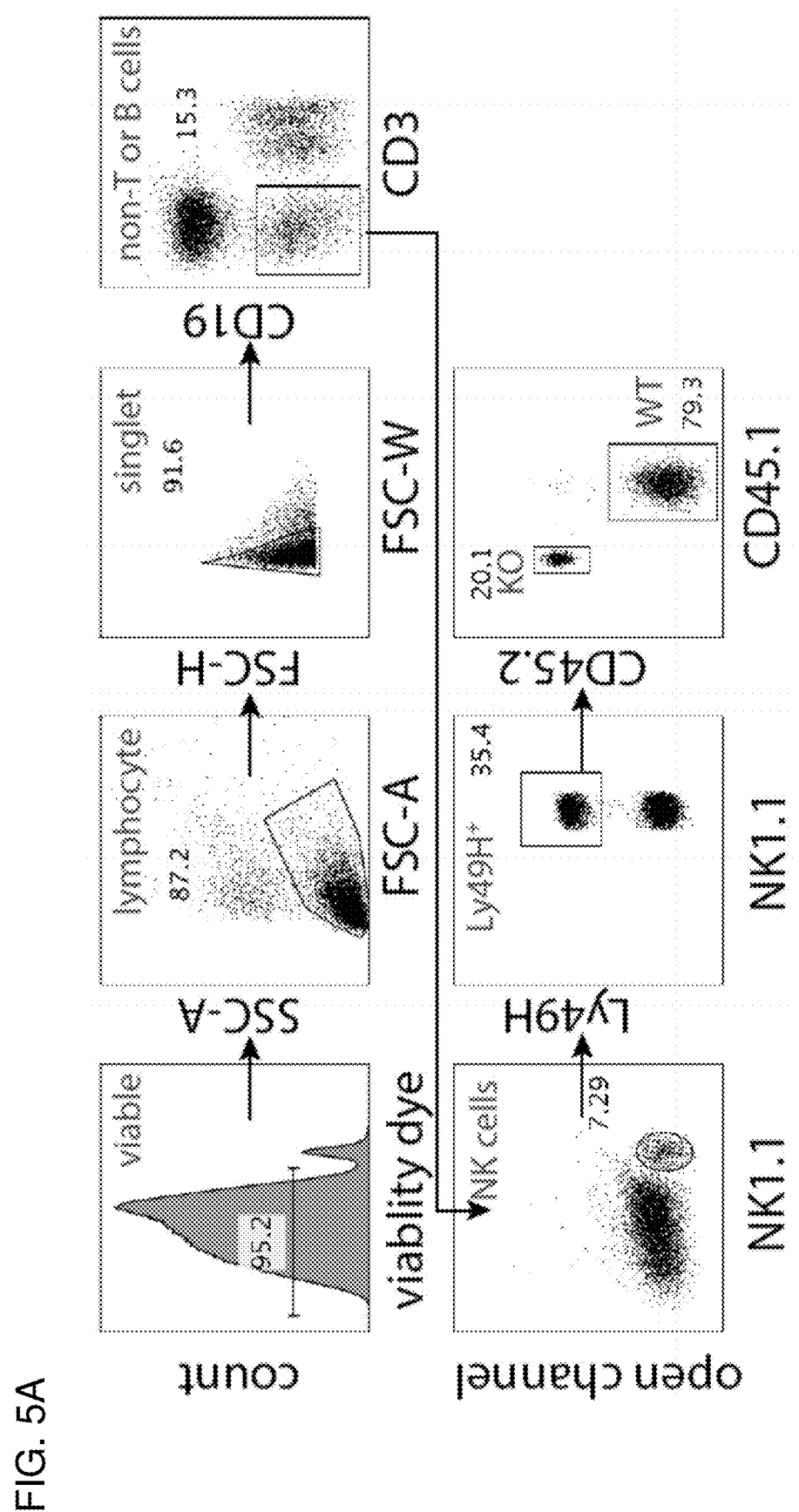
FIG. 5A-FIG. 5D show the dispensable function of IRE1α/XBP1 in NK cell priming, cytokine production or cytotoxicity.

Recently, adaptive immune features of NK cells have been appreciated to contribute towards host protection against viral infection (O'Sullivan et al. (2015) Immunity 43:634-645; Sun et al. (2014) EMBO J. 33:1295-1303; Cerwenka and Lanier (2016) Nat. Rev. Immunol. 16:112-123; Vivier et al. (2011) Science 331:44-49; Sun and Lanier (2011) Nat. Rev. Immunol. 11:645-657). During MCMV infection in mice, Ly49H-expressing NK cells can recognize infected cells and undergo a proliferative burst to enlarge the overall pool of effector cells, followed by a contraction of these activated NK cells to form a long-lived population of memory NK cells (Zawislak et al. (2013) Proc. Natl. Acad. Sci. USA 110:6967-6972; Sun et al. (2011) J. Immunol. 186:1891-1897). To identify whether IRE1α promotes antiviral immunity of NK cells by regulating their adaptive traits, equal numbers of Ly49H$^+$ IRE1$^{NK}$ and CD45.1 congenic wild-type (WT) NK cells were co-transferred into Ly49H-deficient hosts and evaluated the ability of the transferred Ly49H$^+$ cells to expand following MCMV infection (FIG. 4C and FIG. 5A). Whereas the transferred WT NK cells expanded robustly by day 7 PI, their IRE1$^{NK}$ counterparts were dramatically reduced in number (FIGS. 4D and 4E). Moreover, the relative ratio of WT to IRE1$^{NK}$ NK cells remained elevated throughout the time course, ruling out a delayed expansion of the IRE1$^{NK}$ population (FIG. 4E).

Figure 4F:
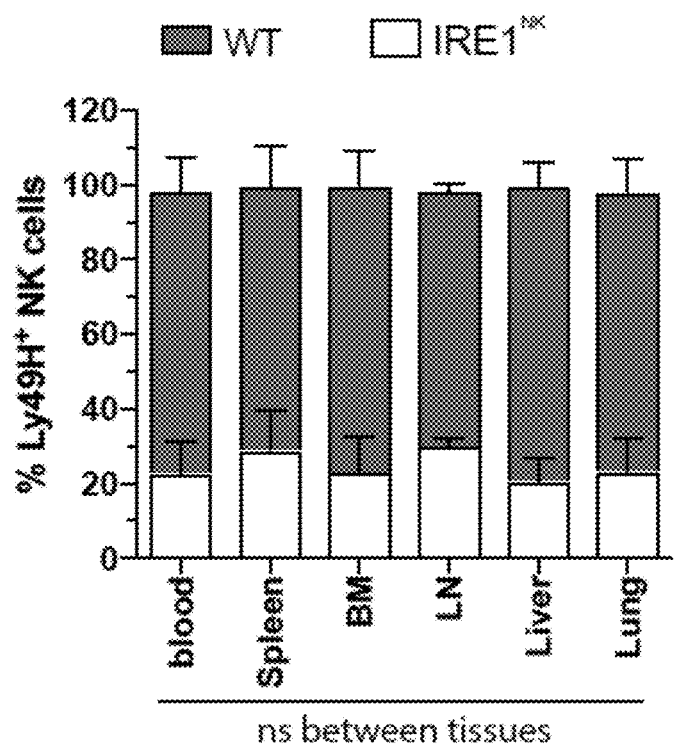
Figure 4G:
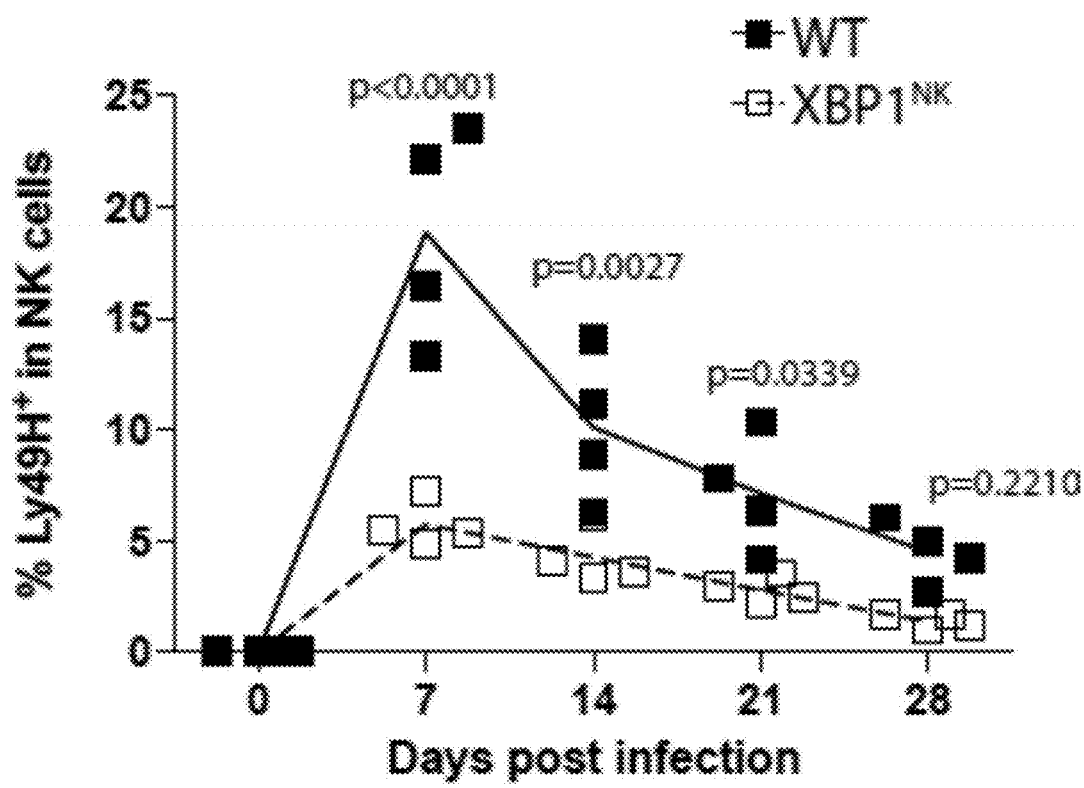
Figure 4H:
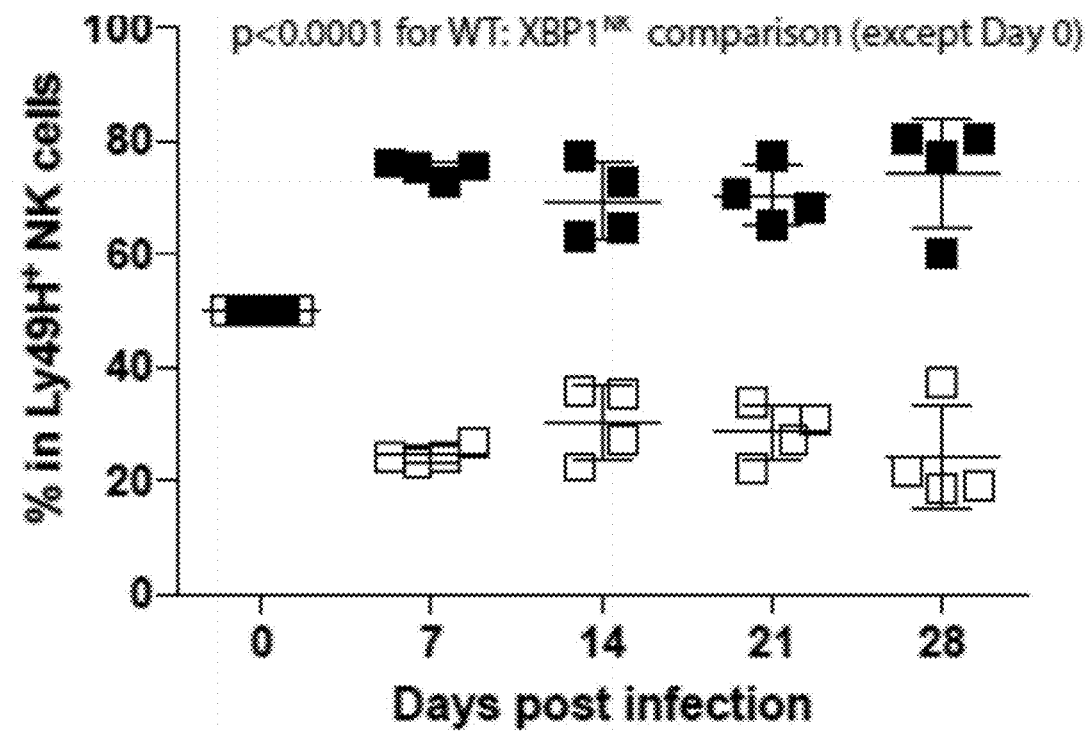
Figure 5B:
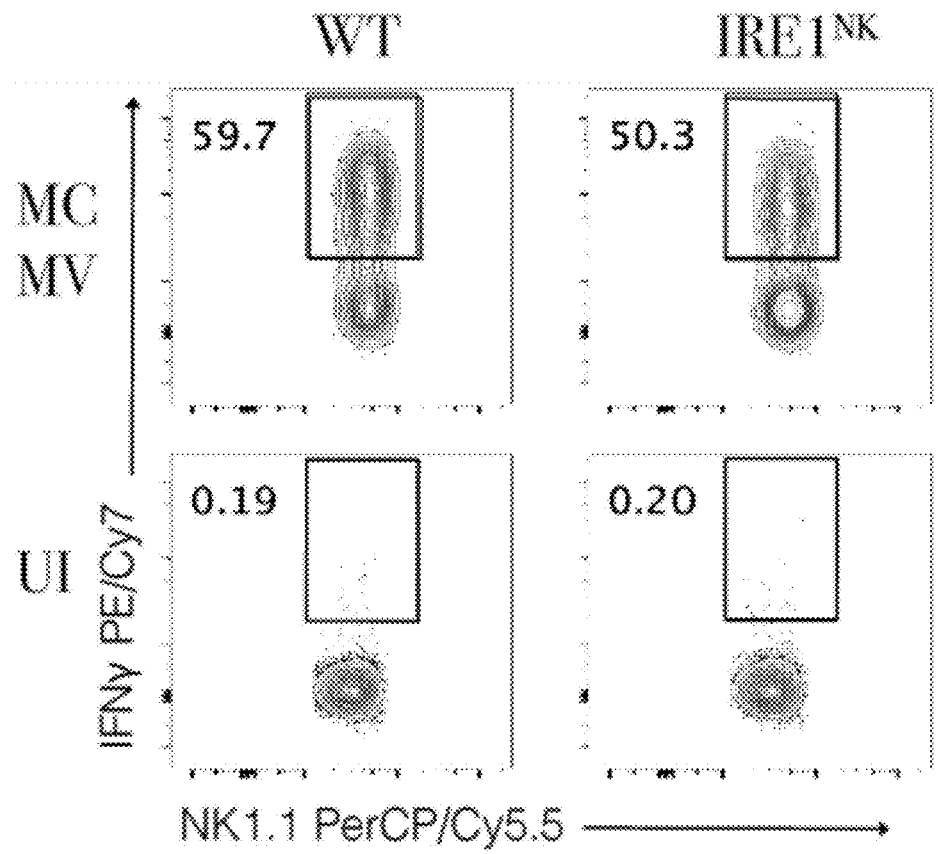
Figure 5B:
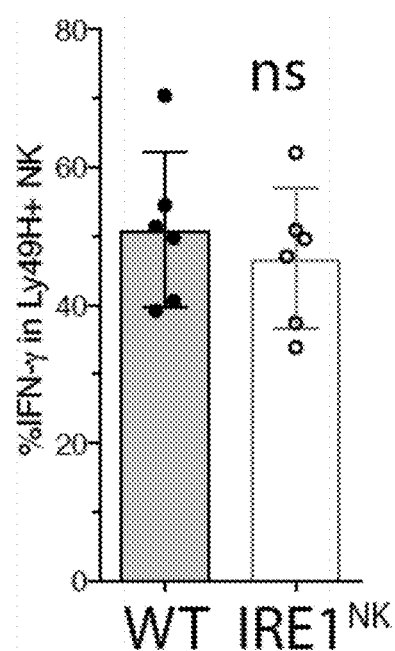
Figure 5C:
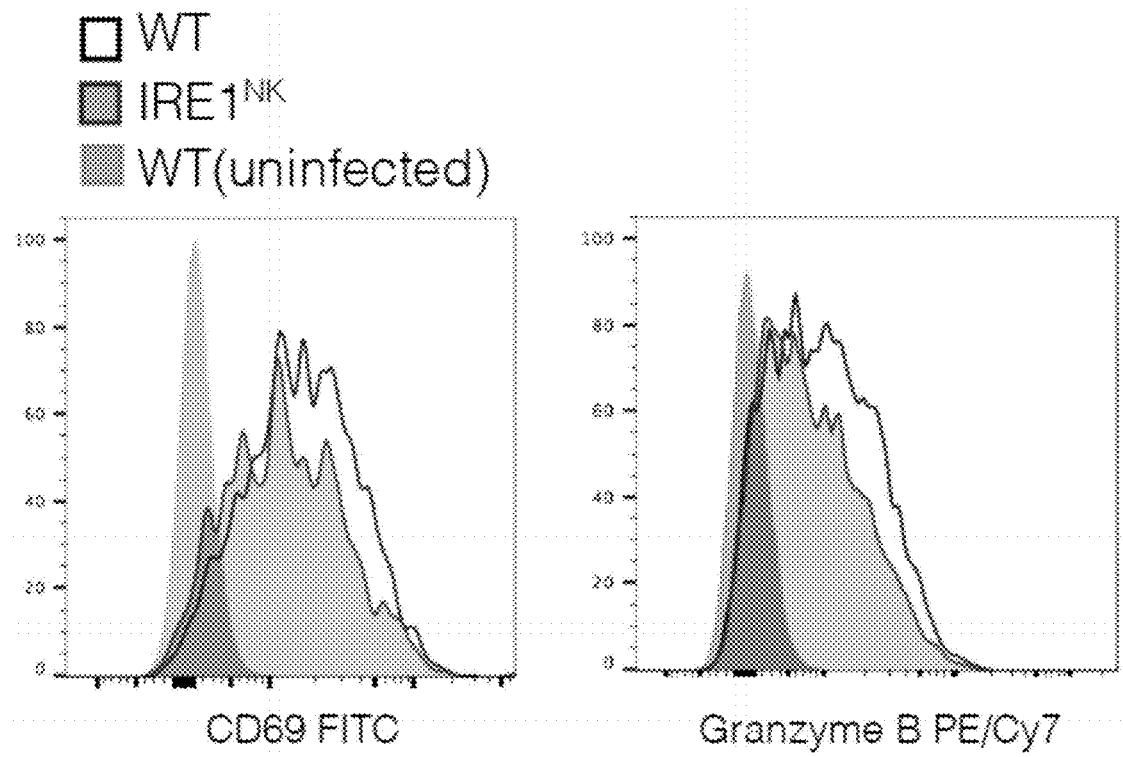
Figure 5C:
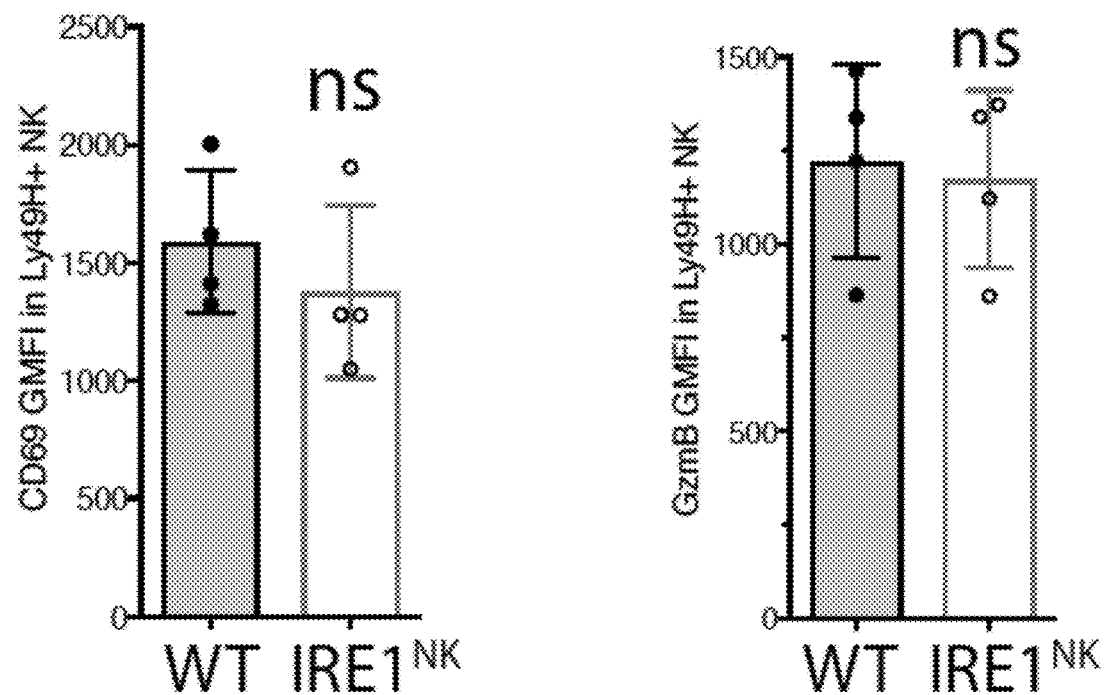
Figure 5D:
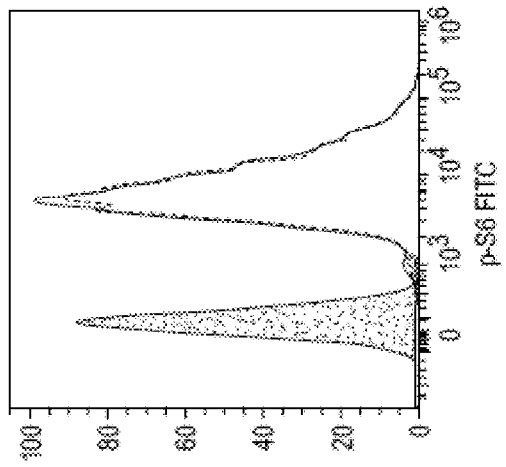
Figure 5D:
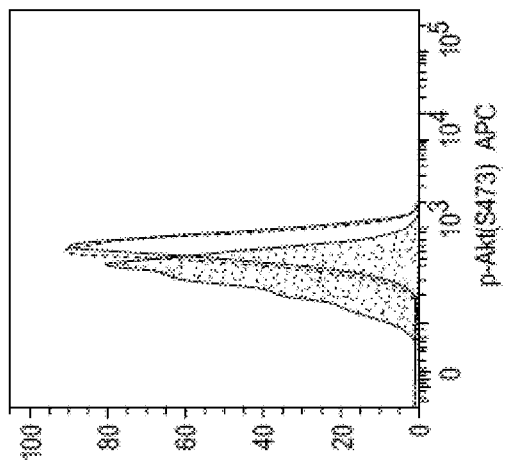
Figure 5D:
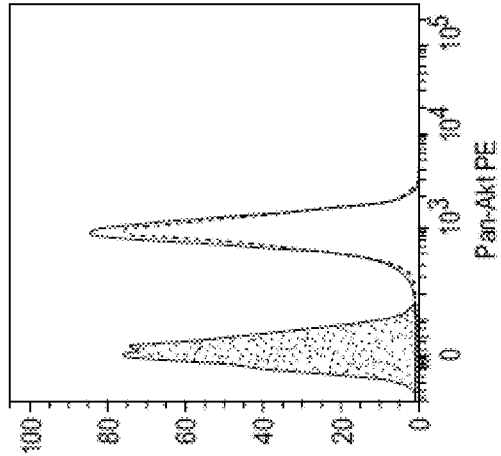
Figure 12:
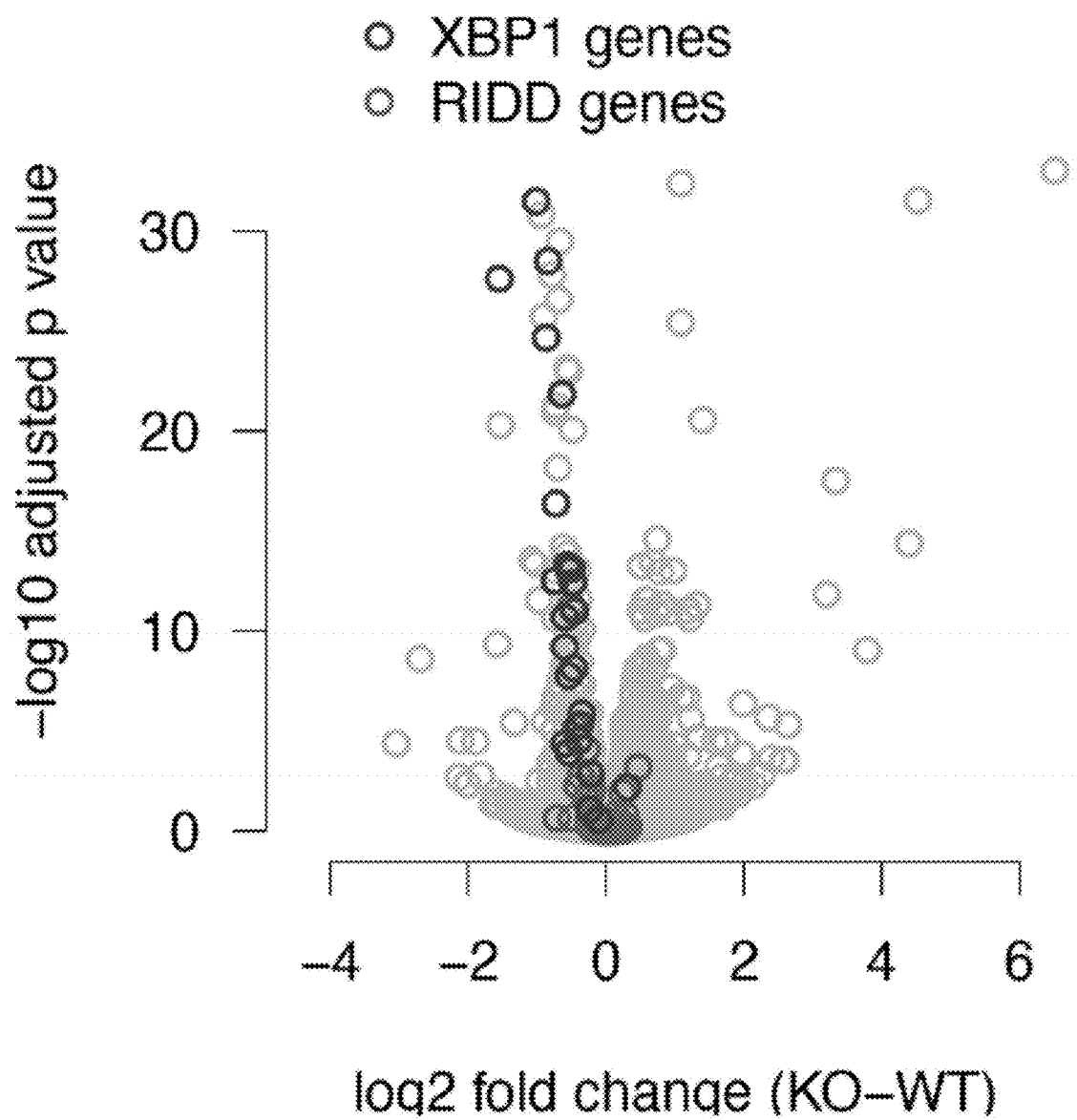
FIG. 12 shows the minimal impact of IRE1α depletion on RIDD in infection-activated NK cells. The volcano plot of RNA-seq analysis showing all genes in IRE1$^{NK}$ versus WT Ly49H$^+$ splenic NK cells harvested from IRE1$^{NK}$ (CD45.2): WT (CD45.1) mixed BM chimera mice day 1.5 PI. RIDD target genes (So et al. (2012) Cell Metab. 16:487-499) and XBP1 target genes (So et al. (2012) Cell Metab. 16:487-499) are highlighted in red and blue, respectively.

The diminished presence of IRE1$^{NK}$ cells in peripheral blood were not due to selective aberrant trafficking, as a similar deficiency was also observed in spleen, liver, lung, bone marrow, and lymph nodes (FIG. 4F). Consistent with the findings in IRE1$^{NK}$ cells, a similar expansion defect was observed in NK cells lacking its downstream substrate XBP1 (from mice denoted as XBP1$^{NK}$, FIGS. 4G and 4H, and FIGS. 3B-3C and 3F). Transcriptomic analysis revealed no change in expression of well-defined IRE1-dependent decay of mRNA (termed "RIDD") target genes (FIG. 12), indicating that IRE1α functions primarily via XBP1 rather than by RIDD in NK cells to drive clonal expansion during viral infection. In contrast to the defect in expansion, NK cell activation, cytokine production and cytotoxicity on a per cell basis was unaffected by the absence of IRE1α (FIGS. 5B and 5C) or XBP1. Levels of Akt/mTOR signaling were unchanged in IRE1$^{NK}$ cells consistent with the placement of IRE1α/XBP1 downstream of mTOR (FIG. 5D). Taken together, these findings indicated an important and specific cell-intrinsic function for the IRE1α/XBP1 pathway in promoting clonal expansion of NK cells following viral infection.

Example 5: Control of NK Cell Proliferation but not Survival by IRE1α/XBP1

Figure 6A:
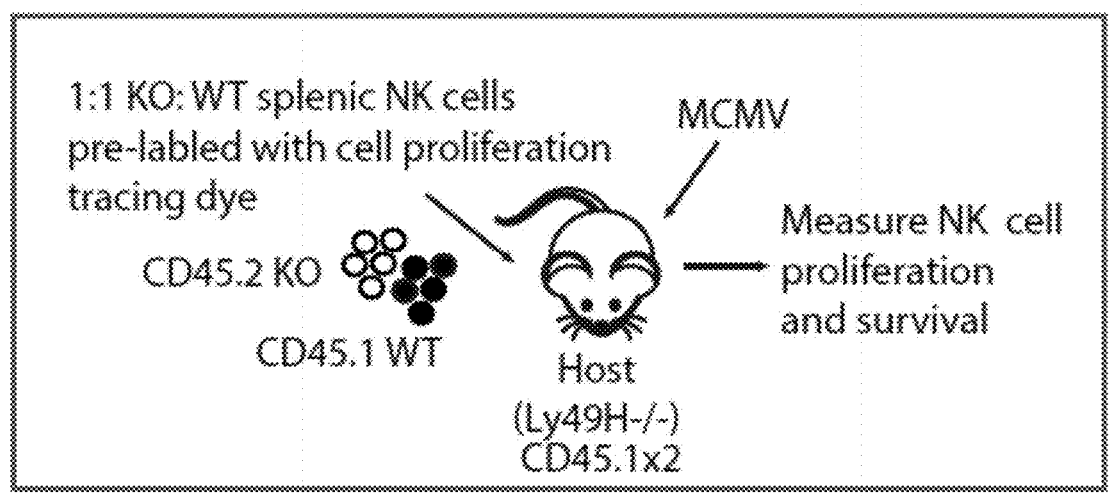
Figure 6B:
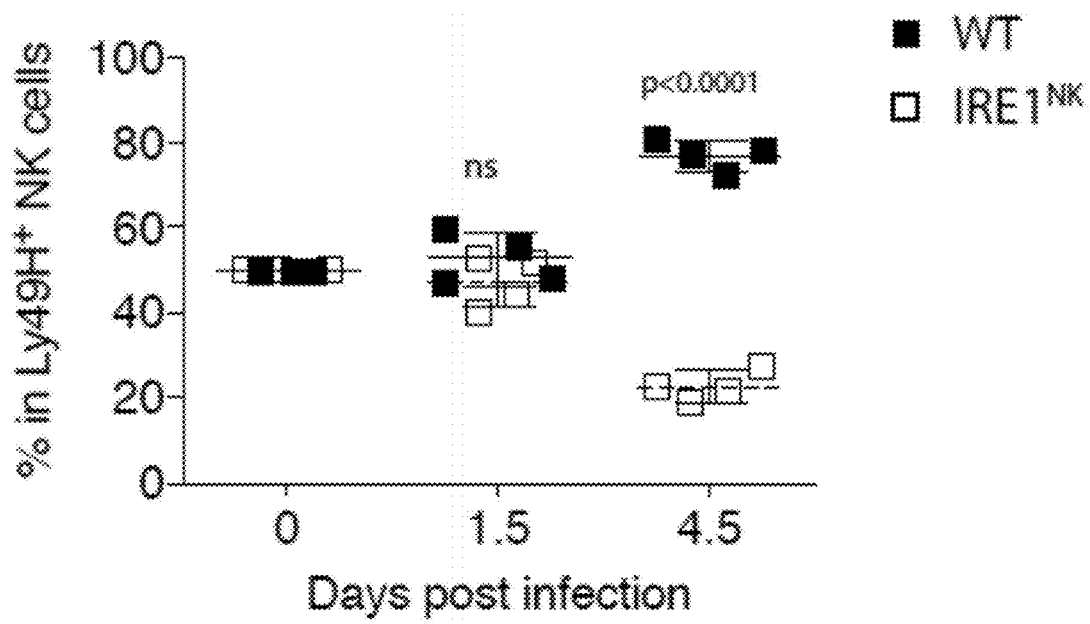
Figure 6D:
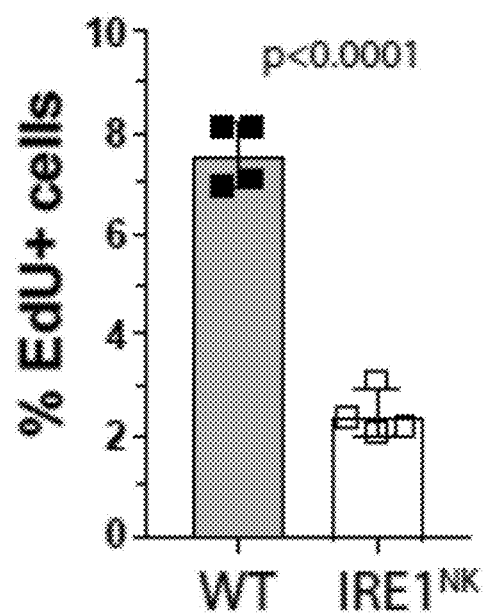
Figure 6E:
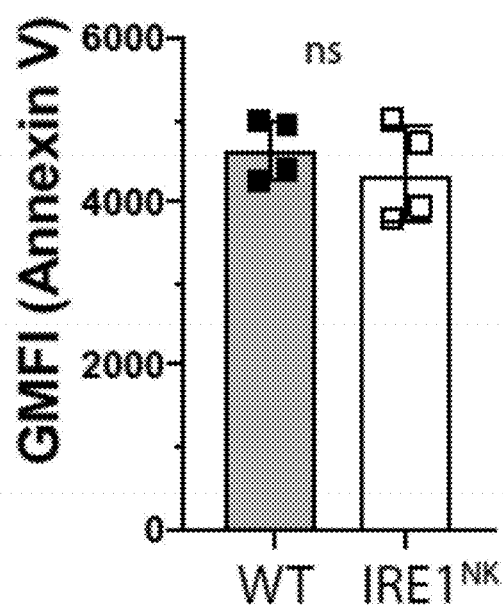
Figure 6F:
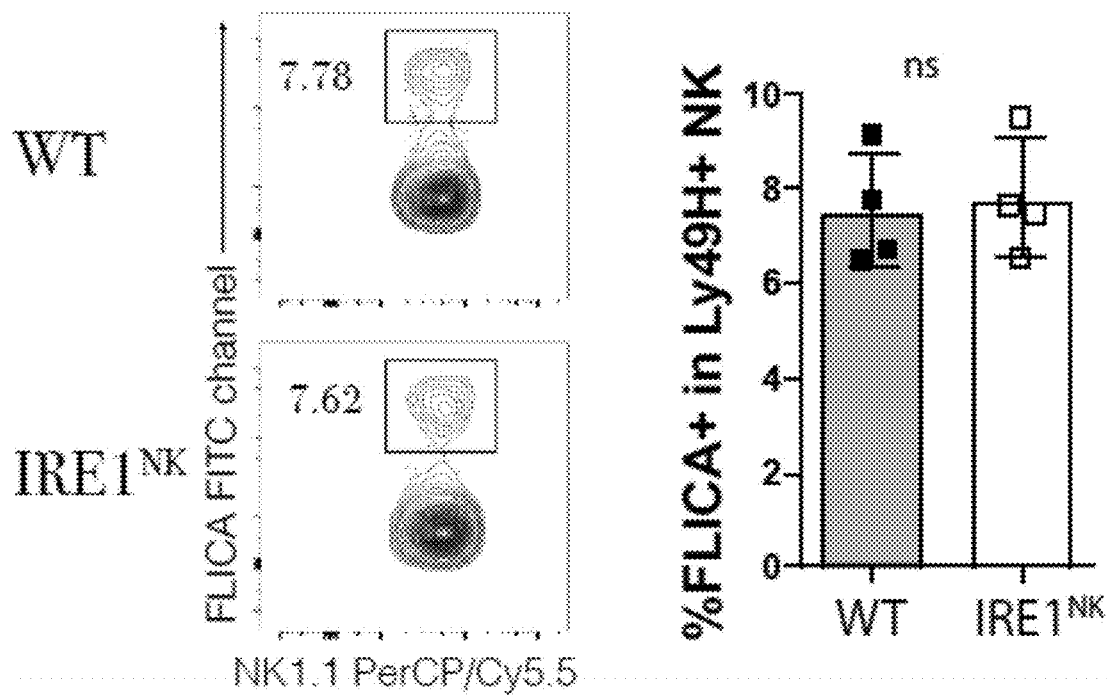

It was next determined whether the IRE1α/XBP1 pathway controls proliferation or survival/apoptosis in activated NK cells, either of which could explain the expansion defect following viral infection. Co-transfer of Ly49H$^+$ IRE1$^{NK}$ and CD45.1 congenic WT NK cells labeled with a cell proliferation tracing dye into MCMV-infected Ly49H− deficient recipients confirmed that IRE1α deficiency markedly impaired MCMV-driven proliferation in vivo (FIGS. 6A-6C). The diminished proliferative capacity of IRE1$^{NK}$ Ly49H$^+$ NK cells was corroborated by a significant decrease in the ability of these cells to incorporate EdU (5-ethynyl-2'-deoxyuridine) (FIG. 6D). In contrast to their proliferation defect, IRE1$^{NK}$ cells did not exhibit enhanced apoptosis, as determined by staining for the apoptotic indicator Annexin V (FIG. 6E) or for activated caspases (FIG. 6F). Collectively, these findings highlighted a specific requirement for IRE1α in the proliferation but not the survival of activated NK cells during viral infection.

Because IRE1α activation is induced to a similar extent in both antigen-specific Ly49H$^+$ and bystander Ly49H$^−$ (Dokun et al. (2001) Nat. Immunol. 2:951-956) NK cells during MCMV infection (FIG. 1C), it was assessed whether IRE1α also regulates the cytokine-driven NK cell proliferation that occurs independently of Ly49H-m157 engagement. Indeed, even adoptively transferred Ly49H$^−$ NK cells showed impaired proliferation in the absence of IRE1 (FIG. 6C), albeit to a lesser extent than the Ly49H$^+$ NK cell population during MCMV infection.

Example 6: IRE1α/XBP1 Drives NK Cell Homeostatic Proliferation

Figure 7A:
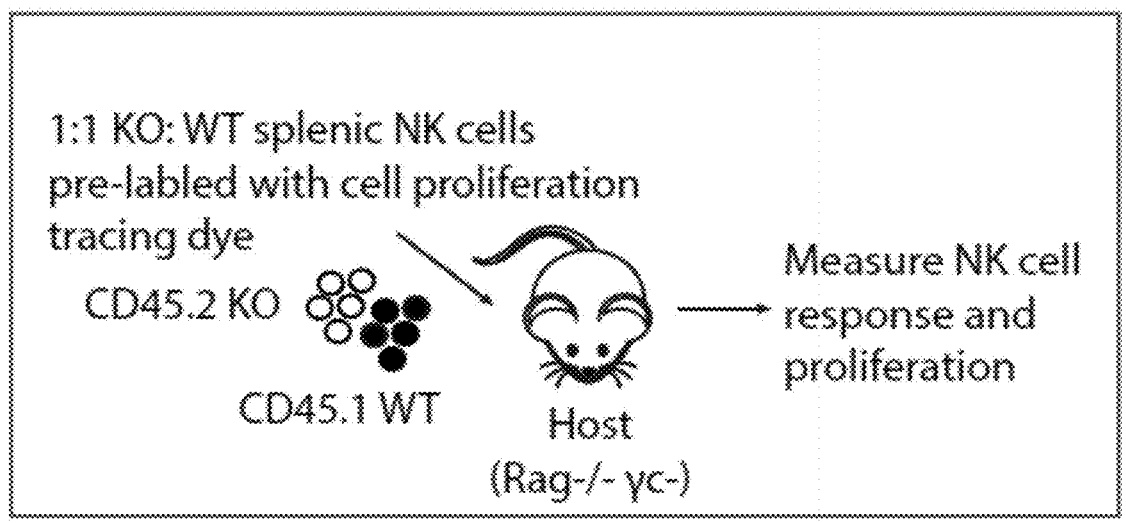
Figure 7B:
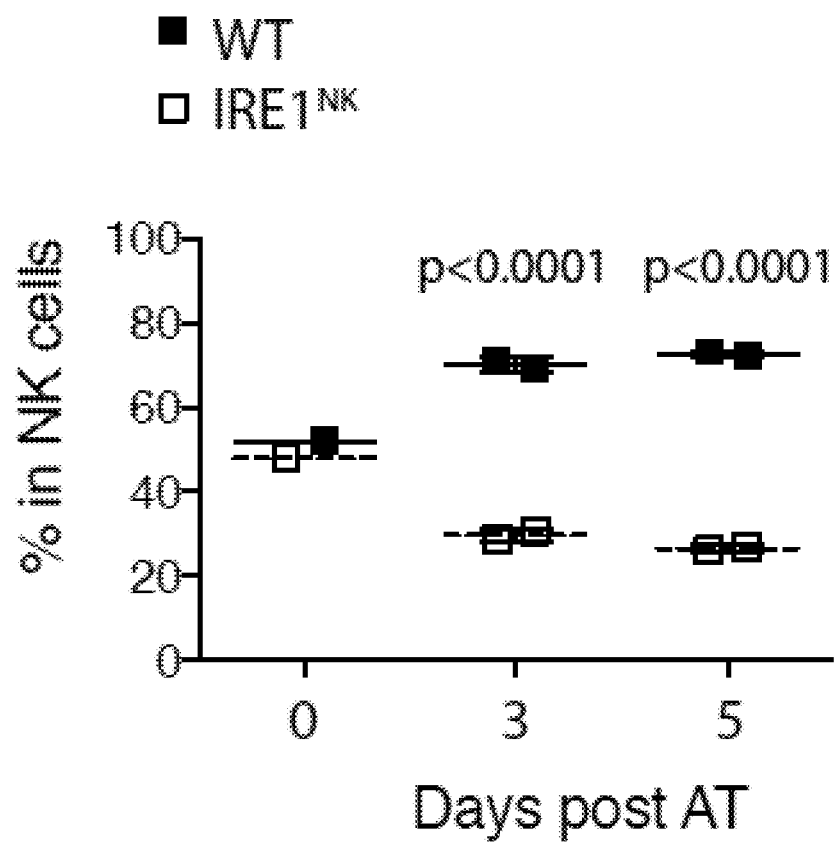
Figure 7C:
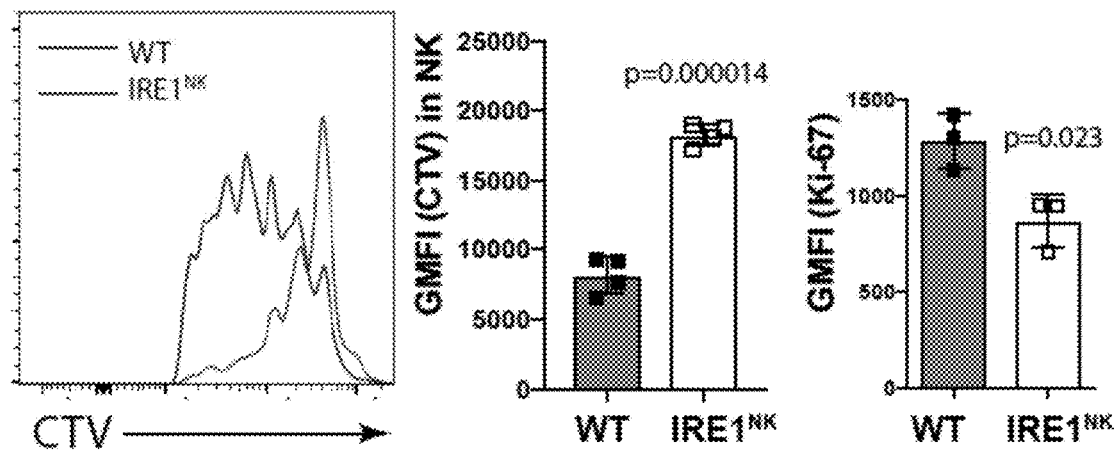

Beyond the NK cell response to pathogens and proinflammatory cytokines induced during infection, robust NK cell expansion can also be triggered by lymphopenia (i.e. homeostatic proliferation) (Sun et al. (2011) *J. Exp. Med.* 208:357-368). Co-transfer of equal numbers of CD45.1 congenic WT and IRE1$^{NK}$ splenic NK cells into lymphocyte-deficient (recipient Rag2$^{-/-}$ Il2rg$^{-/-}$ mice) hosts (FIG. 7A) demonstrated that IRE1α deficiency leads to fewer homeostatically-driven NK cells (~2.5 fold lower) (FIG. 7B) due to a lower proliferation rate (FIG. 7C). Thus, although IRE1α/XBP1 appears to be dispensable for NK cell development and basal homeostasis at steady state (FIGS. 3B-3F), IRE1$^{NK}$ cells exhibit dramatically compromised homeostatic proliferation during lymphopenia.

Figure 7D:
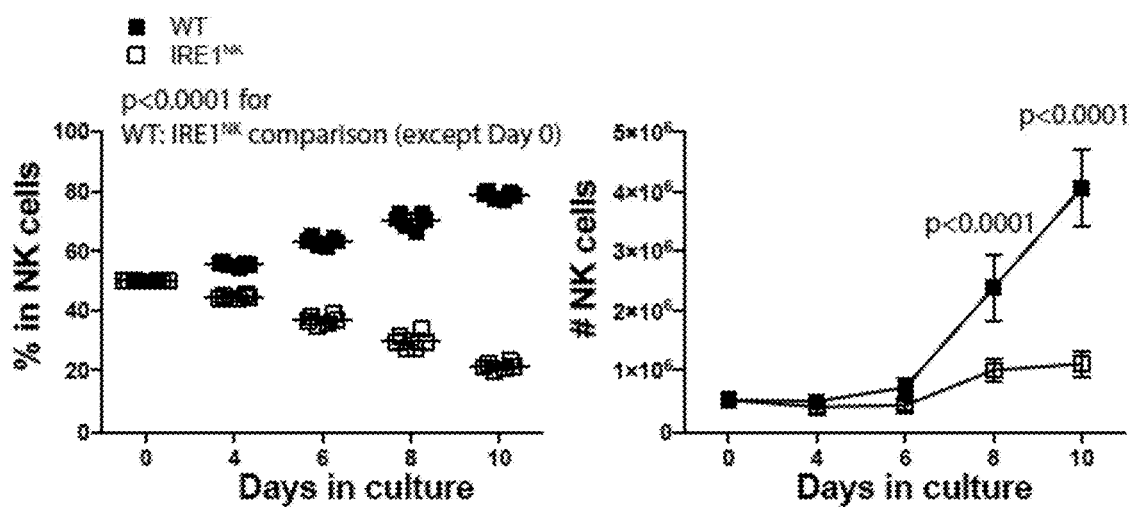
Figure 7F:
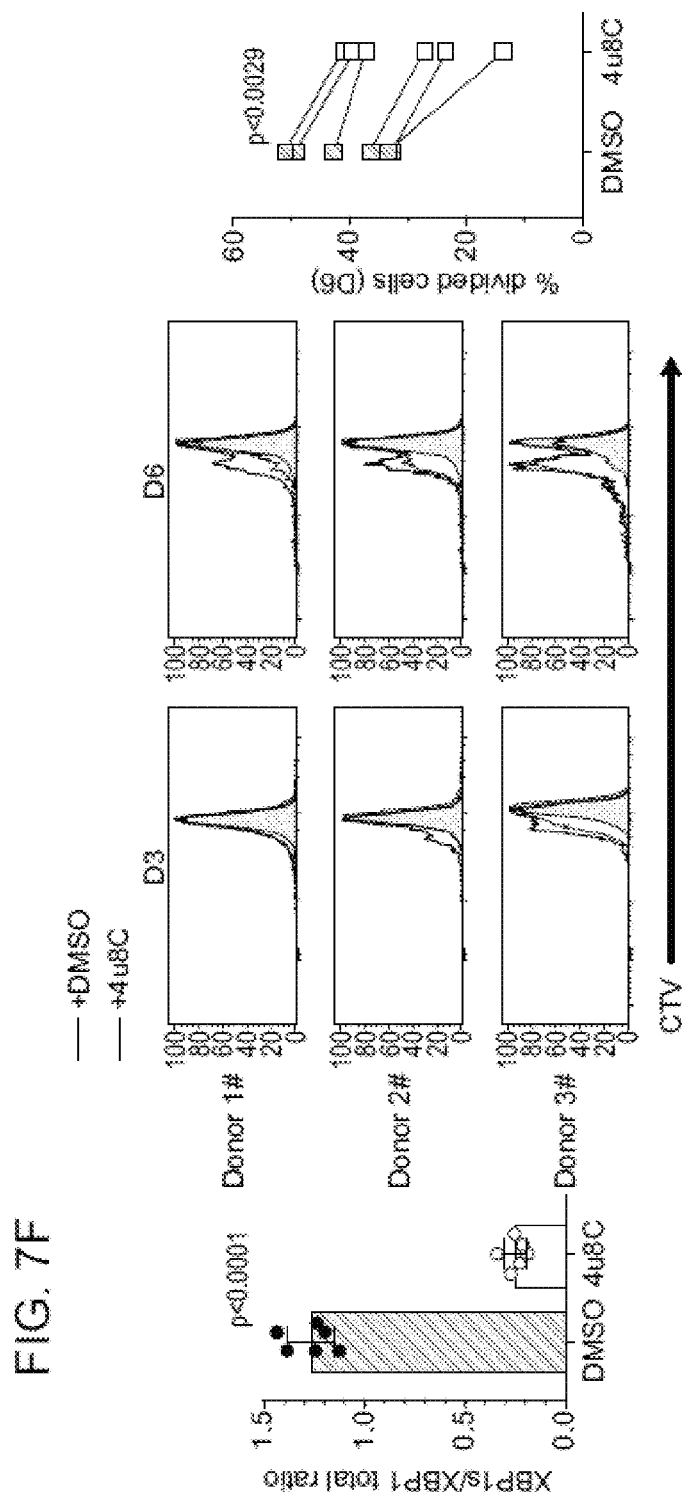
Figure 7G:
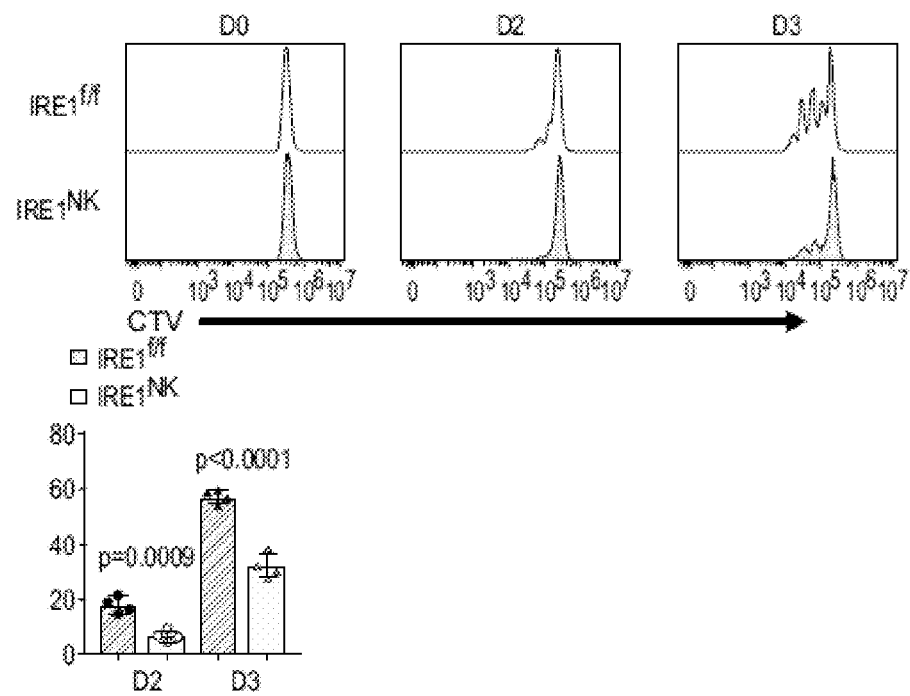
Figure 7H:
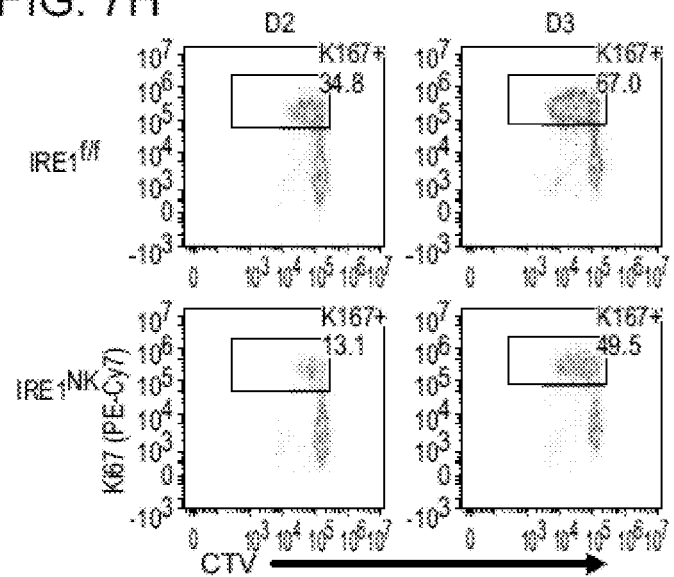

IL-2 and IL-15 are widely utilized for ex vivo expansion of NK cells, as these cytokines are important for proliferation and maintenance of NK cells during development, homeostasis, and immune responses (Mao et al. (2016) *Blood* 128:1475-1489; Yang et al. (2016) *Nat. Commun.* 7:12730; Rautela and Huntington (2017) *Curr. Opin. Immunol.* 44:1-6; Wagner et al. (2017) *J. Clin. Invest.* 127:4042-4058). IL-2 and IL-15 treatment of NK cells from mouse spleen, BM and human PBMCs induced XBP1 splicing (FIGS. 1F and 1G), indicating that cytokines of the common gamma chain family also induce the IRE1α/XBP1 pathway for homeostatic expansion of NK cells. Moreover, a 1:1 co-culture of CD45.1 congenic WT and IRE1$^{NK}$ NK cells with IL-2 and IL-15 revealed that IRE1$^{NK}$ NK cells were continually outcompeted by WT cells (FIG. 7D). Interestingly, IRE1$^{NK}$ cells did not 'blast' (a common characteristic of proliferating cells) as much as their WT counterparts (FIG. 7E). Consistently, IRE1$^{NK}$ cells showed a proliferative defect compared to IRE1$^{f/f}$ littermate control cells cultured with IL-2 and IL-15 (FIGS. 7G and 7H). Of note, IRE1$^{NK}$ cells express normal levels of the relevant cytokine receptors (FIG. 3D), ruling out the possibility that the expansion defect is a secondary consequence of hyposensitivity to cytokine signaling due to lower levels of their target receptors.

Figure 7I:
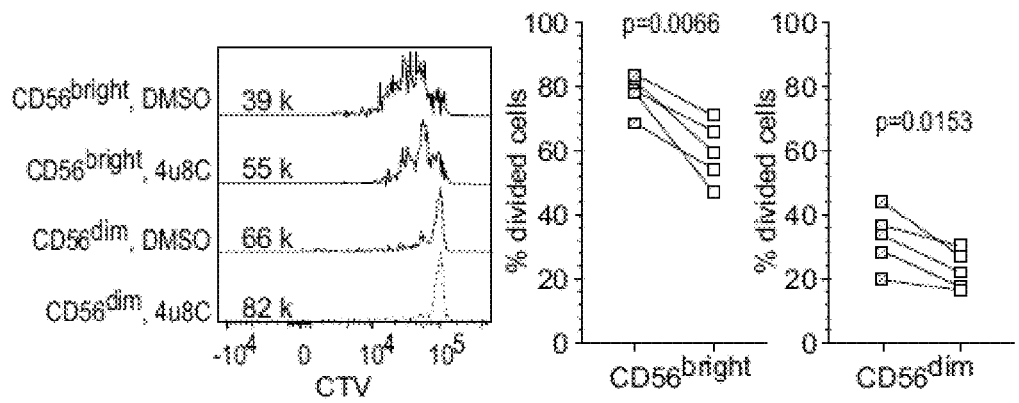
Figure 7J:
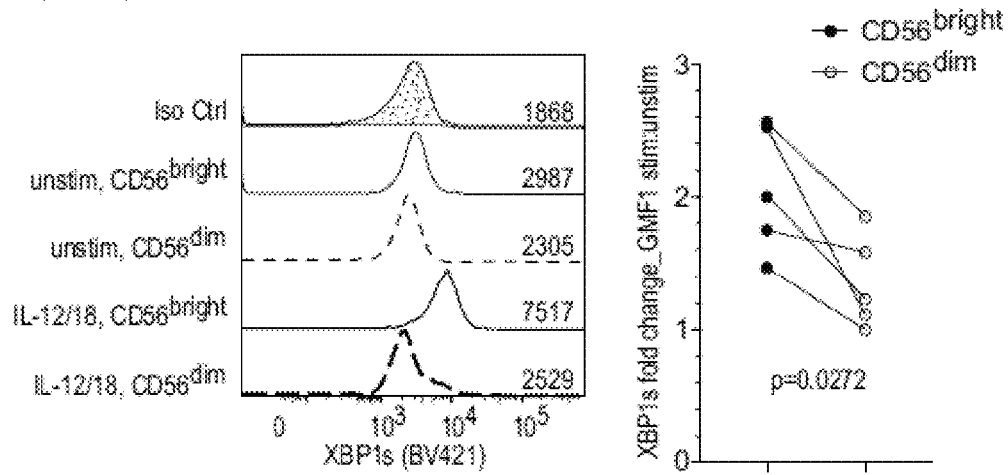

Consistent with the genetic deficiency in IRE1$^{NK}$ cells, pharmaceutical blockade of IRE1α activity using 4μ8c (Cross et al. (2012) *Pro. Natl. Acad. Sci. USA* 109:E869-E878)—a small molecule inhibitor of the IRE1α RNase domain—led to a significant reduction in proliferation of primary human NK cells cultured in IL-2 and IL-15 (FIG. 7F). Interestingly, 4μ8C primarily hindered the proliferation of CD56$^{bright}$ NK cells (FIG. 7I), a subset of human NK cells with higher proliferative capacity compared to their CD56$^{dim}$ counterparts (Wagner et al. (2017) *J. Clin. Invest.* 127:4042-4058). The differential requirement of IRE1α/XBP1 was corroborated by a much more robust induction of XBP1s protein levels in CD56$^{bright}$ NK cell subsets after cytokine stimulation (FIG. 7J). Thus, IRE1α/XBP1 has a conserved function between mouse and human NK cells to support their growth and proliferation and IRE1 is differentially required for the proliferation of the CD56bright NK cell, a subset of NK cells in human that is known to be highly proliferating, compared to their CD56dim counterparts.

Example 7: IRE1α/XBP1 Promotes Oxidative Phosphorylation in NK Cells

Figures 8A, 8B:
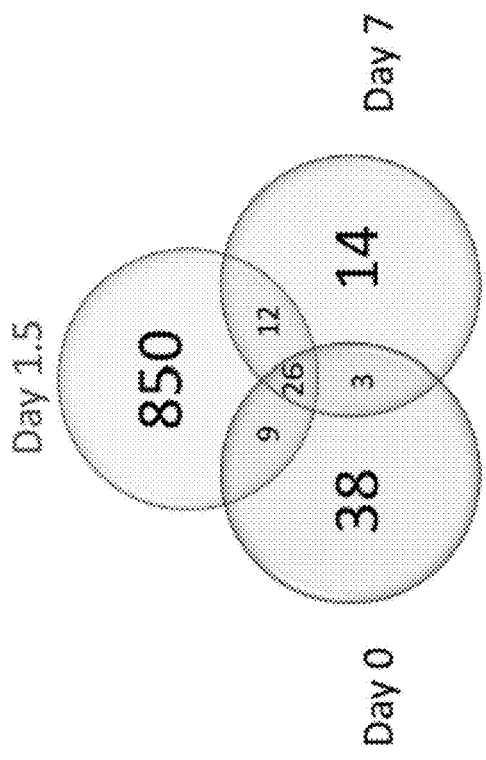
FIG. 8A-FIG. 8H show that IRE1$^{NK}$ RNA-seq analysis highlights Myc as an XBP1 target gene.

Given that the IRE1α/XBP1 pathway specifically controls the proliferation of activated NK cells during infectious/inflammatory states and during lymphopenia, unbiased approaches was used to identify the key cellular processes and molecular mediator(s) downstream of IRE1α/XBP1 in proliferating NK cells. To this end, mixed IRE1$^{NK}$ (CD45.2): WT (CD45.1) bone marrow chimera mice were generated (Sun et al. (2009) *Nature* 457:557-561) (FIG. 3E) and whole genome transcriptome analysis was performed on IRE1$^{NK}$ and WT Ly49H$^+$ NK cells harvested at day 0, 1.5, and 7 PI. The IRE1$^{NK}$ cells showed an overall transcriptome profile similar to their WT counterparts prior to infection, with 76 genes differentially expressed at day 0 but at the peak of primary expansion at day 7 PI, displayed 55 genes that were differentially expressed (FIG. 8A). Importantly, the gene expression profile of IRE1$^{NK}$ cells at day 1.5 PI was markedly distinct from WT NK cells, with 897 genes differentially expressed in the absence of IRE1α (FIG. 8A).

Figure 13:
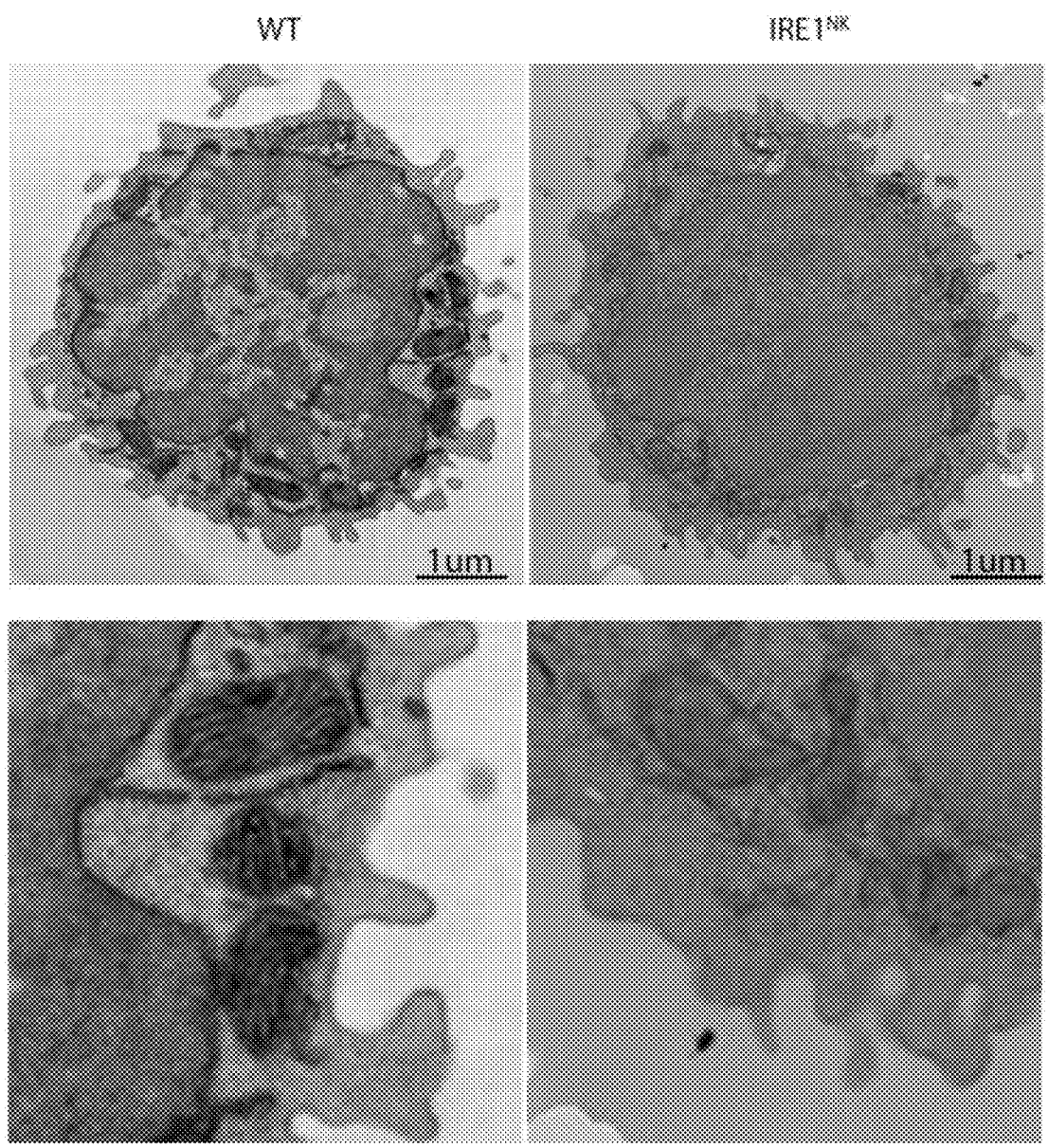
FIG. 13 shows the representative electron microscopy of IRE1$^{NK}$ versus WT Ly49H$^+$ splenic NK cells harvested from IRE1$^{NK}$(CD45.2): WT (CD45.1) mixed BM chimera mice day 7 PI. The high-resolution plots at bottom show mitochondrial morphology. n=3 mixed BM chimera mice.
Figure 14A:
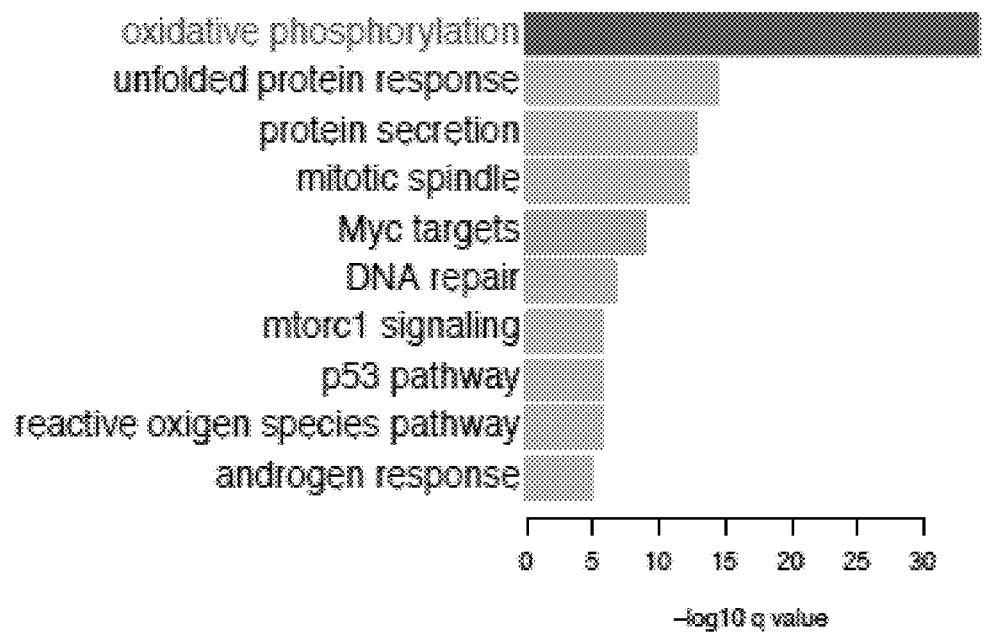
FIG. 14A-FIG. 14C show that IRE1 supports NK cell OXPHOS and mitochondrial function.
Figure 14B:
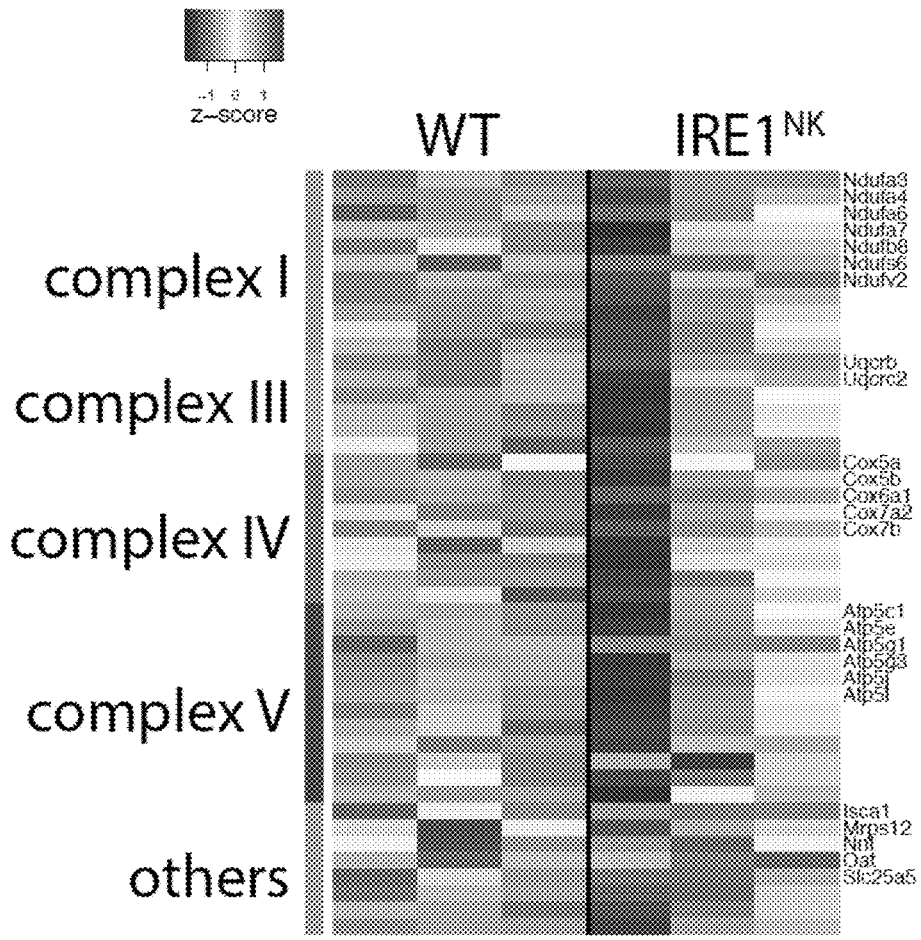
Figure 14C:
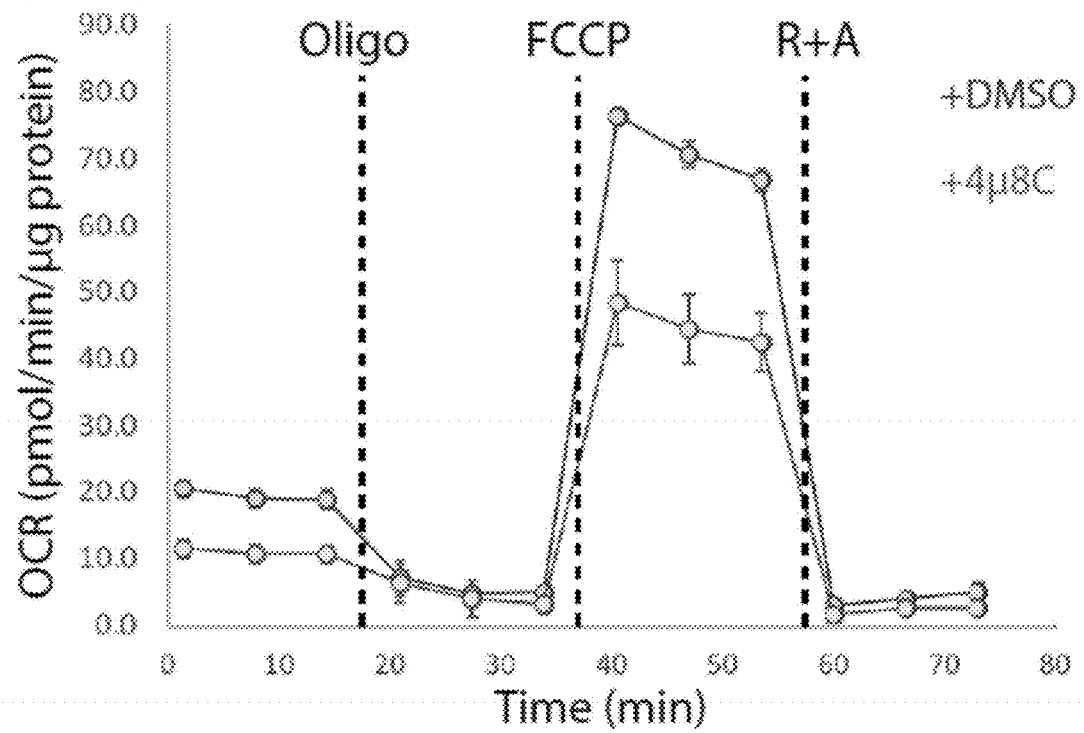
Figure 14C:
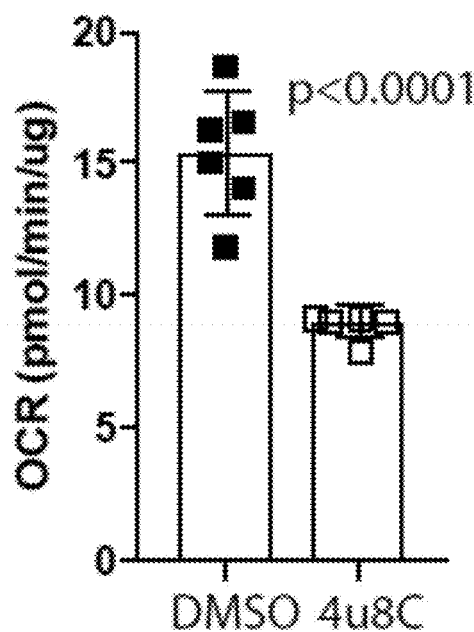
Figure 14C:
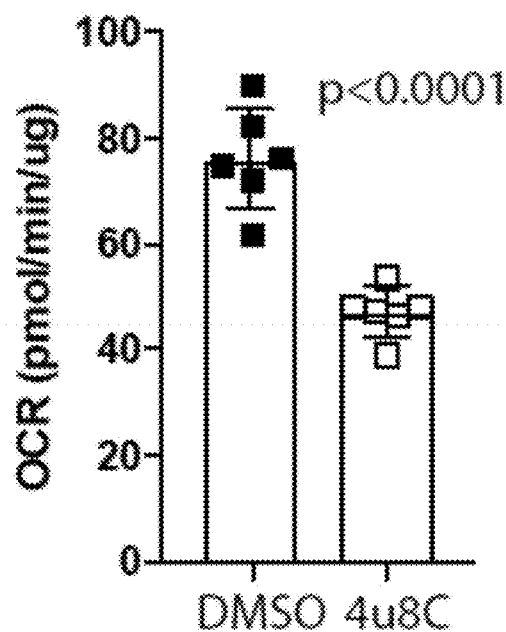

Activated immune cells undergo robust metabolic responses, which play an indispensable role in regulating immune cell function and long-term fitness (Buck et al. (2017) *Cell* 169:570-586; Buck et al. (2015) *J. Exp. Med.* 212:1345-1360). It has been demonstrated that activation of NK cell oxidative phosphorylation (OXPHOS) and glycolysis is essential for robust NK cell responses (Loftus et al. (2018) *Nat. Commun.* 9:2341; O'Sullivan and Sun (2017) *J. Mol. Biol.* 429:3577-3586). Interestingly, OXPHOS was highlighted as the top downregulated cellular process in IRE1NK cells by GO analysis (FIGS. 14A and 14B). Metabolic flux analysis on IL-12 and IL-18 activated human primary NK cells showed significantly decreased levels of OXPHOS and reduced maximal respiration rate upon blockade of IRE1α activity with 4μ8C (FIG. 14C). Consistent with the observation that the absence of IRE1α led to highly compromised OXPHOS, electron microscopy revealed disrupted mitochondrial morphology on sorting-purified IRE1NK cells during MCMV infection (FIG. 13). Collectively, the molecular, cellular and metabolic evidence indicates a critical role of the IRE1α/XBP1 pathway in supporting OXPHOS in NK cells.

Figure 8C:
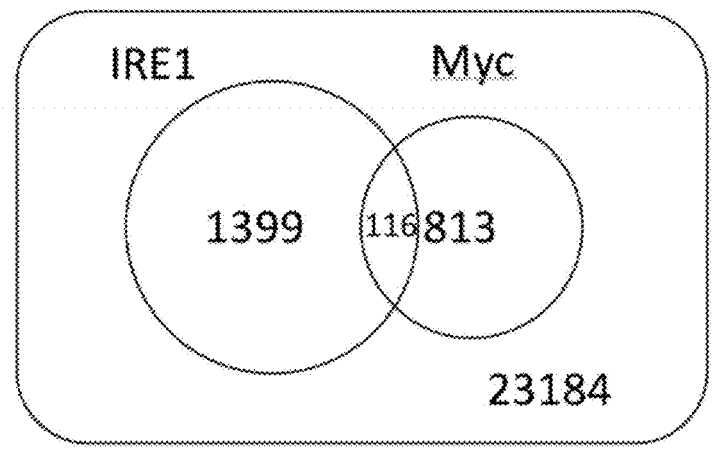

Example 8: XBP1 Promotes NK Cell Proliferation in Part by Direct Transactivation of c-Myc Expression To further identify key molecular mediators of proliferation in IRE1$^{NK}$ cells, the QIAGEN Ingenuity Pathway Analysis platform was utilized. As a validation of this approach, both XBP1 (top 1, p=2.66$^{-38}$) and IRE1α (gene name Ern1, top 6, p=6.23$^{-8}$) were identified among the top upstream regulators in IRE1$^{NK}$ cells (FIG. 8B). Surprisingly, transcription factor Myc (N-Myc, top 2, p=3.93$^{-28}$; c-Myc, top 5, p=4.75$^{-8}$) was also predicted to be reduced in IRE1$^{NK}$ cells compared to WT NK cells. The Myc signaling pathway was also highlighted by GO analysis (FIG. 9A), and there was significantly reduced expression of Myc targets that control cell proliferation or cellular processes highly related to cell growth in IRE1$^{NK}$ (cells (FIG. 9B). Although Myc is known to control a range of biological processes including cell growth, protein synthesis and cell metabolism (Morrish and Hockenbery (2014) *Cold Spring Harb. Perspect. Med.* 4:a014225; Riggelen et al. (2010) *Nat. Rev. Cancer* 10:301-309), its importance in NK cell responses is less well studied. Interestingly, although there is a significant overlap between IRE1α-regulated and c-Myc-regulated genes identified in MCMV-primed NK cells (FIG. 8C), Myc has not previously been described as a canonical target of the IRE1/XBP1-mediated UPR pathway.

The kinetics of Myc expression in differentiating NK cells, and its potential correlation with the IRE1α/XBP1 pathway were investigated. N-Myc was undetectable in NK cells at all time points following MCMV infection, whereas basal levels of c-Myc mRNA were observed in naïve NK cells (FIG. 9C). No appreciable expression of c-Myc protein at baseline was detected (FIG. 9C), which is attributed to the instability of c-Myc protein secondary to multiple degradation mechanisms (Farrell and Sears (2014) Cold Spring Harb. *Perspect. Med.* 4:a014365). Following MCMV infection, NK cells robustly upregulated c-Myc mRNA, and protein levels were now easily detectable (FIG. 9C). Furthermore, in MCMV-infected ERAI mice, levels of c-Myc protein correlated with IRE1α activity (FIG. 9C). Taken together, these data indicated that engagement of both the IRE1α/XBP1 UPR and c-Myc are important during NK cell priming.

Figure 8D:
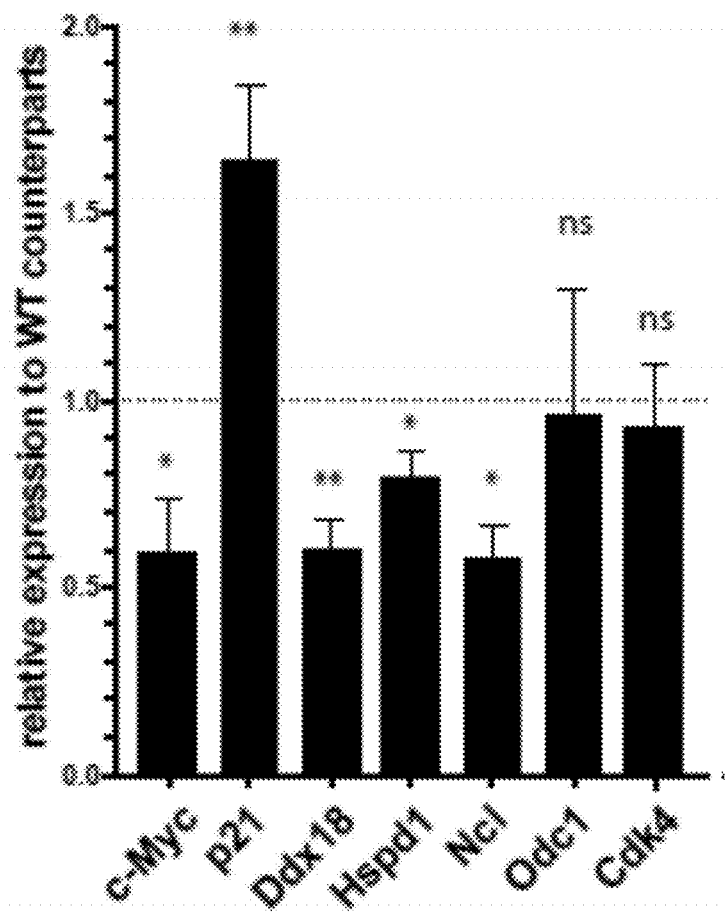
Figure 8E:
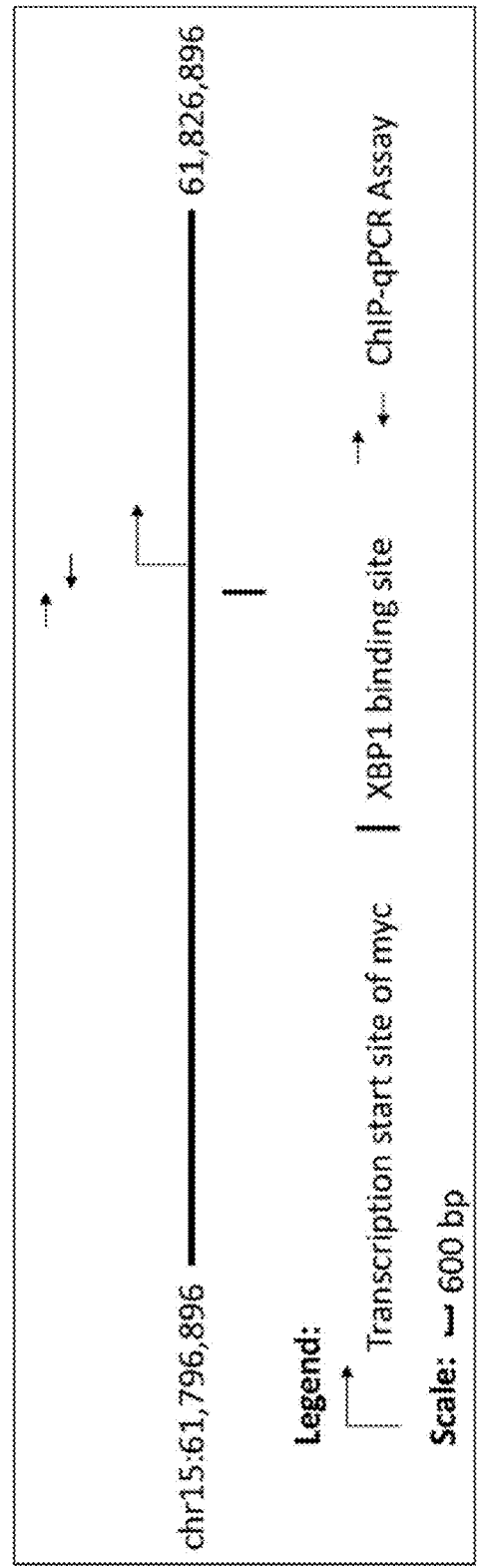
Figure 8F:
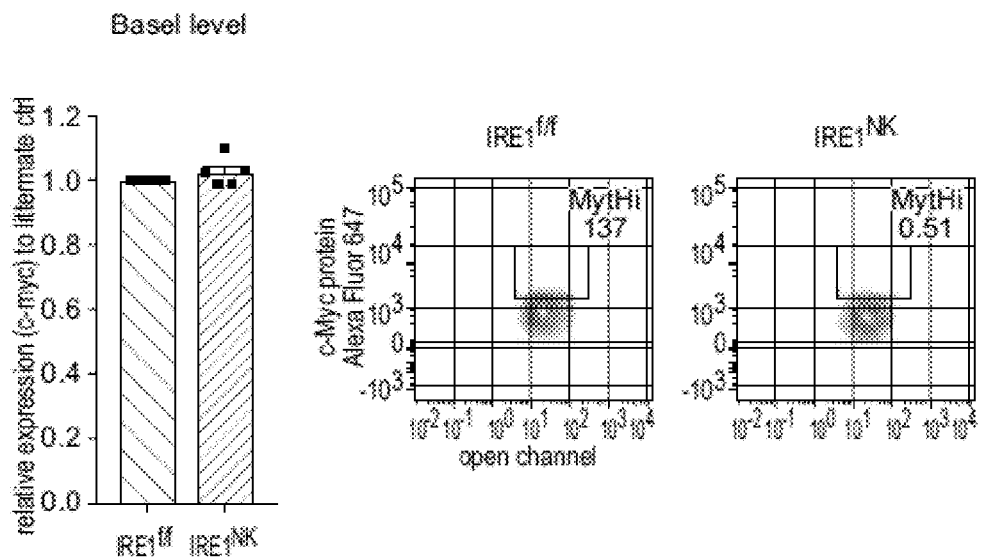
Figure 8G:
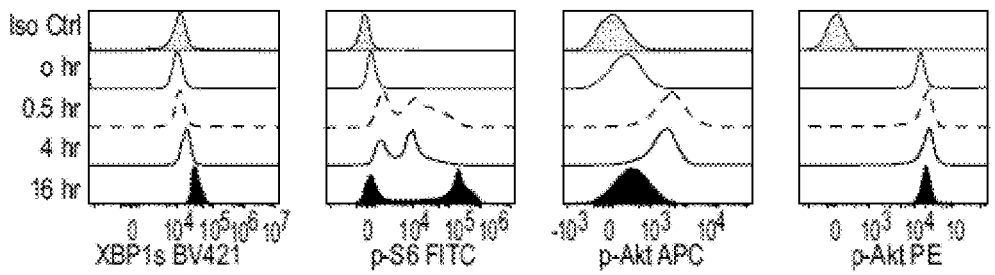
Figure 8H:
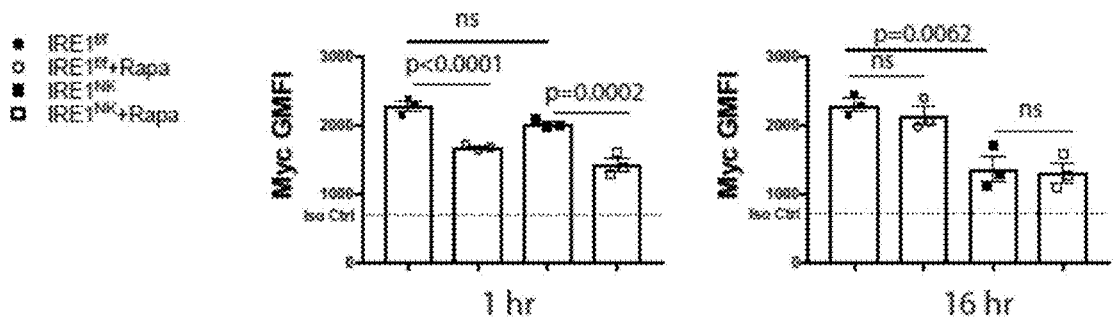
Figure 9F:
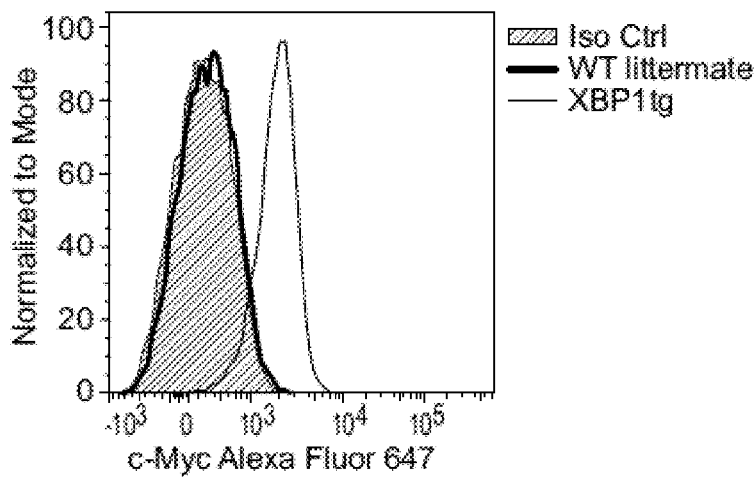
Figure 9G:
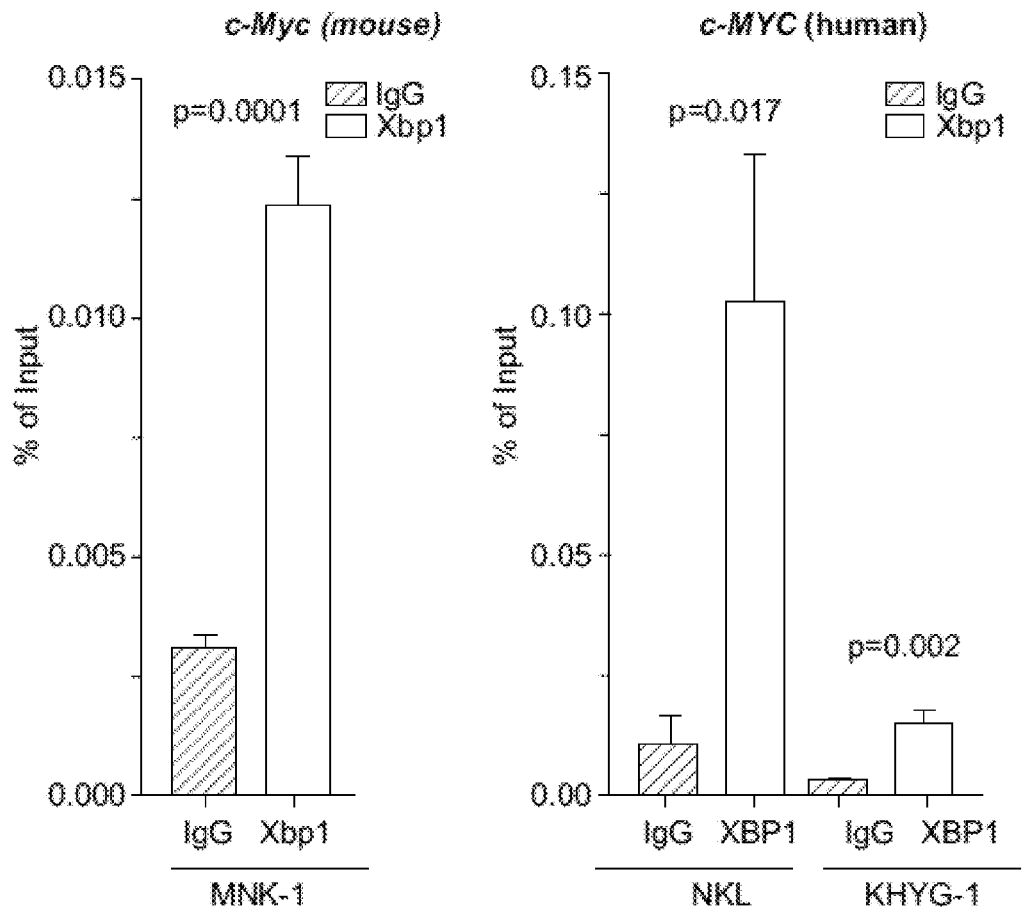
Figure 9H:
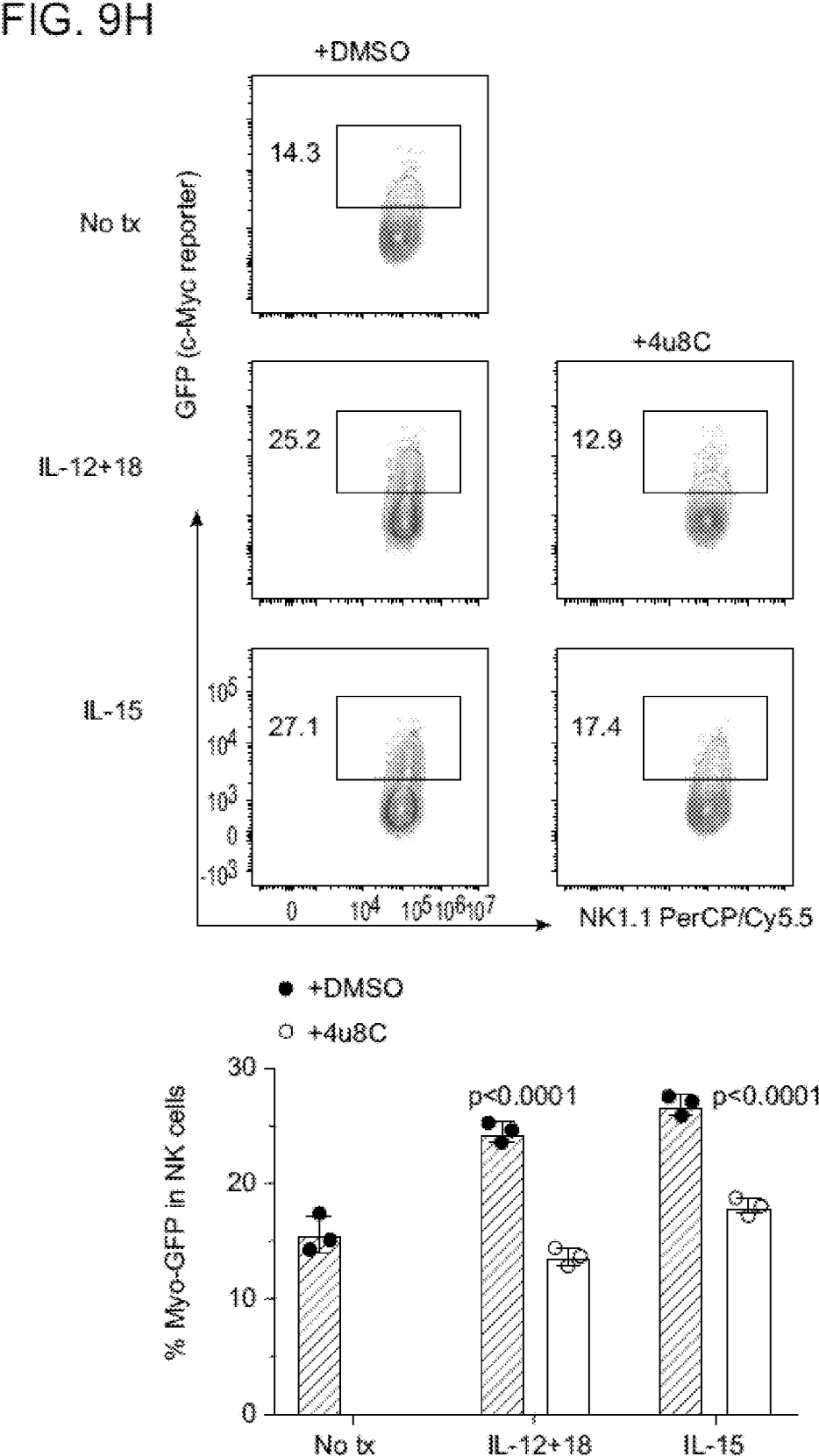
Figure 9I:
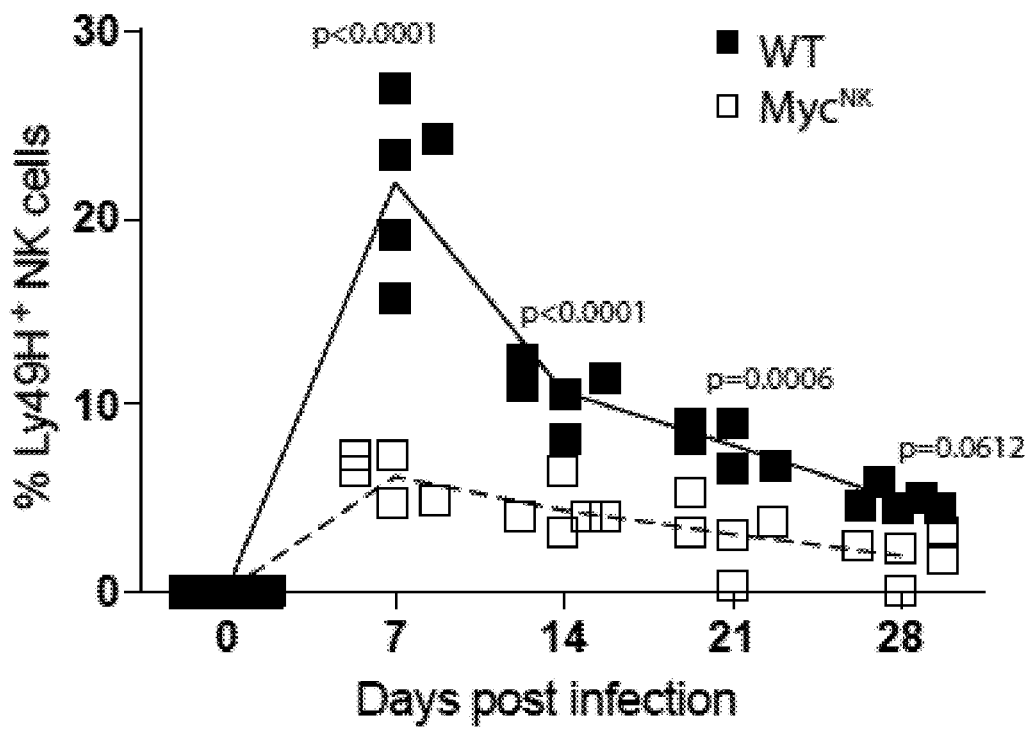
Figure 9I:
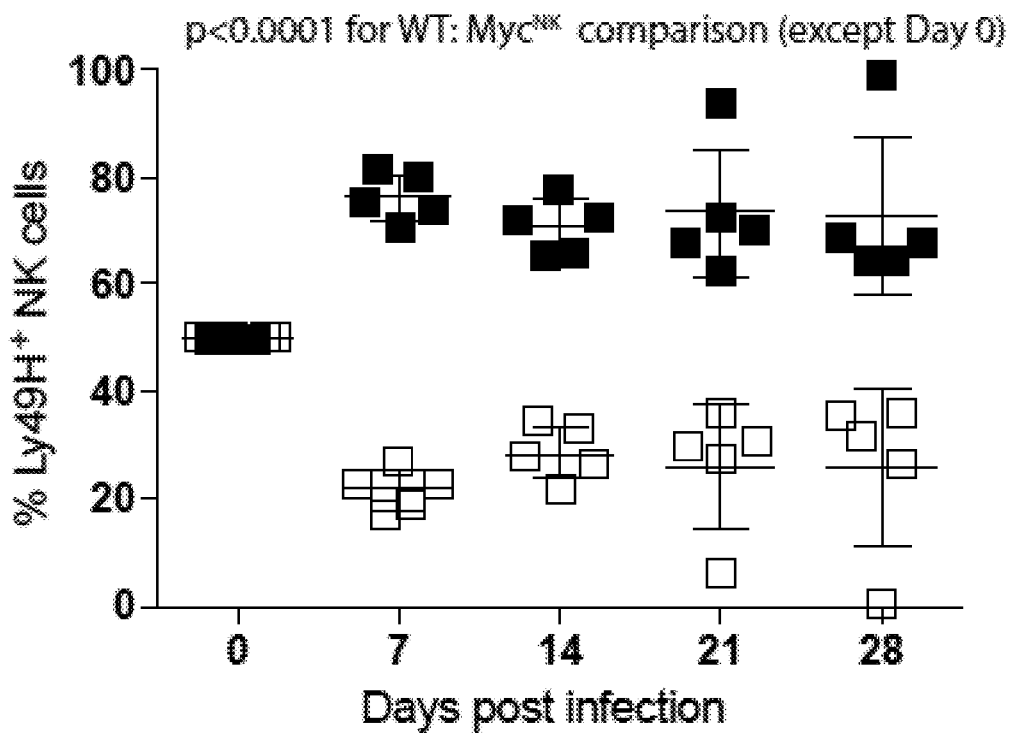
Figure 9J:
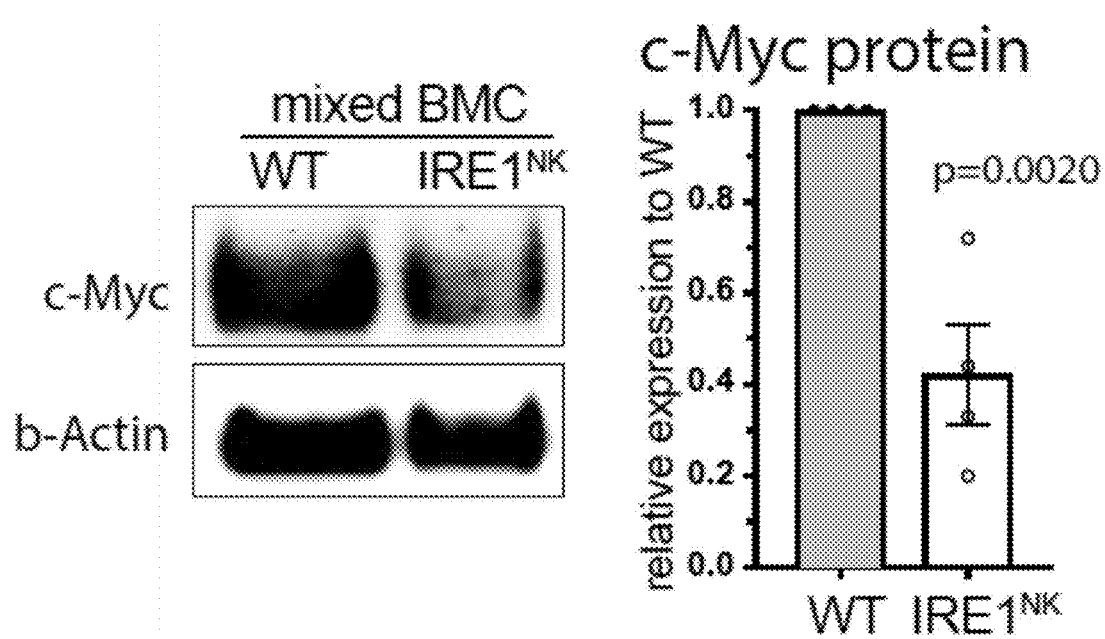

To investigate whether the IRE1α/XBP1 pathway is required for c-Myc induction, c-Myc expression in IRE1$^{NK}$ cells during MCMV infection was measured. The basal levels of c-Myc mRNA and protein were unaffected by the absence of IRE1α in naïve NK cells (FIG. 8F). During MCMV infection, c-Myc transcript and protein levels were significantly diminished in IRE1$^{NK}$ cells compared to WT counterparts (FIGS. 9D and 9J). Furthermore, suboptimal upregulation of canonical c-Myc targeting genes was observed in IRE1$^{NK}$ (cells (FIG. 8D). Consistent with the notion that c-Myc acts as a transcriptional repressor of the cell cycle checkpoint protein p21 (Lu et al. (2018) *Cancer Res.* 78:64-74), mRNA levels of Cdkn2a were significantly upregulated by depletion of IRE1α (FIG. 8D). Because c-Myc expression was not completely eradicated in the absence of IRE1α, complementary upstream mechanisms can exist (i.e., mTOR, FIG. 8H). Similar to viral infection, induction of the c-Myc protein during homeostatic proliferation was also impaired in IRE1$^{NK}$ cells (FIG. 9E). Examination of XBP1 overexpression transgenic mice revealed highly upregulated c-Myc expression in NK cells compared to littermate controls (FIG. 9F). Together, these results strongly indicated that activation of the IRE1α/XBP1 axis regulates c-Myc expression in NK cells.

XBP1s acts as a versatile transcription factor that canonically facilitates adaptation to ER stress by regulating distinct sets of target genes involved in protein folding and quality control (Lee et al. (2003) *Mol. Cell. Biol.* 23:7448-7459). Putative XBP1-binding sites (Clauss et al. (1996) *Nucleic Acids Res.* 24:1855-1864) were found in both human and mouse c-Myc promoter regions (FIG. 8E). Chromatin immunoprecipitation assays performed on a mouse NK/ILC cell line (MNK-1) phenotypically and functionally similar to primary mouse NK cells (Allan et al. (2015) *Mucosal. Immunol.* 8:340-351), and on two human NK cell lines derived from patients with aggressive NK leukemia/lymphoma (NKL (Robertson et al. (1996) *Exp. Hematol.* 24:406-415) and KHYG-1 (Frazier et al. (2013) *J. Immunol.* 190:6198-6208)) revealed a robust enrichment of XBP1 binding to the c-Myc promoter region (FIG. 9G), indicating that XBP1 directly influences transcription by binding at the c-Myc locus. A c-Myc reporter mouse strain (referred to as Myc$^{GFP}$) was also utilized to assess the extent to which c-Myc promoter activation is dependent on IRE1α. Myc$^{GFP}$ NK cells were stimulated in vitro, in the presence or absence of 4μ8c. Whereas c-Myc reporter GFP was induced upon treatment with either IL-15, or IL-12 and IL-18 in cells in the absence of 4μ8c, GFP induction was largely impeded within hours of IRE1α blockade (FIG. 9H). It was concluded that IRE1α positively regulates c-Myc transcription in activated NK cells by direct binding of XBP1 to the c-Myc promoter.

To evaluate the requirement for c-Myc in the expansion of activated NK cells, mice that harbor NK cells with haploinsufficiency in c-Myc were generated (referred to as Myc$^{NK}$, FIG. 16). If IRE1α/XBP1 regulates NK cell expansion primarily via its impact on c-Myc, Myc$^{NK}$ cells would show a similar defect to IRE1$^{NK}$ cells. Indeed, when equal numbers of Myc$^{NK}$ and CD45.1 congenic WT Ly49H$^+$ NK cells were co-transferred into Ly49H-deficient recipients and infected with MCMV, it was observed that WT NK cells outcompeted Myc$^{NK}$ cells during the entire course of the response (FIG. 9I). Thus, c-Myc deficiency impairs clonal expansion of NK cells in a manner similar to NK cells lacking IRE1α or XBP1.

Figure 15A:
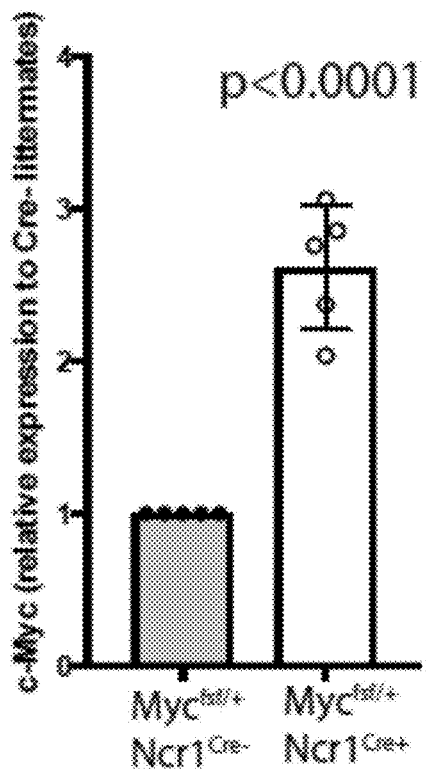
FIG. 15A-FIG. 15E show the restoration of c-Myc in the absence of IRE1 rescues the NK cell proliferation defect.
Figure 15B:
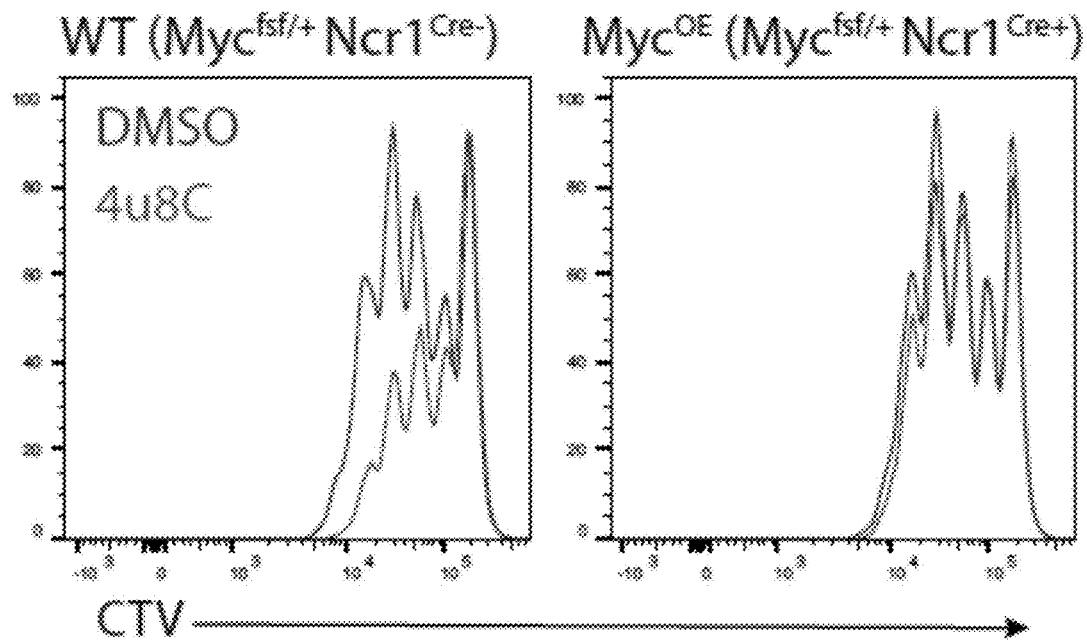
Figure 15C:
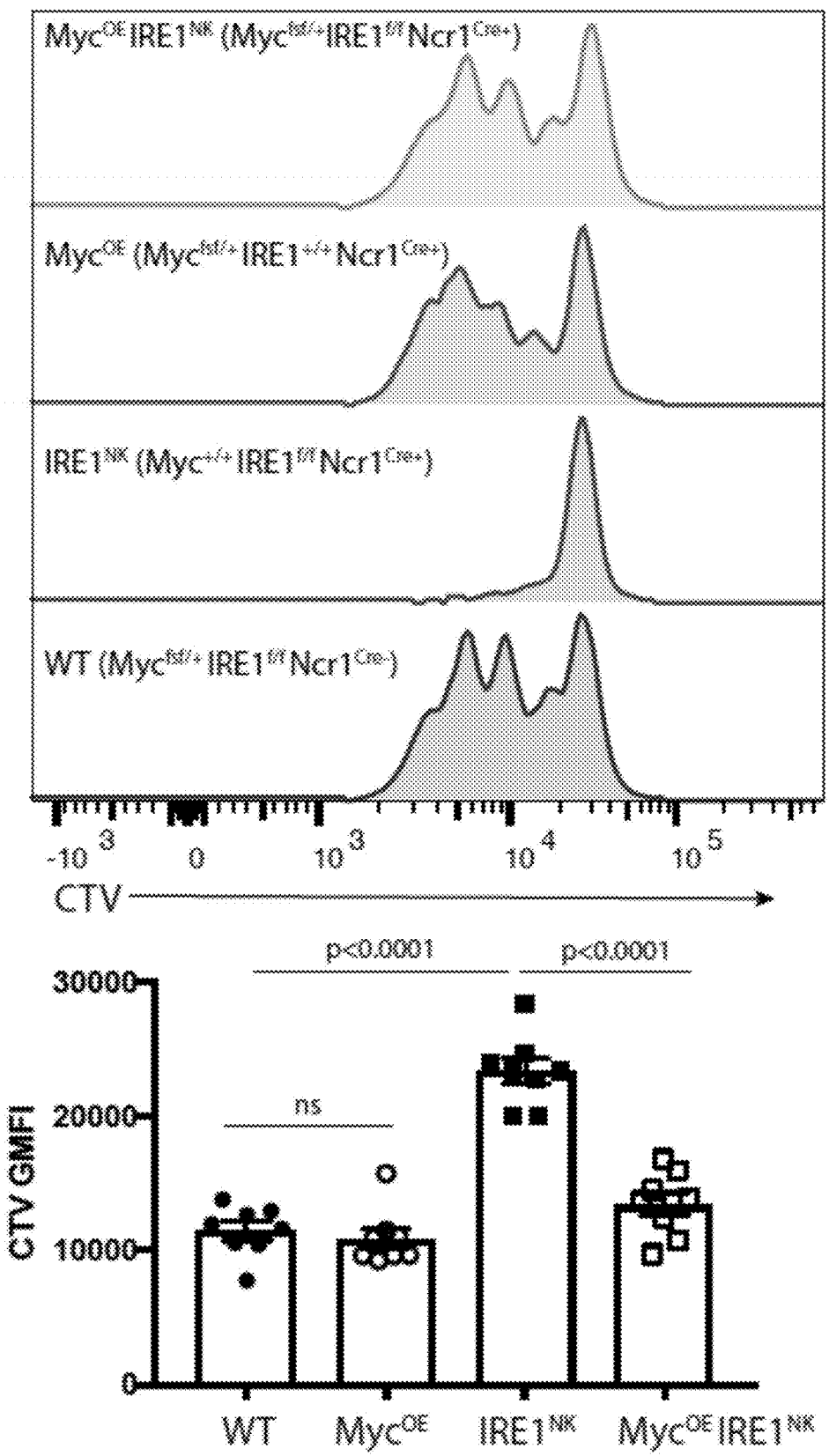
Figure 15D:
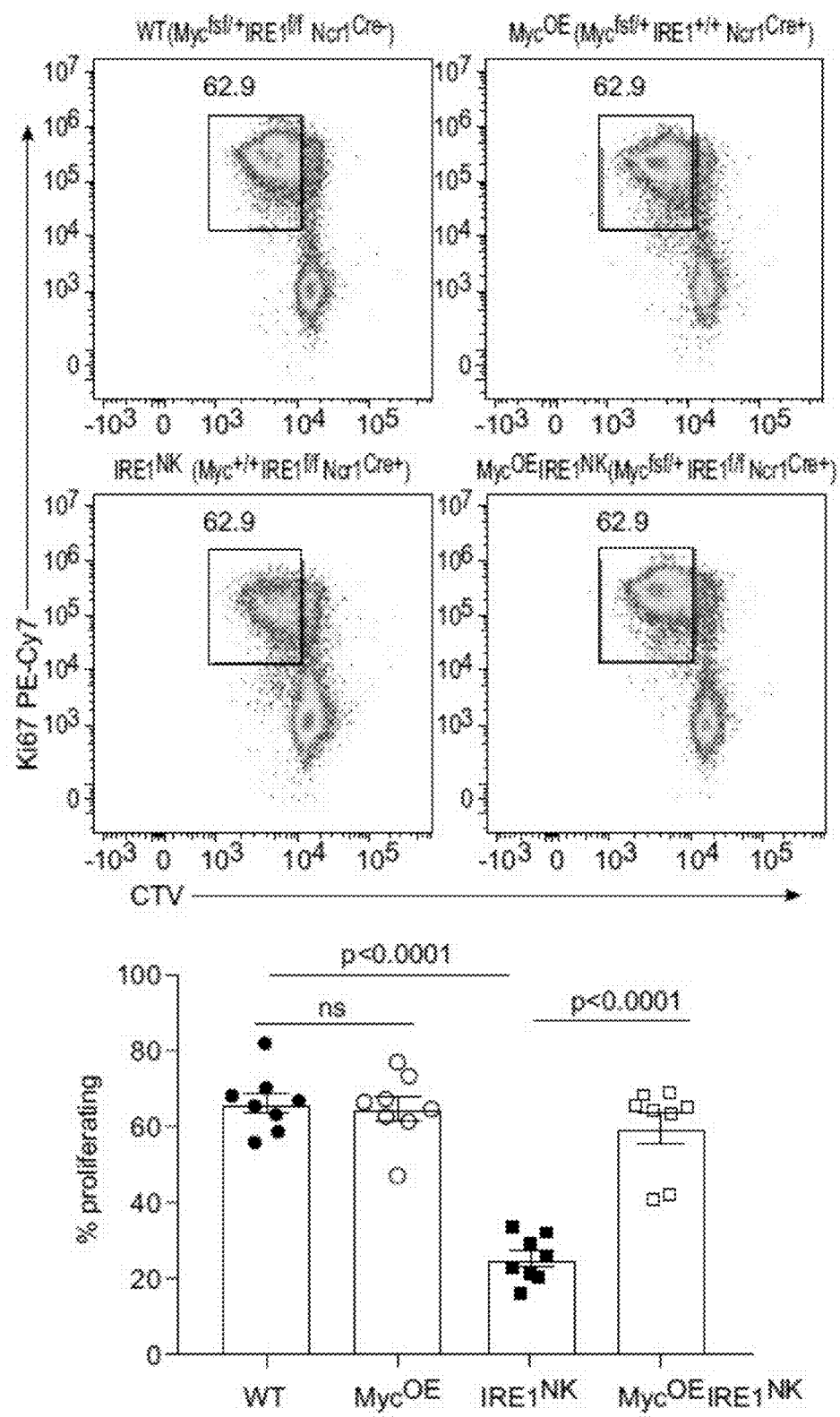
Figure 15E:
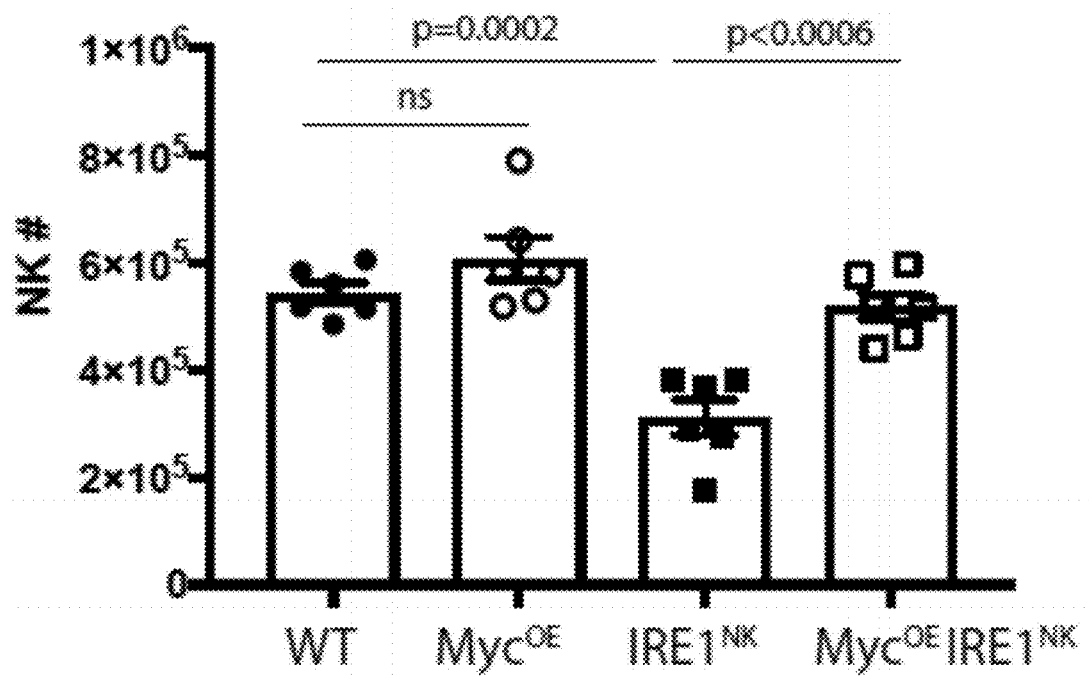
Figure 16A:
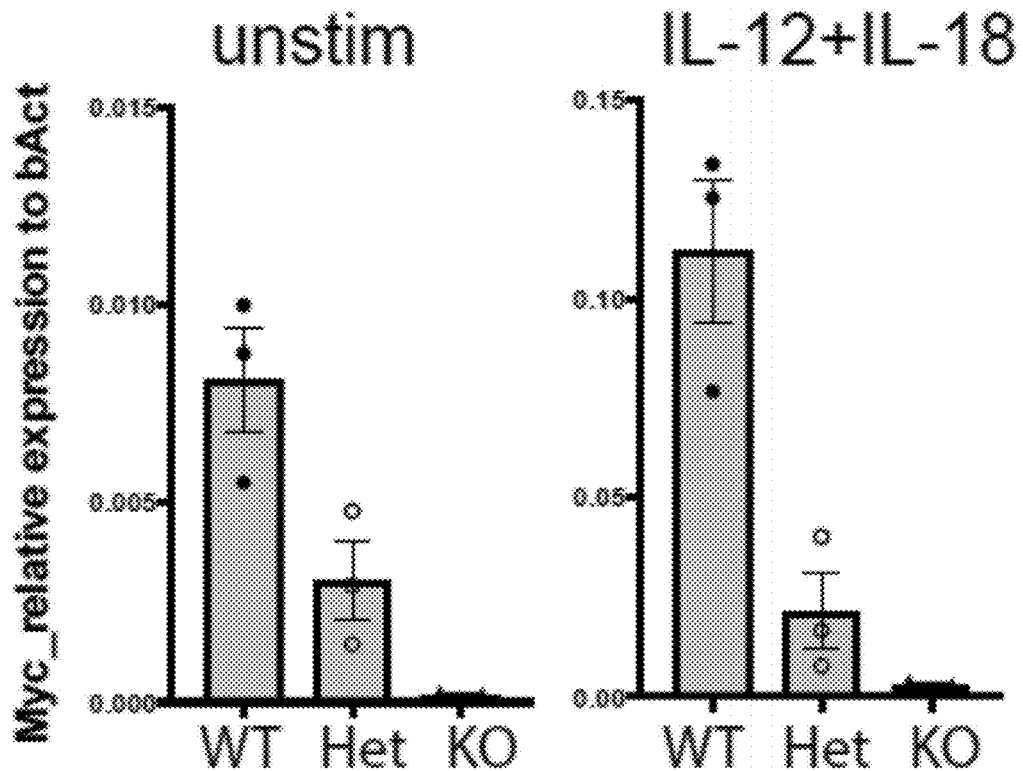
Figure 16B:
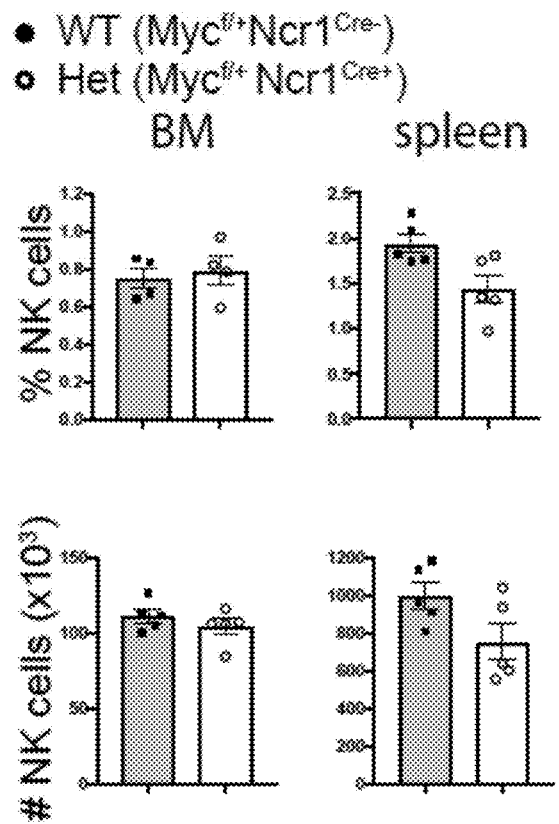
Figure 16C:
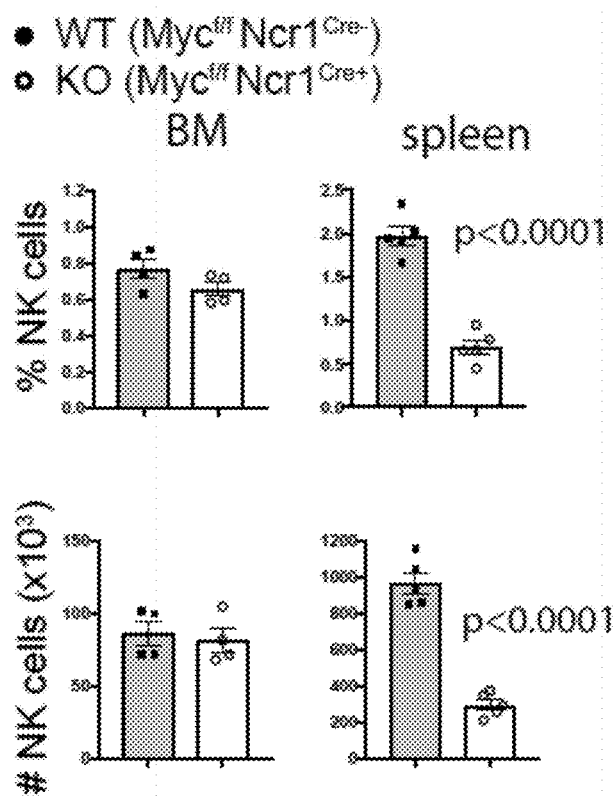
Figure 16D:
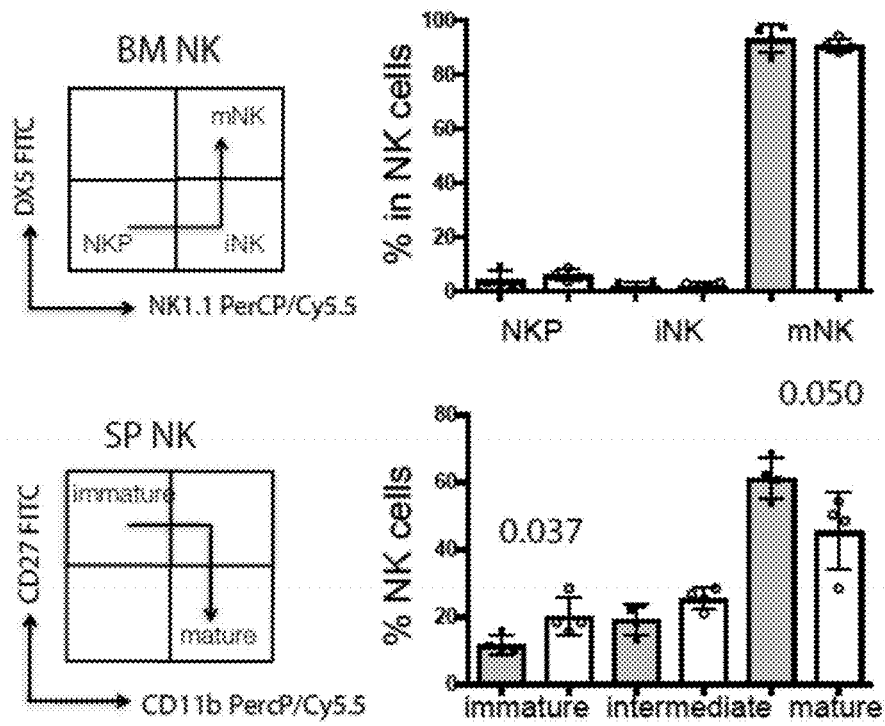
Figure 16E:
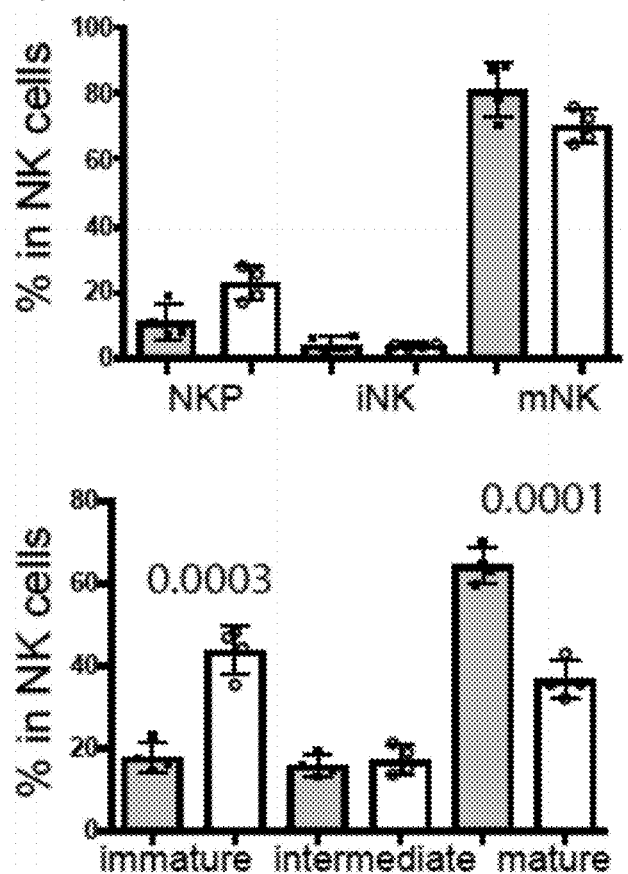
Figure 16F:
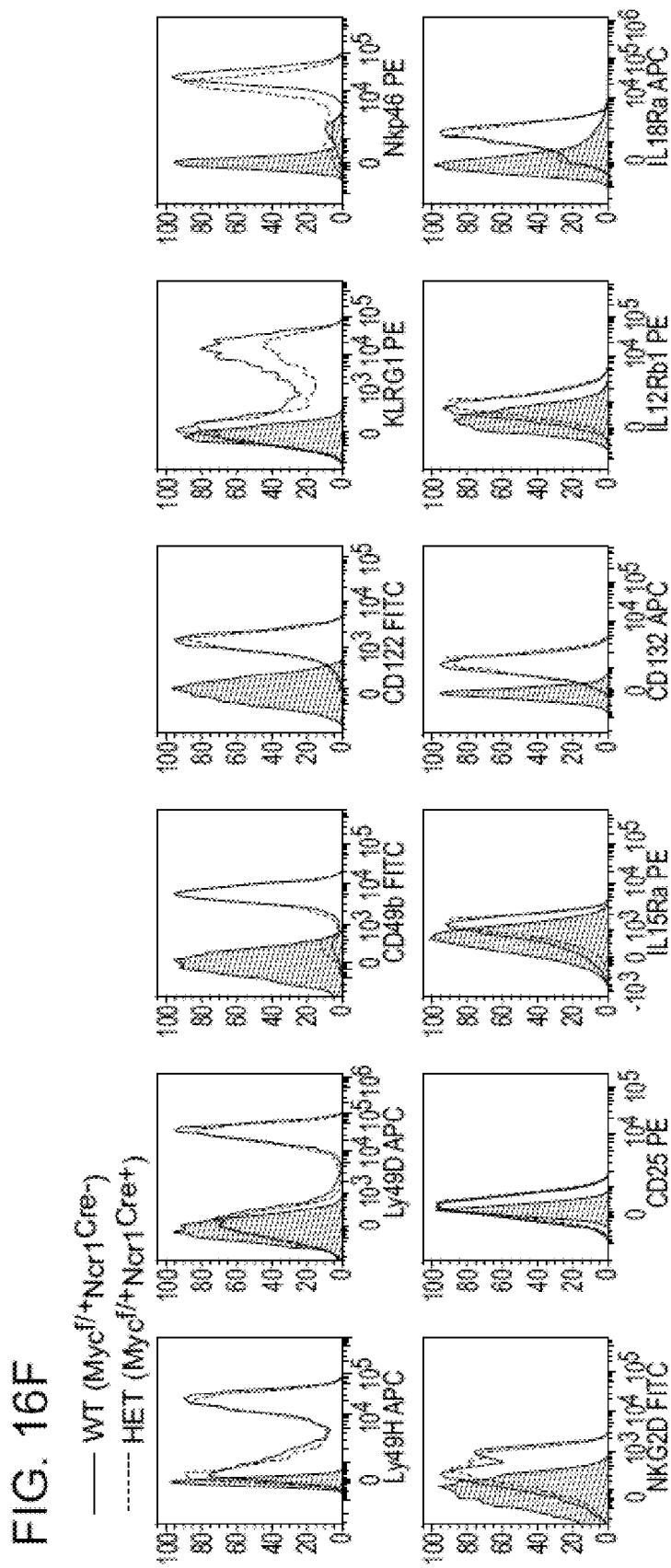

To formally test the hypothesis that IRE1α/XBP1 functions at least in part by regulating c-Myc in activated NK cells to facilitate their proliferation, mice that harbor NK cells with overexpression of c-Myc were generated (Myc$^{fsf/+}$ Ncr1$^{Cre+}$, referred to as Myc$^{OE}$). Levels of c-Myc were moderately elevated by 2-fold in Myc$^{OE}$ NK cells compared to their littermate controls (FIG. 15A), although this conferred no appreciable advantage in proliferation during in vitro expansion (FIGS. 15B-15E). If c-Myc is a primary mediator of IRE1α/270 XBP1 activity, overexpression of c-Myc should restore NK cell proliferation when IRE1α is pharmaceutically blocked or genetically depleted. Indeed, it was found that during in vitro expansion, NK cells from WT littermates (Myc$^{fsf/+}$ Ncr1$^{Cre+}$) were impaired in proliferation after treatment with 4μ8C; however, NK cells from Myc$^{OE}$ mice were largely rescued from this defect and proliferated to a comparable extent as in the DMSO-treated control group (FIG. 15B). Thus, the requirement of IRE1α/XBP1 for NK cell proliferation can be partially bypassed by the moderate overexpression of c-Myc. Myc$^{OE}$ mice were further crossed with the IRE1$^{NK}$ mice to overexpress c-Myc in NK cells with genetic deletion of IRE1α. The delayed proliferation observed in IRE1$^{NK}$ cells was significantly alleviated by restoration of c-Myc via genetic overexpression (FIGS. 15C-15E). Collectively, these findings reveal a novel XBP1-Myc axis that regulates NK cell expansion during infection and homeostatic proliferation.

Example 9: Requirement for IRE1α/XBP1 in NK Cell-Mediated Antitumor Immunity

Figure 10A:
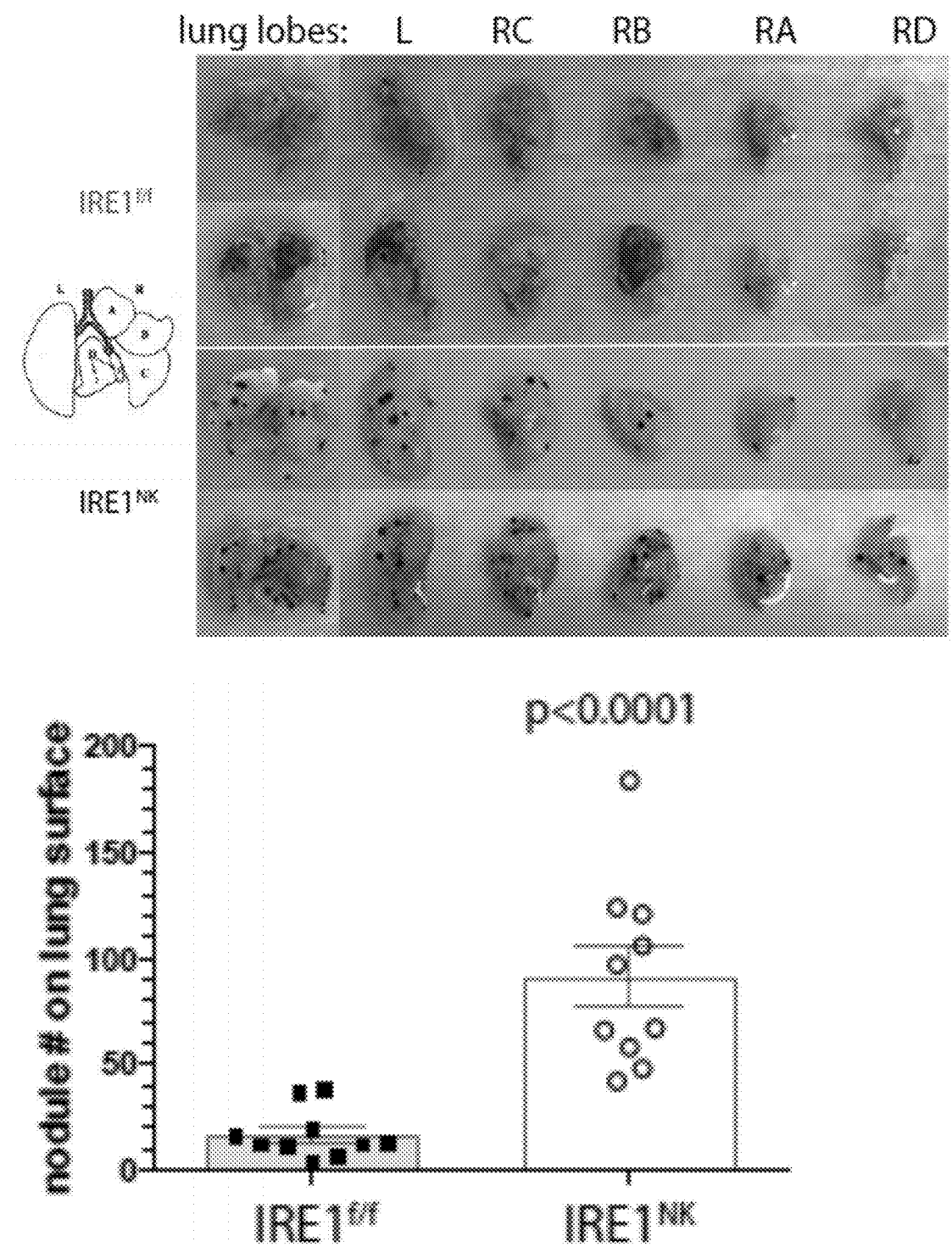
FIG. 10A-FIG. 10I shows the intrinsic requirement of IRE1α/XBP1 for NK cell-mediated antitumor immunity.
Figure 10B:
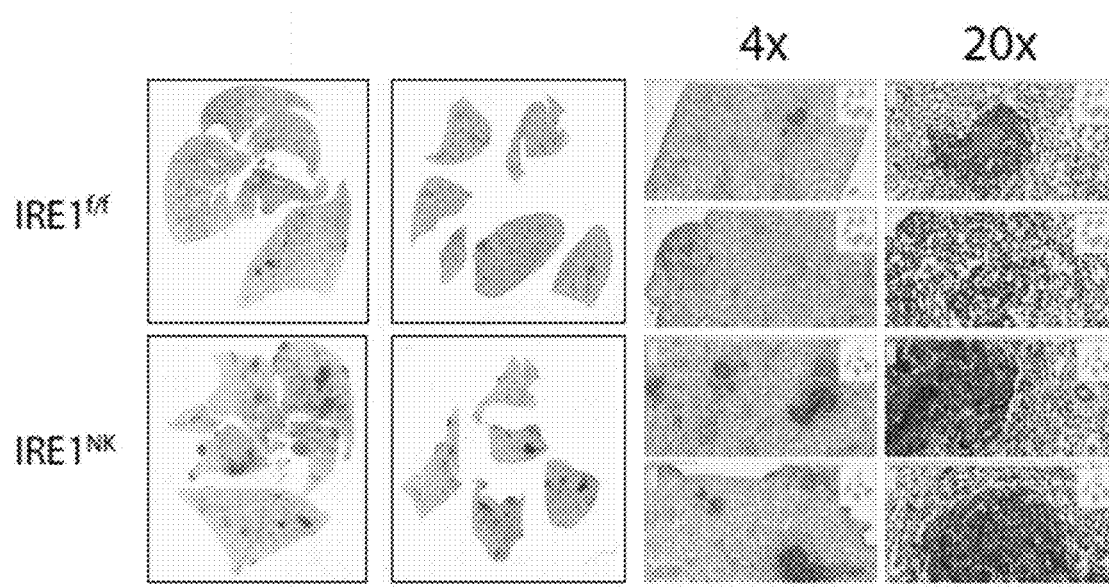
Figure 10C:
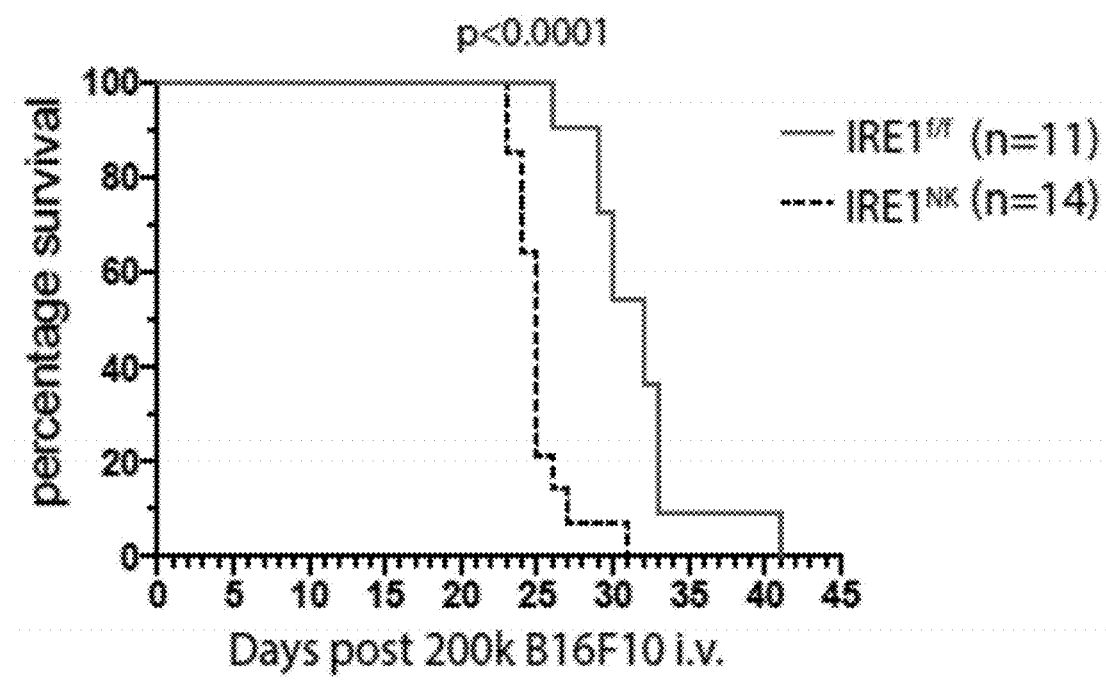
Figure 10D:
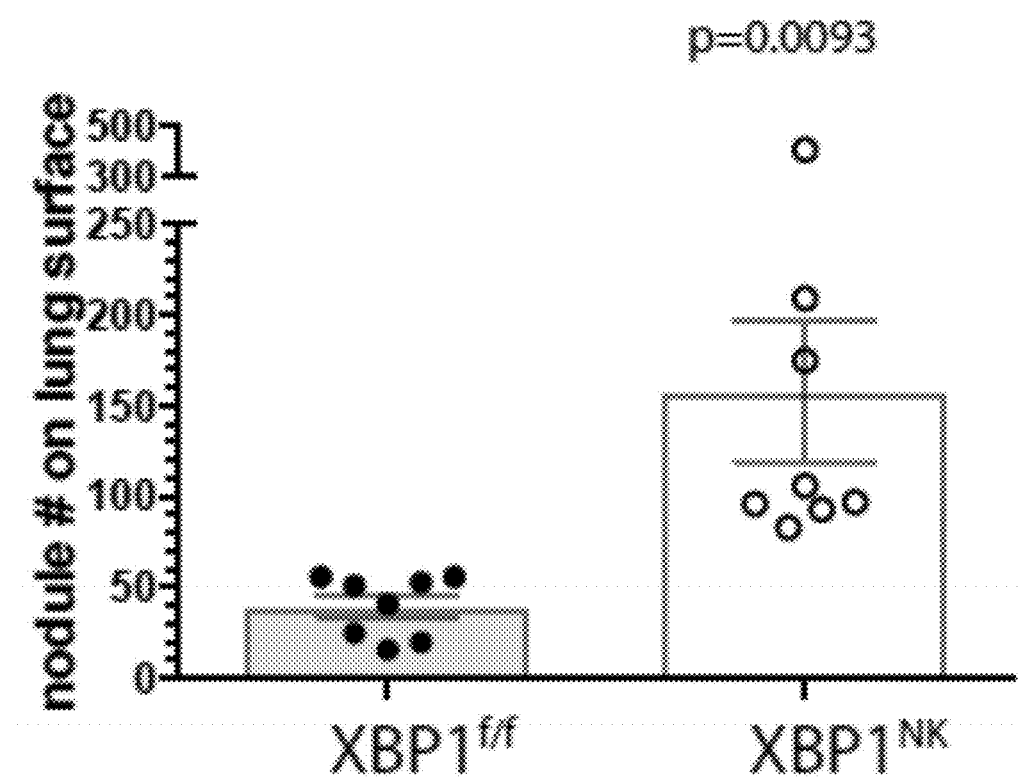
Figure 10E:
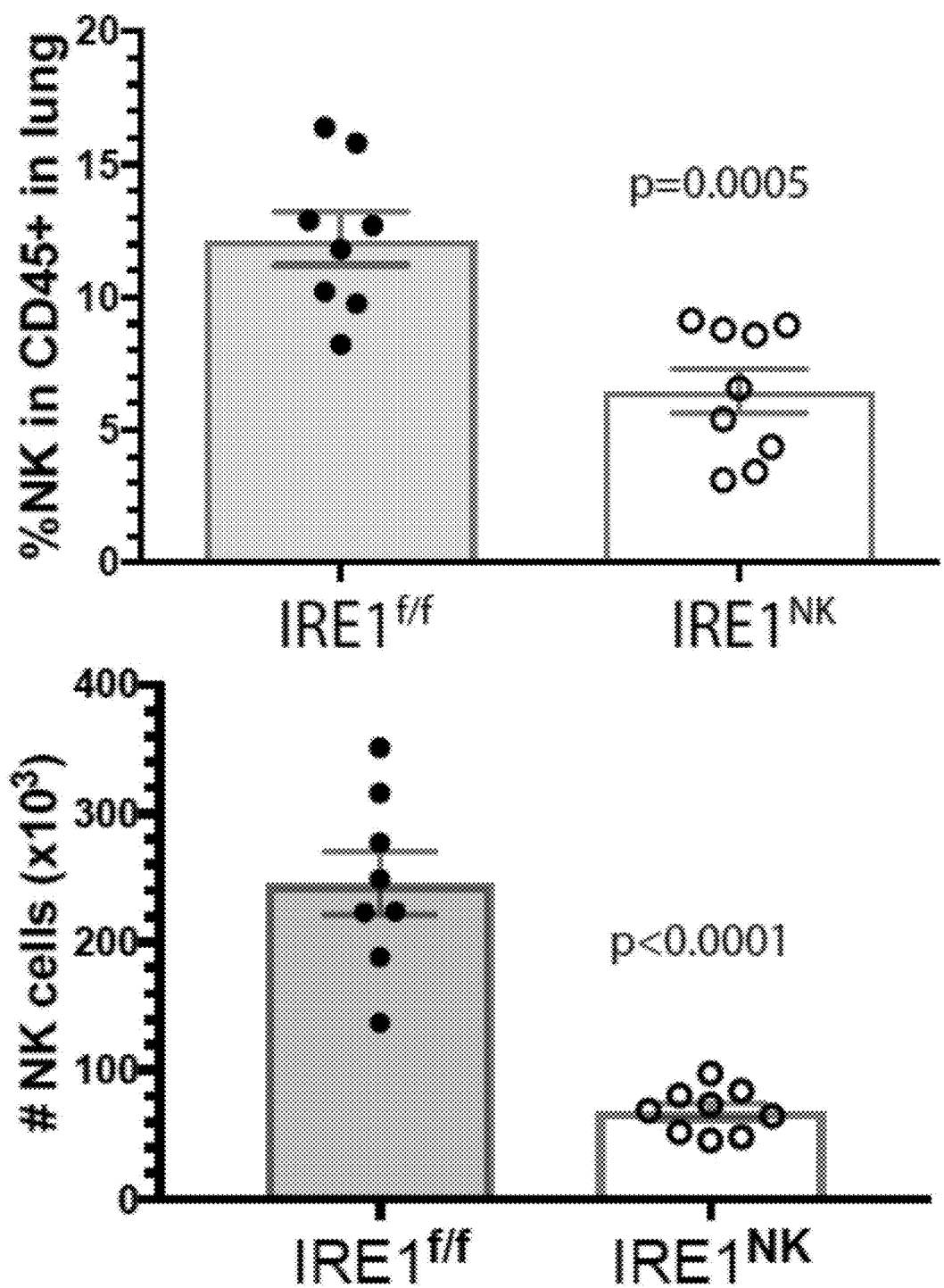

In addition to antiviral responses, NK cells have been demonstrated to play an important role in the host antitumor response (Foley et al. (2014) *Immunol. Rev.* 258:45-63; Ruggeri et al. (2002) *Science* 295:2097-2100; Ni et al. (2012) *J. Exp. Med.* 209:2351-2365; Molgora et al. (2017) *Nature* 551:110-114; Bottcher et al. (2018) *Cell* 172:1022-1037). The experimental intravenous B16 melanoma model provides a potent functional measurement of NK cell-mediated antitumor protection (Werneck et al. (2008) *J. Immunol.* 180:8004-8010). Thus, B16F10 tumor cells were introduced to IRE1$^{NK}$ mice and their IRE1$^{f/f}$ littermates by intravenous injection. Strikingly, while the majority of IRE1$^{f/f}$ mice were protected from lung colonization by the tumor at day 10 after inoculation, mice with IRE1α-deficient NK cells exhibited significantly more melanoma nodules (FIG. 10A) and micro-metastatic lesions (FIG. 10B). Inversely correlating with the increased tumor burden, survival of melanoma-bearing IRE1$^{NK}$ mice was significantly decreased (FIG. 10C). Similar to IRE1$^{NK}$ mice, XBP1$^{NK}$ mice also failed to control melanoma growth (FIG. 10D), consistent with a role for XBP1 downstream of IRE1 in NK cells. Similar to the defect in expansion in IRE1$^{NK}$ cells during viral infection, the lungs from tumor-inoculated IRE1$^{NK}$ mice displayed a 50-70% reduction in percentages and absolute numbers of infiltrating NK cells compared to counterparts from IRE1$^{f/f}$ littermates (FIG. 10E), along with significantly decreased levels of proliferation marker Ki-67

Figure 10F:
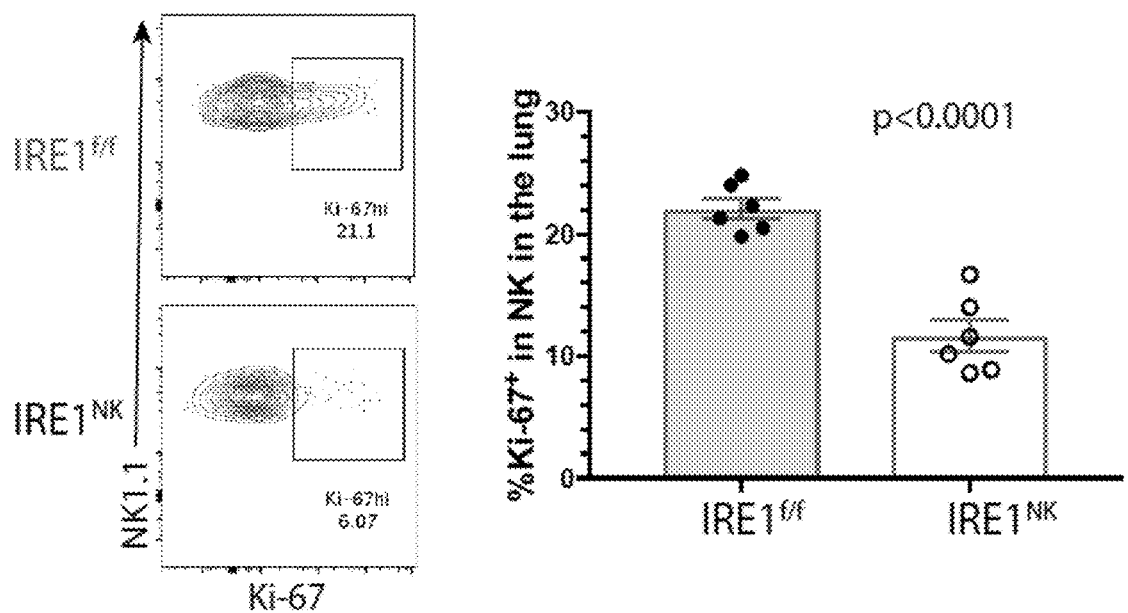
Figure 10G:
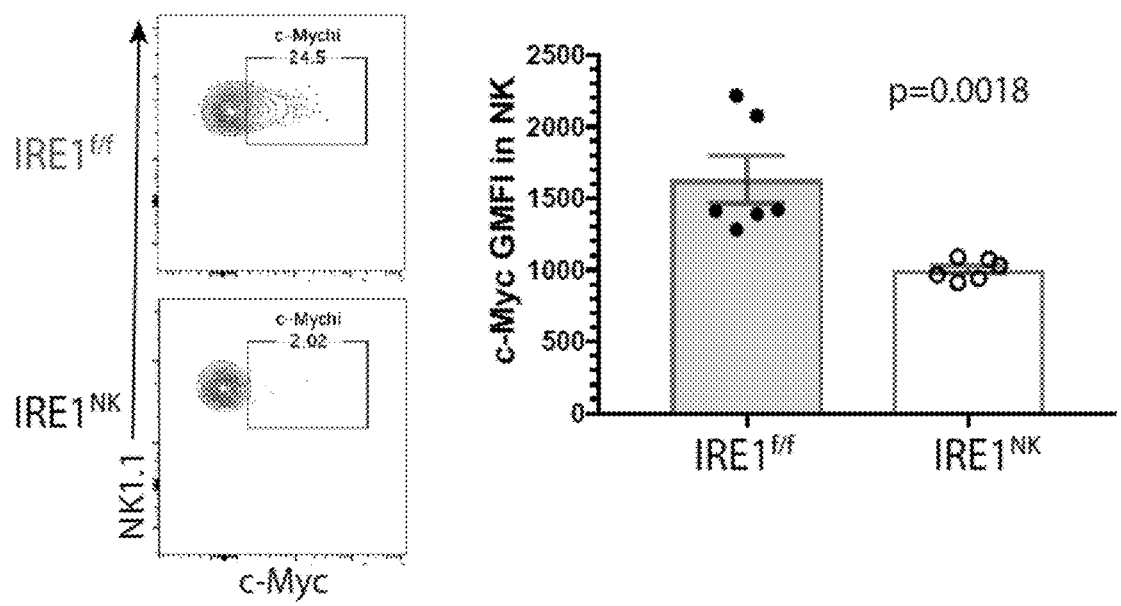
Figure 11A:
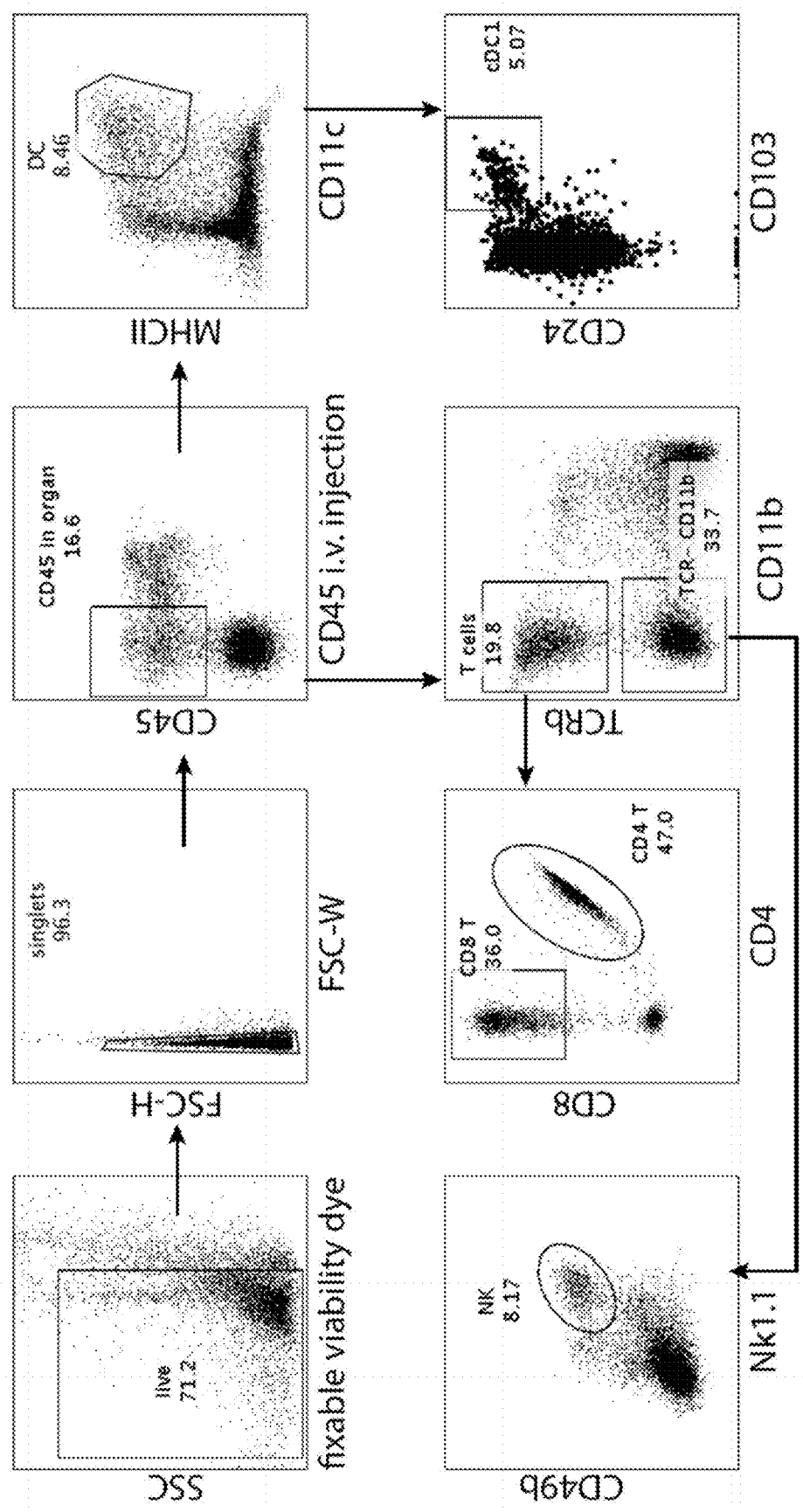
FIG. 11A-FIG. 11D show that IRE1α-driven NK cell expansion is associated with presentation of immune cell types beneficial to tumor control and that IRE1α in NK cells promote IFN-γ production in tumor infiltrated lymphocytes.
Figure 11B:
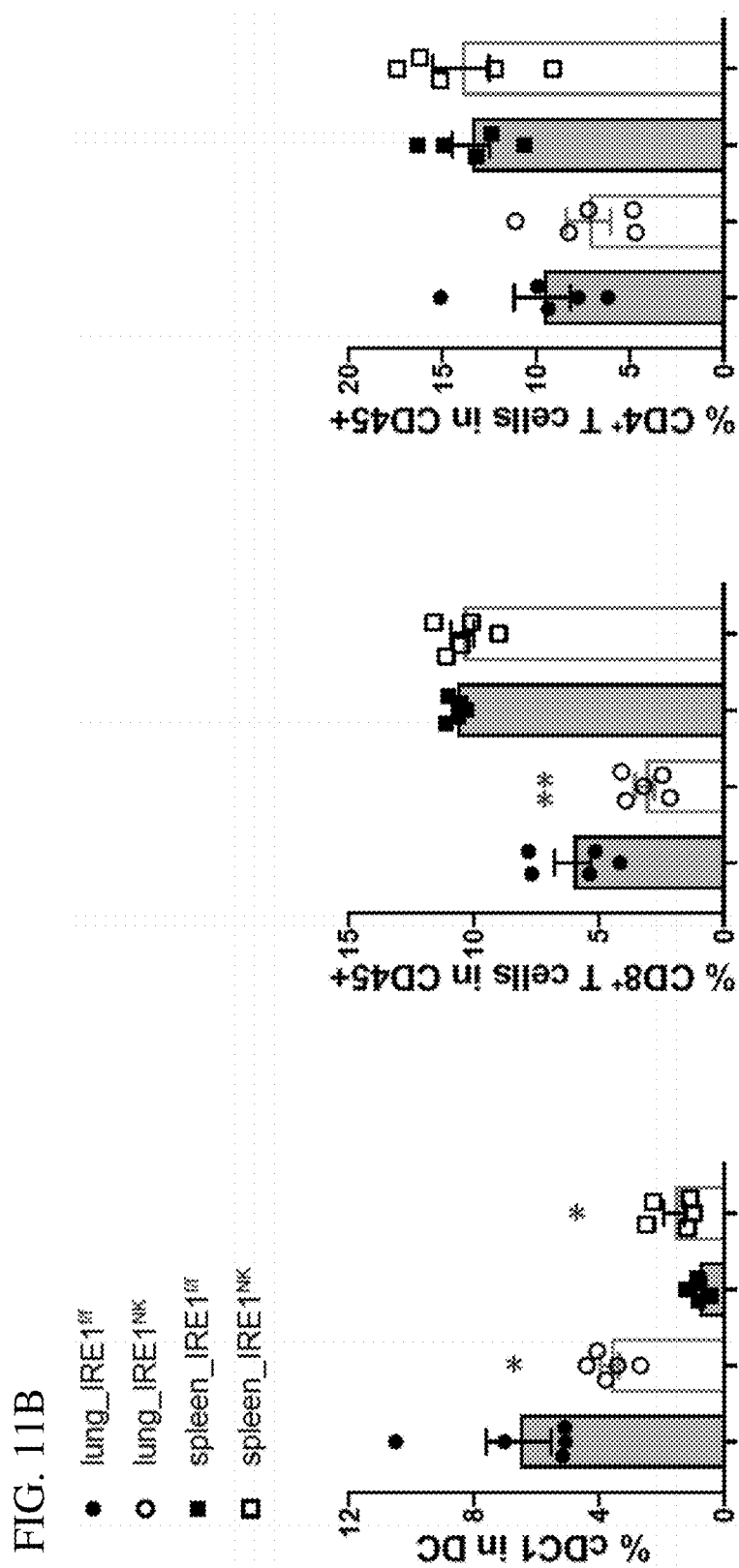
Figure 11C:
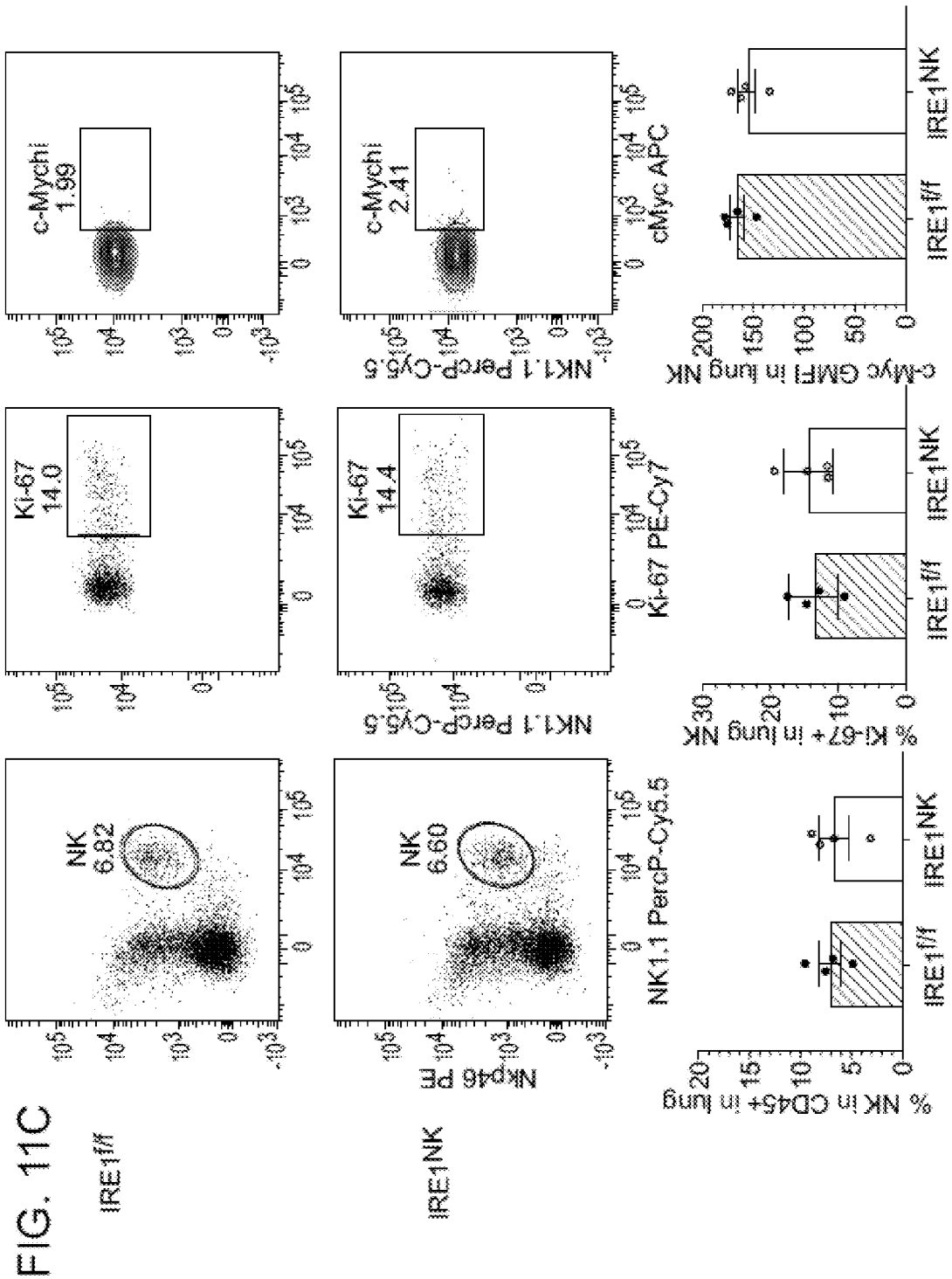

(FIG. 10F) and transcription factor c-Myc (FIG. 10G). Of note, the decreased number of NK cells and decreased levels of Ki-67 and c-Myc (FIGS. 10E-10G) are only apparent following tumor injection, as no changes were detected in tumor-free animals (FIG. 11C and FIG. 3F).

Figure 10H:
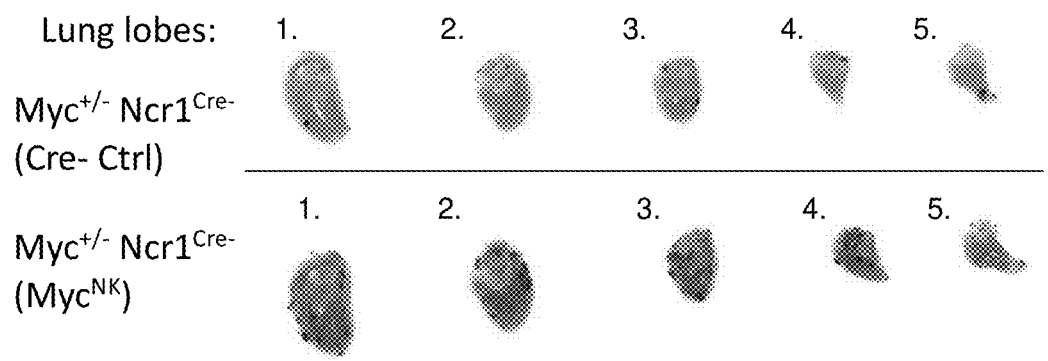
Figure 10H:
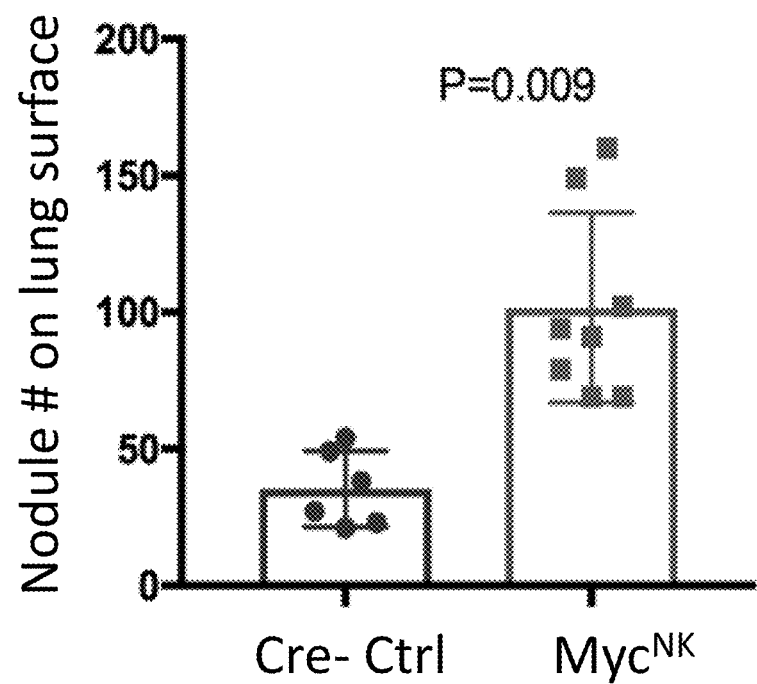
Figure 10I:
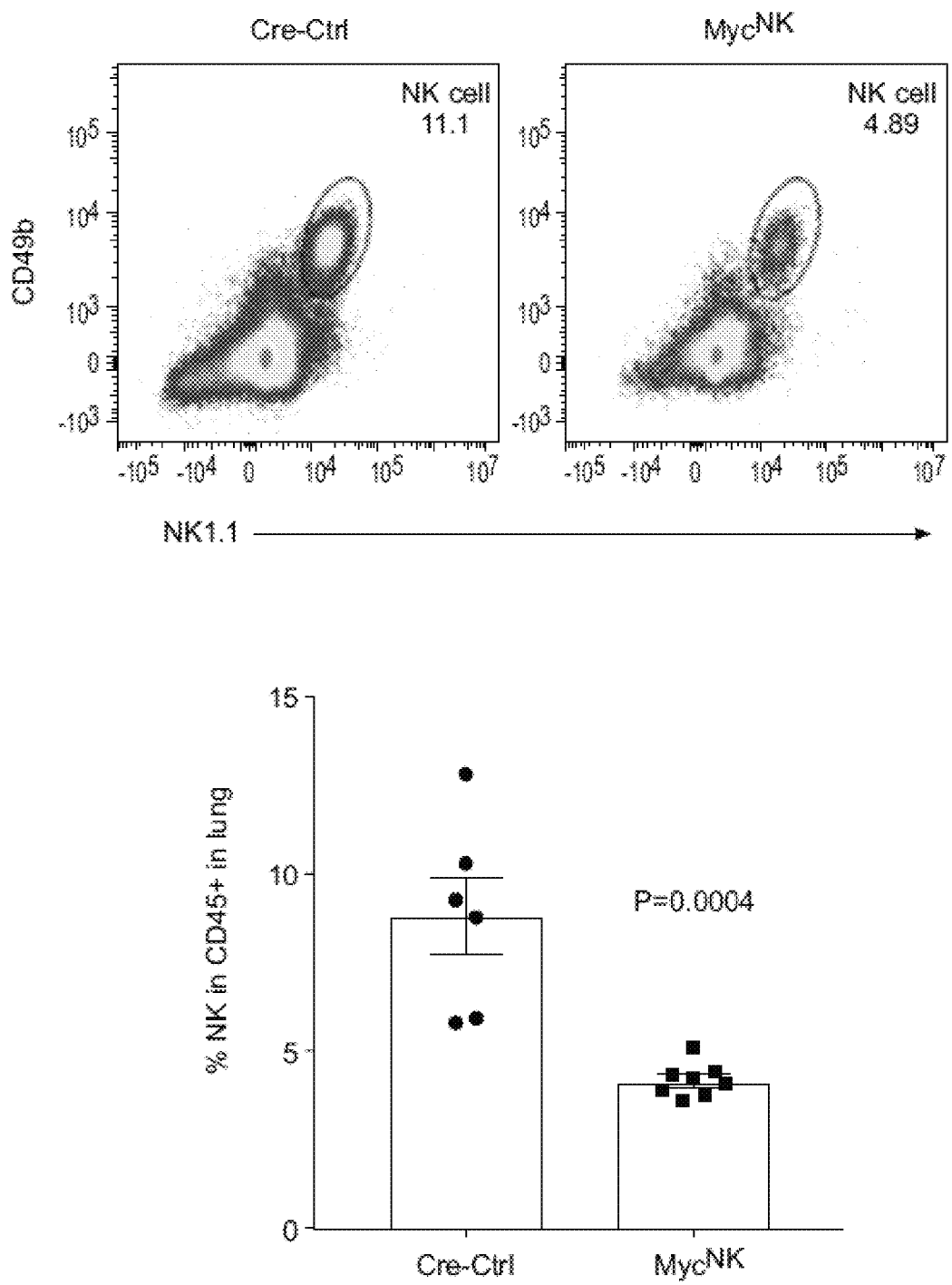
Figure 11D:
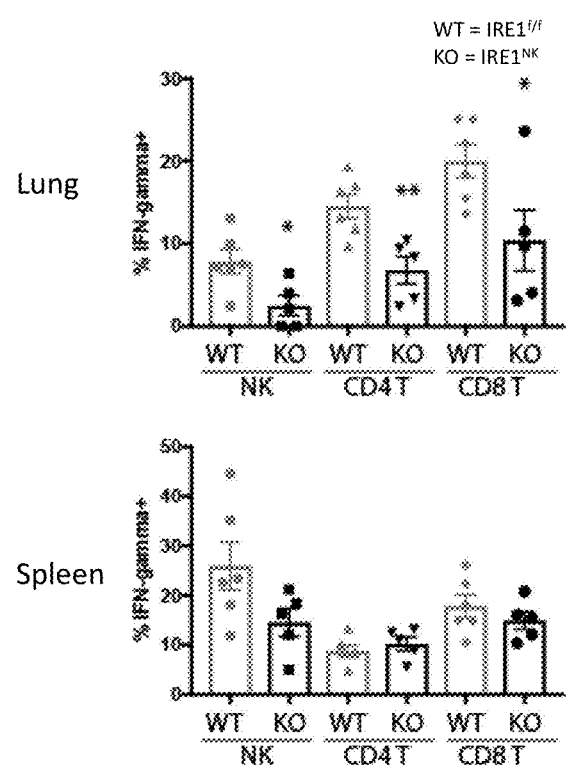

Importantly, Myc$^{NK}$ mice phenocopied the defect of IRE1$^{NK}$ and XBP$^{NK}$ in tumor control (FIG. 10H). Inversely correlating with the increased tumor burden, percentages of infiltrating NK cells in tumor-inoculated Myc$^{NK}$ mice were significantly reduced compared to counterparts from Myc-competent littermates (FIG. 10I), thereby consistently demonstrating an essential role of the IRE1α-XBP1-Myc axis in NK cell-mediated antitumor immunity. Finally, besides its central role in promoting NK cell expansion, IRE1α in NK cells is also positively associated with enhanced infiltration of immune cell types beneficial to tumor control (FIG. 11B) and with production of a main antitumor cytokine, IFN-γ, in tumor infiltrated lymphocytes (FIG. 11D). Collectively, these findings reveal a novel IRE1α-XBP1-Myc axis that regulates NK cell expansion in cancer and versatilely benefits NK cell-driven antitumor immunity.

Example 10: Requirement for IRE1α/XBP1 in NK Cell Memory

Besides their innate cytotoxic and immunostimulatory activity, recent studies have demonstrated that NK cells are capable of generating immunological memory such that they undergo a proliferative burst in response to initial stimulation and generating long-lived memory cells that respond more robustly upon re-stimulation (Romee et al. (2012) *Blood* 120:4751-4760). For example, inflammatory cytokines induce memory-like NK cells that have enhanced antitumor activity compared to naïve NK cells (Romee et al. (2016) *Science Transl. Med.* 8:357ra123). In contrast to adaptive immune cells, such as T cells and B cells, cytokine-induced, memory-like NK cells (CIML) are not restricted to specific antigen and thus offer a new opportunity in developing cell-based immunotherapy. Strikingly, small molecule blockade of IRE1α led to highly compromised antitumor function of human primary CIML NK cells, as evidenced by the significantly reduced IFN-γ production (FIG. 17C). Similarly, IRE1$^{NK}$ mice showed decreased IFN-γ levels in the tumor infiltrated NK cells at a late time point (FIG. 11D), which is consistent with a critical role of IRE1α/XBP1 in antitumor function of long-maintained memory NK cells. Of note, IRE1α/XBP1 differentially promotes IFN-γ production in memory NK cells, whereas IRE1α/XBP1 has minimal impact on naïve NK cells during acute, primary responses to infection (FIG. 5B). Thus, the IRE1α/XBP1 pathway is crutial for generation of NK cell memory and harnessing this pathway may further enhance the antitumor activity of NK cell-based immunotherapy.

Taken together, these findings demonstrated that the IRE1α/XBP1 pathway is required for optimal expansion of NK cells and NK cell memory to facilitate host protection against NK cell-sensitive cancer.

It was demonstrated herein that the IRE1α/XBP1 branch of the ER stress response is a key signaling pathway in NK cells that is important for their function in viral infection, homeostatic proliferation and cancer. NK cells lacking either the upstream sensor IRE1α or its downstream substrate XBP1 fail to expand in response to MCMV infection, lymphopenia or melanoma. Mechanistically, it was found that this highly evolutionarily conserved branch of the UPR directly regulates c-myc signaling and mitochondrial respiration to control cell proliferation in NK cells. These data indicated that the mammalian immune system has evolved a mechanism to incorporate a common cellular stress process to enhance antiviral immunity. The fact that this highly conserved pathway has also been demonstrated to be co-opted by invading pathogens to ensure their survival in host cells (Xuan et al. (2009) *J. Virol.* 83:3463-3474; Qian et al. (2012) *J. Virol.* 86:6712-6723; Siddiquey et al. (2018) *J. Virol.* 92:e00896-18) provides intriguing evidence for host-virus coevolution.

The host immune system participates in controlling viral infection primarily through early activation of innate NK cells followed by an adaptive response by CD8$^+$ killer T cells. NK cells can recognize infected cells without prior sensitization and counteract infection by initiating effector functions including cytotoxicity, cytokine production, and proliferation (Morvan and Lanier (2016) *Nat. Rev. Cancer* 16:7-19). However, less is known about the key intrinsic regulators that control their function or expansion (Beaulieu et al. (2014) *Nat. Immunol.* 15:546-553; Rapp et al. (2017) *Sci. Immunol.* 2:eaan3796; Madera et al. (2018) *J. Immunol.* ji1700416). Described herein is the identification of ER stress as an important component of NK cell expansion in vivo during MCMV infection. CMV is the leading viral cause of birth defects in human newborns and is a common and dangerous pathogen in immunocompromised individuals (including cancer and transplant patients) (Orange et al. (2006) *Curr. Opin. Allergy Clin. Immunol.* 6:399-409). To date, no effective vaccine against CMV is available (Sun and Lanier (2017) Cold Spring Harb. *Perspect. Biol.* a029512). Recapitulating the findings in MCMV-infected mice, it was demonstrated that human primary NK cells activate the IRE1α/XBP1 pathway in response to the pro-inflammatory cytokines present during CMV infection and rely on this pathway for optimal ex vivo expansion. Activation of the IRE1 branch of the ER stress pathway serves useful in developing new vaccine strategies for host control of pathogens by harnessing NK cell compartment.

In patients and animal models, impaired NK cell function is associated not only with recurring viral infection, but also with an increased incidence of various malignancies (Morvan and Lanier (2016) *Nat. Rev. Cancer* 16:7-19; Vivier et al. (2012) *Nat. Rev. Immunol.* 12:239-252; Orange et al. (2013) *J. Allergy. Clin. Immunol.* 132:515-525). Recent studies have begun to uncover the cellular and molecular mechanisms underlying the pivotal role in cancer immuno-surveillance of NK cells, whose "primed" cytotoxicity is elicited by activating receptor signaling (Barrow et al. (2018) *Cell* 172:534-548; Ferrari de Andrade et al. (2018) *Science* 359:1537-1542), and by their ability to recruit other immune cells into the tumor microenvironment (Bottcher et al. (2018) *Cell* 172:1022-1037). A cell-intrinsic requirement for IRE1α/XBP1 signaling in NK cell-mediated antitumor responses was demonstrated herein. Importantly, the failure to control melanoma lung metastasis is associated with an impaired expansion of the NK cell compartment, providing an in vivo indication that IRE1-driven NK cell expansion is critical for tumor immunosurveillance. The deficiency in NK cell expansion correlates with reduced recruitment of type 1 conventional dendritic cells and CD8$^+$ T cells (FIGS. 11A-11B), consistent with the notion that NK cells not only function as direct killers but also potentiate an antitumor microenvironment that promotes cancer immune control (Bottcher et al. (2018) *Cell* 172:1022-1037).

NK cells have recently attracted attention for their potential use as immune-based therapies (Ferrari de Andrade et al. (2018) Science 359:1537-1542; Rabacal et al. (2016) *Proc. Natl. Acad. Sci. USA* 113:5370-5375; Andre et al. (2018)

Cell 175:1731-1743; Van Montfoort et al. (2018) Cell 175: 1744-1755; Barry et al. (2018) Nat. Med. 24:1178-1191). This has been best documented in the setting of hematopoietic cell transplantation (HCT) in patients with leukemia (Foley et al. (2014) Immunol. Rev. 258:45-63). Alloantigen-specific NK cells have been shown to benefit such patients by providing graft-versus-tumor function while simultaneously preventing T cell-mediated graft-versus-host disease (Ruggeri et al. (2002) Science 295:2097-2100). Leukemia patients undergoing immunoablative treatments before HCT often become susceptible to CMV (Sun and Lanier (2017) Cold Spring Harb. Perspect. Biol. a029512), highlighting the key role of NK cells in eliminating both tumor and virus in this setting. In addition, NK cells are known to be the first lymphocytes to reconstitute the bone marrow of patients following HCT (Foley et al. (2014) Immunol. Rev. 258:45-63). However, the magnitude of and mechanism underlying NK cell homeostatic proliferation in the setting of lymphopenia are poorly understood (Zawislak et al. (2013) Proc. Natl. Acad. Sci. USA 110:6967-6972; Sun et al. (2011) J. Exp. Med. 208:357-368; Rabacal et al. (2016) Proc. Natl. Acad. Sci. USA 113:5370-5375; Pahl et al. (2018) Cancer Immunol. Res.). It was demonstrated that although unnecessary for normal NK cell expansion during development, the IRE1α/XBP1 signaling pathway is indispensable for the homeostatic proliferation of mature NK cells in vivo in response to lymphopenia-induced stress, and for IL-15-driven homeostatic-like proliferation (Ali et al. (2015) Front. Immunol. 6:355) of human primary NK cells largely provided by the CD56$^{bright}$ highly proliferative subset. These findings provide strong mechanistic justification for incorporating NK cells into adoptive cellular immunotherapy strategies to target cancer in patients following immunoablative treatment (Morvan and Lanier (2016) Nat. Rev. Cancer 16:7-19; Vivier et al. (2012) Nat. Rev. Immunol. 12:239-252), and indicate that pre-treatment of NK cells with a combination of cytokines (for instance, IL-15, IL-12 and IL-18 that are now being used in the clinic) can further increase the therapeutic efficiency of adoptive NK cell transfer.

The IRE1α-XBP1 branch of the ER Stress or Unfolded Protein Response is best known for its role in the development of normal "professional" secretory cells such as fetal hepatocytes, pancreatic acinar cells, plasma cells, eosinophils and Paneth cells (Lee et al. (2011) Proc. Natl. Acad. Sci. USA 108:8885-8890; Lee et al. (2008) Science 320: 1492-1496; Kaser et al. (2008) Cell 134:743-756). Depletion of XBP1 in neurons protects mice from neurodegenerative diseases by increasing autophagy (Vidal et al. (2012) Hum. Mol. Genet. 21:2245-2262; Martinez et al. (2016) Cell Rep 14:1382-1394; Hetz and Papa (2018) Mol. Cell 69:169-181). However, emerging evidence has demonstrated its key function in promoting intrinsic tumor growth in a number of malignancies including triple negative breast cancer (Chen et al. (2014) Nature 508:103-107; Xie et al. (2018) J. Clin. Invest. 128:2339-2355). It was demonstrated herein that vigorous activation of IRE1α/XBP1 is required for normal NK cell function in combating MCMV infection, lymphopenia and melanoma. It has been shown that this pathway is also beneficial in modulating macrophage-mediated inflammatory responses to bacterial infection (Martinon et al. (2010) Nat. Immunol. 11:411-418). In contrast, overactivation of IRE1α/XBP1 can drive pathology. For example, IRE1α/XBP1 drives pathologic autoantibody production in plasma cells in systemic lupus erythematosus (Todd et al. (2009) J. Exp. Med. 206:2151-2159), drives neurodegenerative diseases by controlling autophagy in neurons (Vidal et al. (2012) Hum. Mol. Genet. 21:2245-2262; Martinez et al. (2016) Cell Rep 14:1382-1394; Hetz and Papa (2018) Mol. Cell 69:169-181), and drives malignancies including triple negative breast cancer and myeloma by promoting intrinsic tumor growth (Chen et al. (2014) Nature 508:103-107, Xie et al. (2018) J. Clin. Invest. 128:2339-2355). And in sharp contrast to its protective role in activating NK cell immunity against MCMV and melanoma described herein, overactive IRE1α/XBP1 signaling in dendritic cells (Cubillos-Ruiz et al. (2015) Cell 161:1527-1538) and CD4+ T cells (Song et al. (2018) Nature 562:423-428) can cripple anti-tumor immune responses against ovarian cancer. The highly pleiotrophic functions of this pathway and the unique molecular mechanisms that govern those functions in different organs and different cell types can explain the disparate effects of overactivation or silencing of this branch of the UPR. For example, the signaling pathways upstream of IRE1α/XBP1 activation vary among cell types. In macrophages, activation is induced through Toll-like receptor signaling while in NK cells, as shown here, both IL-12/STAT4 and mTOR signaling pathways act as critical upstream regulators of IRE1α/XBP1 under infectious/inflammatory conditions. Indeed mTOR is also situated downstream of IL-15 (Mao et al. (2016) Blood 128:1475-1489; Marcais et al. (2014) Nat. Immunol. 15:749-757) and IL-12 (Loftus et al. (2018) Nat. Commun. 9:2341) (also see FIG. 8G), and is essential for NK cell development and antitumor responses (Yang et al. (2018) Elife 7:e35619). Consistent with the data in NK cells, a recent publication demonstrated that mTOR drives IRE1α/XBP1 activation in liver in response to food perception (Brandt et al. (2018) Cell 175:1321-1335), as well as in lung Th2 cells and fibroblasts in fibrotic disease (Hsu et al. (2017) Sci. Rep. 7:14272; Zheng et al. (2018) Sci. Rep. 8:8905).

The unexpected and important finding that XBP1 directly controls the transcription of c-Myc and its downstream target genes in NK cells was evidenced by promoter binding and transactivation assays and by the demonstration that restoration of c-Myc largely rescues the proliferation defect in IRE1α-deficient NK cells. This appears paradoxical in light of the recent finding that the oncogene c-Myc acts upstream of the IRE1α/XBP1 pathway to drive tumorigenesis in transformed cells (Zhao et al. (2018) J. Clin. Invest. 128:1283-1299). However, this discrepancy can be explained by the differing functions and downstream consequences of IRE1α signaling in normal versus transformed cells and in cells belonging to different lineages. One clear difference between transformed versus normal cells is that the former are addicted to constitutively activated c-Myc while the latter display negligible levels of c-Myc at baseline, requiring external stimuli to be induced. Although c-Myc is among the best-studied oncogenes and tumor-intrinsic Myc activity has been reported to program an immune suppressive microenvironment that is obligatory for tumor progression (Kortlever et al. (2017) Cell 171:1301-1315), its regulation and direct function in cells of the immune system is less well understood (Chou et al. (2014) Nat. Immunol. 15:884-893; Bianchi et al. (2006) Blood 107: 3992-3999; Gnanaprakasam and Wang (2017) Genes (Basel) 8(3)). A recent study indicated that c-Myc is essential for upregulation of metabolic responses in IL-2/IL-12-activated mouse NK cells ex vivo (Loftus et al. (2018) Nat. Commun. 9:2341). In human NK cells ex vivo, c-MYC is thought to function downstream of IL-15 to enhance effector function (Cichocki et al. (2009) Blood 113:3245-53). Here, the in vivo evidence of an essential role for c-Myc acting downstream of IRE1α/XBP1 to drive NK cell expansion during MCMV infection, lymphopenia and anti-tumor immunity was provide. Consistent with the observations that ablation of the IRE1α/XBP1 axis in NK cells results in compromised tumor surveillance, it was recently reported that c-MYC levels were significantly decreased in NK cells from cancer patients compared to healthy donors (Zakiryanova et al. (2017) *Immun. Inflamm. Dis.* 5(4):493-502), indicating a protective role of c-MYC in NK cell-mediated antitumor immunity in human disease.

Finally, the finding that IRE1α supports mitochondrial function and morphology in NK cells was unexpected given that it has been recently described that depletion of IRE1α/XBP1 helps to restore the metabolic fitness of T cells in ovarian cancer (Song et al. (2018) *Nature* 562:423-428). Intriguingly, 25 of the 46 differentially expressed OXPHOS genes in IRE1α-deficient NK cells are known to be regulated by c-Myc (Morrish and Hockenbery (2014) *Cold Spring Harb. Perspect. Med.* 4:a014225) (FIG. 14A). Thus, the dysregulated metabolism observed here can be in part a consequence of impaired Myc signaling (Loftus et al. (2018) *Nat. Commun.* 9:2341) which is in turn at least partly responsible for the failure of IRE1α-deficient NK cells to expand appropriately in vivo in response to viral infection, lymphopenia and malignancy.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject having a condition that would benefit from upregulation of an immune response comprising administering to the subject a therapeutically effective amount of a composition comprising natural killer (NK) cells modified to increase the copy number of XBP1.

2. The method of claim 1, wherein
   a) the NK cells are derived from the subject who is treated with the composition; or
   b) the NK cells are derived from a different subject who is not treated with the composition.

3. The method of claim 1, wherein the condition is an infection, optionally wherein the infection is a viral infection, bacterial infection, protozoan infection, parasite infection, fungal infection, or helminth infection.

4. The method of claim 1, wherein the condition is a viral infection caused by a virus selected from the group consisting of CMV, human immunodeficiency virus (HIV), hepatitis B virus (HBV), hepatitis C virus (HCV), influenza A virus, Epstein-Barr virus (EBV), human herpes simplex virus (HSV) type 1 and type 2, respiratory syncytial virus (RSV), human papilloma virus (HPV), lymphocytic choriomeningitis virus (LCMV), Zika virus, Rift Valley fever virus (RVFV), dengue virus (DENV), chikungunya virus (CHIKV), enterovirus (EV), and human adenovirus (HAdV).

5. The method of claim 4, wherein the composition promotes antiviral immunity in the subject or promotes clonal expansion of NK cells upon viral infection in the subject, decreases viral titers in the subject, or increases overall survival rate.

6. The method of claim 1, wherein the condition is a bacterial infection caused by *Listeria monocytogenes, Mycobacterium tuberculosis*, or *Salmonella typhimurium*.

7. The method of claim 1, wherein the condition is a parasite infection caused by *Plasmodium* or *Cryptosporidium*, further optionally wherein the *Plasmodium* is malaria parasite.

8. The method of claim 1, wherein the condition is a fungal infection caused by *Aspergillus*, optionally wherein the *Aspergillus* is *Aspergillus fumigatus*.

9. The method of claim 1, wherein the condition is lymphopenia.

10. The method of claim 1, wherein the condition is cancer, optionally wherein the cancer is a NK cell-sensitive cancer or the cancer is selected from the group consisting of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, thyroid cancer, and cervical cancer.

11. The method of claim 1, wherein the composition promotes antitumor immunity in the subject.

12. The method of claim 1, wherein the composition increases the amount of NK cells infiltrating a tumor, increases the amount of type 1 conventional dendritic cells or CD8+ T cells infiltrating a tumor, or reduces the number of proliferating cells in the cancer or reduces the volume or size of a tumor comprising the cancer cells.

* * * * *